(12) United States Patent
Gold et al.

(10) Patent No.: US 8,114,404 B2
(45) Date of Patent: *Feb. 14, 2012

(54) METHOD AND COMPOSITION FOR ALTERING A B CELL MEDIATED PATHOLOGY

(75) Inventors: Daniel P. Gold, Del Mar, CA (US); Robert J. Shopes, San Diego, CA (US)

(73) Assignee: MMRGLOBAL, Inc., Los Angeles, CA (US)

(*) Notice: Subject to any disclaimer, the term of this patent is extended or adjusted under 35 U.S.C. 154(b) by 214 days.

This patent is subject to a terminal disclaimer.

(21) Appl. No.: 10/843,703

(22) Filed: May 10, 2004

(65) Prior Publication Data

US 2005/0238645 A1    Oct. 27, 2005

Related U.S. Application Data

(63) Continuation of application No. 09/927,121, filed on Aug. 10, 2001, now Pat. No. 6,911,204.

(60) Provisional application No. 60/224,723, filed on Aug. 11, 2000, provisional application No. 60/224,722, filed on Aug. 11, 2000, provisional application No. 60/279,079, filed on Mar. 23, 2001.

(51) Int. Cl.
    A61K 39/00      (2006.01)
    A61K 39/385     (2006.01)
    A61K 48/00      (2006.01)
    A01N 63/00      (2006.01)
    C07K 16/00      (2006.01)

(52) U.S. Cl. ............... 424/184.1; 424/192.1; 424/193.1; 424/277.1; 424/93.1; 424/93.2

(58) Field of Classification Search .......................... None
    See application file for complete search history.

(56) References Cited

U.S. PATENT DOCUMENTS

| | | |
|---|---|---|
| 3,969,287 A | 7/1976 | Jaworek et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,338,397 A | 7/1982 | Gilbert et al. |
| 4,399,216 A | 8/1983 | Axel et al. |
| 4,444,878 A | 4/1984 | Paulus |
| 4,468,464 A | 8/1984 | Cohen et al. |
| 4,512,922 A | 4/1985 | Jones et al. |
| 4,634,665 A | 1/1987 | Axel et al. |
| 4,661,586 A | 4/1987 | Levy et al. |
| 4,704,362 A | 11/1987 | Itakura et al. |
| 4,745,051 A | 5/1988 | Smith et al. |
| 4,816,249 A | 3/1989 | Levy et al. |
| 4,816,397 A | 3/1989 | Boss et al. |
| 4,840,896 A | 6/1989 | Reddy et al. |
| 5,053,224 A | 10/1991 | Koprowski et al. |
| 5,078,996 A | 1/1992 | Conlon, III et al. |
| 5,122,464 A | 6/1992 | Wilson et al. |
| 5,149,625 A | 9/1992 | Church et al. |
| 5,162,111 A | 11/1992 | Grabstein et al. |
| 5,179,017 A | 1/1993 | Axel et al. |
| 5,227,159 A | 7/1993 | Miller et al. |
| 5,229,496 A | 7/1993 | Deeley et al. |
| 5,254,534 A | 10/1993 | Tachibana et al. |
| 5,281,699 A | 1/1994 | Chang et al. |
| 5,334,379 A | 8/1994 | Pillai et al. |
| 5,478,556 A | 12/1995 | Elliot et al. |
| 5,580,561 A | 12/1996 | Cercek et al. |
| 5,602,007 A | 2/1997 | Dunn et al. |
| 5,612,035 A | 3/1997 | Howell et al. |
| 5,650,150 A | 7/1997 | Gillies |
| 5,679,347 A | 10/1997 | Porcelli et al. |
| 5,679,356 A | 10/1997 | Bonnem et al. |
| 5,728,377 A | 3/1998 | Sarris et al. |
| 5,789,206 A | 8/1998 | Tavtigian et al. |
| 5,792,445 A | 8/1998 | Tournier et al. |

(Continued)

FOREIGN PATENT DOCUMENTS

| | | |
|---|---|---|
| CA | 2139756 | 1/1994 |
| EP | 0874054 B1 | 9/1985 |
| EP | 0351876 A2 | 1/1990 |
| EP | 0370656 A1 | 5/1990 |
| EP | 0183350 B1 | 1/1992 |

(Continued)

OTHER PUBLICATIONS

Benvenuti et al. Gene Therapy 2001 8:1555-1561.*
Alvaro et al. Journal of Biomedicine and Biotechnology. 2009 vol. 2010, pp. 1-17.*
Accolla, et al., "Monoclonal antibodies specific for carcinoembryonic antigen and produced by two hybrid cell lines," Proc Natl Acad Sci. USA, 77(1):563-566 (1980).

(Continued)

*Primary Examiner* — Chun Dahle

(74) *Attorney, Agent, or Firm* — McKee, Voorhees & Sease, P.L.C.

(57) ABSTRACT

The present invention provides a method for altering a B cell mediated pathology in a patient. This method comprises administering a composition comprising at least one and/or two chimeric proteins. Each chimeric protein comprises at least a portion of either the $V_H$ or $V_L$ region of a immunoglobulin molecule from particular B cells from a patient having a B cell mediated pathology, and an immunoglobulin constant region. The genes encoding $V_H$ and/or $V_L$ regions and the genes encoding immunoglobulin constant regions are isolated and inserted into an expression vector. The chimeric proteins are produced by introducing the expression vectors into insect cell lines. The chimeric proteins are purified using antibody affinity columns, and then chemically conjugated to an immunogenic carrier, keyhole-limpet hemocyanin (KLH). Since the conjugates comprise chimeric proteins made specifically from particular B cells from a patient having B cell mediated pathology, when it is administered to such a patient, with or without a cytokine, such as granulocyte-macrophage-CSF, or a chemokine, it can induce immune responses to alter such a B cell mediated pathology.

44 Claims, 27 Drawing Sheets

U.S. PATENT DOCUMENTS

| | | | |
|---|---|---|---|
| 5,861,164 | A | 1/1999 | Howell et al. |
| 5,891,429 | A | 4/1999 | Clark et al. |
| 5,891,432 | A | 4/1999 | Hoo |
| 5,895,646 | A | 4/1999 | Wang |
| 5,900,238 | A | 5/1999 | Gombotz et al. |
| 5,904,920 | A | 5/1999 | Dranoff et al. |
| 5,929,196 | A | 7/1999 | Kissel et al. |
| 5,942,221 | A | 8/1999 | Clark et al. |
| 5,942,253 | A | 8/1999 | Gombotz et al. |
| 5,972,334 | A | 10/1999 | Denney, Jr. |
| 5,980,911 | A | 11/1999 | Corner et al. |
| 6,063,905 | A | 5/2000 | Capra et al. |
| 6,080,409 | A | 6/2000 | Laus et al. |
| 6,083,521 | A | 7/2000 | Acemoglu et al. |
| 6,083,703 | A | 7/2000 | Wang et al. |
| 6,087,110 | A | 7/2000 | Wang et al. |
| 6,096,313 | A | 8/2000 | Jager et al. |
| 6,120,807 | A | 9/2000 | Gombotz et al. |
| 6,274,175 | B1 | 8/2001 | Gombotz et al. |
| 6,309,632 | B1 | 10/2001 | Agosti |
| 6,312,690 | B1 | 11/2001 | Edelman et al. |
| 6,312,718 | B1 | 11/2001 | Popescu et al. |
| 6,331,415 | B1 | 12/2001 | Cabilly et al. |
| 6,338,953 | B1 | 1/2002 | Boyce et al. |
| 6,338,962 | B1 | 1/2002 | Boyce |
| 6,342,216 | B1 | 1/2002 | Fidler |
| 6,348,449 | B1 | 2/2002 | Weiner et al. |
| 6,361,948 | B1 | 3/2002 | Tricoli et al. |
| 6,911,204 | B2 * | 6/2005 | Gold et al. .................. 424/141.1 |

FOREIGN PATENT DOCUMENTS

| | | |
|---|---|---|
| EP | 0382381 B1 | 5/1993 |
| EP | 0326149 B1 | 8/1993 |
| EP | 0799897 A1 | 10/1997 |
| EP | 0874054 A2 | 3/1998 |
| FR | 2658432 | 8/1991 |
| FR | 2658432 A1 | 8/1991 |
| JP | 62-089621 | 4/1987 |
| JP | 62-230729 | 9/1987 |
| JP | 64-027492 | 1/1989 |
| JP | 01-193227 | 8/1989 |
| JP | 02-002390 | 1/1990 |
| JP | 02-076820 | 3/1990 |
| JP | 10-295379 | 11/1998 |
| JP | 10295379 | 11/1998 |
| JP | 2000-256209 | 9/2000 |
| WO | WO 88/00832 | 2/1988 |
| WO | WO 91/05046 | 4/1991 |
| WO | WO 92/08495 | 5/1992 |
| WO | WO 93/20835 | 10/1993 |
| WO | WO 94/01133 | 1/1994 |
| WO | 9520672 | 8/1995 |
| WO | WO 96/07740 A1 | 3/1996 |
| WO | WO 96/10395 | 4/1996 |
| WO | WO-96-12014 A1 | 4/1996 |
| WO | WO-96-17954 A1 | 6/1996 |
| WO | WO 97/13502 | 4/1997 |
| WO | WO 97/29769 | 8/1997 |
| WO | WO 97/35008 | 9/1997 |
| WO | 9741244 | 11/1997 |
| WO | WO 98/16246 | 4/1998 |
| WO | WO 98/30577 A1 | 7/1998 |
| WO | WO-98-55657 A1 | 12/1998 |
| WO | WO 99/29732 | 6/1999 |
| WO | WO 99/46392 | 9/1999 |
| WO | WO 99/52562 | 10/1999 |
| WO | WO-99-55886 A1 | 11/1999 |
| WO | WO 99/57981 | 11/1999 |
| WO | WO-99-66070 A1 | 12/1999 |
| WO | WO 00/06733 | 2/2000 |
| WO | WO 00/47228 | 8/2000 |
| WO | WO-00-47228 A1 | 8/2000 |

OTHER PUBLICATIONS

Adams, et al., "Molecular cloning of mouse immunoglobin heavy chain messenger ribonucleic acids coding for, mu, alpha, gamma1, gamma2 and gamma3 chains,"Biochemistry, 19:2711-2719 (1980).

Advani, et al., "Granulocyte-Macrophage Colony-Stimulating factor (GM-CSF) as an adjunct to autologous hemopoietic stem cell transplantation for lymphoma," Annals of Internal Medicine, 116 (3):183-189 (1992).

Altmann, et al., "Insect Cells as Hosts for the Expression of Recombinant Glycoproteins," Glycoconjugate Journal, 16:109-123 (1999).

Amster "Synthesis of part of a mouse immunoglobin light chain in a bacterial clone," Nucleic Acids Research, 8(9):2055-2065 (1980).

Arden, et al., "Human T-Cell Receptor Variable Gene Segment Families," immunogenetics, 42:455-500 (1995).

Azuma et al., "Stimulation of host defence mechanism with synthetic adjuvants and recombinant cytokines against viral Infection in mice," In Friedman et al., ed., Microbial Infections, Plenum Press, New York, pp. 253-263 (1992).

Backman and Ptashne, "Maximizing gener expression on a plasmid using recombination in vitro," Cell, 13:65-71 (1978).

Baltimore et al., "Expression of the Abelson murine leukemia virus genome and of transfected• immunoglobin genes" Journal of Cellular Biochemistry, 12th Annual UCLA Symposia Abstracts, Suppl. 7A Abstract 0224 (1983).

Banerji, et al., "Expression of beta-Globin gene is enhanced by remote SV40 DNA sequences," Cell, 27:299-308 (1981).

Benvenuti, F. et al., "Anti-idiotypic DNA vaccines for lymphoma immunotherapy require the presence of both variable region genes for tumor protection," Gene Therapy 7:605-611 (2000).

Selmayr, M. et al., "B-cell lymphoma idiotypes chimerized by gene targeting can induce tumor immunity," Cancer Gene Therapy 7(3):501-506 (2000).

Veelken, H. et al., Rapid expression cloning of B cell lymphoma-derived immunoglobulin genes for anti-idiotypic vaccination nad functional analyses of Fab-fragments,: Blood 90(10) (Suppl1 PAR), pp. 515A (Nov. 15, 1997) Abstract.

Favrille Investor Relations Press Release [ retrieved on Jul. 7, 2008], retrieved from the internet: www.favrille.com, pp. 1-2.

Arnold Freedman, et al., "Placebo-Controlled Phase III Trial of Patient-Specific Immunotherapy With Mitumprotimut-T and Granulocyte-Macrophage Colony-Stimulating Factor After Rituximab in Patients With Follicular Lymphoma", Journal of Clinical Oncology, vol. 27, No. 18, Jun. 20, 2009, pp. 3036-3043.

Alice Hastings, et al., "Production and Characterization of a Murine/Human Chimeric Anti-Idiotype Antibody That Mimics Ganglioside", Cancer Research 52, pp. 1681-1686, Apr. 1, 1992.

Kathleen N. Potter, et al., "Antibody Production in Insect Cells", American Chemical Society, Aug. 18, 1995, Department of Microbiology, University of Texas Southwestern Medical Center, Dallas, Texas, Chapter 4, pp. 41-55.

Jasper Zu Putlitz, et al., "Antibody Production in Baculovirus-Infected Insect Cells", Bio/Technology, vol. 8, pp. 651-654, Jul. 1990.

Bianchi, A. and Massala, M., "Idiotypic vaccination in B-cell malignancies," Mol. Med. Today:Reviews:435-441 (1997).

De Cerio, A. et al., "Anti-iditotype antibodies in cancer treatment," Oncogene 26:3594-3602 (2007).

Li, Y. et al., "Tumor-specific recognition of human myeloma cells by idiotype-induced CD8+ cells," Blood 96(8):2828-2833 (2000).

Liang, M. et al., "Baculovirus expression cassette vectors for rapid production of complete human IgG from phage display selected antibody fragments," J. Immunol Methods 247:119-130 (2001).

Mottershead, D. et al., "Baculoviral display of functional scFv and synthetic IgG-binding domains," Biochem Biophys. Res. Comm. 275:84-90 (2000).

Nature Biotechnology:Biopharmaceutical Benchmarks:Table 1 and Table 2, 8 pages, undated, Mar 27, 2008.

Poul, M. et al., "Cassette baculovirus vectors for the production of chimeric, humanized, or human antibodies in insect cells," Eur. J. Immunol. 25:2005-2009 (1995).

Poul, M. et al., "Design of cassette baculovirus vectors for the production of therapeutic antibodies in insect cells," Immunotech. 1:189-196 (1995).

Reavy, B. et al., "Expression of functional recombinant antibody molecules in insect cell expression systems," Protein Expression and Purification 18:221-228 (2000).

Ward, V.K. et al., "Generation of an expression library in the baculovirus expression vector system," J. Virological Methods 53:263-272 (1995).
Beers, et al (eds.), "Lymphomas" The Merck Manual, Ch. 139:955-962 (1999).
Bendandi, "Role of anti-idiotype vaccines in the modern treatment of human follicular lymphoma," Expert Rev. Anticancer Ther., 1(1):65-72 (2001).
Bendandi, et al., "Complete Molecular Remissions Induced by Patient-Specific Vaccination Plus Granulocyte-monocyte Colony-Stimulating Factor Against Lymphoma," Nature Medicine, 5:1171-1177 (1999).
Berinstein, et al., "Idiotypic Variation in a Human B Lymphoma Cell Line," The Journal of Immunology, vol. 144, No. 2:752-758 (1990).
Bernard, et al., "Sequences of Mouse Immunoglobin Light Chain Genes Before and After Somatic Changes," Cell 15:1133-1144 (1978).
Bixler and Pillai, "Augmentation by interleukins of the antibody response to a conjugate vaccine against Haemophillus Influenza B," in Atassi, ed., Immunobiology of Proteins and Peptides VI, Plenum Press, New York, pp. 185-190 (1991).
Bonnem, et al., "Summary of Preclinical/Clinical Phase I Studies with Granulocyte-Macrophage Colony Stimulating Factor (GM-CSF)," Investigational New Drugs: The Journal of New Anticancer Agents, Abstract 235, 7(4)407 (1989).
Bonnem and Morstyn, "Granulocyte macrophage colony (GM-CSF) Current Status and Future Development," Seminars in Oncology, 15(5)(Suppl. 5):46-51 (1988).
Bonnem, "Alpha interferon: The potential drug of adjuvant therapy: Past achievments and future challenges," Eur. J. Cancer, 27(Suppl. 4):S2-S7 (1991).
Bonnem, "Granulocyte-Macrophage colony stimulating factor—issues in patient management," in Maroum, et al., eds., Colony-Stimulating Factors in Clinical Practice, International Congress and Symposium Series No. 184, Royal Cociety of Medicine Services Limited, London, pp. 17-22 (1992).
Bonnem, "Granulocyte-Macrophage Colony-Stimulating Factor: Unrealized Potential," in Murphy, ed., Blood Cell Growth Factors: Their Present and Future Use in Hematology and Oncology, AlphaMed Press, Dayton, Ohio, pp. 3-20 (1991).
Bonnem, "Granulocyte-macrophage colony-stimulating factor (GM-CSF): Biology and potential clinical utility," in Oldham, ed., Principles of Cancer Biotherapy, 2nd ed., Marcel Dakker, Inc. New York, Chapter 20, pp. 585-596 (1991).
Boss and Emtage, "Expression of an Immunoglobin Light Chain Gene in *Escherichia coli*," Gene Expression, Alan R. Liss, Inc., New York, pp. 513-522 (1983).
Brown et al., "Antiidiotype Antibody Therapy of B-Cell Lymphoma," Seminars in Oncology, 16:199-210 (1989).
Brown et al., "The Prognostic Significance of Immunophenotype in High-grade Non-Hodgkins Lymphoma," Histopathology, vol. 14: 621-627 (1989).
Brown, et al., "Treatment of B-Cell Lymphomaswith Anti-idiotype Antibodies Alone and in Combination with Alpha Interferon," Blood, 73(3):651-661 (1989).
Campbell, et al., "Idiotype Vaccination Against Murine B Cell Lymphoma. Humoral and Cellular Requirements for the Full Expression of Antitumor Immunity," The Journal of Immunology, 145:1029-1035 (1990).
Campbell, et al., "Immunotherapy of Established Murine B Cell Lymphoma, Combination of Idiotype Immunization and Cyclophosphamide," The Journal of Immunology, 145:1029-1036 (1988).
Carayannopoulos, et al., "Recombinant Human IgA Expressed in Insect Cells," Proc. Natl. Acad. Sci., vol. 91:8348-8352 (1994).
Casares, et al., "Antigen-Specific Downregulation of T-Cells by Doxorubicin Delivered through a Recombinant MHC II-Peptide Chimera," Nature Biotechnology, 19:142-147 (2001.
Caspar, et al., "Idiotype Vaccines for Non-Hodgkin's Lymphoma Induce Polyclonal Immune Responses That Cover Mutated Tumor Idiotypes: Comparison of Different Vaccine Formations," Blood, vol. 90 (9):3699-3706 (1997).

Caton, et al., "Influenza Virus Hemagglutinin-specific Antibodies Isolated from a Combinatorial Expression Library are Closely Related to the Immune Response of the Donor" Proc. Natl. Acad. Sci., vol. 88:6450-6454 (1990).
Chen and Levy, "Induction of Autoantibody Responses to GM-CSF by Hyperimmunization with an Id-GM-CSF Fusion Protein," The Journal of Immunology, 154:3105-3117 (1995).
Chen, et al., "Idiotype-Cytokine Fusion Proteins as Cancer Vaccines, Relative Efficacy of IL-2, IL-4 and Granulocyte-Macrophage Colony-Stimulating Factor," The Journal of Immunology, 153:4775-4787 (1994).
Cheson, et al., "Report of an International Workshop to Standardize Response Criteria for Non-Hodgkin's Lymphomas." J Clin Oncol., 17(4):1244 (1999).
Chunduru, "Explotation of the V beta8.2 T Cell Receptor in Protection against Experimental Autoimmune Encephalomyelitis Using a Live Vaccinia Virus Vector," J. Immunol., 156:4940-4945 (1996).
Chung, et al., "Functional three-domain single-chain T-cell receptor," Proc. Natl.Acad. Sci. USA, 91:12654-12658 (1994).
Clark and Croce, "An autonomously replicating vector for mammalian cells," Plasmids and Transforming Vectors, Fed. Proc. 1983, Abstract 2364.
Clark, et al., "Comparison of Human and Mouse T-Cell Receptor Variable Gene Segment Subfamilies," Immunogenetics, 42:531-540 (1995).
Cleary, et al., "Clustering of Extensive Somatic Mutations in the Variable Region of an Immunoglobin Heavy Chain Gene from a Human B Cell Lymphoma," Cell Press, 44:97-106 (1986).
Colman, et al., "Interactions of mouse immunoglobin chains with *Xenopus* Oocytes," J. Mol. Biol., 160:459-474 (1982).
Daley, et al., "Idiotype-Specific Transplanation Resistance to MOPC-315: Abrogation by Post-Immunization Thymectomy," The Journal of Immunology, 120(5) (1978).
Doenecke, et al., "Rapid Amplification of cDNA ends (RACE) Improves the PCR-based Isolation of Immunoglobulin Variable Region Genes from Murine and Human Lymphoma Cells and Cell Lines," BTS Leukemia, 11:1787-1792 (1997).
Dolby et al., "Cloning and Partial Nucleotide Sequence of Human Immunoglobin mu chain cDNA from B cells and mouse-human hybridomas," Proc. Natl. Acad. of Sci. USA, 77(10):6027-6031.
Dranoff, et al., "Vaccination with Irradiated Tumor Cells Engineered to Secrete Murine Granulocyte-Macrophage Colony-Stimulating Factor Stimulates Potent, Specific and Long-Lasting Anti-Tumor Immunity," Proc. Natl. Acad. Sci. USA, 90(8):3539-3543 (1993).
Dumann et al., "Influence of Thymopentin on Antibody Response, and Monocyte and T Cell Function in Hemodialysis Patients who Fail to Respond to Hepatitis B Vaccination," Nephron, 55:136-140 (1990).
Edelman, et al., "Obtaining a functional recombinant anti-rhesus (D) antibody using the baculovirus-insect cell expression system," Immunology, 91:13-19 (1997).
Eilat, et al., "Secretion of a Soluble Chimeric gamma.delta T-cell receptor—immunoglobin heterodimer," Proc. Natl. Acad. Sci. USA., 89:6871-6875 (1992).
Engel, et al., "High-Effiency Expression and Solubilization of Functional T Cell Antigen Receptor Heterodimers," Science, 256:1318-1321 (1992).
Falkner and Zachau, "Expression of Mouse Immunoglobin genes in Monkey Cells," Nature, 298:286-288 (1982).
Friedmann, et al., "Introduction of the Human HPRT Gene into Mammalian Cells by an Infectious Retroviral Vector," Control of Phospholipid Metabolism, Fed. Proc. 1983, Abstract 1736.
Fujisawa, et al., "Direct Expression of Hepatitis B Surface Antigen Gene in *E. coli*,"Nucleic Acids Research, 11(11):3581-3591 (1993).
Fuliano, et al., "La Timopentina Come Terapia Adiuvante Nella Vaccinazione Anti-Epatite B in Soggetti non-O Iporesponsivi," Minerva Medica, 81(5):407-413 (1990).
George, et al., "Idiotypic Vaccination as a Treatment for a B Cell Lymphoma," The Journal of Immunology, vol. 141:2168-2174 (1988).
Gillies and Tonegawa, "Expression of Cloned Immunoglobulin Genes Introduced into Mouse L Cells," Nucleic Acids Research, 11(22):7981-7997 (1983).

Gillies, et al., "A Tissue-Specific Transcription Enhancer Element is Located in the Major Intron of a Rearranged Immunoglobulin Heavy Chain Gene," Cell, 33:717-728 (1983).

Gillies, et al., "Biological Activity and In Vivo Clearance of Antitumor Antibody/Cytokine Fusion Proteins," Bioconjugate Chem., 4:230-235 (1993).

Glennie and Stevenson, "Univalent Antibodies Kill Tumor Cells In-Vitro and In-Vivo," Nature, 295:712-714 (1982).

Gold, "TCR V Gene Usage in Autoimmunity," Current Opinion in Immunology, 6:907-912 (1994).

Gold, et al., "T-Cell Receptor Peptides as Immunotherapy for Autoimmune Disease," Critical Reviews Immunol., 17:507-510 (1997).

Gough, "The Rearrangements of Immunoglobulin genes," in Tooze, et al., eds., Trends in Biochemical Sciences, Reference Edition, vol. 6, International Union of Biochemistry and Elsevier/north Holland, 1981, pp. 203-205.

Gough, et al., "Molecular Cloning of Seven Mouse Immunoglobulin kappa Chain Messenger Ribonucleic Acids," Biochemistry, 19:2702-21710 (1980).

Grabstein, et al., "Induction of Macrophage Tumoricidal Activity by Granulocyte-Macrophage Colony-Stimulating Factor," Science, 232:506-508 (1986).

Greenberg, "Adoptive T Cell Therapy of Tumors: Mechanisms Operative in the Recognition and Elimination of Tumor Cells," Advances in Immunology, 49:281-355 (1991).

Gregoire, et al., "Engineered secreted T Cell Receptor alpha.beta heterodimers," Proc. Natl. Acad. Sci USA, 88:8077-8087 (1991).

Guarente, et al., "Improved Methods for Maximizing Expression of a Cloned Gene: a Bacterium That Synthesizes Rabbit beta-Globin," Cell, 20:543-553 (1980).

Hasemann, et al., "High-Level Production of a Functional Immunoglobulin Heterodimer in a Baculovirus Expression System," Proc. Natl. Acad. Sci. 87:3942-3946 (1990).

Hasemann, et al., "Mutational Analysis of Arsonate Binding by a CRIA+ Antibody, VH and VL Junctional Diversity are Essential for Binding Activity," The Journal of Biological Chemistry, 266:7626-7632 (1991).

Hasemann, et al., "Mutational Analysis of the Cross-Reactive Idiotype of the A Strain Mouse," the Journal of Immunology, 147:3170-3179 (1991).

Heath and Playfair, "Cytokines as immunological adjuvants," Vaccine, 10(7):427-434 (1992).

Hess, et al., "The Effect of Granulocyte-Macrophage-Colony-Stimulating Factor (GM-CSF) on Hepatitis B Vaccination in Haemodialysis Patients," Journal of Viral Hepatitis, 3:149-153 (1996).

Heufler, et al., Granulocyte/Macrophage Colony-Stimulating Factor and Interleukin 1 Mediate the Maturation of Murine Epidermal Langerhans Cells into Potent Immunostimulatory Dendritic Cells, J. Exp. Med., 16792:700-05 (1988).

Hinuma, et al.,"A Novel Strategy for Converting Recombinant Viral Protein into High Immunogenic Antigen," Federation of European Biochemical Societies 288:138-142 (1991).

Hitzman, et al., "Secretion of Human Interferons by Yeast," Science 219:620-625, Hitzeman, 1983.

Hozumi, et al., "Characterization of a Mouse DNA Clone containing an Immunoglobulin Variable Region Gene," Nucleic Acids Research, 5(6):1779-1799 (1978).

Hsu, et al., "Tumor-Specific Idiotype Vaccines in the Treatment of Patients with B-Cell Lymphoma—Long Term Results of a Clinical Trial," Blood 89(9):3129-3135 (1997).

Hsu, et al., "Vaccination of Patients with B-Cell Lymphoma Using Autologous Antigen-Pulsed Dendritic Cells," Nature Medicin, 2:52-58 (1996).

Huse, et al., "Generation of a Large Combinatorial Library of the Immunoglobulin Repertoire in Phage Lambda," Science, 246(4935):1275-1281 (1989).

Jaffee, et al., "Novel Allogenic Granulocyte-Macrophage Colony-Stimulating Factor—Secreting Tumor Vaccine for Pancreatic Cancer: A Phase I Trial of Safety and Immune Activation," Journal of Clinical Oncology, 19(1):145-156 (2001).

Jiang, et al., "Murine CD8+ Cells that Specifically Delete Autologous CD4+ T Cells Expressing Vb8 TCR: A Role of the Qa-1 Molecule," Immunity, 2:185-194 (1995).

Kappler, et al., "Binding of a soluble •• T-Cell receptor to Superantigen/Major histocompatability complex ligands," Proc. Natl. Acad. Sci. USA, 91:8462-8466 (1994).

Kemp and Cowan, "Direct Immunoassay for Detecting *Escherichia coli* Colonies that contain Polypeptides encoded by cloned DNA Segments," Proc. Natl. Acad. Sci. USA, 78(7)4520-4524 (1981).

Knuth, et al., "Cellular and Humoral Immune Responses against Cancer: Implications for Cancer Vaccines,"Current Opinion in Immunology, 3:659-664 (1991).

Kumar, et al., "Recombinant T Cell Receptor Molecules Can Prevent and Reverse Experimental Autoimmune Encephalomyelitis," J Immunol., 159:5150-5156 (1997).

Kurokawa, et al., "Expression of Human Immunoglobulin E epsilon chain cDNA in *E. coli*," Nucleic Acids Research, 11(10):3077-3085 (1983).

Kurucz, et al., "A Bacterially Expressed Single-Chain Fv Construct from the 2B4 T-Cell Receptor," Proc. Natl. Acad. Sci. USA. 90:3830-3834 (1993).

Kwak, et al., "Combined Syngenic Bone Marrow Transplantation and immunotherapy of a murine B-Cell Lymphoma: Active Immunizationwith Tumor Derived Idiotypic Immunoglobulin," Blood, 76(11):2411-2417 (1990).

Kwak, et al., "Idiotypic Vaccination as Therapy for Multiple Myeloma," Seminars in Hematology, 36:34-37 (1999).

Kwak, et al., "Induction of Immune Responses in Patients with B-Cell Lymphoma Against the Surface-immunoglobulin Idiotype Expressed by their Tumors," N. Eng. J. Med, 327:1209-1215 (1992).

Kwak, et al., "Transfer of Myeloma Idiotype-Specific Immunity froim an Actively Immunized Marrow Donor," The Lancet, 345:1016-1020 (1995).

Kwak, et al., "Vaccinantion with Syngeneic, Lymphona-derived Immunoglobulin Idiotype Combined with Granulocyte/Macrophage Colony Stimulating Factor Primes Mice for a Protective T-Cell Response," Proc. Natl. Acad. Sci. USA. 93:10972-10977 (1996).

Lau and Kan, "Construction of Recombinant DNA Libraries Using Expression Cosmid Vectors That Can Shuttle Between Bacteria and Mammilian Cells," Plasmids and Transforming Vectors, Fed Proc. 1983, Abstract 2362, p2161.

Lebowitz, et al., "Soluble, High-Affinity Dimers of T-Cell Receptors and Class II Major Histocompatibility Complexes: Biochemical Probes for Analysis and modulation of Immune Responses," Cell Immune., 192:175-184 (1999).

Leslie, et al., "Humoral Immune Responses in Mice Using Gamma Inulin Preparations as Adjuvants for Hepatitis B Vaccines," Immunol. Cell Biol., 68:107-112 (1990).

Levitisky, et al., "Immunization with Granulocyte-Macrophage Colony-Stimulating Factor-Transduced, but not 87-1-Transduced, Lymphoma Cells Primes Idiotype-Specific T Cells and Generates Potent Systemic Antitumor Immunity," J. Immunol., 156(10)3858-3865 (1996).

Levy, "Cytokine Fusion Proteins with Enhanced Immunogenicity," NIH Grant No. 1R01AI037219-01 (1994).

Levy, et al., "Mutational Hot Spots in Ig V region Genes of Human Follicular Lymphomas," J. Exp Med., 168(2):475-489 (1988).

Lieschke and Burgess, "Granulocyte Colony-Stimulating Factor and Granulocyte-Macrophage Colony-Stimulating Factor," Part 1, New England Journal of Medicine, 327(1):28-35, 1992.

Lieschke and Burgess, "Granuocyte Colony-Stimulating Factor and Granulocyte-Macrophage Colony-Stimulating Factor,"Part 2, New England Journal of Medicine, 327(2):99-106, 1992.

Lieschke, et al. "Effect of Bacterially Synthesized Recombinant Human Granulocyte-Macrophage Colony in Patients with Advanced Malignancy," Annals of Internal Medicine, 110:357-364 (1989).

Lin, et al., "Expression of T Cell Antigen Receptor Heterodimers in a Lipid-Linked Form," Science, 249:677-679 (1990).

Maecker and Levy, "Spontaneous T Cell Antigen Receptor Variants of a Human T Leukemia Cell Line," J. Immunol., 141:2994-3002 (1985).

Malkovska, et al., "Human T Cells in hu-PBL-SCID Mice Proliferate in Response to Daudi Lymphoma and Confer anti-tumor immunity," Clin. Exp. Immunol., 96:158-165 (1994).

Maloney, et al., "Monoclonal Anti-Idiotype Antibody Therapy of B-Cell Lymphoma: The Addition of a Short Course of Chemotherapy Does Not Interfere with the Anti-Tumor Effect nor Prevent the Emergence of Idiotype-Negative Variant Cells," Blood, 80(6):1502-1510 (1992).

Martin et al., "Recombinant Human Granulocyte-Macrophage Colony-Stimulating Factor (rhGM-CSF) in the treatment of Chronic Hepatitis B," American Association for the Study of Liver Disease. Abstracts of Papers, 16(2 Pt. 2):67A, Abstract 89 (1992).

Massaia, et al., "Idiotype Vaccination in Human Myeloma: Generation of Tumor-Specific Immune Responses After High-Dose Chemotherapy," Blood, 94:673-683 (1999).

Masucci, et al., "Chemotherapy and Immunotherapy of Colorectal Cancer," Med. Oncol. & Tumor Pharmacother., 8(3):207-220 (1991).

Masucci, et al., "GM-CSF Augments the Cytotoxic Activity of Monouclear Cells in Adcc Using MAb 17-1A. Both alpha-IFN and TNF-alpha Acts Synergistcally," Sixth NCI-EORTC Symposium on New Drugs in Cancer Therapy, Amsterdam, Mar. 7-10, 1989. Abstract 143.

Masucci, et al., "Granulocyte-Monocyte Colony-Stimulating Factor Augments the Interleukin-2-induced cytotoxic activity of human lymphocytes in the absence and presence of mouse or chimeric monoclonal antibodies (mAb 17-1A)," Cancer Immunol. Immunother., 31:231-235 (1990).

McCune and Marquis, "Interleukin 1 as an Adjuvant for Active Specific Immunotherapy in a Murine Tumor model," Cancer Research 50:1212-1215 (1990).

McKeever, et al., "Immunization with Soluble BDC 2.5 T Cell Receptor-Immunoglobulin Chimeric Protein: Antibody Specificity and Protection of Nonobese Diabetic Mice against Adoptive Transfer of Diabetes by Maternal Immunization," J. Exp. Med. 184:1755-1768 (1996).

Meeker, et al., "A Clinical Trial of Anti-Idiotype Therapy for B Cell Malignancy," Blood, 65:1349-1363 (1985).

Meeker, et al., "Emergence of Idiotype Variants During Treatment of B-Cell Lymphoma with Anti-Idiotype Antibodies," N.Eng.J.Med, 312:1658-1655 (1985).

Mercereau-Puijalon, et al., "Expresion of Cloned Eukaryotic Genes in Microorganisms," in Perterson, et al., eds., Expressions of Cloned Eukaryotic Viral and Cellular Genes, Academic Press, 1981, pp. 295-303.

Meuer, et al., "Low Dose Interleukin-2 Induces Systemic Immune Responses Against HBsAg in Immunodeficient Non-Responders to Hepatitis B Vaccination," The Lancet, Jan. 7, 1989, pp. 15-18.

Meuer, et al., "Monocyte Defect in Hemodialysis Patients Supports Nonresponsiveness to Hepatitis B Vaccination and Development of HBsAG Carrier State," in Zukerman, ed., Viral Hepatitis and Liver Disease, Alan R. Liss, Inc., New York, pp. 711-713 (1988).

Meuer, et al., "Selective Blockade of the Antigen-Receptor-Mediated Pathway of T Cell Activation in Patients with Impaired Primary Immune Responses," J. Clin. Invest. 80:743-749 (1987).

Miller, et al., "Treatment of B-Cell Lymphoma with Monoclonal Anti-Idiotype Antibody," N. Eng. J. Med., 306(9):517-522 (1982).

Minty, et al., "Molecular Cloning of the MCP-3 Chemokine Gene and Regularion of its Expression," Eur. Cytokine Netw., 4(2):99-110 (1993).

Monk, et al., "Heavy-Chain Mutants Derived from Y2b Mouse Myeloma: Characterization of Heavy-Chain Messenger Ribonucleic Acid, Proteins, and Secretion in Deletion Mutants and Messenger Ribonucleic Acid in Y2a Mutant Progent," Biochemistry, 20:2330-2339 (1991).

Morrison, "Transfer and Expression of Immunoglobulin genes," Ann. Rev. Immunol., 2:239-256, (1984).

Morrissey, et al., "Granulocyte-Macrophage Colony_Stimulating Factor Augments the Primary Antibody Response by Enhancing the Function of Antigen-Presenting Cells," Journal of Immunology, 139(4):1113-1119 (1987).

Morstyn, et al., "Pharmacology of Colony-Stimulating factors," in Abbott, et al., eds., Trends in Pharmacological Sciences, 10:154-159 (1989).

Moxon, "The Scope of Immunisation," the Lancet, Feb. 24, 1990, pp. 448-451.

Mroczkowski, et al., "Secretion of Thermostable DNA Polymerase Using a Novel Baculovirus Vector," J. Biol Chem. 269:13522-13528 (1994).

Mulligan and Berg, "Expression of Bacterial gene in Mammalian Cells," Science 209:1422-1427 (1990).

Mulligan and Berg, "Selection for Animal Cells that express the *Escherichia coli* gene Coding for Xanthine-guanine Phosphoribosyltransferase," Proc. Natl. Acad. Sci. USA, 78(4):2072-2076 (1981).

Mullinax, et al., "Identification of Human Antibody Fragment Clones Specific for Tetanus Toxoid in Bacteriophage A Immunoexpression Library," Proc. Natl. Acad. Sci. USA., 87(2):8095-8099 (1990).

Myers and Gustafson, "Adjuvants for Human vaccine Usage: A Rational Design," Chapter 32 in Cryz, Ed., Vaccines and Immunotherapy, pergamon Press, Inc., new York, 1991, pp. 404-410.

Nelson, et al., "Tumor-Specific Cytotoxic T-Lymphocyte Response After Idiotype Vaccination for B-Cell, Non-Hodgkin's Lymphoma," Blood, 88:580-589 (1996).

Nesbit, et al., "Production of a Functional Monoclonal Antibody Recognizing Human Colorectal Carcinoma Cells from a Baculovirus Expression System," Immunol. Methods, 151:201-208 (1992).

Neuberger, "Expression and Regulation of Immunoglobulin Heavy Chain Gene Transfecting into Lymphoid Cells," EMBO Journal, 2(8):1373-1378 (1983).

Nisonoff and Rivers, "Recombination of a Mixture of Univalent Antibody Fragments of Different Specificity," Archives of Biochemistry and Biophysics, vol. 93, Academic Press, new York and London, pp. 460-462 (1961).

Novotny, et al., "Soluble, Single-Chain T-Cell Receptor Fragment Endowed with Antigen-Combining Properties," Proc. Natl. Acad. Sci. USA., 88:8646-8650 (1991).

O'Brien, et al., "Cloning and Sequencing of the cDNA for Ovine Granulocyte-Macrophage Colony Stimulating Factor (GM-CSF)," Immunology and Cell Biology 69:51-55 (1991).

Ochi et al., "Functional Immunoglobulin M Production After Transfection of Cloned Immunoglobulin Heavy and Light Chain Genes into Lymphoid Cells," Proc. Natl. Acad. Sci. USA., 80:6351-6355 (1983).

Ochi et al., "Transfer of a Clonded Immunoglobulin Light-Chain Gene to Mutant Hybridoma Cells Restores Specific Antibody Production," Nature 302:340-342 (1983).

Odendahl, et al., "Distributed Peripheral B Lymphocyte Hemostatis in Systemic Lupus Erythematosus," J Immunol., 165(10):5970-5979 (2000).

Offner, et al., "Vaccination with BV8S2 Protein Amplifies TCR-Specific Regulation and Protection Against Experimental Autoimmune Encephalomyelitis in TCR BV862 Transgenic Mice," J. Immunol., 161:2178-2186 (1998).

Ogawa, et al., "Increase in CD95 (Fas/APO-1)-Positive CD4+ and CD8+ Cells in peripheral Blood Derived from Patients with Autoimmune Hepatitis or Chronic Hepatitis C with Autoimmune Phenomena," J. Gastroenterol. Hepatol., (1):69-75 (2000).

O'Herrin, et al., "Analysis of the Expression of Peptide—Major Histocompatability Complexes Using High Affinity Soluble Divalent T Cell Receptors," J. Exp. Med., 186(8):1333-1345 (1997).

Oi et al., "Immunoglobulin Gene Expression in Transformed Lymphoid Cells," Proc. Natl. Acad. Sci. USA, 80:825-829 (1983).

Okada, et al., "TCR Vaccines for Active Immunotherapy of T Cell Malignancies," J. Immunol., 159:5516-5527 (1997).

Okayama and Berg, "A cDNA Cloning Vector That Permits Expression of cDNA Inserts in Mammalian Cells," Molecular and Cellular Biology 3(2):280-289 (1983).

Opdenakker, et al., "Human Moncyte Chemotactic Protein-3 (MCP-3): Molecular Cloning of the cDNA and Comparison with other Chemokines," Biochem. Biophys. Res. Comm., 191(2):535-542 (1993).

Orlandi, et al., "Cloning Immunoglobulin Variable Domains for Expression by the Polymerase Chain Reaction," Proc. Natl. Acad. Sci. USA, 86(10):3833-3837 (1989).

Pardoll, "Gene-Targeted Immunotherapy of Renal Cancer," Grant No. 1U01CA061551-01 (Abstract), http://commons.cit.nih.gov/crisp3/CRISP_LIB, accessed Sep. 4, 2002.
Pellicer et al., "Altering Genotype and Phenotype by DNA-Mediated Gene Transfer," Science, 209:1414-1421 (1980).
Picard and Schaffner, "Correct Transcription of a Cloned Mouse Immunoglobulin Gene In-Vivo," Proc. Natl. Acad. Sci. USA 80:417-421.
Potter, et al., "Anti-Idiotypic Antibody D12 and Superantigen SPA Both Interact with Human VH3 Encoded Antibodies on the External Face of the Heavy Chain Involving FR1, CDR2 and FR3," Molecular Immunology, 35:1179-1187 (1998).
Potter, et al., "Staphylococcal Protein A Binding to VH3 Encoded Immunoglobulins," Intern. Rev. Immunol., 14:291-308 (1997).
Potter, et al., "Staphylococcal Protein A Simultaneously Interacts with Framework Region 1, Somplementarity-Determining Region 2, and Framework Region 3 on Human VH3-Encoding IgS1," The Jornal of Immunology, 157:2982-2988 (1996).
Potter, et al., "The Cross Reactive Idiotypes Recognized by the Monoclonal Antibodies 9G4 and LC1 are Located in Framework Region 1 of Two Non-Overlapping Subsets of Human VH4 Family Encoded Antibodies," Scand J. Immunol., 40:43-49 (1994).
Proost, et al., "Human Monocyte Chemotactic Proteins-2 and -3: Structural and Functional Comparison with MCP-1," J. Leukoc. Biol., 59 (1):67-74 (1996).
Quiroga et al. "Recombinant •-Interferon as Adjuvant to Hepatitis B Vaccine in Memodialysis Patients," Hepatology, 12(4):661-663 (1990).
Raso and Griffin, "Hybrid Antibodies with Dual Specificity for the Delivery of Ricin to Immunoglobulin-bearing Target cells," Cancer Research, 41:2073-2078 (1981).
Rauser and Kaiser, "demonstration of Anti-HuD Specific Oligoclonal Bands in teh Cerebrospinal Fluid from Patients with Paraneoplastic Syndromes Qualitative Evidence of Anti-HuD Specific IgG-Synthesis in the Central Nervous System," J. Neuroimmunol., 111(1-2):241-244 (2000).
Reeves, et al., "Construction and Transfer into Mammalian Cells of a Vector Containing Insect Histone Genes," in Lurquin, et al., eds., Genetic Engineering in Eukaryotes, Plenum Press, New York, pp. 73-85 (1983).
Rice and Baltimore, "Regulated Expression of Immunoglobulin kappa Gene Introduced into a Mouse Lymphoid Cell Line," Proc. Natl. Acad. Sci. USA. 79:7862-7865 (1982).
Rice, et al., "Expression of Immunoglobulin Genes Introduced into Mouse Lymphoid Cell Lines," Journal of Cellular Biochemistry, Suppl. 7A:133 (Abstract 0341) (1983).
Roberts, "A lac Promoter System for the Overexpression of Prokaryotic and Eukaryotic Genes in *E. coli*," in Rodriguez, et al., eds., Promoters, Strucutre and Function, Praeger Publishers, New York, 1982, pp. 452-461.
Roberts, et al., "A General Method for Maximizing the Expression of a Cloned Gene," Proc. Natl. Acad. Sci. USA. 76(2):760-764 (1979).
Roberts, et al., "Synthesis of Simian Virus 40 t Antigen in *Escherichia coli*.," Proc. Natl. Acad. Sci. USA 76(11):5596-5600 (1979).
Rowen, et al., "The Complete 685-Kilobase DNA Sequence of the Human beta T Cell Receptor Locus," Science, 272:1755-1762 (1996).
Ruberti, et al., "The Use of the RACE Method to Close Hybridoma cDNA when V region Primers Fail," Journal of Immunological Methods, 173:33-39 (1994).
Sakato, et al., "Suppression of MOPC-167 growth In Vivo by Immunization Against the Idiotype of the MOPC-167 Myeloma Protein," Microbiol Immunol., 23:927-931 (1979).
Sambrook, et al., "Cloning into Bacteriophage M13 Vectors and Transfection of Competent Bacteria," in Molecular Cloning. A Laboratory Manual, 2nd ed., Cold Spring Harbor Laboratory Press, New York, 1989, pp. 4.33-4.34.
Santolini, et al., "Amplification of IL-2-Driven T Cell Proliferation by Recombinant Human IL-3 and Granulocyte-Macrophage Colony-Stimulating Factor," J. Immunol., 141(20):519-526 (1988).
Schrader, "Peptide Regulatory Factors and Optimization of Vaccines," Molecular Immunology, 28(3):295-299 (1991).

Sims, et al., "Somatic Mutation in Genes for the Variable Portion of the Immunoglobulin Heavy Chain," Science, 216:309-311 (1982).
Sinclair, et al., "PCR Strategies for Isolation of the 5' End of an Immunoglobin-encoding Bovine cDNA," Gene 167:285-289 (1995).
Singh and O'Hagan, "Advances in Vaccine Adjuvants," Nature Biotech, 17:1075-1081 (1999).
Smith, et al., "Direct Evidence for an Intracellular Role for IFN-γ Microinjection of Human IFN-γ Induces la Expression on Murine Macrophages", J. Immunol., 144(5):1777-1782 (1990).
Southern and Berg, "Transformation of Mammalian Cells to Antibiotic Resistance with a Bacterial Gene under Control of teh SV40 Early Region Promoter," Journal of Molecular and Applied Genetics, 1:327-341 (1982).
Stafford and Queen, "Cell-Type Specific Expression of a Transfected Immunoglobulin Gene," Nature, 306:77-79 (1983).
Stevenson and Gordon, "Immunization with Idiotypic Immunoglobulin Protects Against Development of B Lymphocytic Leukemia, but Emerging Tumor Cells can Evade Antibody Attack by Modulation," J. Immunol., 130(2):970-973 (1983).
Steward et al., "Clinical Studies with Recombinant Human Granulocyte Macrophage Colony Stimulating Factor," international Journal of Cell Cloning, 8:335-346, Suppl. 1 (1990).
Steward et al., "Recombinant Human Granulocyte Macrophage Colony Stimulating factor (rhGM-CSF) given as Daily Short Infusions—a Phase I Dose-Toxicity Study," Br. J. Cancer. 59:142-145 (1989).
Subramani, "Expression of the Mouse Dihydrofolage Reductase Complementary Deoxyribonucleic Acid in Simian Virus 40 Vectors," Molecular and Cell Biology, 2:854-864 (1981).
Sullivan and Mandell, "The Role of Cytokines in Infection," Current Opinion in Infectious Diseases, 4:344-349 (1991).
Summary in Molecular Cloning. A Laboratory Manual, Mantitis, et al., eds., Cold Spring Harbor Laboratory, New York p. 433 (1982).
Tan, et al., "Expression and purification of a secreted functional mouse/human chimaeric antibody against bacterial endotoxin in baculovirus-infected insect cells," Biotechnol. Appl. Biochem. 30:59-64 (1999).
Taniguchi, et al., "Expression of the human fibroblast interferon gene in *Escherchia coli*," Proc. Natl. Acad. Sci. USA, 77(9):5230-5233, 1980.
Tao and Levy, "Idiotype/Granulocyte-Macrophage Colony-Stimulating Factor Fusion Protein as a Vaccine for B-Cell Lymphoma," Nature, 362(6422):755-758 (1993).
Tessier, et al., "Enhanced Secretion from Insect Cells of a Foreign Protein Fused to the Honeybee Melittin Signal Peptide," Gene, 98:177-183 (1991).
Tonegawa, "Somatic Generation of Immune Diversity", Nobel Lecture, Dec. 8, 1987.
Vainiene, et al., "Natural Immunodominant and Experimental Autoimmune Encephalomyelitis-protective Determinants within the Lewis Rat V beta8.2 Sequence Include CDR2 and Framework 3 Idiotypes," J. Neurosci. Rsrch., 43:137-145 (1996).
Valle, et al., "Anti-ovalbumin monoclonal antibodies interact with their antigen in internal membranes of *Xenopus*-oocytes," Nature, 300:71-74 (1982).
Valle, et al., "Synthesis and Secretion of Mouse Immunoglobulin Chains from *Xenopus* Oocytes," Nature, 291:338-340 (1981).
Van Hall, et al., "identification of a Novel Tumor-Specific CTL Epitope presented by RMA, EL-4, and MBL-2 Lymphomas Reveals Their Common Origin," J. Immunol., 165:869-877 (2000).
Vandenbark, et al., "Human TCR as Antigen: Homologies and Potentially Cross-Reactive HLA-DR2-Restricted Epitopes Within the AV and BV CDR2 Loops," Critical Reviews Immunol., 20:57-83 (2000).
Vose, et al., "Granulocyte-monocyte colony-stimulating factor(GM-CSF): Answers or More Questions?," Annals of Internal Medicine, 116(3):261-262 (1992).
Waisman, et al., "Suppresive Vaccination with DNA encoding a Variable Region gene of the T-Cell receptor prevents autoimmune encephalomyelitis and activates Th2 Immunity," Nature Med., 2(8):899-905 (1996).
Walsh, Biopharmaceutical Benchmarks—2003, Nature Biotechnology, 21(8):865-870 (2003).

Ware, et al., Human CD8+ Lymphocyte Clones Specific for T Cell Receptor VB Families Expressed on Autologous CD4+ T Cells, Immunity, 2:177-184 (1995).

Warren and Catz, "Kinetic Profiles of Cerebrospinal Fluid Anti-MBP in Response to Olntravenous MBP Synthetic Peptide DENP85VVHFFKNIVTP96RT in Multiple Sclerosis Patients," Mult. Scler., 6(5):300-311 (200).

Weber, et al., "Specific low-affinity recognition of major histocompatability complex plus peptide by soluble T-cell receptor," Nature, 356:793-796, 1992.

Wetzel, et al., Expression in *Escherichia coli* of a chemically synthesized gene for a 'mini-C' analog of human proinsulin, Gene, 16:63-71 (1981).

Wigler, et al., "Transformation of Mammalian Cells with Genes from Procaryote and Eucaryotes," Cell, 16:777-785 (1979).

Williams, et al., "Cytoplasmic Inclusion Bodies in *Escherichia coli* Producing Biosynthetic Human Insulin Proteins," Science, 215:687-689 (1982).

Wilson, et al., "Results of a Phase I clinical Trial of T-Cell receptor peptide vaccine in patients with Multiple Sclerosis. I. Analysis of T-Cell Receptor Utilization in CSF Cell Populations," J. Neuroimmunol., 76:15-28 (1997).

Young, et al., "Comparison of the Effects of IL-3, Granulocyte-Macrophage Colony-Stimulating Factor in Supporting Monocyte Differentiation in Culture,"J. Immunol., 145(2):607-615 (1990).

Zhang, et al., "Cutting Edge: A Role for B Lymphocyte Stimulator in Systemic Lupus Erythmatosys," J. Immunol., 166(1):6-10 (2001).

Zhang, et al., "Increased Frequency of Interleukin 2-responsive T Cells Specific for Myelin Basic Protein and Proteolipid Protein in Peripheral Blood and Cerebrospinal Fluid of Patients with Multiple Sclerosis," J. Exp. Med. 179:973-984 (1994).

Potter, Kathleen N., et al., "Antibody Production in the Baculovirus Expression System", Intern. Rev. Immunol., vol. 10, 1993, pp. 103-112, Harwood Academic Publishers GmbH, USA.

\* cited by examiner p2Bac DNA Sequence

```
GCAGTTCGTTGACGCCTTCCTCCGTGTGCCGAACACGTCGAGCGGGTGGTCGATGACCAGCGGGCGTGCCGCACGCACG
CACAAGTATCTGTACACCGAATGATCGTCGGGCGAAGGCACGTCGGCCTCCAAGTGGCAATATTGGCAATTCGAAATA
TATACAGTTGGGTTGTTTGCGCATATCTATCGTGGGCATGTCGGCGTTGGGACGTCCGAACGTTGATTTGCATGCAAGCCGAAA
TTAAATCATTGCGATTAGTGCGATTAAAACGTTGTACATCCTCGCTTTAATCATGCCGTCGATTAATCGCAATCGA
GTCAAGTGATCAAAGTGTGGAATAATGTTTTCTTTGTATTCCGAGTCAAGCGCAGCGCAGTCGCACGTCAAGAATTAACAATGCGCCCG
CTTGTAAGTTAGTTTCATTAATGCAACTATGATAGAGATCAAATAAAGCGCGAATTAATAGCTTGGACGCAACGTGCACGATCTG
TGTCGCATCTCAACACGACTATGATTTGATTGTAATAAGTTTTACGAAGCGATGCATGACGTTAAAACTATTAAGCCATTATTCCAATCGACCGTTAG
TGCACGCGTTCCGGCACGAGCTTTGATTGTAATAAGTTTTACGAAGCGATGACGTTAAACTATTAAGCCATCCAATCGACCGTTAG
GCCCAAAGAACTGCCGACTACAAAATTACCGAGTATGTCGGTGACGAATGCATCGTATAACGTGTGGAGTCCGTCATTAGAGC
TCGAATCAGGACCGCTGGTGCGAGAAGCCGCAAGCTACATTTTAATTGTCCCGACTCATTGTTACATGCTGTTAACGCTGTTAACGCTGTGAAGTGTGAAGAATCGTTAG
GTCATGTTAGACAAGAAAGCTACATTTTAATTGTCCCGACTCATTGTTACATGCTGTTAACGCTGTGAAGTGTGGTGCAACTGCA
TATTCTACAATGGCGGGTTTGTCAAAATTCCGACTGCGATTGTACATGCTGTTAACGCTGTTAACGGCTCCGCCATACACGG
GAATTAAAATTCCAATTTAAAAACGCAGAGAAACATTGTATGAAAGAATGCGTAGAAGGAAGAAGAAAAATGT
CGTCGACATGCTGAACAACAAGATTAATATGCCTCCGTGTATAAAAATATTGAACGATTTGAAAGAAAACAATGTAC
CGCGGCGGTATGTGAAGAGAGTTTATACTAAACTGTTACATTGCAAACTGTGGTTTCGTGTGCCAAGTGTGAAAC
CGATGTTTAATCAAGGCTCTGACGCATTTGTATAAACACCACCAACTGAAAATGAAAACTGCATGCATCTCTTTTAATCAA
ATCCCAAGATGTGTATAAACCTATTTGTAATTCCTATTTGTAATTGTGCGACAAGCTCTGTCGTTGCTGGCAACTGCA
AGGGTCTCAATCCTATTTGTAATTGTCACAGTTCATTTTGTTTTTATTAAGATACAAAC
CAAACGCAACAAGAACATTGTAGTATTCTATAATTGAAAACGCGTAGTTATATAAACTGATATTTTAAATCA
TTTTCCTTCTCTTTTTTTGTGTCATAAATATATGTCTCTTTCGGAGTGTGCTTAATTAACATAGTTATCATTTAAATTATACGTATA
GTATTCCTTCTCTTTTTTGTGTCATAAATATATGTCTCTTTCGGAGTGTGCTTAATTAACATAGTTATCATTTAAATTATACGTATA
GAGTAAATTTTGTGTCATAAATGTTCTCGGCAGTGCGCAGTGCGGCGGATGCTTCTTTGCGGGTCAAGGCACGCACACCG
TTACACAGTGCTATTTCTACAATATGTTCCGGCAGTGTTCGGCGGATGCTTCTTTGCGGGTCAAGGCACAGTGCAACCCG
ATCGTCGGTTTTGTACAATATGTTGTACGAACGTTGTACGAACCGTTAAACAAAACAGTTCACCTCCACCATTTTTTTAGCAGCACCG
GATTAACATAACTTTCCAAAATGTTTACGAACCATTGTAATGAAGACGCACAAACTAATATCACAAACTGGAAATGTCATCAA
AGCAGTTGTTGTTGTAAAATTAACAGCATGCTATTGTCTTCCCAATCCTCCCCGTCCTGCCACCCACC
TATATAGTTGCTGATATCTCCCCAGCATGCCTATTGTCTTCCCAATCCTCCCCGTCCTGCCACCCACC
CCCCAGAATAGAATGACACCTACTCAGACAATGCGATGCAATTTCCTCATTTATTAGGAAGGACAGTGGGAGTGGCAC
CTTCAGGGTCAAGAAGGACACTAGTATACCGCGGGAGGGCAAACAACAGATGCCTGCAACTAGAAGGCACAGTCGACTGATCAG
CGAGTCTAGTTGACTAGTAGTGATGCCTATTAATTACAAAATGATTTGATAATAAATTCATAGTCCCCTGTTGTAAGTGATGGCTATTCTGA
AATGTAATTTACAGTATATGTTTAATTAATATACAAATGATTTCATAGTCCCCTGTTGTAAGTGATGCGTATTCTGA
TGGGTTGAATTAAAGGTCCCGGCATCCTCAATGCATAATTCATAGTCCCCTGTTCTGCGAGGATATCATGGAGATAATTAA
ATCTTTGTAAAATAGCACACAAGACTCCAACGCGTTTGCGTTTATTTTCGTTGCTCGAGGATATCATGGAGATAATTAA
AATGATAACCATCTCGCAAATAATAAGTATTTACTGTTTTCGTAACAGTTTTGTAATAAAAAACCTATAATATTCC
```

FIGURE 3A

```
GGATTATTCATACCGTCCCACCATCGGGCGTGTAGCGGATCCGAGCTCGAGATCTGCAGCTGGTACCATGGAATTCGAA
GCTTGTCGTTGGATGGAAAGGAAAAGAGTTCTACAGGAAACTTGGACCCGCTTCATGGAAGACAGCTTCCCCATTGTTA
ACGACCAAGAAGTGATGGTTTCCTTGTCGTCAACATGCGTCCCACTAGACCCAACGTTGTTACAAATTCCTGGCC
CAACACGCTCTGCGTTGCGACCCGCATCAGCCTGGCTAAGACCTATGTACCTCATGACGTGATTAGGATCGTCGAGCCTTCATGGGTGGCAGCAA
TCGAACAGTTACCGCATCAGCCTGGCTAAGACGTCATCGATCGTGTCATCTGAAGTTTCTCCTTGAAGTTCATCGATGTCCCTGGTGTTCAAAGTAAGGAGTTTGCACCAGACGCACCTCTGTTCACTGGTCTGGCCTGCACACCGTAAGAG
GAGGAAATTCTCCTTGAAGTTCATCGATACATTGTTATTAGTACATTTTATAATCTTAGGCTGGTATGTTAGAGCGAAAATCAAATGATTTTCAGCGTCT
GTATTATCTGAATTTAATAATTCATTAAATATTAAATCCTCAATAGATTTGTAAAATAGTTTCAACGCCACAACTTGTGACCAACAGGGTTGTTTCC
TTATATCTGAATTTAATAATTCATTAAATATTAAATCCTCAATAGATTTGTAAAATAGTTTGTAGCAGCAATCTAGCTT
CGAACCGATGGCTGGACTATCTAATGATTTCGCTCAACGCCACAAACTTGTAGCAGCAATCTAGCTT
TGTCGATATCGTTCGTTTGTTTTGTTAATAAGGTTCGACGTCGTTCAAATATTATGCGCTTTGTATTTCTTTCA
TCACTGTCGTTAGTGTACAATTGACTCGCTCGTCGTCCAACCTCGTCGTCTAGAAGTTGCTTCCGAGACGATTTGCCATAGCC
TAGCTTTATTAGCCGATTATCGTCGTCCAACCTCGTCGTCTAGAAGTTGCTTCCGAGACGATTTGCCATAGCC
ACACGACGCCTATTAATTGTGTCGCTAACACGTCCGGCTAACTCTACTAATGTGCGCAAATCTACCCGGTGGAGGCGA
CGGCGTTTTGGGCGGGTTTCAATCTAACTGTCCGGCTAACTCTACTAATGTGCGGTTGTCCGGTGGAGGCGA
GTGGTAACATTTCAGACGCACCTAATGGCGGGAGGTGCTGATGGAGCGCGGTTTGATGATAATCTACCATCGGTGGAGGCGA
GGCGGGCTGGCGGGGAGGCGCAAATCTAACTATTGTACGGTTCGTGCTCAAATGCGTTGGCTCAAATGTCTCTTTAGG
CAACACAGTCGACACCTCCACTATTGTACTGCTTCCAACAATTGTTCTGCTGTCTCAAATGCGTTGAGGTTCCGTCGGCATTGCTGATTT
TTCGTTTCTAATAGCTTCAGACATTGCTTCAACAATTGTTCTGCTGTCTAAGGTCAGGGTTGAGGTTCCGTCGGCATTGTGGTGA
GCGCGGGCAATTCAGACATTGCTTCAACAATTGTTCTGCTGTCTAAGGTCAGCCCGATCCAGAGAAGGTGGTTGGCGG
CGGTGCCGCCGTATAATTGTTCTGCTTCGAGGCCTTAAGCGTACACGCTAATCGTACACGATAAGTTTATGTATTAATTGACCCAGGACACCCTCGC
CAACGGAAGTCGTCTGCTTCGAGGCCTTATTCGCTTTAATCGTACACGATAAGTTTATGTATTAATTGACCCAGGACACCCTCGC
TCTGCTATAAGCATTGTAATTCGCACGCTCGAGTTGAATTCGCTCAATGTATTAATGTTGGCGAGACACCTCGC
AAGAGATTGTCTGACTCGAGTTTGTCACACATTGATACGTCGTCGAATCCGCACGAATCGTAGGTCGATACGCCGT
TGTCGTCGACTCGAGTTTGTCACACATTGATACGTCGTCGAATCCGCACGAATCGTAGGTCGATACGCCGT
TCTAACGACAATATGTCCATAGTGTGCACCTGCACTCCAGTACAATCTGCTCTGATGCCGCATAGTTAAGCCAGCCGGACACCC
GCCAACACCCGCTGACGCGCCCTGTCTGACGGGCCCTGTCCCGGAAACGCGCGAGTCTAGTTCGTAACAAGCTGAACGGCCTCCGGGA
GCTGCATGTGTCAGAGGTTTTCACCGTCATCACCGAAACGCGCGAGGAAGAGGCCTGATCAGCAGTGGGTCCATGTCGATACGCCTATTTTATAG
GTAATGTCATGATAATAATTCAAATATGTTTCTTAGACGTCAGGTGCATGAGCACAGTGGGTTACATCGAACTGGATCTCAACAGCGG
ATTTTCTAAATACATTCAACATTTCAAATATGTTTCTTAGACGTCAGGTGCATGAGCACACTATTCTCAGAATGACTTGTCGTATGGCGCGGTAT
AGAGTATGAGTATTCAACATTTCGCCCGAAGAAGCTAAAGATCAGTTTTCCAATGAGTCCGCCATACACTATTCTCAGAATGACTTGTCGTATGGCGCGGTAT
GAAACGCTGGTGAAAGTAAAAGATATTCAACAACGTCGGAAGACGACGAATGACCATACACGTCCCAATCGGAACTGGAGACACGGATGCC
TAAGATCCTTGAGAGTTTCGCCCCGAAGACAACGTCGGAAGACTGACTTCTCAGAATGACGTCGCCCATACGGATGCCCATACCAGAGAGC
TATCCCGTATTGACGCCGGGCAAGAGCAACGTCGGATGCCATGAGGACGGGACCATACACAGCCGGAATGACGGCCTCGTAGCAATGGCA
GTCACAGAAAGCATCTTCTGACAACGATCGGAGCAACCGGAGCGACGCCGGAATGACGGCCTACCAACCGTAACGGGGATCATGTAACTC
GGCCAACTTACTTCGGTCGGACCTCGACCACCGGATGCCAACGCGAACCGGAATGACGCGACTAACCAACCGTAACGGGGATCATGTAACTC
GCCTGATCGTTGGGACCGGAGCTGAATGACGGGACGCGAACCCAAACGCGAACGGAATGAACACCGATGCCGGACACAATCTAACTGA
ACAACGTTGGCAAACTATTAACTGGCGAACTACTTACTCTAGCTCCCGGCAACAATTAATAAGAGACTGGATGGAGGCGGA
```

FIGURE 3B

TAAAGTTGCAGGACCACTTCTGCGCTCGGCTGGCCCTTCCGGCTGGCTGGTTTATTGCTGATAAATCTGGAGCCGGTGAGCGTG
GGTCTCGCGGTATCATTGCAGCACTGGGGCCAGATGGTAAGCCCTCCCGTATCGTAGTTATCTACACGACGGGAGTCAG
GCAACTATGGATGAACGAAATAGACAGATCGCTGAGATAGGTGCCTCACTGATTAAGCATTGGTAACTGTCAGACCAAGT
TTACTCATATATACTTTAGATTGATTTAAAACTTCATTTTAATTTAAAGGATCTAGGTGAAGATCTTTTTGATAATC
TCATGACCAAAATCCCTTAACGTGAGTTTTCGTTCCACTGAGCGTCAGACCCCGTAGAAAAGATCAAAGGATCTTCTTGA
GATCCTTTTTTTCTGCGCGTAATCTGCTGCTTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGATACCAAATACTGTCCTTCTAGTGTAGCCGT
AGTTAGGCCACCACTTCAAGAACTCTGTAGCACCGCCTACATACCTCGCTCTGCTAATCCTGTTACCAGTGGCTGCTGCC
AGTGGCGATAAGTCGTGTCTTACCGGGTTGGACTCAAGACGATAGTTACCGGATAAGGCCAGCCAGCGGTCGGGCTGAACGGG
GGGTTCGTGCACACAGCCCAGCTTGGAGCGAACGACCTACACCGAACTGAGATACCTACAGCGTGAGCATTGAGAAAGCG
CCACGCTTCCCGAAGGGAGAAAGGCGGACAGGTATCCGGTAAGCGGCAGGGTCGAACAGGAGAGCGCACGAGGGAGCTT
CCAGGGGGAAACGCCTGGTATCTTTATAGTCCTGTCGGGTTTCGCCACCTCTGACTTGAGCGTCGATTTTTGTGATGCTC
GTCAGGGGGGCGGAGCCTATGAAAAACGCCAGCAACGCGGCCTTTTACGGTTCCTGGCCTTTTGCTGGCCTTTTGCTC
ACATGTTCTTTCCTGCGTTATCCCTGATTCTGTGGATAACGTATTACCGCCTTTGAGTGAGCTGATACCGCTCGCCGC
AGCCGAACGACCGAGCGCAGCGAGTCAGTGAGCGAGGAAGCGGAAGAGCGCCCAATACGCAAACCGCCTCTCCCCGCG
TTGGCCGATTCATTAATGCAGGTTAACCTGGCTTATCGAAATTAATACGACTCACTATAGGGAGACCGGAGATCGATCT
GTCGA

FIGURE 3C

FIGURE 4
pTRABac/9F12 DNA Sequence

```
GCAGTTCGTTGACGCCTTCCTCCGTGTGGCCGACACGTCGAGCGGGTGGTCGATGACCAGCGCGTGCCGCACGCGACG
CACAAGTATCTGTACACCGAATGATCGTCGGGCGAAGGCACGTCGGCTCCGCCAAGTGCAATATTGGCAAATTCGAAATA
TATACAGTTGGGTTGTTTGCGCATATCTATCGTGGCGTTGGGCATGTACGTCCGAACGTTGATTGCATGCAAGCCGAAA
TAAATCATTGCGATTAGTGCAAAGTGTGGAATAAATGTTTTCTTTGTATCCGAGTCAAGCGCAGCGCGTATTTTAACAAACTAGCCAT
GTCAAGTGATCAAAGTGTGGAATAAATGTTTTCTTTGTATCCGAGTCAAGCGCAGCGCGTATTTTAACAAACTAGCCAT
CTTGTAAGTTAGTTTCATTAATGCAACTTTATCCAATAATATTATGTATCGCACGTCAAGAATTAACAATGCGCCCG
TTGTCGCATCTCAACACGACTATGATAGAGATCAAATAAAGCGCGAATTAAATAGCTTGCGACGCAACGTGCACGATCTG
TGCACGCGGTTCCGGCACGAGCTTTGATTGTAATAAGTTTTACGAAGCGATGACATGACCCCGTAGTGACAACGATCAC
GCCCAAAAGAACTGCCGACTACAAATTACCGAGTATGTCGGTGGCGAATGTCGATTAAAACTCGTATAACGTGGAGTCCGCTAG
TCGAATCAGGACCGCTGGTGCGAGAAGCCGCGAAGTATGGCGAATGCATCGTATAACGTGTGGAGTCCGCTCATTGAGC
GTCATGTTTAGACAAGAAAGCTACATATTTAATTGATCCGATGATTTATTGATAAATTGACCCTAACTCCATACACGG
TATTCTACAAGTGGCGGGTTTGGTCAAATTTAAAAAAACGCAGCAAGAATGCCTCCCGTGTATAAAAAAAATATTGAACGATTGAAAGAAAACAATGTAC
GAAATTAAAAATTCAATTTAAAAAACGCAGCAAGAATGCCTCCCGTGTATAAAAAAAATATTGAACGATTGAAAGAAAACAATGTAC
CGTCGACATGCTGAACAACAAGATTAATATGCCTCTAAACTGTTATACTGTTACATTGCAAACGTGGTTTCGTGTGCCAAGTGTGAAAAC
CGCGCGGCGTATGTACAGGAAGAGAGGTTTATACTAACTGTTACATTGCAAACGTGGTTTCGTGTGCCAAGTGTGAAAAC
CGATGTTTAATCAAGGCTCTGACGCATTTCTACAACCACGACTCCAAGTGTCGGGTGAAGTCATGCATCTTTAATCAA
ATCCCAAGATGTGTATAAACCACCAAACTGCCAAAATGAAAACAATTAAAAATGCTAAATTGTTTTTTATTAACGATACAAAC
AGGGTCTCAATCTTCAATTATTGTAATTATTGCAAAATGCCAAAATGAAAACAATTAAAAATGCTAAATTGTTTTTTATTAACGATACAAAC
CAAACGCAACAAGAACATTGTAGTATTATCTATAAACGCGTAGTTATTTCACATAACTAGTATTATTCACATAGACGCCTTGTCGTCTTCTTC
TTTCAAATGATTCACAGTTAATTGCGACAATATATTTATTTCTCCTCATAAAATAATTAACATAGTTATTATCCGTATCTATCGTATA
GTATTCCTTCTCTTTTGTTCTCGGTAGTTCTCATTTTGTCATAAATATATGTCTTTCGGAGTATGGGGTGTATAGTAATTATTAA
GAGTAAATTTTGTTCTCGGTAGTTCTCATTTTGTCATAAATATATGTCTTTCGGAGTATGGGGTGTATAGTAATTATTAA
TTACAACAGTGCTATTTTGTACAATATGTTGCCCGGCATAGTACGCAGCTTCTCTAGTTCTAATTACACCATTTTTAGCAGCACCG
ATCGTCGGTTTGTGTTACAATATGTTGCCCGGCATAGTACGCAGCTTCTCTAGTTCTAATTACACCATTTTTAGCAGCACCG
GATTAACATAACTTTCCAAATGTTGTTAAAATAACAGCCATTGTACGAACCGTTAAAGTAATGAGACCACAAACTGAAATGTCTATCA
AGCAGTTGTTTGTTGTTAAAATAACAGCCATTGTACGAACCGTTAAAGTAATGAGACCACAAACTGAAATGTCTATCA
TATATAGTTGCTGATATCTCCCCAGCCTGCTATTGTCTTCTTCCCAATCTCCCCCTTGCTGTCCTGCGTCCCCACCCACC
```

Figure 4 (Cont.)

```
CCCCAGAGAATAGAATGACACCTACTCAGACAATGCGATGCAATTTCCTCATTTTATTAGAAAGGACAGTGGAGTGGCAC
CTTCCAGGTCAAGGAAGGCACGGGGAGGCAAACAACAGATGGCTGGCAACTAGAAGGCACAGTCGAGGCTGATCAG
CGAGCTCTAGTCTAGACTATTATTACCCGAGACAGGGAGAGCTCTTCGCTGTAGTGGTTGTGCAGAGCCTCATGC
ATCACGGAGCATGAGAAGACGTTCCCCTGCTGCCACCTGCTGAGCTTGCTGTAGAGGAAGAAGGAGCC
GTCGGAGTCCAGCACGGGAGGCGTGGTTGTAGTGCTGACCTGAGCTGTCTCCCACTCCACGGCGATGTCGC
TGGGATAGAAGCCTTTGACCAGGCAGGTCAGGCTGTTCTTGGTCCTGTTCTTGGTCAGCTCATCCGGATGGGGGCAGGGTAC
ACCTGTGTTCTCGGGCTGCCCTTTGGCTTTTGTGCTTTGGATGTGTTTCTCGATGGGGCTGGGAGGGCTTTGTTGTTGAGACCTT
GCACTTGTACTCCTTGCCATTCAGCCAGTCCTGGTGCACCTCACGTACACCAGTTGAACTTGACCTTCAGGTCTTCG
GCTCCTCCACGTCCACCACGCATGTGACCTCAGGGTGCCGGTGGGCATGTGCAGATGTGAGTTGCACAAGATTGGGCTCAACTTTCT
TGGCTCACGTCACGGTCCCCCCAGGGCTTGCGGCTTGATTGTGATTCACGTTCAGGTGCCGGTGGGCATGTGCAGATGTGAGTTCTGGGTGCCCAAGCTGCTGAGGGCACGTC
GAAGACTGACGGTCTCCCCCAGGGCTTGCGGCTTGATTGTGATTCACGTTCAGGTGCTGATTGTGCTTGTGGGCTCTGGAGGGCACGTC
TGTCCACCTTGGTGGTCGAGGGAGTAGAGTCCTGAGGACTAGTCCTTGAGCAGCAGCAGCCCCTTGGTGTGACCAGGGCCGTGACCAGGAGTGTGCAGCGCTGTCT
ACCAGCGTGACACCGTCCAGGGGAAGACCGATGGGCCACTGTTTTCCCGCTTTCTCTGAGAATTGTCTCCAGCCACCTCAGCCCCATCCGGAGCCTGACCCAGAGCGCCGTGTCCGCGACCCAGCTGCAGCTCTGCATAATATG
GTTCAAGTCAGATAGTAGTGGGCCAGTAGATAGCGTGTTCAATAATAGCGCACTGTTGTACTAATAGCGCACTGTTGTACTAATAGCGCACTGTTCATGGAATTGTCTCTGAGAATTGTCTCTGAGAGTTGCATAATATG
GCCGCGTACGATTGTAAATAAATATTGTGGTTGATATCTTTGAATCTTTGTTGAATTGAAATAGCACACAGACTCCAGCGTTGGCATCTCAAATGCCGTTTGGCGTTTTATTTCTTTGCTCGA
CTGCTAAAGCTGAATCTGTCCGATAGTGAAGAAATGTAAGAAGAAATGTACAGTATATTACAGTGAAGAAATGTAAGAAATGTACAGTAATATCAAATGATTGATAATAATCTT
GCCGCGTACGATTGTAAATAAATATTGTGGTTGATATCTTTGAATCTTTGTAAAATAGCACACAGACTCCAGCGTTGGCATCTCAAATGCCGTTTGGCGTTTTATTTCTTTGCTCGA
GTAAGTCAGGTATTTCTGAATCTTTGTAAAATAGCACACAGACTCTCGAAATAATAGATAACCATCTCGAACATCTCCACCATCTGGGCGGTCTAGCGGATCCATGGTGGGACCCTGCA
AAAAAACCTATAAATATTCCGGATTATTCATACCGTCTGAGCCTAGGCTACAGAGACATCATCCTGATTAGCACGAGTATTAGCACCTATTAAATTGGTA
TCCCTGTCTGCAGAAACCAGGGAGAAGCCCCTAACTCACTTCACTCCTTATGCAACCAATTTGCAAGTTGGGTCCCATCAAGTTCA
TCAGCAGAAACCAGGTCGGACAGATTTCACTCACTTCCACCATCAGCAGTCTGCCAAGTGGATATGAAGACTGTGGCTGCACCAAGTCTTCATCTT
CAGAGTTCCAACACCGTCACTTCGCCCTGGACACTGCCTCTGTTGCTGTGCTGAATAACTTCTATCCCAGAGGCCA
CCCGCCATCTGATGACCGTCACTTCGCCCTGGACACTGCCTCTGTTGCTGTGCTGAATAACTTCTATCCCAGAGGCCA
```

Figure 4 (Cont.)

AAGTACAGTGGAAGGTGATAACGCCCTCCAATCGGGTAACTCCCAGGAGAGTGTCACAGAGCAGGACAGCAAGGACAGC
ACCTACAGCCTCAGCAGCTCGACCCTGAGCTGACAAAGCAGACTACGCAAAGCAGAGAAACAAAGTCTACGCCTGAAGTCACCCA
TCAGGGCCTGAGCTCGCCCGTCACAAAGAGCTTCAACAGGGAGAGTGTTAATAGAAGCTTGTCGTTGGATGGAAGGAA
AAGAGTTCTACAGGAAACTTGCGTCCCACTAGACCCGCTTCATGGAAGACAGCTTCCCATTGTTAACGACCAAGAAGTGATGGATGTT
TTCCTTGTGTCAACATGCGTCCCACTAGACCCAACCGTTGTTACAAATTCCTGCCCAACACGCTCGCGTTGCGACCC
CGACTATGTACCTCATGACGTGATTAGAGATCGTCAGCCTTCATGGGCAGCAACAACGAGTACCCATCAGCCTGG
CTAAGAAGGGCGGCGCTGCCCAATAATGAACCTTCACTCTGAGTACACCAACTCGTTGAACAGTTCATCGATCGTGTC
ATCTGGGAGAACTTCTACAAGCCCATCGTTACATCGGTACCGACTCTGCTGAAGAGGAGAAATTCTCCTTGAAGTTTC
CCTGGTGTTCAAATGTACATTTAAGCGAGTTTGCACCAGACGTCTGCGTAGATTCTGCGTTGTTGATTACAGACAATTGTACGTATTAAACACGATACATTGTT
ATTAGTACATTATTAAGCGTAGATTCTGCGTTGTTGATTACAGACAATTGTCAGCGTCTTTATATCTGAATTTAAATATTAA
AATTTATAATCTTTAGGTGTATGTTAGAGCGAAATCAAATGATTTTCAAACAAGGTTGTTTTCCGAACCGATGGCTGGACTACTA
ATCCTCAATAGATTTGTAAAATAGGTTTCGATTAGTTCAAAATCTTGTAGCAGCAATCTAGCTTTGTCGATATTCGTTTGTTTTG
ATGGATTTCGCTCAACGCCACAAAGGTTCGACGTCGTTCAAAATTGTATATGCGCTTTGTATTTCTTCATCGTCGTTAGTGTACAATTG
TTTTGTAATAAAGGTTCGACGTCGTTCAAAATTGTATATGCGCTTTGTATTTCTTCATCGTCGTTAGCCGATTATCG
ACTCGACGTAAACACGTTAAATAAGCTAGCTTGGACATATTTAACATGGGCGTGTTAGCTTTATTAGGCCTATTAATTGTCTC
TCGTCGTCCCAACCCTCGTCTTAGAAGTTGCTTCCGAAGACGATTTTGCCATAGCCACACGACGCTATTAATTGTGTC
GGCTAACAGTCCGCGATCAAATTTGTAGTTGAGCTTTTTTGAATTATTTCGATTGCGGCGTTGGTAACATTTCAGACGCAAA
ATCTAACTGTGCCCGATTTTTAATTCAGACAACACGTTAGAAAGCGATGGTGCAGGCGATGTGGAGGCGTGGCGGGGCGGAGGCGG
TCTACTAATGGCGGCGGTGGTGGCGGCGGATGCAGACGGCGGTTTTGGTTTGACCGGTGAGGTTCGCTCGAGACGAGTGCATTGTGTGGCTGAGCGGCACCTCAACTA
AGGCGGAGGTGGTGGCGGCGGCGGCGCCGTTTTTTGGTTTGACCGGTGAGGTTCGCTCGAGACGAGTGCATTGTGTGGCGGCACCTCAACTA
TTGTACTGGTTTCGGGCGCCGTCTAAAGGTGCAGGCGGGTTGAGGCGCACGCGGCCACCGGCTGCACAACGGAAGGTCGTCTGCTTCGA
AATTGTTGTCTGTGGTGGTGTTCGCGCCACGATTGTGGCGCACACATTGGAATACAAATCGTAAAAATCTGTATAAGCATTGTAATTTC
TGGTTTAGTTTGTTGGGCGTGGTGGTGGTGCCGATATTTAACACCGCTCAATGTAAGCATTGTAGTGGCGAGACACTTCGCTGTCGAGTTCTAG
GCTATCGTTACCGTCCGTGCCGATATTTAACACCGCTCAATGTAAGCATTGTAGTGGCGAGACACTTCGCTGTCGAGTTCTAG
GCCCGATAACAAGCTTTTCATTTTCATTGTATGATATACATAAGGTTATGTATTAATTGTAGCCGCATATGAGCCGCCCT
GTGCACTCTCAGTACAATCTGCTCTGATGCCGCTTACGACAGACAAGCTGTAAAGACACCGGTCAATGTATAGGTTAATGTCATGATATAATGT
CCGTCATCACCGAAACGCCGAGAGAAAGCGGCCTCGTGATACGCCTATTTTATAGGTTAATGTCATGATATAATGT

Figure 4 (Cont.)

TTCTTTAGACGTCAGGTGGCACTTTTCGGGGAAATGTGCGCGGAACCCCTATTGTTATTTTCTAAATACATTCAAATA
TGTATCCGCTCATGAGACAATAACCCTGATAAATGCTTCAATAATATTGAAAAAGGAAGAGTATGAGTATTCAACATTTC
CGTGTCGCCCTTATTCCCTTTTTGCGGCATTTTGCCTTCCTGTTTTGCTCACCAGAAACGCTGGTGAAAGTAAAAGA
TGCTGAAGATCAGTTGGGTGCACGAGTGGGTTACATCGAACTGGATCTCAACAGCGGTAAGATCCTTGAGAGTTTTCGCC
CCGAAGAACGTTTTCCAATGATGAGCACTTTTAAAGTTCTGCTATGTGGCGCGGTATTATCCCGTATTGACGCCGGGCAA
GAGCAACTCGGTCGCCGCATACACTATTCTCAGAATGACTTGGTTGAGTACTCACCAGTCACAGAAAAGCATCTTACGGA
TGGCATGACAGTAAGAGAATTATGCAGTGCTGCCATAACCATGAGTGATAACACTGCGGCCAACTTACTTCTGACAACGA
TCGGAGGACCGAAGGAGCTAACCGCTTTTTTGCACACAACGATGCCTAGCAACATGGGGGATCATGTAACTCGCCTTGATCGTTGGGAACCGGAG
CTGAATGAAGCCATACCAAACGACGAGCGTGACACCACGATGCCTGTAGCAACGTTGCGCAAACTATTAAC
TGGCGAACTACTTACTCTAGCTTCCCGGCAACAATTAATAGACTGGATGGAGGCGGATAAAGTTGCAGGACCACTTCTGC
GCTCGGCCCTTCCGGCTGGTTATTGCTGATAAATCTGGAGCCGGTGAGCGTGGGTCTCGCGGTATCATTGCAGCA
CTGGGGCCAGATGGTAAGCCCTCCCGTATCGTAGTTATCTACACGACGGGAGTCAGGCAACTATGGATGAACGAAATAG
ACAGATCGCTGAGATAGGTGCCTCACTGATTAAGCATTGGTAACTGTCAGACCAAGTTTACTCATATATACTTTAGATTG
ATTTAAAACTTCATTTTAATTTAAAGAGATCTAGTGAAGATCAAGAATCCTTTTTTGATAATCTCATGACCAAAATCCCTTAACGT
GAGTTTTCGTTCCACTGAGCGTCAGACCCCGTAGAAAAGATCAAAGGATCTTCTTGAGATCCTTTTTTCTGCGTAAT
CTGCTGCTTGCAAACAAAAAAACCACCGCTACCAGCGGTGGTTTGTTTGCCGGATCAAGAGCTACCAACTCTTTTTCCGA
AGGTAACTGGCTTCAGCAGAGCGCAGATACCAAATACTGTCCTTCTAGTGTAGCCGTAGTTAGGCCACCACTTCAAGAAC
TCTGTAGCACCGCCTACATACCTCGCTCTGCTAATCCTGTTACCAGTGGCTGCTGCCAGTGGCGATAAGTCGTGTCTTAC
CGGGTTGGACTCAAGACGATAGTTACCGGATAAGGCGCAGCGGTCGGGCTGAACGGGGGGTTCGTGCACACAGCCCAGCT
TGGAGCGAACGACCTACACCGAACTGAGATACCTACAGCGTGAGCATTGAGAAAGCGCCACGCTTCCCGAAGGAGAAAG
GCGGACAGGTATCCGGTAAGCGGCAGGGTCGGAACAGGAGAGCGCACGAGGGAGCTTCCAGGGGGAAACGCCTGGTATCT
TTATAGTCCTGTCGGGTTTCGCCACCTCTGACTTGAGCGTCGATTTTTGTGATGCTCGTCAGGGGGGCGGAGCCTATGGA
AAAACGCCAGCAACGCGGCCTTTTTACGGTTCCTGGCCTTTTGCTGGCCTTTTGCTCACATGTTCTTTCCTGCGTTATCC
CCTGATTCTGTGGATAACCGTATTACCGCCTTTGAGTGAGCTGATACCGCTCGCCGCAGCCGAACGACCGAGCGCAGCGA
GTCAGTGAGCGAGGAAGCGGAAGAGCGCCCAATACGCAAACCGCCTCTCCCCGCGCGTTGGCCGATTCATTAATGCAGGT
TAACCTGGCTTATCGAAATTAATACGACTCACTATAGGGAGACCGGCAGATCGATCTGTCGA

FIGURE 6A pTRABacHuLCκHCλ1 DNA Sequence

```
GCAGTTCGTTGACGCCTTCCTCCGTGTGGCCGAACACGTCGAGCGGGTGGTCGATGACCAGCGGCGTGCCGCACCGACGCACAAGTAT
CTGTACACCGAATGATCGTCGGCGAAGGCACGTCGGCCTCCAAGTGGCAATATTGGCAATTCGAAATATATCAGTTGGGTTGTTT
GCGCATATCTATCGTGGCGTTGGGCGCATGTACGTCCGAACGTTGCATGCAAGCCGAATTAAATCATTGCGATTAGTCGATTAA
AACGTTGTACATCCTCGCTTTAAACAAACTAGCCATCTTGTAAGTTAGTTTCATTTAATGCAATCAAAGTGTGAATAATGTTTCTTTG
TATTCCCGAGTCGACACGTCAAGAATTAACAATGCGCCCGTTGTCGCATCTCAACACGACTATGTAATAAGTTTTTACGAAGCGAATTAAATA
GCTTGCGACGCAACGTGCACGATCTGTCCGGCACGCGTTCCGGACACCCAAAAGAACTGCCGACTACAAAATTACCGAGTATGTCGGTGATTGTAATAAGTTTTACGAAGCGATGACATGACCCCC
GTAGTGACAACGATCACGCCCAAAAGAACTGCCGACTACAAAATTACCGAGTATGTCGGTGACGTTAAAACTATTAAGCCATCCAATCG
ACCGTTAGTCGAATCAGGACCGCTGGTGCGAGAAGCCGCGAATATGCGAATGATATAACGTGTGGAGTCCGCTCATTAGAGCG
TCATGTTTAGACAAGAAAGCTACATATTTCCGATGATTTATTGATCCCGTAACTCCATACACGTATCTACAA
TGGCGGGGTTTGGTCAAATTTCCGACTGCAATGTCGTGTTAACGGCTCCGCCCACTATTAATGAAATTAAAAATTCCAATT
TTAAAAACGCAGCAAGAGAACATTGTATGAAGAAAGAAAATGTCGTCGACATGCGTAGAAGAGTTTATACTAAA
ATGCCTCCGTGTATAAAAAAATATTGAACGATTTGAAAGAAACAATGTACCGCGGCGGTATGTACAGGAAGAGTTTATACTAAA
CTGTTACATTGCAAACGTGGTTTCGTGTGCCAAGTGTGAAAACCGATGTTTAATCAAGGCTCTACAACCACGACTCCA
AGTGTGTGGGTGAAGTCATGCATCTTTAATCAAATCCCAAGATGTGTATAAAAAAATGCCAAAAATGAAAACTGTCGACAAG
CTCTGTCCGTTGCTGGCAACTGCAAGGGTCTCAATCCTATTGTTGTAATTATTGAATAATAAACAATTATAAATGCTAAATTGTTTT
TATTAACGATACAAACCAAACGCAACAAGAACATTGTAGTATTATCTATAATAACGCTAGTTATAATCGCTGAGGTAATATT
AAAATCATTTCAAATGATTCACAGTTAATTGCGACAATATAATTTATTTTCACATAAACTAGACGCCTTGTCTTCTATCTTCTTCGT
ATTCCTTCTCTTTCATTTTCATTTTCCTCATAAAATTACAGTATTATCGTATCCATATATGTATCTATCGTATAGAGTAAATTTT
TTGTTGTCATAAATATATATGTCTTTTTAATGTCTTGCTTTGCTTAGTTCTTCCGGCATAGTTTGGGATGTATACCGGCGATAGTTTCTGTAATTTACAACAGTGCTATTTTC
TGGTAGTTCTTCGGAGTGTGTTCTTGTTCTTCAATTATATCACACCATTTTTTAGCGAGCAGTGTTGTTAAAATAACAGCCATTGTAACGTAATGAGACGCAC
CATAGTACGCAGCTTCACCTCCCTTTTCTATACTATTGTCTGCGAGCAGTGTCTGATATCTCCCAGCATGCCTGCTATTGTCTTCCCAATCCTCCCC
AACAAAAACGTTCACAACACTGGAAATGTCTATCAATATATAGTTGCTGATATATTGTTAAAATAACAGCCATTGTAATGAGACGCAC
CTTGCTGTCCGTGCCCCCACCCCCCAGAATAGAATGACACCTACTCAGAATGCGATGCAATTCCTCATTTTATTAGGAAAGA
```

Figure 6A (Cont.)

CAGTGGGAGTGGCACCTTCCAGGTCAAGGAAGGCACGGGGAGGGCAACAACAGATGGCTGCAACTAGAAGGCACAGTCGAGGCT
GATCAGCGAGCTCTAGACTATTATTTACCCGGAGACAGGAGAGAGCTCTTCTGCGTTAGTGGTTGTGCAGAGCCTCATGCATC
ACGGAGCATGAGAAGACGTTCCCCTGCTCACCTGTTCTCCACGGTGAGCTTGCTGTAGAGGAAGGAGCCGTCGGAGTCCAG
CACGGGAGGCGTGGTCTTGTAGTTGTTCCAGCCATTGCTCTCCACTCACGGCGATGTCGCTGGGATAGAAGCCTTTGACCA
GCAGGTCAGGCTGACCTGGTTTCTCGATGGGGCTGGGAGGCTGTACACCTGTGGTTCTCGGGGCTGCCCTTTGGCT
TTGGAGATGGTTTTCTCGATGGGGCTGGGAGGCTGTGTTGTTGGAGACCTTGCTCACTGTTGTCTTGGCATTATCAGCCAGTCCTGTCAG
GACGGTGAGGACGCTGACCACACGGTACGTCTTCTGTGGCTCACGTCCACCACGCATGTGACCTGGGCACGTGGGCATGAGGGTG
CGTACCAGTTGAACTTGACCTGCAGGTCTTCGTGGCCTTTGTGATTGCAGGACTGTGGGCAGGTCTTGCGCCCCAAGCTCTGG
TCCTTGGGTTTGGGGGAAGAGAAGAACTGACGGTTCACCTGGGCTCGAGGGAGTAGTCTTGACCAGCAGCCCAGAGTTTGTCACA
AGATTTGGGCTCAACTTTCTTGTCACGCTGTCACCACCGTGAGGGATGCTCGGGGAAGTAGTCGGTTGCAGCAGCCCAGGGCCGCTGGTCAGGCGCT
AGGGCACGGTCACGACACCGGTTCGGGGAAGACCGATGGGCCCACTAGTGGCCCCAGGAATTCATGCGCCGCTACGAGGCGCTGCTCTTGGAGA
GAGTTCCACACACACCGGTTCGGGGAAGACCGATGGGCCCACTAGTGGCCCCAGGAATTCATGCGCCGCTACGAGGCGCTGCTCTTGGAGA
GGGTGCCAGGGGAAGACTATTTTAATTAATATACAAATGATTTGATAATAATTCTTATTGTGCCGCTACATATGTGTTGGGTTGAATTAAAGT
TTACAGTATAGTATTTTAATTAATATACAAATGATTTGATAATAATTCTTATTGTGCGTATTCTGAATCTTTGTAAATAGCACACAGACTC
CCCGGCATCCTCAAATGCATAATATCATAATGATTTTCTTGCTGAAGTGATGCGTATTTCTGTAAGTGATGCGTATTTCTGAATCTTTGTAAATAGCACACAGACTC
CAACGCGTTTGGCGTTTATTTTCTTGCTGAGGATATCATGAGATATTAAAATGATAACCATCTCGCAAATAAATAAGTATTTAC
TGTTTCGTAACAGTTTTGTAATAAAAAACCTATAAATATTCGGATTATTCATACCGTCATCATCTTCCCGCCATCTGATGAGCAGTTGAAATCT
GGTGGGACCCTGCATGCTGTGCCGTGCGGTGCGTGCCTGAATAACTTCTATCCCAGAGACAGCCTCAGGCTGAAGTACAGTGGAAGTGGATAACGCCCTCCAATCGGG
GGAACTGCCTCTGTTGCCGTGCGGTGCGTGCCTGAATAACTTCTATCCCAGAGACAGCCTCAGGCTGAAGTACAGTGGAAGTGGATAACGCCCTCCAATCGGG
TAACTCCCCAGGAGAGTGTCACAGCCCTGCGAAGTCACCCATCAGGGCTCGACGGAAACTTGGACACCCGTTCATGGAAGACAGCTTCAACAGGGAGAGTGTTAATAG
AGAAACACAAAGTCTACGCCCTGCGAAGTGAAAGAGTTCTACAGGGAAACTTGGACACCCGTTCATGGAAGACAGCTTCAACAGGGAGAGTGTTAATAG
AAGCTTGTCGTTGGATGATGTTTCCTTGTTGTCAACATGCGTGATTAGGATCGTCGAGCCTTCAACATGGTGGGCAGCAACAACGAGTACCGCATCAGCCTGGCT
AGAAGTGATGATGTTTCCTTGTTGTCAACATGCGTGATTAGGATCGTCGAGCCTTCAACATGGTGGGCAGCAACAACGAGTACCGCATCAGCCTGGCT
GCGACCCGACTATGTACCTCATGACCTGATTAGGATCGTCGAGCCTTCAACATGGTGGGCAGCAACAACGAGTACCGCATCAGCCTGGCT
GCGACCCGACTATGTACCTCATGACCTGATTAGGATCGTCGAGCCTTCAACATGGTGGGCAGCAACAACGAGTACCGCATCAGCCTGGCT
AAGAAGGCGGCCGCTGCCAATAATGAACCTTCACTCTGAGTACACCAACTCGTTGAACAGTTCATCGTGTCCTTGTTCAAAGTAAAGG
CTTCTACAAGCCCATCGTTACATCGGTTACACCGTCCGGCGTATTAAAACGATACATTGTTATTAGTACATTATTAAGCGCTAGATTCT
AGTTTGCACCAGACGCACCTCGTTCACTGTTACGTATTTAATAAATTCATTAAATTTATAATCTTTAGGTGGTATGTTAGAGCGAAAT
GTGCGTTGTTGATTTACAGACAATTGTTGTACGTATTTAATAAATTCATTAAATTTATAATCTTTAGGTGGTATGTTAGAGCGAAAT

Figure 6A (Cont.)

CAAATGATTTTCAGCGTCTCTTTATATCTGAATTTAAATATTAAATCCTCAATAGATTTGTAAAATAGGTTTCGATTAGTTTCAAACAAGG
GTTGTTTTTCCGAACCGATGGCTGGACTATCTAATGGATTTCGCTCAACGCCACAAAACTTGCCAAATCTTGTAGCAGCAATCTAGCT
TTGTCGATATTCGTTGTGTTTGTTTTGTAATAAAGGTTCGACGTCGTTCAAAATATTATGCGCTTTTGTATTCTTTCATCACTGTC
GTTAGTGTACAATTGACTGACGTAAACACGTTAAATAAAGCTAGCTTGGACATATTTAACATCGGGCGTGTTAGCTTTATTAGCCGA
TTATCGTCGTCGTCCCAACCCTCGTTAGAAGTTGCTTCCGAAGACGATTTGCCATAGCCACACGACGCCTATTAATTGTGTCGGC
TAACACGTCCGCGATCAAATTGTAGTTGAGCTTTTTGAATTATTTCTGAATGCCGTGTTTTGGGCGTTTTGGGGGTTTCAATCTAACTGTGC
CCGATTTAATTCAGACAACACGTTAGAAAGCGATGGTGCAGGCGGTGTAACATTTCAGACGGCAAATCTACTAATGGCGGCGGTGT
GGAGCTGATGATAAATCTACCATCGGTGAGGCGAGGCGGGGCCAGGCGGAGTTGTGGCGGTGATGCAGACGG
CGGTTAGGCTCAAATGTCTCTTAGGCAACACAGTCGGCACCTCAACTATTGTCTCGTCTAAAGGTGCAGCGGTTGAGGTTCCGTCGC
TGAGACGAGTGCGATTTTTTCGTTTCTAATAGCTTCCAACAATTGTGTCTGTCGGAGCGCTGGGCACCGGCCTGCTGGGAGAAGGTGGTGGCGG
ATTGGTGGAGCGGCCAATTCAGACATCGATGGTGGTGGCACGATTGTGGGCAATTCAATATATATAAGCTAAAAATCTGCTATAAGCATTGTA
CGGTGCCGCCCGGTATAATTGTTCTGGTTTAGTTTGTTGTTCGGCACGATTGTGGGCAGGCCCCTGGCTGCACAACGGAAG
GTCGTCTGCTTCGAGGCAGCGGTTACCGTCGCCGATATTTAACAACCGCTCAGTGGCGAGACACTTCGAGTTCGAGTTCACCTAAATC
ATTTCGCTATCGTTTACCGTCGTCCGCGATATTTTACTACAGCATTGTAGTGCCGAGACACTTCGAGTTCGAGTTGTCACCTAAATC
GATAACAAGCCTTTCATTTTACTACAGCATTGTAGTGCCGCGTTCTAACGACAAATATGTCCATATGGCACTCTCAGTACAATCTGC
GTATGTGTATGATACATAAGGTTATGTATTAATGTTAGCCGCGTTCTAACGACAAATATGTCCATATGGCACTCTCAGTACAATCTGC
TCTGATGCGGCATAGTTAAGCCAGCCCCGGAGCTGCATGTGTCAGAGGTTTCTTAGAGTGGCACTTTCAGGTGCCACTTTCGGGGAAATGTGCGCGAACCCT
CAGACAAGCTGTGACCGTCTCCGGGAGCTGCATGTGTCAGAGGTTTCTTAGAGTGGCACTTTCAGGTGCCACTTTCGGGGAAATGTGCGCGAACCCT
TACGCCTATTTTATTTTCTAAATACATTCAAATGTAATGTCATGATAATATGTATCCGCTCATGAGACAATAACCCTGATAAATGCTTCAATATATTGAAAAAGGAA
ATTTGTTTATTTTCTAAATACATTCAAATGTAATGTCATGATAATATGTATCCGCTCATGAGACAATAACCCTGATAAATGCTTCAATATATTGAAAAAGGAA
GAGTATGAGTATTCAACATTCCGTGTCGCCCTTATTCCGCCGCGAGTGGGTGCACAGCGGTTACATCGAACTGGATCTCAACAGCGGTAAGATCCTTGAGAGTTTT
TGAAAGTAAAGATGCTGAAGATCAGTGGGTGCACAGCGGTTACATCGAACTGGATCTCAACAGCGGTAAGATCCTTGAGAGTTTT
CGCCCGAAGAACGTTTCCAATGATGAGCACTGTTAAAGTTCTGTATACTCCACCAGTCAGAATGACTTACGCCGGGCAAGAGCA
ACTCGGTCGCCGCATACACTATTCTCAGAATGACTCTCAGAATGACTCTCAGAATGACTCTCAGCCGATGCCATGCAACTAA
GAGAATTATGCAGTCGTGCCAACATGGGGATCATGTAACCATGAGTGATAACTCGGCCAACTTACTTCTGACAACGATGAAGCCATACCAAACGACGAGCGTGA
GCTTTTTGCACAACATGCCCTGAGCAATGGCAACAACGTTGCGCAACTATTAACTGGCGAACTACTTACTCTAGCTTCCCGCAACAATTAATAG
CACCACGATGCCTGTAGCAATGGCAACAACGTTGCGCAACTATTAACTGGCGAACTACTTACTCTAGCTTCCCGCAACAATTAATAG
ACTGGATGGAGGCGATAAAGTTGCAGGACCACTTCTGCGCTCGGTCTTATGCTGATAAATCTGGAGCCGGT

Figure 6A (Cont.)

```
GAGCGTGGGTCTCGCGGTATCATTGCAGCACTGGGCCAGATGGTAAGCCCTCCCGTATCGTAGTTATCTACACGACGGGAGTCAGC
AACTATGGATGAACGAAATAGACAGATCGCTGAGATAGGTGCCTCACTGTGAGATTAAGCATTGTCAGACCAAGTTACTCATATA
TACTTTAGATGATTAAAACTTCATTTTTAATTTAAAAGGATCTAGGTGAAGATCTCTTTTGATAATCTCATGACCAAAATCCCTTAAC
GTGAGTTTTCGTTCCACTGAGCGTCAGACCCCGTAGAAAAGATCAAAGCAACAACTCTTTTTCGCGTAATCTGCTGC
TTGCAAACAAAAAAACCACCGCTACCAGCGGTGGTTTGTTTGCCGGATCAAGAGCTACCAACTCTTTTTCCGAAGGTAACTGGCTTCAG
CAGAGCGCAGATACCAAATACTGTCCTTCTAGTGTAGCCGTAGTTAGGCCACCACTTCAAGAACTCTGTAGCACCGCCTACATACCTCG
CTCTGCTAATCCTGTTACCAGTGGCTGCTGCCAGTGGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGAACGACCTACACCGAACTGAGATACCTACAGCGTGA
GCATTGAGAAAGCGCCACGCTTCCCGAAGGGAGAAAGGCGGACAGGTATCCGGTAAGCGGCAGGGTCGGAACAGGAGAGCGCACGAGGG
AGCTTCCAGGGGGAAACGCCTGGTATCTTTATAGTCCTGTCGGGTTTCGCCACCTCTGACTTGAGCGTCGATTTTTGTGATGCTCGTCA
GGGGGCGAGCCTATGGAAAAACGCCAGCAACGCGGCCTTTTTACGGTTCCTGGCCTTTTGCTGGCCTTTTGCTCACATGTTCTTTCC
TGCGTTATCCCCTGATTCTGTGGATAACCGTATTACCGCCTTTGAGTGAGCTGATACCGCTCGCCGCAGCCGAACGACCGAGCGCAGCG
AGTCAGTGAGCGAGGAAGCGGAAGAGCGCCCAATACGCAAACCGCCTCTCCCCGCGCGTTGGCCGATTCATTAATGCAGGTTAACCTGG
CTTATCGAAATTAATACGACTCACTATAGGGAGACCGGCAGATCGATCTGTCGA
```

FIGURE 6B pTRABacHuLCλHCγ1 DNA Sequence

```
GCAGTTCGTTGACGCCTTCCTCCGTGTGGCCGAACACGTCGAGCGGGTGGTCGATGACCAGCGGCGCTGCCGCCACGCGACGCACAAG
TATCTGTACACCGGAATGATCGTCGGGCCGAAGGCACGTCGGCCTCCAAGTGCAATATTGGCAAATTCGAAAATATACAGTTGGG
TTGTTTGCGCATATCTATCGTGGCCGTTGGGCATGTACGTCCATGCGCCAATCGTTGATTTGCATGCAAGCCGAAATTAAATCATTGCGATTAG
TGCGATTAAAACGTTGTACATCCTCGCTTTAAATCATGCCGTCGATTAAATCGCGCAATCGAGTCGAGTCAAGTGATCAAGTGTGAATA
ATGTTTTCTTTGTATTCCGAGTCAAGCGCAGCCGTATTTTAACAAACTAGCCATCTGTCGCATCTCAACACGACTATGAGTTCATTAATGCAACTT
TATCCAATATATTATGTATGCGAATTAAATAGCTTGCGACGCAACGTGCACGATCTGTCACGCGTTCCGACGCGTTTGATTGTAATAAGTTTTTA
CGAAGCGGATGACATGACCCCCGTAGTGACAACCGTTAGTCGAATCGACCGTTAGACAAGAACCGCTGGTGCGAAGACCTGTGCGGAAGTATGGCGAATGCATCGTAT
TAAAACTATTAAGCCATCCGCTCATTAGAGCGTCATGTTTAGACAAGAAGCTACATATTTCCGGACTGCATGCTGTTAACGGCTC
GACCCTAACTCCATACACGGTATTCTACAATGGCGGGTTTTGGTCAAAATTCCAATTTTAAAAAACGCAGCAACATTTGATATGAAAGAATGCGTAGAAGGAAAG
CGCCCACTATTAATGAAATTAAAAATTCCAATTTTAAAAAACGCAGCAGAAACATTTGTATGAAAGAATGCGTAGAAGGAAAG
AAAAATGTCGTCGACAAGAGAAAAATATGCCTCCGTGTAAACTAATATGCCAAGCGGCTCGTGCCAAGTGTGAAAAACCGAT
ACCGCGCGGGTATGTACAGGAGGAGGTTTATACTACAACCACGACTCCAAGTGTGGGTGAAGCTCGTCCGTTGCTGCCAAGTGTGAAACCGAT
GTTTAATCAAGGCTCTGACGCCATTTCTACACAACGTGCACAAAAAATGAAAAATCAAGTTGTTTTATTAACGATACAAACCAAACGCAACAAGAACATTTGT
GTGTATAAAACCACCAAACTGCCAAAAAATGAAAACAATTATAAATGCTAAATTGTTTTTATTAACGATACAAACCAAACGCAACAAGAACATTTGT
TTGTAATTATTGAATAATTGAAAACGCGTAGTTATAATCGCTGAGGTAATATTTAAAATCATTTTCAAATGATTCACAGTTAATTGCG
AGTATTATCTATAATTTTATTTTCACATAAACGCGTAGTTATAATCGCTGAGGTAATATTTTCTCTTCTTCGTATTCCTTCTCTTTTCATTTTTCATATAAATATGTCTTTTT
ACAATATAATTTTATTTTCACATAAACTAGACGCCTTGTCGTCTTGTCGAGGTAATATTGTATTCAACACAGTGCTATTTTCGGAGTGTGTTGCTT
AATGGGGTGTATAGTACCGCTGCGCAGTCTATCCATATATGTTTTCTGTAATTACAACACAGTGCTATTTTCGGAGTGTGTTGCTT
TAATTATTAAATTTATATAATCAATGAATTTGGGATCGTCGGTTTTGTACAAATGTTGCCGGCATAGTACGCAGCTTCTTCTAGT
TCAATTACACCATTTTTTAGCAGCACCGGATTAACATAACTTTCAAAATGTTACGAACCGTTAAACAAAAACAGTTCACCTCC
CTTTCTATACTATTGTCTGCGAGCAGTTGTTTGTTAAAAATAACAGCCATTGTAATGAGACGCACAAACTAATATCACAAAC
TGGAAATGTCTATCAATATATAGTTGCTGATATCTCCCCAGCATGCCTATTGCTCTTCCCAATCCTCCCCCTGTCTTCCTGTCCTGCC
```

Figure 6B (Cont.)

```
CCACCCCACCCCCAGAATAGAATGACACCTACTCAGACAATGCGATGCAATTCCTCATTTATTAGGAAAGGACAGTGGGAGTG
GCACCTTCCAGGGTCAAGGAAGGCACGGGGAGGGGCAACAACAGATGCCTGGCAACTAGAAGGCACAGTCGAGGCTGATCAGCG
AGCTCTAGACTATTATTACCGGAGACAGGAGAGGCTCTTCTGCGTAGTGGTTGTGCAGAGCCTCATGCCTCGGAGTCGAGCA
GCATGAGAAGACGTTCCCCTGCTGCCACCTGCTCTTGTCCACGGTGAGCTTGCTGTAGAGGAAGAAGGAGCCGTCGGAGTCCAGCA
CGGGAGGCGTGGTCTTGTAGTTGTTTCTCCGGCTCATTGCTCCTCCCATTGCTCTCCCGATGCGATGTCGCTGGGATAGAAGCCTTTGACC
AGGCAGGTCAGGCTGACCTGGTTCTTGGTCAGCTCATCCGGGATGGGGCAGGGTGTACACCTGTGGTTCTCGGGGCTGCCCTTT
GGCTTTGAGATGGTTTTCTGATGGGGCTGGGAGGGCTTTGTTGGAGACCTTGCACTCTCCTTGCCATTCAGCCAGTCCT
GGTGCAGGAACGGTGAGGACGCTGACCACGGTACGTGCTGTTGTACTGCTCTCACGTGTGGCTTGATCAGGAGTTCAGTGCTGGGCACGGTGGCATG
ACGCGTCCACGTACCAGTTGAACTTGAGGGTTTGGGGCTCAACTTCTTCTGTCCACCTGGTGCTGAGGAGTCCTGAGGACTGTAGGACAGCCCAGGCCGCTG
GATCATGAGGGTGTCTGGGTTTGTCACAGATTTGGGCTCAACTTCTTCTGTCCACCTGGTGCTGAGGAGTCCTGAGGACTGTAGGACAGCCCAGGCCGCTG
TGTGAGTTTTGTCACAGATTTGGGCTCAACTTCTTCTGTCCACCTGGTGCTGAGGAGTCCTGAGGACTGTAGGACAGCCCAGGCCGCTG
TGGGTGCCCAAGCTGCTGGAGGGCACGGTCACCTGAGTTCTGAGGCGCTGAGTTCCAGGGCCTGAGTTCGGGGAAGTAGTCCTTGACCGAGCCGTTCGGGGAAGTAGTCATGCGG
CACGCGCTGGTGCAGGGCGCCTGAGTTCGGGGAAGTAGTCCTTGACCGAGCCAGTGTAGTCCTTGACCGAGCCAGTGTAGTCCTTGACCGAGCCAGTGTAGTCCTTGACCGAGCCAGTG
TGCCCCCGTACGATTGTTAAATAAAATGTAATTTACAGTAGTATTTAATTAATATACAAATGATTTGATAATAATTCTTATTTAACT
CCGGCGTACGATTGTTAAATAAAATGTAATTTACAGTAGTATTTAATTAATATACAAATGATTTGATAATAATTCTTATTTAACT
ATAATATATTGTGTTGGGTTGAATTAAAGTCCCGGCATCCTCAAATGCATATGCGTTTGGCGTTTCTTCTTGCTCGAGGATATCATGGAGATAATTA
TTTCTGAATCTTTGTAAATAGCACACAGGACTCCAACGCGTTTGGCGTTTATTTCTTGCTCGAGGATATCATGGAGATAATTA
AATGATAACCATCTCGCCAATAAGTATTTACTGTTTTCGTAACAGTTTTGTAATAAAAAACCTATAAATATTCCGATT
ATTCATACCGTCCACCATCGGGCGTGCTAGCGATCCATGGTGGACCCTGCATCGTGCTCTAGCTCTAGCCTCACC
CAGTGTCACTCTGTTCCGCCCTCCTGAAGGCTTCAAGCCACACTGGTGCTGTCTCATAAGTGACTTCTACCCGG
GAGCCGTGACAGTGGCCTGAAGGCAGATAGCAGCCCCGTCAAGGCAGTCAGCCTGAGAACCCTCCAAACAAAGCAACAAC
AAGTACGCGGCCAGCAGTGGCCCCTGAGCCTGACGCGCTGACAGAATAGCAGCCCCGTCAAGGCAGTCAGCCTGAGAACCCTCCAAACAAAGCAACAAC
GAGCACCGTGGACCGGCCAGCAGTGGCCCCTGAGCCTGACGCGCTGACAGAAGAACGCCACAAGCTACAGCTGCCAGGTCACGCATGAAGG
AACTTGGACCCGCTCATGGAAGACAGTTCCCCATTGTTAACGACCAAGAAGTGATGATGTTTCCTTGTTGTCAACATGCGT
CCACTAGACCCAACCGTTGTTACAAATTCCTGGCCAACAGCGCTCTGCGTTGCACACGCTCTGCGTTGCACACGCTCTGCGTTGCACACGCTCTGCGTTGCACACGCTCTGCGTTGCACACGCTCTGCGTTGCACACGCTCTGCGTTGCACACCCGACTATGTACCTCATGACGTGATTAG
GATCGTCGAGCCTTCATGGGTGGCAGCAACTCGTTCGAACAGTTCATCGTCATCGTTCCCTGGTGTTCAAAGTAAAGGAGTTTGCACCAGACGCACCTCTGTT
TTCACTCTGAGTACACCAACTCGTTCGAACAGTTCATCGTCATCGTTCCCTGGTGTTCAAAGTAAAGGAGTTTGCACCAGACGCACCTCTGTT
ACCGACTCTGCTGAAGAGGAGAAATTCTCATTGTTATTATTGTAATGTTATTATTAAGCGCTAGAATTCTTAGGTGTATGTTAGAGCGAAATCAAATGATTTCAGCGTCT
CACTGGTCCGCGTATTTAATAAACACGATACATTGTTATTATTAAGCGCTAGAATTCTTAGGTGTATGTTAGAGCGAAATCAAATGATTTCAGCGTCT
ATTGTTGTACGTATTTAATTAATTCATTAAATTATAATCTTAGGTGTATGTTAGAGCGAAATCAAATGATTTCAGCGTCT
TTATATCTGAATTAAATATTAAATCCTCAATAGATTTGTAAAATAGGTTTCGATTAGTTTCAAACAAGGGTGTTTTCCAACC
```

Figure 6B (Cont.)

```
GATGGCTGGACTATCTAATGGATTTCGCTCAAGCGCCACAAAACTTGCCAAATCTTGTAGCAGCAATCTAGCTTTGTCGATATTCG
TTTGTGTTTGTTTGTGTAATAACGTTAAATAAAGCTAGCTTGGACATATTAACATCGGGCGTGTTAGCTTTATTAGGCCGATTATCGT
AATTGACTCGACGTAAACACGTTAAATAAAGCTAGCTTGGACATATTAACATCGGGCGTGTTAGCTTTATTAGGCCGATTATCGT
CGTCGTCCCAACCCTCGTCGTTAGAAGTTGCTTCCGAAGACGATTTTGCCATAGCCACACGACGCCTATTAATTGTCGCTAAC
ACGTCCGGATCAAATTGTAGTTGAGCTTTTTGGAATTATTCTGATTGCGGGCGTTTTGGGCGGTTTCAATCTAACTGTGCC
CGATTTAATTCAGACAACACGTTAGAAAGCGATGGTGCAGGCGGTGTAACATTTCAGACGGCAAATCTACTAATGGCGCGGTG
GTGGAGCTGATGATAAATCTACCATCGGTGGAGGCCAGGCGGGGCTGGCGCGGGGGCTGCCCGAGGCGGAGGTGGTGCCGGTGATGCA
GACGGCGTTTAGGCTCAAATGTCTCTTTAGGCAACAGTCGGCACCTCAACATTGTGTCTGTGTGGAGGCGCTGAAGTGTAGGCACGGGA
GACCGGTCTGAGACGAGTGCGATTTTTTCGTTCTAATAGCTTCCAACAATCGATGGTGGTTGTGTTGTCGCCACGATTGTGGGCACCGGCGCAGGCGCGC
GTTCCGTCGGCATTGGTGGAGCGGGCGCCGGTATAAATTGTCTCTGTTTACCGTCGTTACCGTCGATATTTACTACAGCAGCATTGTGGCGAGACACTTCGCTGTCGTCGAC
GAAGTGTGGCGGCGGTGCCGGTCGTCGTCTGCTCGAGGCAGCGCTTGGGGTGGTGGCCAATTCAATATTATAATTGGAATACAAATCGTAAA
TGGCTGCACAACGGAAGGTCGTCGTCTGCTCGAGGCAGCGCTTGGGGTGGTGGCCAATTCAATATTATAATTGGAATACAAATCGTAAA
AATCTGCTATAAGCATTGTAATTTCGCTATCGTTACCGTCGATATTTACTACAGCAGCATTGTGGCGAGACACTTCGCTGTCGTCGAC
GATTGTCTCAAGCTCCGATAACAAGCCTTTTCATTTTACTACAGCAGCATTGTGGCGAGACACTTCGCTGTCGTCGAC
TCGAGTTCTATAGTGTCACCTAGTAATCGTATGTGTATGATACATAAGGTTATGTATTAATTGTAGCCGCGTTCTAACGACAATATGT
CCATATGGTGCACTCTGCTCTCCCGGCATCCGCTTACAGACAAGCTGTGACCGTCTCCGGAGCTGCATGTGTCAGAGTTTCACCGTC
TGACGGGCTTGTCGTCCCGGAGCCGCTGATACGCCTATTTGTTTATTTTCTAAATACATTCAAATATGTATCCGCTCATGAGA
ATCACCGAAACGCGCGAGAGGAAAAGGCCCTCGTCGATACGCCTATTTGTTTATTTTCTAAATACATTCAAATATGTATCCGCTCATGAGA
CAGGTGGCACTTTTCGGGGAAATGTGCGCGAACCGGTGTAAGAAGCCTCGGGACCCCTATTTGTTTATTTTCTAAATACATTCAAATATGTATCCGCTCATGAGA
CAATAACCCTGATAAATGCTTCAATAATATTGAAAAAGGAAGAGTATGAGTATTCAACATTCCGTGTCGCCCTTATTCCCTTTTT
TGCGGCATTTGCCTTCCCTGTTTTTGCTCACCCAGAAGATCCTTGGAAGATCCTTGGAAGATCAGTTGGGTGCACGAGTGG
GTTACATCGAACTGGATCTCAACAGCGGTAAGATCTCCCGTATTCGACGCCGGCAAGAGCAACTCGGTCGCCGCCATACACTATTCTCAGAATGACTT
GGTTGAGTACTCACCAGTCACAGAAAAGCATTCTACGGATGCATGACAGTAAGACAGTTGAGAATTATGCAGTGCTGCCATAACCATGAGTG
ATAACACTGCGGCCAACTTACTTCTGACAACAGATCGGAGGACCGAAGGAGCTAACCGCTTTTTTGCACAACATGGGGATCATGTA
ACTCGCCTTGATCGTTGGGAACCTGGAACCGGAATGAAGCCATAACGAAACGACGAGCGTGACACCACGATGCCTGTAGCAATGGCAAC
AACGTTGCGCAAACTATTAACTGGCCCTTCCGGCTGAAGCTACTTACTGCGAACAATTAATAGACTGATGAGGCGGATAAAGTTG
CAGGACCACTTCTGCTCGGCCTTCCCGGCCCTTCCGGCTGAAGCCCTCGGTCGTCATTGCTGATAAATCTGGAGCCGGTGAGCGTGGGTCTCGCGTATC
ATTGCAGCACTGGGCTGAGATAGGTGCCTCACTGATTAAGCATTGGTAACGTCAGACCAAGTTACTCATATATACTTTAGATTGATT
TAGACAGATCGCTGAGATAGGTGCCTCACTGATTAAGCATTGGTAACGTCAGACCAAGTTACTCATATATACTTTAGATTGATT
TAAAACTTCATTTTCATTTTAAAGGATCTAGGTGAAGATCCTTTTGATAATCTCATGACCAAAATCCCTTAACGTGAGTTTTCG
```

Figure 6B (Cont.)

TTCCACTGAGGGTCAGAGACCCCGTAGAAAAGATCAAAGGATCTTCTTGAGATCCTTTTTTTCTGCGCGTAATCTGCTGCTTGCAAAC
AAAAAACCACCGCTACCAGCGGTGGTTTGTTTGCCGGATCAAGAGCTACCAACTCTTTTTCCGAAGGTAACTGGCTTCAGCAGAG
CGCAGATACCAAATACTGTCCTTCTAGTGTAGCCGTAGTTAGGCCACCACTTCAAGAACTCTGTAGCACCGCCTACATACCTCGCT
CTGCTAATCCTGTTACCAGTGGCTGCTGCCAGTGGCGATAAGTCGTGTCTTACCGGGTTGGACTCAAGACGATAGTTACCGGATAA
GGCGCAGCGGTCGGGCTGAACGGGGGGTTCGTGCACACAGCCCAGCTTGGAGCGAACGACCTACACCGAACTGAGATACCTACAGC
GTGAGCATTGAGAAAGCGCCACGCTTCCCGAAGGAGAAAGGCGGACAGGTATCCGGTAAGCGGCAGGGTCGGAACAGGAGAGCGC
ACGAGGGAGCTTCCAGGGGGCGGAGCCTATGGAAAAACGCCAGCAACGCGGCCTTTTTACGGTTCCTGGCCTTTTGCTGGCCTTTTGCTC
ATGCTCGTCAGGGGGGCGGAGCCTATGGAAAAACGCCAGCAACGCGGCCTTTTTACGGTTCCTGGCCTTTGCTGGCCTTTTGCTC
ACATGTTCTTTCCTGCGTTATCCCCTGATTCTGTGGATAACCGTATTACCGCCTTTGAGTGAGCTGATACCGCTCGCCGCAGCCGA
ACGACCGAGCGCAGCGAGTCAGTGAGCGAGGAAGCGGAAGAGCGCCCAATACGCAAACCGCCTCTCCCCGCGCGTTGGCCGATTCA
TTAATGCAGGTTAACCTGGCTTATCGAAATTAATACGACTCACTATAGGGAGACCGGCAGATCGATCTGTCGA

FIGURE 6C pTRABacHuLCκHCγ1 + Stuffers DNA Sequence

```
GCAGTTCGTTGACGCCTTCCTCCGTGTGGCCGAACACGTCGAGCGGGTGGTCGATGACCAGCGGCGGGTGCCGCACGCGACGCACAAG
TATCTGTACACCGAATGATCGTCGGGCGAAGGCACGTCGGCCTCCAAGTGGCAATATTGGCAATTCGAAATATATACAGTTGGG
TTGTTTGCCGATCTATCTATCGTGTGGCCGTTGGCATGTACGTCCGAACGTTGATTTGCATGCAAGCCGAAATTAAATCATTGCGATTAG
TGCGATTAAAACGTTGTACATCCTCGCTTTTAATCATGCCGTGATTAAATCGCCAGTCGAGTCAAGTGATCAAAGTGTGAATA
ATGTTTCTTTGTATTCCCGAGTCAAGCGCAGCGTATTTAACAACTAGCCATCTGTAAGTTAGTTTCATTAATGCAACTT
TATCCAATAATATATTATGTATCGCACGTCAAGAATTAACAATGCCCGTTGTCGCATCTCAACACGACTATGATAGAGATCAAA
TAAAGCGCGAATTAAATAGCTTGCGACGCAACGTGCACGATCGTGTGCACGCGTTCCGGCACGCTTTGATTGTAATAAGTTTTTA
CGAAGCGATGACATGACCCCCGTAGTGACAACGATCACGCCCAAAAGAACTGCCGACTACAAATTACCGAGTATGTCGGTGACGT
TAAAACTATTAAGCCATCATCCAATCGCTCATTAGAGCGTCATGTTTAGACAAGAAAGCTACATATTTAATTGATCCCGATGATTTTATTGATAAATT
AACGTGTGGAGTCCGCTCATTAGAGCGTCATGTTTAGACAAGAAAGCTACATATTTAATTGATCCCGATGATTTTATTGATAAATT
GACCCTAACTCCATACACGGTATTCTACATGCCGGGTTTTGGTCAAATTTGTCAAAAACGCAGCAGAGAAACATTTGTAAAGAATGCGTAGAAGGAAAG
CGCCCTAACTCCATACACGGTATTCTACATGCCGGGTTTTGGTCAAATTTGTCAAAAACGCAGCAGAGAAACATTTGTAAAGAATGCGTAGAAGGAAAG
AAAAATGTCGTCGACATGCTGAACAACAAGATTTTATACTAACAGTGTTACATTGCAAACGTGGTTCGTGTGCCAAGTGTGAAAACCGAT
ACCGCGCGGGTATGTACAGGAAGAGTTTATACTAACAGTGTTACATTGCAAACGTGGTTCGTGTGCCAAGTGTGAAAACCGAT
GTTAATCAAGGCTCTGACGCCATTCTACACACGACTGTGAAGTCATGCATCTTTTAATCAAATCCCAAGAT
GTGTATAAACCACCACGACTGCCAAAAATGAAAAATATAAAATGCTAAATTGTTTTTATTAACGATACAAAACCAAACGCAACAAGAACATTTGT
TTGTAATTATTGAATAATAAAACAATTATAAAATGCTAAATTGTTTTTATTAACGATACAAAACCAAACGCAACAAGAACATTTGT
AGTATATCTATAATTGAAAACGCGTAGTTATAATCGCTGAGGTAATATTTCAAATGATTCACAGTTAATTTGCG
ACAATATAATTTATTTCACATAACTAGACGCCTTGTCTTCTTCGTATCTATCGTATCTATCGTATAGAGTAAATTTTTGTCATAAATATATGTCTTTTT
AATTAACATAGTTATTATCGTATCCATATATGTATCTATCGTAATTTACAACAGTGCTATTTTCTCGGAGTCTTCGGAGTGTGTGCTT
AATGGGGTGTATAGTTACGGGATCGCGCATAGTTTTCTGTAATTTACAACAGTGCTATTTTCTCGGAGTCTTCGGAGTGTGTGCTT
TAATTATTAAATTTATAATAATGAATTGGATCGGTTTGTACAATATGTTGTACGAACCGTTAAACAAAAACAGTTCACCTCC
TCAATTACACCATTTTTAGCAGCACCGATTAACAACTTTCCAAAATGTTGTTGTTAAAATAACAGCACACAAACTAATACACAAAC
CTTTTCTATATTGTCGAGCAGTGTTGCTGATATCGTCCCAGCATGCCCTGCTATTGTCTTCCCAATCCTCCCCTGCCCCCCCAAACAGC
TGGAAATGTCTATCAATATATAGTTGCTGATATCGTCTCCCAGCATGCCCTGCTATTGTCTTCCCAATCCTCCCCTGTCCTGCC
```

Figure 6C (Cont.)

```
CCACCCCCACCCCCAGAATAGAATGACACCTACTCAGACAATGCGATGCAATTTCCTCATTTTATTAGGAAAGGACAGTGGGAGTG
GCACCTTCCAGGGTCAAGGAAGGCACGGGGGAGGGCAAACAACAGATGCTGGCAACTAGAAGGCACAGTCGAGGCTGATCAGCG
AGCTCTAGTCTAGACTATTACCGGAGAGACAGGAGAGGCTCTTCTGCGTGTAGTGGTTGTGCAGAGCCTCATGCATCACGGA
GCATGAGAAGACGTTCCCCTGCTGCCACCTGCTCTTGTCCACGGTGAGCTTGCTGTAGAGGAAGAAGGAGCCGTCGAGTCCAGCA
CGGGAGGCGGTGGTCTCTTGTAGTTGTTCCCCATTGTCTCCTCCACGGCGATGTGCTGGGATAGAAGCCTTTGACC
AGGCAGGTCAGGCTGACCTGGTTCTTGGTCAGTCATCCCGGATGGGGGACAGGGTGTACACCTGTCACTTGTACTCCTGCCAGTCCT
GGCTTTGGAGATGGTTTCTCGATGGGGCTGGAGGCTTTGTTGAGACCTTTGTACTGTCTCTCCCGCCTTTGTCTTGGCATTATGCACCTCC
GGTGCAGGACGGTGAGGACGCTGACCAGTTGAACTTGACCTTCTCTCCTCACCTGCACCGTCCCGACTGCTGGGTCCGGA
ACGCCGTCCACGTACCAGTTGAACTTGGGGTTTTGGGGAAGAGAAGACTGACGGTCCCCCAGAGTCAGGTCTGGGCACGGTCCGGCATG
GATCATGAGGGTGTCCTTGGCTCAACTTTCTTGTCCACCTTGGTGTGCTGGGAGTAGAGTCCTGAGGACTGTAGGACAGCCGGAAGGTGTG
TGGGTGCCCAAGCTGCTGGAGGGCGCCTGAGTTCGGGAGTAGCTCCTGAGGACTAGTCTTATCAAACTAGTGCAACGTTGACTAAGAATTT
CACGCCGTCAGGGTCTCTTGGAGGAGAGGTGCCAGGAAGACCGATGGGCCTTATCAAACTAGTGCAACGTTGACTAAGAATTCTTA
CATGCGGCCGCGTACGATTGTAAATAAATGTAATTTACAGTATATTTAATTAATACACAAATGATTGATAATAATCTTA
TTTAACTATATATTTCTGAATCTTTGTAAATAGCACACAGGACTCCAACGCGTTTGGCGTTTCGTAACAGTTTTGTAATAAAAACCTATAAATATT
ATAATTAAAATGATAACCATCTCGCAAATAAATAAGTATTTTACTGTTTCGTAACAGTTTTGTAATAAAAACCTATAAATATT
CCGGATTATTCATACCGTCCCACCATGGGCGTGCTAGCGATCCATGGTGGGACCCATGAGCAGTTGAAATCTGAACTCGGGTAACTCCCAGGAGAGTGTCACAGAGC
CCTTTGATAACACCAAGTGTCTTCATCTTCCCCGCACGTCTTTCATCTTGATGAGCAGTTGAAATCTGAACTCGGGTAACTCCCAGGAGAGTGTCACAGAGC
TAACTTCTATCCCAGAGAGCCAAAGTACAGTGGAAGTGGAAGTTGAAGCCCTCAGCAGCACCCTCAGCAGCTAGCCTGAGCCCTCAGAGAGCCTGCAAACACAGTCTACGCCTGC
AGGACAAGGACAGCACCTACAGCCCTGAGCTCGCCCGTCGAGCTCCACAAGAGCTTCAACAGGGAGAGTGTTAATAGAAGCTTGTCGTTGGATGGAA
GAAGTCACCCATCAGGCCTGAGCTCTACAGGGAAACTTGGACCGTCCACTAGACCCAACCAGTTGTTAACGACCAAGAAGTGATGATGTTT
AGGAAAAGAGTTCTACAGCAGTGTCTCCACTAGACCCAACCAGTTGTTAACGACCAAGAAGTGATGATGTTT
TCCTTGTTGTCAACATGACGTGATTAGGATCGTCGAGCCTTCATGGGTGGGCAGCAACAACGAGTACCGCATCAGCCTGGCTAAGAAGGCGG
GTACCTCATGACGTGATTAGGATCGTCGAGCCTTCATGGGTGGGCAGCAACAACGAGTACCGCATCAGCCTGGCTAAGAAGGCGG
CGGCTGCCCCAATAATGAACCTTCACTCTGAGTACACCAACTCGTTCGAACAGTTCATCGATCGTGTCATCGTCGGAGAACTTCTACA
```

Figure 6C (Cont.)

AGCCCATCGTTACATCGGTACCGACTCTGCTGAAGAGGAGGAAATTCTCCTGGTGTTCAAAGTAAAGGAGTTT
GCACCAGAGCGCCACCTCTGTCACTGGTCCGGCGTATTAAAACGATAAATTAAGCGCTAGATTCTGT
GCGTTGTTGATTTACAGACAATTGTGTACGTATTTCATTAATTTATAATTATACATCTTAGGTGGTATGTTAGAGCGAAAA
TCAAATGATTTCAGCGTCTTTATATCGAATTTAAATTATTAAATCCTCAATAGATTTGTAAAATAGGTTTCGATTAGTTCAAAC
AAGGGTTGTTTTCCGAACGATGGCTGGACTATCTAATGATTTTCGCTCAACGCCACAAACTTGCCAAATCTGTAGCAGCAA
TCTAGCTTTGTCGATATTCGTTGTGTTTTGTTTTGTAATAAAGGTTGACGTCGTTCAAAATATATGCGCTTTGTATTCTTT
CATCACTGTCGTTAGTGTACAATTGACTCGACGTAAACACGTTAAATAAACTAGCTTGGACATATTTAACATCGGCGTGTTAGC
TTTATTAGGCCGATTATCGTCGTCCCAACCCTCGTCGTTAGAAGTTGAGCTTTTGAATTATTCTGATTGCGGGCGTTTTGGCG
TATTAATTGTCGGCTAACACGTCGCCCGATCAAATTGTAGTTGAGTTTTGAGCTTTGAGAAAGCGATGGTGCAGGCGGGTAACATTTCAGACGGCAA
GGTTTCAATCTAACTGTGCCCGATTTAATTCAGACAACACGTTAGAAACGATGGTGCAGGCGGGTAACATTTCAGACGGCAA
ATCTACTAATGGCGGGCGGTGGTGGAGCTGATGATAAATCTACCATCGGTGAGGCTGGCGGGAGGCG
GAGGTGGTGGCGCCCGTTTTGGTTGAGCGGTTTAGCTCAACACAGTCGCACCTCCAACAATTGTGTCTGTCGTC
TCGGGCGCCGTTTTGGTTGACCGGTCTGAGACGAGTGCGATTTTTTCGTTCTAATAGCTTCCAACAATTGTGTCTGTCGTC
TAAAGGTGCAGCGGGTTCCGTCGAGGTTCCGTCGGAGCGGGGCCAATTCAGACATCGATGGTGGTTCCGGTGGAGCCG
CTGGAATGTTAGGCACGGAGAAGGTGGTGGCGCGGTGTGCCGGTATAATTGTTCTGTTAGTTGTTCGCACGATTGTG
GCACCCGGCCAGGCGCCGCTGCTGCTATAAATCGTAATGTTGTAAATTCGCTCGATATTTAACCGTCTCAATGT
AAGCAATTGTATTGTAAAGAGATTGTCCAAGCTGTCTCAAGCTCCGCACGCCGATAACAAGCCTTTTCATTTTACTACAGCATTGTAGTGCGA
GACACTTCGCTGTCGTCGACTCGAGTTCGAGATCGAGTTTCCCGACACGCGATACAACAAGCCTTTCATTTTACTACAGCATTGTAGTGCGA
GCGTTCTAACGACACAATATGTCCATATGGTGCACTCCAGTAACACCGTCTAAATCGTCATAAATCGTCTGTATGCGTATAAGCCAGCCCGACACCCGC
CAACACCCGCTGACGCCCTGACGCGGCTTGTCTGTCTCCCGGCATCCGCTTACAGACAAGCGTGACACGTCTCCGGAGCTGCATG
TGTCAGAGGTTTCACCGTCATCACCGAAACGCGCGAGAGGCGCCTATTGCCTCGTGATACGCCTATTTGTTATTTTTCTAAATACATCAA
AATAATGGTTTCTTAGACGTCAGTGCCACTTCGGGAAATGCGCCGGAACCCCTATTGCCCGAATATTGAAAGGAAGTATGAGTATTCAACATTCCGT
ATATGTATCCGCTCATGAGACAATAACCCTGCATTTGCCTTTCCTTGTTTTTGCTCACCCAGAAACGCTGGTGAAAGTAAAAGATGCTGAAGA
GTCGCCCTATTCCCCTTTTTTTGCGGCATTTGCCTTCCTGTTTTTGCTCACCCAGAAACGCTGGTGAAAGTAAAAGATGCTGAAGA
TCAGTTGGGTGCACGAGTGGGTTACATCGAACTGGATCTCAACAGCGGTAAGATCCTTGAGAGTTTTCGCCCCGAAGAACGTTTTC
CAATGATGAGCACTTTTAAAGTTCTGCTATGTGGCGCGGTATTATCCCGTATTGACGCCGGGCAAGAGCAACTCGGTCGCCGCATA

Figure 6C (Cont.)

CACTATTCTCAGAATGACTTGGTTGAGTACTCACCAGTCACAGAAAGCATCTTACGGATGCATGACAGTAAGAGAATTATGCAG
TGCTGCCATAACCATGAGTGATAACACTGCGGGCCAACTTACTTCTGACAACGATCGGAGGACCGAAGGAGCTAACCGCTTTTGC
ACAACATGGGGATCATGTAACTCGCCTTGATCGTTGGGAACCGAGCTGAATGAAGCCATACCAAACGACGAGCGTGACACCACG
ATGCCTGTAGCAATGCAACAACGTTGCGCAACTATTAACTGGCGAACTACTTACTCCGGCTTCCTAGCTTCCCGGCAACAATTAATAGACTG
GATGGAGGCGGATAAAGTTGCAGGACCACTTCTGCGCTCGGCCCTTCCGGCTGGTTTATTGCTGATAAATCTGGAGCCGGTG
AGCGTGGGTCTCGCGGTATCATTGCAGCACTGGGGCCAGATGGTAAGCCCTCACTGATTAAGCATTGGTAACTGTCAGACCAAGTTACTC
GCAACTATGGATGAACGAAATAGACAGATCGCTGAGATAGGTGCCTCACTGATTAAGCATTGGTAACTGTCAGACCAAGTTACTC
ATATATACTTTAGATTGATTTAAAACTTCATTTTTAAAAGGATCTAGGTGAAGATCCTTTTTGATAATCTCATGACCAAAA
TCCCTTAACGTGAGTTTTCGTTCCACTGAGCGTCAGACCCCGTAGAAAGATCAAAGGATCTTCTTGAGATCCTTTTTTTCTGCGC
GTAATCTGCTGCTTGCAAACAAAAAAACCACCGCTACCAGCGGTGGTTTGTTTGCCGGATCAAGAGCTACCAACTCTTTTTCCGAA
GGTAACTGGCTTCAGCAGAGCGCAGATACCAAATACTGTCCTTCTAGTGTAGCCGTAGTTAGGCCACCACTTCAAGAACTCTGTAG
CACCGCCTACATACCCGCTCTGCTAATCCTGTTACCAGTGGCTGCTGCCAGTGGCGATAAGTCGTGTCTTACCGGGTTGGACTCA
AGACGATAGTTACCGGATAAGGCCGCAGCGGTCGGGCTGAACGGGGGGTTCGTGCACACAGCCCAGCTTGGAGCGAACGACCTACAC
CGAACTGAGATACCTACAGCGTGAGCATTGAGAAAGCGCCACGCTTCCCGAAGGGAGAAAGGCGGACAGGTATCCGGTAAGCGGCA
GGGTCGGAACAGGAGAGCGCACGAGGGAGCTTCGTCGGGTATCTTTATAGTCCTGTCGGGTTTCGCCACCTCTGA
CTTGAGCGTCGATTTTTGTGATGCTCGTCACATGTTCTTTCCTGCGTTATCCCCTGATTCTGTGGATAACCGTATTACCGCCTTTGAGTGAGCTG
CTTTTGCTGGCCTTTTGCTCACATGTTCTTTCCTGCGTTATCCCCTGATTCTGTGGATAACCGTATTACCGCCTTTGAGTGAGCTG
ATACCGCTCGCCGCAGCCGAACGACCGAGCGCAGCGAGTCAGTGAGCGAGGAAGCGGAAGAGCGCCCAATACGCAAACCGCCTCTC
CCCGCGCGTTGGCCGATTCATTAATGCAGTTAACCTGGCTTATCGAAATTAATACGACTCACTATAGGGAGACCGGCAGATCGAT
CTGTCGA

FIGURE 6D pTRABacHuLCλHCγ1 + Stuffers DNA Sequence

```
GCAGTTCGTTGACGCCTTCCTCCGTGGCCGAACACGTCGAGCGGGTGGTCGATGACCAGCGGCGTGCCGCACGCGACGCAC
AAGTATCGTACACCGAATGATCGTCGGGCGAAGGCACGTCGGCCTCCAAGTGCAATATGGCAATTCGAAATATATACA
GTTGGGTTGTTTGCGCATATCTATCGTGCGTTGGGCATGTACGTCCGAACGTTGATTGCATGCAAGCCGAAATTAAATCAT
TGCGATTAGTGCGATTAAAACGTTGTACATCCTGCGTTTAATCATGCCGTCGATTAAATCGCGCAATCGAGTCAAGTGATCA
AAGTGTGGAATAATGTTTCTTTGTATTCCGAGTCAAGCCAGCGGCGTCAAGAATTAACAAGCCATCTTGTAAGTTAGTTT
CATTTAATGCAACTTTATCCAATAATATATGTATCGCACGTCAAGAATTAACAATGCGCCCGTTGTCGCATCTCAACACG
ACTATGATAGAGATCAAATAAAGCGCGAATTAAATAGCTTGCGACGCAACGTGCACGATCTGTGCACGCGTTCCGGCACGAGC
TTTGATTGTAATAAGTTTTACGGTGACGTTAAAACATTATAAGCCATCGACAACGATCACGCCCAAAGAACTGCCGACTACAA
AATTACCGAGTATGTCGGTGACGTTAAAACTATTAACGTGTGGAGTCCGCTCATTAGAGCGTCATGTTTAGACAAGAAGCTACATATT
CCGCGAAGTATGCGAATGCATCGTATAAACGTGTGGAGTCCGCTCATTAGAGCGTCATGTTTAGACAAGAAGCTACATATT
AATTGATCCCGATGATTTATTGTACATGCTGTTAACGGCTCCGCCCACTATTAATGAAATTAAAATTCCAATTTAAAACGCAGCAAG
CCGGACTGCGATTGTACATGCTGTTAACGGCTCCGCCCACTATTAATGAAATTAAAATTCCAATTTAAAACGCAGCAAG
AGAAACATTTGTATGAAAGAATGCGTAGAAGAAAAGAACAATGTCGTGAACATGCGGCGTATGTACAGGAAGAGGTTATACTAAACTGTT
TATAAAAAAATATTGAACGATTTGAAAGAAAAACAATGTACCGCGGCGTATGTACAGGAAGAGGTTATACTAAACTGTT
ACATTGCAAACGTGGTTCGTGTGCCAAGTGTGAAAACGATGTTAATCAAGCTCTGACGCATTCTACAACCACGACTCC
AAGTGTGTGGGTGAAGTCATGCAGTCCAAGTGTGAAATCAAGCTCTGACGCATTCTACAACCACGACTCC
CGACAAGCTCTCCGTTGCCTTGCTGGCAACTGCAACACAAACCAACAGAACATTGTAGTATCTATTAATTGAAAACGCGTAGTTAT
TAAATTGTGTTTTTATTAACGATACAAACCAACAGAACATTGTAGTATCTATTAATTGAAAACGCGTAGTTAT
AATCGCTGAGGTAATATTTAAATCATTTCAAATGATTCACAGTTAATTGCGACAATATAATTTATTTCACATAAACTA
GACGCCTTGTCGTCTGTCGTTAATCATTTCAAATGATTCACAGTTAATTGCGACAATATAATTTATTTCACATAAACTA
ATATATGTATCATCGTATAGAGTAAATTTTTGTTGTCATAAATATATGTCTTTTTAATGGGTGTATAGTACCGCTGC
GCATAGTTTTCTGTAATTTACAACAGTGCTATTTCTGGAGTGTGCTTTAATTATTAAATTTATATAA
TCAATGAATTTGGGATCGTCGGTTTTGTACAATGTTGCCGGCATAGTACCGCAGCTTCTTCAGTTCAATTACACCATTTTT
TAGCAGCACCGGATTAACATAACTTTCCAAAATGTTGTACGAACCGTTAAACAAAACAGTTCACCTCCTTTCTATCTAT
TGTCTCGCGAGCAGTTGTTGTTGTTAAAAATAACAGCCATTGTAATGAGACGCACAAACTAATATCACAACTGAAATGTCT
```

Figure 6D (Cont.)

ATCAATATATAGTTGCTGATATCTCCCCAGCATGCCTGCTATTGTCTTCCAATCCTCCCCCTGCTGTCTTGCCCCACCCA
CCCCCAGAATAGAATGACACCTACTCAGACAATGCGATGCAATTCCTCATTTTATTAGGAAAGGACAGTGGAGTGGCACC
TTCCAGGGTCAAGGAAGGCACGGGGGAGGGCAAACACAGATGGCTGCAACTAGAAGGCACAGTCGAGGCTGATCAGCGAG
CTCTAGTCTTAGACTATTATTTACCCGGAGAGACAGGAGAGGCTCTTCTGCGTGTAGTGGTTGTGCAGAGCCTCATCACGG
AGCATGAGAAGACGTTCCCCTGCTGCCACCTGCTCTTGTCCACGGTGAGCTTGCTGTAGAGGAAGAAGGAGCCGTCGGAGTCC
AGCACGGGAGGCGGTGGTCTTGTAGTTGTCTCCGGCCATTGCTTCCGGCCATTGTCTCCACGCGATGTGCTGCTGGATAGAAGCC
TTTGACCAGGCAGGTCAGGCTGACCTGGTTCTTGGTCAGTCATCCCGGATGGGGCAGGGTGTACACCTGTGGTTCTCGGG
GCTGCCCTTTGCTTTGGAGATGGTGTTTCTCAGGAGACGTTGAAACCTGTCAGGGTCTTCGTGGCTCTTCCACCACCACGCATG
TTCAGCCAGTCCTGTGTGCAGACGCCGTCCACGTTGACCAGTTGAACTTGACCTTCGTGGCTCACGTCCACCACCACGCATG
GGCATTATGCAGCCTCCACGCCGTCCACGTTGACCAGTTGAACTTGACCTTCGTGGCTCACGTCCACCACCACGCATG
TGACCTCAGGGGTCCGGAGATCATGAGGGTCTTGGGTTTTTGGGGAAGAGAAGACTGACGCGTCCCCCAGGAGTTCA
GGTGCTGGGCACGGTGGGCATGTGTGAGTTTTGTCACAAGATTTGGGGCTCAACTTCTTGTCCACCTTGGTGTTGCTGGGCTT
GTGATTCACGTTGCAGATGCCGGACAGCCCGGGAAGTGTGCACGCCGCTGTCTTGAGGCGCTGCTCGAGTCGTTCGGGAAG
AGGACTGTAGGACAGCCGGACAGCAGCCAGGCAGTGTGCACGCCCGGGAAGTGTGCACGCCGTCGAGGGAGACCGATGGGCC
TAGTCCTTGACCAACTAGTGCAACCGTTGACTAAGAATTCATGCGCCGCGTAACTATAATAATTTACAGTATAGTAT
CTTATCAAACTAGTGCAACCGTTGACTAAGAATTCATGCGCCGCGTAACTATAATAATTTACAGTATAGTAT
TTTAATTAATATACAAATGATTGATAATAATTCTTATTGTAAGTGATGCGTATTTCTGAATCTTTGTAAATAGCACACAGACTCCA
CCTCAAATGCATAATATCATAGTCCCCTTGTTGTAAGTGATGCGTATTTCTGAATCTTTGTAAATAGCACACAGACTCCA
ACGGGTTTGGCGTTTATTTCTTCTGCTCGAGATATCATGGAGATATAATTCCGATTATCATCGGTCCACCATCGGGCGTGCTA
TTACTGTTTTCGTAACAGTTTGTAATAAAAAACCTATAAATATTCCGATTATCATCGGTCCACCATCGGGCGTGCTA
GCGGATCCATGGTGGACCCTGGGACCTTGCAGCCAACAAGGCCACACTGTGTGTCTCATAAGTGACTTCTACCCCGGAGCCGTGACAGTGGCC
CCTCCCTCTGAGGAGTTCAAGCCAACAAGGCCACACTGTGTGTCTCATAAGTGACTTCTACCCCGGAGCCGTGACAGTGGCC
TGGAAGGCAGATAGCAGCCCCGTCAAGGCGAGTGGAGACCCCACAAAGCACGCTGCCAGGTCACGCATGAAGGGAGCACGTGG
CAGCTACCTGAGCGCTGACGCCCCTACAGAATGTTCATAGTAAAGCTTGTTGATGGAAAGAGTTCTACGGAAACTTGG
AGAAGACAGTGGCCCCTACAAGAGAAGACAGCAGCTTCCCATTGTTAACGACCAAGAAGTGATGATGTTTCCTTGTTGTCAACATGCGTCCAC
ACCCGGCTTCATGCAGGAGTCTGCCCAACACGCTCTGCCTTGTTACAAATTCCTGGCCGACTACTACGTAACGACTGATTAGGA
TAGACCCAACCGTTGTTACAAATTCCTGGCCGACTACTACGTAACGACTGATTAGGA

Figure 6D (Cont.)

TCGTCGAGCCTTCATGGGTGGCAGCAACAACGAGTACCGCGCATCAGCCTGGCTAAGAAGGGCGGGGCTGCCCAATAATGAAC
CTTCACTCTGAGTACACCAACTCGTTCGAACAGTTCATCGATCGTGTCATCTGGGAGAACTTCTACAAGCCCATCGTTTACAT
CGGTACCGACTCTGCTGAAGAGGAAATTCTCCTTGAAGTTTCCCTGTGTTCAAAGTAAAGGAGTTTGCACCAGACGCAC
CTCTGTTCACTGGTCCGGCGTATTAAAACACGATACATTGTTATTAGCGCTAGATTCTGTGCGTTGTTGA
TTTACAGACAATTGTTGTTATATCTGTATTTAATAATTCATTAAATCTTTAGGGTGGTATGTTAGAGCGAAATCAAATG
ATTTCAGCGTCTTTATATCTGAATTTAAATATTAAATCCTCAATAGATTTGTAAAATAGTTTCGATTAGTTTCAAACAAGG
GTTGTTTTCCGAACCGATGGCTGGACTATCTAATGATTTCGCTCAACGCCACAAACTTGCCAAATCTGTAGCAGCAAT
CTAGCTTTGTCGATATTCGTTAGTGTACAATTGACTCGTCGTCCCAACCCTCGTCGTTAGAAGTTGCTTCCGAAGACGTAACATGGGCGTG
TTCATCACTGTCGTTATTAGGCCGATTATCGTCGGCTAACACGTGTCGGCTAACACTGTAGTTGAGCTTTTGAATTATTTCTGATTGCGGGC
ACGACGCCTATTAATTGTCGGCTAACACTGTCGGCTAACACTGGAAGCGGCAGCAAGCGTTAGAAAGCGTTAGAGCGCGTGGTAAC
GTTTTTGGGCGGGTTCAATCTACTAATGCGGCGGTGCGGGTGTTAGGCTTAGGCAACACAGTCGGCA
ATTTCAGACGGCAAATCTACTAATGGCGGGCGGTGCGGGTGATGCAGAGCGGTTAGGCTCAGAGCGAGTGCTCTTTAGCTCAATAAGCT
CGGGGCAGGGCGAGGCGGAGGTTCGGGCGCCGTTTGGTTTGACCGGTCTGAGACGAGTGCTGATTTTCCTTCTAATAGCT
CCTCAACTATTGTACTGGTTCGTCTGTCTCTAAAGTGCAGCGGGTTGAGGTTCCGGTGAGGTTCCGGTGAGGCGGGCAATTCAGACAT
TCCAACAATTGTGTCTCTCGTCTCTAAAGTGCAGCGGGTTGAGGTGAGGTTCAGCGTGAGCGGGTGCCGCCGGTATAATTGTT
CGATGGTGGTGGTGTTCGCGCACGATTGTGGCAATTCAATATTATAATTGGAATACAAATCGTAAAAATCTGCTATAAGCATTGTAATTCGCTATC
CTGGTTTAGTTGTTCGCGCACGATTGTGGCAATTCAATATTATAATTGGAATACAAATCGTAAAAATCGTAAAGAGATTGTCTCAAGCTCCGACGCCGATAA
AGCGCTTGGGGTGCCGATATTTAACAACCGCTAAGTAAGCAATTGTATTGTAAAGAGATTGTCTCAAGCTCCGACGCCGATAA
GTTTACCGTGCCGATATTTTACTACAGCATTGTAGTGGCGAGACACTTCGCTGTCGTCGACTCGAGTTCTATAGTGTCACCTAAAT
CAAGCCTTTTCATTTTCATTACAGCATAAGGTTATGTATAATTGTAGCCGCGTTCTAACGACAATATGTCCATATGTGCACTCTCAGTAC
CGTATGTGTATGATACATAAGGTTATGTATAATTGTAGCCGCGTTCTAACGACAATATGTCCATATGTGCACTCTCAGTAC
AATCTGCTCTGATGCCGCATAGTTAAGCCAGCCCCGACAGTTAAGCCAGCCCCGACAGCGGCCCTGACGGGCTTGTCTGCTCC
CGGCATCCGCTTACAGACAAGCTGTGACCGTCTCCGGAGCTGCATGTGCAGAGGTTTTCACCGTCATCACCGAAACGCCG
AGAGGAAAAGGGCCTCGTAGATACGCCCTATTTTATAGGTTAATGTCATGATAATAATGTTCTTAGACGTCAGGTGCACTTT
TCGGGGAAATGCGCGGAACCCTGTTAATTTGTTATTTTCTAAATACATTCAAATATGTATCGCTCATGAGACAATAACCT
GATAAATGCTTCAATAATATTGAAAAGGAAGAGTATGAGTATTCAACATTCCGTGCGCCCTTATTCCCTTTTGCGCA

Figure 6D (Cont.)

TTTGCCTTCCTGTTTTGCTCTCACCCAGAGAAACGCTGGTGAAAGTAAAGATGTGAAGATCAGTTGGGTGCACGAGTGGGTTA
CATCGAACTGGATCTCAACAGCGGTAAGATCCTTGAGAGTTTTCGCCCCGAAGAACGTTTTCCAATGATGAGCACTTTTAAAG
TTCTGCTATGTGGCGCGGTATTATCCCGTATTGACGCCGGGCAAGAGCAACTCGGTCGCCGCATACACTATTCTCAGAATGAC
TTGGTTGAGTACTCACCAGTCACAGAAAAGCATCTTACGGATGCATGACAGTAAGAGATAATTATGCAGTGCTGCCATAACCAT
GAGTGATAACACTGCGGCCAACTTACTTCTGACAACGATCGGAGGACCGAAGGAGCTAACCGCTTTTTGCACAACATGGGGG
ATCATGTAACTCGCCTTGATCGTTGGGAACCGGAGCTGAATGAAGCCATACCAAACGACGAGCGTGACACCACGATGCCTGTA
GCAATGGCAACAACGTTGCGCAAACTATTAACTGGCGAACTACTTACTCTAGCTTCCCGGCAACAATTAATAGACTGGATGGA
GGCGGATAAAGTTGCAGGACCACTTCTGCGCTCGGCCCCTTCCGGCTGGTTATTGCTGATAAATCTGGAGCCGGTGAGC
GTGGGTCTCGCGGTATCATTGCAGCACTGGGGCCAGATGGTAAGCCCTCACTGATTAAGCATTGGTAACTGTCAGACCAAGTTA
GCAACTATGATGAACGAAATAGACAGATTCATTTTAAAGGATCGTAGGTGAAGATCCTTTTGATAATCTCATGA
CTCATATATACTTTAGATTGATTTAAACTTCCACTGAGTTTTCGTTCCACTGAGCGTCAGACCCCGTAGAAAAGATCAAAGGATCTTCTTGAGATCCTTTT
CCAAAATCCCTTAACGTGAGTTTTCGTTCCACTGAGCGTCAGACCCCGTAGAAAAGATCAAAGGATCTTCTTGAGATCCTTTT
TTTCTGCGCGTAATCTGCTGCTTGCAAACAAAAAAACCACCGCTACCAGCGGTGGTTTGTTTGCCGGATCAAGAGCTACCAAC
TCTTTTTCCGAAGGTAACTGGCTTCAGCAGAGCGCAGATACCAAATACTGTCCTTCTAGTGTAGCCGTAGTTAGGCCACCACT
TCAAGAACTCTGTAGCACCGCCTACATACCTCGCTCTGCTAATCCTGTTACCAGTGGCTGCTGCCAGTGGCGATAAGTCGTGT
CTTACCGGGTTGGACTCAAGACGATAGTTACCGGATAAGGCCGCGAACGGGGGTTCGTGCACACAGCCCAG
CTTGGAGCGAACGACCTACACCGAACTGAGATACCTACAGCGTGAGCATTGAGAAAGCGCCACGCTTCCCGAAGGGAGAAAGG
CGGACAGGTATCCGGTAAGCGGCAGGGTCTGACTTGAGCGTCGATTTTTGTGATGCTCGTCAGGGGGGCGGAGCCTATGTATCTTTAT
AGTCCTGTCGGGTTTCGCCACCTCTGACTTGAGCGTCGATTTTTGTGATGCTCGTCACATGTTCTTCCTGCGTTATCCCTGATTCTG
CAGCAACGCGGCGAGTATTACCGCCTTTTTACGGTTCCTGGCCTTTTGCTGGCCTTTTGCTCACATGTTCTTCCTGCGTTATCCCTGATTCTG
TGGATAACCGTATTACCGCCTTTGAGTGAGCTGATACCGCTCGCCGCAGCCGAACGACCGAGCGCAGCGAGTCAGTGAGCGAG
GAAGCGGAAGAGCGCCCAATACGCAAACCGCCTCTCCCCGCGCGTTGGCCGATTCATTAATGCAGCTGGCACGACAGGTTTCCCGACTGGAAAGCGGGCAGTGAGCGCAACGCAATTAATGTGAGTTAGCTCACTCATTAGGCACCCCAGGCTTTACACTTTATGCTTCCGGCTCGTATGTTGTGTGGAATTGTGAGCGGATAACAATTTCACACAGGAAACAGCTATGACCATGATTACGCCAAGCGCGCAATTAACCCTCACTAAAGGGAACAAAAGCTGGAGCTCCACCGCGGTGGCGGCCGCTCTAGAACTAGTGGATCCCCCGGGCTGCAGGAATTCGATATCAAGCTTATCGATACCGTCGACCTCGAGGGGGGGCCCGGTACCCAGCTTTTGTTCCCTTTAGTGAGGGTTAATTCTGAGCTTGGCGTAATCATGGTCATAGCTGTTTCCTGTGTGAAATTGTTATCCGCTCACAATTCCACACAACATACGAGCCGGAAGCATAAAGTGTAAAGCCTGGGGTGCCTAATGAGTGAGCTAACTCACATTAATTGCGTTGCGCTCACTGCCCGCTTTCCAGTCGGGAAACCTGTCGTGCCAGCTGCATTAATGAATCGGCCAACGCGCGGGGAGAGGCGGTTTGCGTATTGGGCGCTCTTCCGCTTCCTCGCTCACTGACTCGCTGCGCTCGGTCGTTCGGCTGCGGCGAGCGGTATCAGCTCACTCAAAGGCGGTAATACGGTTATCCACAGAATCAGGGGATAACGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAGCATCACAAAAATCGACGCTCAAGTCAGAGGTGGCGAAACCCGACAGGACTATAAAGATACCAGGCGTTTCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGACACGACTTATCGCCACTGGCAGCAGCCACTGGTAACAGGATTAGCAGAGCGAGGTATGTAGGCGGTGCTACAGAGTTCTTGAAGTGGTGGCCTAACTACGGCTACACTAGAAGAACAGTATTTGGTATCTGCGCTCTGCTGAAGCCAGTTACCTTCGGAAAAAGAGTTGGTAGCTCTTGATCCGGCAAACAAACCACCGCTGGTAGCGGTGGTTTTTTTGTTTGCAAGCAGCAGATTACGCGCAGAAAAAAAGGATCTCAAGAAGATCCTTTGATCTTTTCTACGGGGTCTGACGCTCAGTGGAACGAAAACTCACGTTAAGGGATTTTGGTCATGAGATTATCAAAAAGGATCTTCACCTAGATCCTTTTAAATTAAAAATGAAGTTTTAAATCAATCTAAAGTATATATGAGTAAACTTGGTCTGACAGTTACCAATGCTTAATCAGTGAGGCACCTATCTCAGCGATCTGTCTA
AATTAATACGACTCACTATAGGGAGACCGGCAGATCGATCTGTCGA

METHOD AND COMPOSITION FOR ALTERING A B CELL MEDIATED PATHOLOGY

RELATED APPLICATIONS

This is a continuation application of U.S. application Ser. No. 09/927,121, filed Aug. 10, 2001, now U.S. Pat. No. 6,911,204, which is hereby incorporated by reference in its entirety, including all drawings, tables, and figures, which claims the benefit of U.S. Provisional Application No. 60/224,723, filed Aug. 11, 2000, entitled "Method for Producing an Idiotypic Vaccine," U.S. Provisional Application No. 60/224,722, filed Aug. 11, 2000, entitled "Expression Vectors for Production of Recombinant Immunoglobulin" and U.S. Provisional Application No. 60/279,079, filed Mar. 23, 2001, entitled "Method and Composition for Altering a B Cell Mediated Pathology," each of which is hereby incorporated by reference in its entirety.

FIELD OF THE INVENTION

This invention relates generally to the field of immunology and immunotherapy. More specifically, this invention relates to methods and compositions for altering B cell mediated pathologies, such as B cell malignancies and/or autoimmune diseases.

BACKGROUND OF THE INVENTION

The immune system produces both antibody-mediated and cell-mediated responses. Each type of immune response is regulated by a type of lymphocyte, B cells (for antibody-mediated response) and T cells (for cell-mediated response). B cells initially recognize an antigen when the antigen binds to the IgM and IgD molecules on the B cell's surface. Each B cell clone recognizes only specific antigens due to the unique idiotype of that clone. Upon recognition of the antigen, B cells internalize and process the antigen for presentation via MHC class II molecules. B cells can thereby function as an antigen presenting cell ("APC") for T cells. T cells bind to portions of foreign proteins (antigens) when portions of the protein associate with a major histocompatibility complex molecule ("MHC"), typically on an APC, in which the antigen is digested into fragments and presented on the surface of the APC bound to its MHC.

Several types of cancers have their origin in the circulatory system. Among the major types are: leukemias, a neoplasm of the bone marrow and blood; myelomas, a cancer of B cells; and lymphomas, a group of cancers that originate in the lymphatic system. Lymphomas can be further classified into several groups; one of these groups is the non-Hodgkin's lymphomas which, in turn, forms a diverse group of cancers. Three broad categories of these lymphomas are defined according to the International Working Formulation for tumor classification, low grade, intermediate grade and high grade, which differ in their curability and aggressiveness (Cheson, et al., "Report of an International Workshop to Standardize Response Criteria for Non-Hodgkin's Lymphomas," *J. Clin Oncol.* 17(4):1244, 1999). Overall, these lymphomas collectively rank fifth in the United States in terms of cancer incidence and mortality, and approximately 50,000 new cases are diagnosed each year.

In a recent study which examined fifty-one case isolates of high-grade non-Hodgkins's lymphoma (NHL), forty-three were shown to be derived from B cells while eight were shown to be derived from T cells (Brown et al., *Histopathology* 14:621-27, 1989). Therefore, treatments directed specifically towards pathological B cells would be valuable in the treatment of non-Hodgkin's lymphomas and myelomas.

Initial attempts in the field to develop an immunology-based treatment directed at antigens uniquely produced by malignant B cells involved laboriously isolating and purifying idiotypic (Id) proteins directly from the pathological B cells. This purified protein was first used in model systems to treat the associated lymphoma. It was demonstrated that this active immunization against idiotypic determinants on isolated proteins could produce resistance to tumor growth in a mouse model system (Daley et al., *J. Immunol.* 120(5):1620-24, 1978; Sakato et al., *Microbiol Immunol.* 23(9):927-31, 1979). This phenomenon of resistance to tumor growth has been subsequently reproduced in a number of additional experimental tumor models (Stevenson et al., *J. Immunol.* 130(2):970-03, 1983; George et al., *J. Immunol.* 141(6):2168-74, 1988; Kwak, et al., *Blood* 76(11):2411-17, 1990).

Among the first attempts at bringing this idea and technology into the clinic was very labor intensive and utilized mouse monoclonal antibodies generated against proteins isolated from the patients' individual lymphomas following biopsy. Meeker and coworkers generated mouse monoclonal anti-idiotype antibodies for treatment of eleven patients after most had already undergone conventional lymphoma therapy (Meeker et al., *Blood* 65:1349-63, 1985). Positive results were obtained in roughly half the patients, with one case of apparent remission. In some of the patients, however, the lymphoma cells developed a resistance to the antibody via switching the class of cell surface-expressed antibodies (Meeker et al., *N. Engl J. Med.* 312:1658-65, 1985).

Another way a B cell lymphoma clone developed resistance to anti-idiotypic antibodies is via a somatic mutation in the CDR2 region (Cleary et al., *Cell* 44:97-106, 1986), thereby evading recognition. While this passive immunity approach for treatment has the advantage that it only requires isolation and purification of a relatively minor amount of idiotypic protein from a patient for raising an immune response in a mouse, the usefulness for treating lymphomas with monoclonal antibodies directed at idiotypes is limited. In the absence of a robust and convenient way to produce large quantities of idiotypic protein, however, this could prove to be the only practical way to exploit the abilities of the immune system to directly attack the idiotype of a B cell lymphoma.

Kwak et al. pursued a different approach and attempted the active immunization of patients using proteins purified from their own unique lymphomas in spite of the logistical requirement for isolating large quantities of idiotypic proteins (Kwak et al., *N. Engl, J. Med.* 327:1209-15, 1992). Patients who had minimal or no disease following chemotherapy were treated by vaccination with autologous idiotype proteins. In order to obtain sufficient quantities of idiotypic proteins for vaccination, lymphoma cells obtained by biopsy were fused with an established cell line to facilitate their growth in tissue culture, and the secreted idiotype proteins were purified via chromatography. Large scale application of this method of immunization is precluded due to the extreme labor requirements, technical barriers, and prohibitive costs. Additionally, concerns have recently been raised concerning the viral loads associated with protein production in mammalian cells.

In a following paper, Hsu et al. reported on the phase I/II of the above clinical trial utilizing vaccination of the idiotype conjugated to keyhole limpet hemocyanin (KLH) in the treatment of B-cell lymphoma (Hsu et al., *Blood* 89:3129-35, 1997). After standard chemotherapy, 41 patients with refractory non-Hodgkin's B-cell lymphoma were vaccinated with a tumor-specific idiotype. As per Kwak et al (1992), supra, the tumor-specific idiotype antigens were obtained by chromatographic purification of proteins produced by the patients' hybridomas. These proteins were therefore composed of the entire variable and constant regions of the patient's own immunoglobulin from the patients' lymphomas. The results showed that the generation of an anti-idiotype response correlated with improved clinical outcome. The duration of freedom from disease progression and overall survival of all patients mounting an anti-idiotype cellular immune response were significantly prolonged compared to those patients who did not mount an immune response. This study confirms that patients with B-cell lymphomas can be induced to make a specific immune response against tumor idiotype (Id) protein. Furthermore, the ability to generate an anti-idiotype immune response correlates with a more favorable clinical outcome. However, to treat each individual patient, lymphoma cells obtained by biopsy must be fused to established cell lines in order to allow the production of sufficient protein to vaccinate a typical patient. This process would-be difficult or impractical to use on a commercial scale.

More recently, Bendandi et al. demonstrated idiotypic, patient-specific vaccination-induced remissions in patients with follicular lymphoma (Bendandi et al., Nat. Med. 5:1171-77, 1999). Following standard chemotherapy, twenty patients demonstrating complete clinical remission were vaccinated using patient-specific idiotypic proteins accompanied by granulocyte-monocyte colony-stimulating factor (GM-CSF; see infra.). Molecular analysis of the translocations characteristic of this lymphoma was conducted prior to chemotherapy, at clinical remission and following, vaccination therapy. Eight of eleven patients with detectable, translocations after chemotherapy-induced remission were found to undergo complete molecular remission following this vaccination. Tumor-specific cytotoxic CD8+ and CD4+ T cells were found in 19 of 20 patients. Tumor-specific antibodies were also detected but were not found to be required for remission. Again, this study used idiotypic proteins made up of the entire variable and constant region of the immunoglobulin found associated with the patient's lymphoma and produced by heterohybridoma fusion.

Therefore, directing an immune response to the idiotype of cells is a promising approach, but the above techniques are limited by the requirement of producing sufficient quantities of idiotypic proteins from each patient's lymphoma cells.

The concept of anti-idiotypic immunity against B cell tumors has also been used in the case of multiple myeloma. Results have been reported by Kwak and coworkers regarding its use in enhancing the specific efficacy of allogeneic marrow grafts by pre-immunizing the donor with myeloma IgG isolated from the patient (Kwak et al., Lancet 345 (8956):1016-20, 1995). Also, Massaia and coworkers vaccinated patients in remission following high-dose chemotherapy, followed by peripheral blood stem cell transplantation (Massaia et al., Blood 94:673-83, 1999).

Granulocyte-monocyte colony-stimulating factor (GM-CSF), used above in Bendandi et al.'s study, is a hematopoietic growth factor which stimulates proliferation and differentiation of hematopoietic progenitor cells. This cytokine also plays a role in shaping cellular immunity by augmenting T-cell proliferation (Santoli et al., J. Immunol. 141(2):519-26, 1988). increasing expression of adhesion molecules on granulocytes and monocytes (Young et al., J. Immunol 145 (2):607-15, 1990; Grabstein et al., Science 232(4749):506-08, 1986), and augmenting antigen presentation (Morrissey et al., J. Immunol. 139(4):1113-9, 1987; Heufler et al., J. Exp. Med. 167(2):700-05, 1988; Smith et al., J. Immunol. 144(5): 1777-82, 1990).

Cell-based vaccines genetically engineered to produce GM-CSF have been shown to induce cellular immune responses capable of eliminating systemic lymphomas in preclinical models. This effect is mediated exclusively through activation of the cellular arm of the immune system (Levitsky et al., J. Immuno. 156(10): 3858-65, 1996). Similarly, low doses of free GM-CSF have been shown to enhance the protective anti-tumor immunity induced by idiotype protein-KLH immunization because of its ability to enhance immunity through an effect on the CD8 cells (Kwak et al., Proc. Natl. Acad. Sci. USA 93(20):10972-77, 1996. In one study, GM-CSF was shown to be the best immunomodulator to generate anti-tumor immunity among those tested in a model system (Dranoff, G., Proc. Natl. Acad. Sci. USA 90(8):3539-43, 1993.)

GM-CSF has also been used as a portion of a chimeric protein used to generate an immune response in model systems. Chen and Levy (Chen and Levy, J. Immunol. 154(7): 3105-17, 1995; U.S. Pat. No. 6,099,846) studied the production of mouse monoclonal antibodies using a chimeric protein containing a portion of GM-CSF plus a portion of an antigen of interest, namely an idiotypic region obtained from a murine B-cell tumor, 38C13, both fused to portions of human immunoglobulin chains. Chen and coworkers have also studied fusion proteins where the GM-CSF moiety has been replaced by portions of IL-2 or IL-4 (Chen et al., J. Immunol. 153(10):4775-87, 1994). One explanation for the requirement of including the GM-CSF moiety (or interleukin moiety) was to augment the effect of low levels of chimeric protein produced by the mammalian cell expression system. However, the use of purified GM-CSF co-administered with a chimeric protein to enhance the immune response of a vaccination has not been demonstrated.

With the advent of recombinant DNA technology, heavy and light chain cDNA molecules can now be cloned from hybridomas or from combinatorial libraries employing the polymerase chain reaction (PCR). This recombinant DNA technology allows researchers to manipulate the effector function or the binding function of a selected monoclonal antibody. In addition, combinatorial libraries of immunoglobulins can be generated by cloning a large number of $V_L$ and $V_H$ genes, randomly assorting them to create a library of different binding specificities, expressing them in E. coli, then screening the stochastic library for clones with the desired binding affinities (Huse et al., Science 246(4935): 1275-81, 1989). Using this recombinant approach, human antibodies were cloned with high affinity and specificity for tetanus toxoid from a randomized combinatorial library expressed in E. coli (Mullinax et al., Proc. Natl. Acad. Sci. 87(20):8095-99, 1990). The immunoglobulin genes were cloned from activated B-cells into bacteriophage vectors using the polymerase chain reaction (PCR) with specific primers. The H and L chains were randomly combined and co-expressed in E. coli to comprise a library of $10^7$ members. This combinatorial library was screened with $^{125}$I-tetanus toxoid and 0.2% of the clones displayed binding activity (Mullinax et al., supra). In addition, murine monoclonal antibodies have also been identified using a similar approach (Huse et al., supra; Caton et al., Proc. Natl. Acad. Sci. 87(16): 6450-54, 1990). Winter and co-workers used a plasmid vector to clone immunoglobulin domains by the polymerase chain reaction for expression in bacteria (Orlandi et al., Proc. Natl. Acad. Sci. 86(10):3833-37, 1989).

Newly developed E. coli antibody cloning systems are very useful for the identification of genes encoding desired binding specificities. However, antibodies produced in E. coli are not generally useful for therapeutic applications. Typically, only the antibody antigen binding fragments, Fab or Fv, can be produced as secreted products in bacteria. In the rare instance when a whole chain tetrameric IgG has been produced in E. coli, the $C_{H2}$ domains are not glycosylated. Non-glycosylated antibodies lack the cytolytic activities antibody-directed cellular cytotoxicity (ADCC) and complement activation that make passive immunotherapy so powerful. Mammalian expression systems produce glycosolated antibody and thus circumvent this limitation of the bacterial system. However, recent modifications in the CBER division of the FDA's "Points to Consider" clearly signal their concerns about viral loads associated with monoclonal antibodies produced in mammalian cells. Moreover, it is expected that any engineered antibody produced in a mammalian expression system will be quite expensive ($1500-$5000 per dose). Alternative expression systems that circumvent the difficulties encountered with current mammalian and bacterial systems are therefore highly desirable.

The baculovirus expression system is an attractive alternative to antibody production in E. coli and mammalian cells. The expression of recombinant proteins using the baculovirus system has been demonstrated in the past several years and has emerged as an excellent choice for high yield production (1-100 mg/L) of biologically active proteins in eukaryotic cells. The baculovirus/insect cell system also circumvents the solubility problems often encountered when recombinant proteins are overexpressed in prokaryotes. In addition, insect cells contain the eukaryotic post-translational modification machinery responsible for correct folding, disulfide formation, glycosylation, β-hydroxylation, fatty acid acylation, prenylation, phosphorylation and amidation not present in prokaryotes. The production of a functional, glycosylated monoclonal antibody recognizing human colorectal carcinoma cells from a baculovirus expression system has been recently demonstrated (Nesbit, J. Immunol. Methods 151: 201-208, 1992). Additionally, expression of recombinant IgA has also been demonstrated in baculovirus cells, and this IgA was correctly assembled into heavy chain/light chain heterodimers, N-glycosylated, and secreted (Carayannopoulos et al., Proc. Natl. Acad. Sci. 91:8348-52, 1994, PCT Publication No. WO 98/30577, U.S. Pat. No. 6,063,905). However, the use of baculovirus to express a chimeric idiotypic protein for use as an immunotherapeutic agent to modify a B cell pathology such as B cell malignancies and autoimmune diseases has not been demonstrated.

SUMMARY OF THE INVENTION

The present invention provides a method for altering a B cell mediated pathology in a patient. This method includes administering a composition that contains at least one chimeric protein having at least a portion of a $V_H$ or $V_L$ region of an immunoglobulin variable region and at least a portion of an immunoglobulin constant region. The $V_H$ or $V_L$ region used in this composition is associated with a particular immunoglobulin produced by a B cell from a patient having a B cell mediated pathology. After administering such a composition into a patient, the B cell mediated pathology in the patient is altered.

The present invention also provides a method for altering a B cell mediated pathology in a patient by administering a composition containing two different chimeric proteins. Each chimeric protein has at least a portion of a $V_H$ and/or $V_L$ region of an immunoglobulin chain linked to at least a portion of an immunoglobulin constant region. The $V_H$ and/or $V_L$ regions that are part of the chimeric protein are associated with particular immunoglobulin chains from a B cell of the patient having a B cell mediated pathology.

Specific immunoglobulin chains containing patient-derived unique $V_H$ and/or $V_L$ chains can be developed as therapeutic compositions. They will have therapeutic value for patients suffering from a variety of B cell malignancies or autoimmune diseases. Among the major types of cancers that can be treated are leukemias, myelomas, and lymphomas; among the lymphomas is non-Hodgkin's lymphoma. As an example of the therapeutic value of the instant invention, antigens derived from B cell lymphomas have been used to treat patients.

Suspected self-antigens can be used to affinity purify B cells involved in autoimmune diseases, such as multiple sclerosis (MS) (Warren and Catz, Mult. Scler. 6(5):300-11, 2000), systemic lupus erythematosus (SLE) (Zhang, J. et al., J. Immunol. 166(1):6-10, 2001; Odendahl, M. et al., J. Immunol. 165(10):5970-79, 2000), anti-Hu associated paraneoplastic neurological syndromes (Rauer, S. and Kaiser, R., J. Neuroimmunol. 111(1-2):241-44, 2000); and autoimmune hepatitis (AIH) (Ogawa, S. et al., J. Gastroenterol. Hepatol (1): 69-75, 2000). Other autoimmune diseases which may have B cell involvement include rheumatoid arthritis (RA), myasthenia gravis (MG), autoimmune thyroiditis (Hashimoto's thyroiditis), autoimmune uveoretinitis, polymyositis, scleroderma, and certain types of diabetes. Following the purification of a small number of pathogenic B cells, the variable portion of the immunoglobulins expressed by these cells may be cloned via PCR using the methods described in the invention. Once cloned, the $V_H$ and/or $V_L$ portions of the immunoglobulin chains specifically involved in the B cell pathology can be used to make chimeric proteins which can be expressed in a baculovirus system as described herein.

The immunoglobulin constant regions used in the above compositions and chimeric protein can be from $IgG_1$, $IgG_2$, $IgG_3$, $IgG_4$ $IgA_1$, $IgA_2$, IgM, IgD, IgE heavy chains, and κ or λ light chains or portions thereof. In some of the embodiments, the chimeric protein only contains either the $V_H$ and/or $V_L$ region of an immunoglobulin region with an immunoglobulin constant region. Examples of chimeric proteins include $V_H$-$IgG_{65\ 1}$, $V_L$-κ, and $V_L$-λ. In another embodiment, the composition contains two chimeric proteins that each respectively contains a $V_H$ and $V_L$ region with an immunoglobulin constant region. Examples include $V_H$-$IgG_{\gamma 1}$ and $V_L$-κ, and $V_H$-$IgG_{\gamma 1}$ and $V_L$-λ.

The present invention also provides a method for producing chimeric proteins using recombinant DNA technology and an expression system. This method includes the following steps: (a) isolating genes encoding the $V_H$ or $V_L$ region of an immunoglobulin chain from B cells of a patient having a B cell mediated pathology, (b) inserting the isolated gene encoding the $V_H$ or $V_L$ region of an immunoglobulin chain and the gene encoding an immunoglobulin constant region into an expression vector to allow the expression of a chimeric protein, (c) producing the chimeric protein by introducing the expression vector into insect cell lines and allowing its expression, and (d) isolating the chimeric protein. The method for producing chimeric proteins further includes a step of inserting a gene encoding either the $V_H$ and/or $V_L$ region of an immunoglobulin chain and a gene encoding a second immunoglobulin constant region into the expression vector to allow the expression of the second chimeric protein.

The present invention further provides a composition for altering a B cell mediated pathology in a patient. This composition contains at least one chimeric protein having at least a portion of a $V_H$ and/or $V_L$ region of an immunoglobulin chain and at least a portion of an immunoglobulin constant region. In preferred embodiments, the chimeric proteins may comprise at least a portion of a $V_H$ region of an immunoglobulin chain and at least a portion of an immunoglobulin constant region. The $V_H$ or $V_L$ region that is part of the chimeric protein are associated with a particular immunoglobulin chain from a B cell of a patient having a B cell mediated pathology. The composition further contains a second chimeric protein having at least a portion of a $V_H$ and/or $V_L$ region of an immunoglobulin chain and at least a portion of a second immunoglobulin constant region. In other preferred embodiments, the second chimeric protein may comprise at least a portion of a $V_H$ or $V_L$ region of an immunoglobulin chain and at least a portion of an immunoglobulin constant region. The $V_H$ or $V_L$ region that is part of the chimeric protein is associated with a particular immunoglobulin chain from a B cell of a patient having a B cell mediated pathology.

In one of the embodiments of the invention, the composition comprises two chimeric proteins. The first of the chimeric proteins comprises the entire $V_H$ region and a human constant region of an immunoglobulin $IgG_{\gamma1}$ ($V_H$-$IgG_{\gamma1}$), and the second chimeric protein comprises the entire $V_L$ and a human κ or λ constant region ($V_L$-$C_\kappa$ or $V_L$-$C_\lambda$). In other preferred embodiments, either or both of the chimeric proteins may comprise at least a portion of a $V_H$ and/or $V_L$ region of an immunoglobulin chain, plus a linker region, and at least a portion of an immunoglobulin constant region.

In another embodiment of the invention, the composition contains a single chimeric protein containing either a $V_H$ and/or $V_L$ region from a particular immunoglobulin chain from a B cell of a patient and an immunoglobulin constant region. Examples include chimeric proteins $V_H$-$IgG_{\gamma1}$, $V_L$-κ, $V_L$-λ, $V_L$-$IgG_{\gamma1}$, $V_H$-κ, and $V_H$-λ.

In one of the embodiments of the invention, the expression vector used to express the chimeric proteins is a baculovirus vector. The vector preferably contains two expression cassettes each having a promoter, a secretory signal sequence and a chimeric protein. One expression cassette contains the baculovirus AcNPV p10 promotor linked to the honey bee melittin secretory signal sequence. The other expression cassette has the polyhedrin promotor linked to a human placental alkaline phosphatase secretory-signal sequence. In addition to the listed promoters and signal sequences, other promoters and signal sequences known to those skilled in the art could be used. In some preferred embodiments, the signal sequences are endogenous signal sequences associated with the $V_H$ and $V_L$ genes isolated from patients, or other signal sequences involved in antibody production. The genes encoding the $V_H$ or $V_L$ portions of the immunoglobulin chains, and the genes encoding immunoglobulin constant region are inserted, separately and/or together, into the above expression cassette of the baculovirus vector allowing expression of one or two chimeric proteins. In a preferred embodiment, the constant region of the immunoglobulin heavy chain, such as $IgG_{\gamma1}$, with either the $V_H$ or $V_L$ region, is controlled by the polyhedrin promotor.

Chimeric proteins produced are purified using affinity columns with anti-immunoglobulin antibodies or Ig-binding proteins, such as protein A for the constant, region of an immunoglobulin heavy chain, and protein L for kappa light chains, and/or any other proteins that bind to an immunoglobulin binding domain.

The present invention also contemplates covalently coupling the chimeric proteins to a carrier protein such as keyhole limpet hemocyanin (KLH). The composition of the present invention may also be administered into a patient together with a cytokine such as granulocyte-macrophage-CSF (GM-CSF), or a chemokine such as a monocyte chemotactic protein 3 (MCP 3). Because the present composition of the present invention containing chimeric protein(s) is specifically related to a particular immunoglobulin from B cells of a patient having B cell mediated pathology, administration of this composition induces an immune response against the disease specific idiotype in which particular $V_H$ or $V_L$ segments are involved. Similarly, responses against B cells associated with autoimmune diseases involving B cells that use a restricted repertoire of immunoglobulin V-region segments, such as $V_H$ or $V_L$ segments may induce a therapeutic result. Thus, the administration of the composition of the present invention alters a B cell mediated pathology and/or autoimmune diseases in a patient. The administration routes for the invented composition include but are not limited to oral delivery, inhalation delivery, injection delivery, transdermal delivery, and the like.

All U.S. patents and applications; foreign patents and applications; scientific articles; books; and publications mentioned herein are hereby incorporated by reference in their entirety, including any drawings, figures and tables, as though set forth in full.

BRIEF DESCRIPTION OF THE DRAWINGS

FIG. 3A, 3B, 3C: DNA sequence of baculovirus expression vector p2Bac (SEQ ID NO:5). The sequence is depicted from 5' to 3'. The p2Bac vector contains the AcNPV polyhedrin gene promoter (nucleotides 1 to 120 of the GenBank accession number X06637 (SEQ ID NO:92)) and the AcMNPV p10 promoter (nucleotides 8 to 237 of GenBank accession number A28889 (SEQ ID NO:93)). FIG. 3A represents the first 2720 bases of the sequence; FIG. 3B represents the next 3120 bases of the sequence; and FIG. 3C represents the last 1285 bases of the sequence.

FIG. 4: DNA sequence of the plasmid pTRABac/9F12. This plasmid contains the genes for the heavy and light (κ) chains expressed by the stable human cell-line 9F12. This cell line produces a human IgG1/κ, antibody specific for tetanus toxoid (SEQ ID NO:89). The underlined regions represent sequences encoding mature 9F12 $IgG_1$ (TTTACCC . . . ) and kappa (ATCGACA . . . ) chains, respectively. The sequence is depicted from 5' to 3'.

FIG. 6A: DNA sequence of pTRABacHuLC$_\kappa$HC$_{\gamma1}$ (SEQ ID NO:6). The sequence is depicted from 5' to 3'.

FIG. 6B: DNA sequence of pTRABacHuLC$_\lambda$HC$_{\gamma1}$ (SEQ ID NO:7). The sequence is depicted from 5' to 3'.

FIG. 6C: DNA sequence of pTRABacHuLC$_\kappa$HC$_{\gamma1}$ following modification utilizing the kappa stuff primers (SEQ ID NO:90). The sequence is depicted from 5' to 3'.

FIG. 6D: DNA sequence of pTRABacHuLC$_\lambda$HC$_{\gamma1}$ following modification utilizing the lambda stuff primers (SEQ ID NO:91). The sequence is depicted from 5' to 3'.

DETAILED DESCRIPTION OF THE PREFERRED EMBODIMENTS

Figure 1:
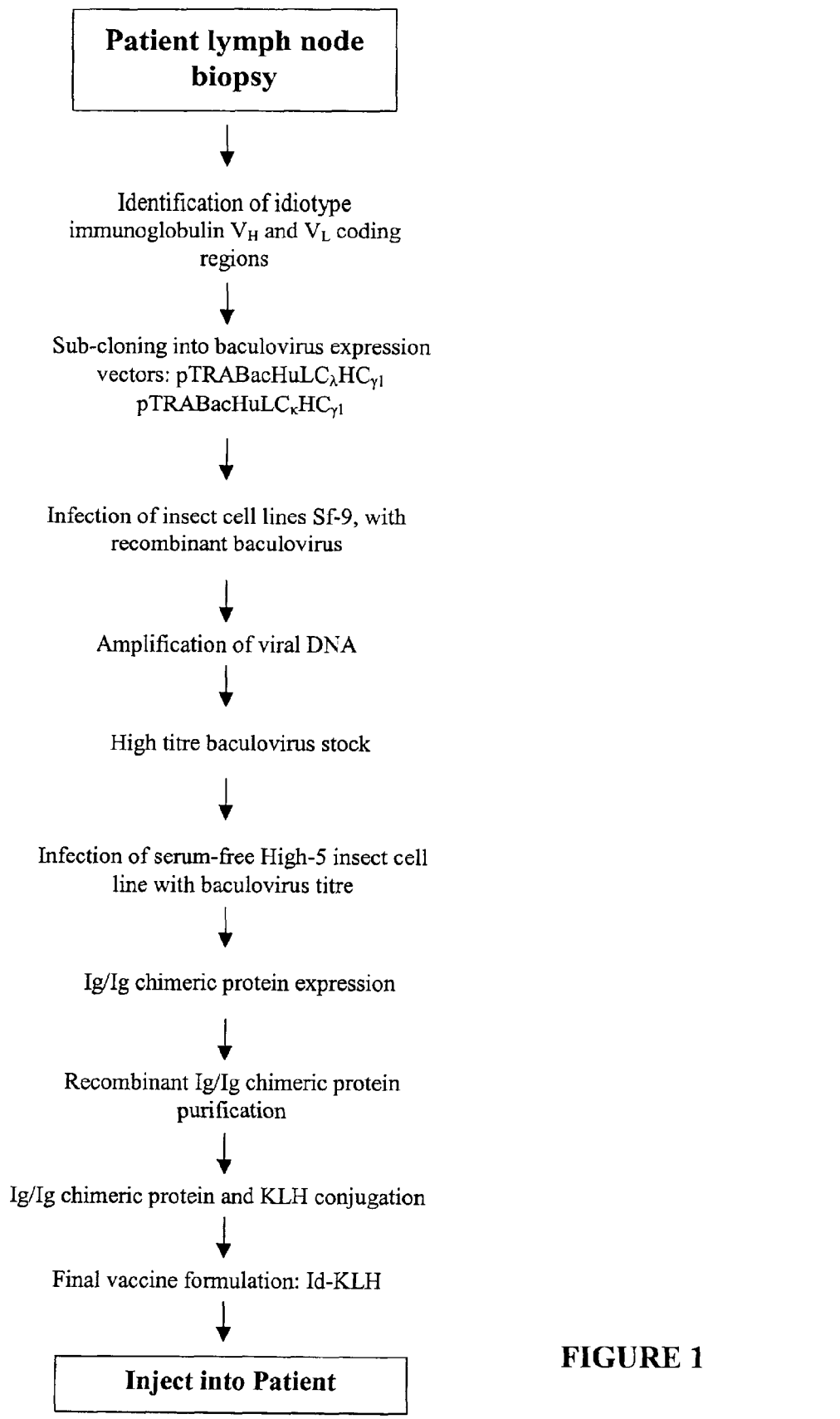
FIG. 1: A general scheme for producing a composition comprising chimeric proteins for $V_H$ or $V_L$ regions of a particular immunoglobulin from B cells from a patient having B cell mediated pathology.

The possibility of evoking an immune response that would recognize and eliminate neoplastic cells while sparing normal tissue represents an exciting approach to the treatment of cancer. Inducing such an immune response is assisted by identifying a unique tumor antigen. B-cell malignancies express a unique antigen, the immunoglobulin idiotype (Id), on their surface. This antigen contains protein sequences from both the variable immunoglobulin heavy and light regions ($V_H$ and $V_L$). Each B-cell harbors a unique genetic sequence used in the production of the immunoglobulin idiotype. Consequently, as most B cell malignancies arise from the clonal expansion of a single B cell, all cells comprising a B-cell malignancy expresses a unique Id protein. Hence, idiotypic protein should serve as an ideal target for immune-based therapy of any B cell malignancy, such as lymphoma or leukemia.

Passive Immunotherapy

Early immunotherapy strategies focused on the use of monoclonal antibodies against tumor-specific idiotype (anti-Id MoAb). This approach resulted in tumor regression and long-lasting remissions in several patients with non-Hodgkin's lymphoma. However many patients experienced eventual relapse (Miller et al., N. Engl. J. Med. 306(9):517-22, 1982; Maloney et al., Blood 80(6):1502-10, 1992; Brown et al., Blood 73(3):651-61, 1989; Brown et al., Semin. Oncol 16(3):199-210, 1989; Meeker et al., Blood 65(6):1349-63, 1985.

One difficulty that arose in the studies described above was that cells of a malignant B or T cell lymphoma could alter their expression of their idiotypic immunoglobulins or T cell receptors. Two examples of this were described in some of the articles listed above (Cleary et al., 1986, and Meeker et al., 1985). It was also shown that T cell leukemia cells could escape anti-idiotypic antibodies by reducing their expression of surface T cell receptor (Maecker et al., J. Immunol. 141:2994-3002, 1985), and this was confirmed for B cell leukemias in an animal model (Stevenson et al., J. Immunol. 130(2):970-3, 1983). Other studies demonstrated that that there is idiotypic variation even within a given human B cell lymphoma (Berinstein et al., J. Immunol. 144(2):752-8, 1990; Levy S, et al., J. Exp. Med. 168(2):475-89, 1988;). Such mutations appeared responsible for the decreased effectiveness of the anti-Id MoAb over time (Berinstein et al., supra; Tao et al., Nature 362(6422):755-8, 1993; Chen et al., J. Immunol. 153(10):4775-87, 1994).

One way to avoid this problem is via the generation and use of a polyclonal antisera against the idiotypic protein. Caspar and co-workers studied the potential of a polyclonal antibody-based therapy in a mouse model system (Caspar et al., Blood 90:3699-706, 1997). These authors vaccinated a mouse using idiotypic proteins from a non-Hodgkin's leukemia patient who had relapsed following successful monoclonal antibody therapy. The resultant polyclonal antibodies recognized idiotypic proteins from both the original tumor and all variants. Therefore, generation of polyclonal antibody response specific to the idiotype of a B cell lymphoma or leukemia would represent an improvement over monoclonal antibody therapy. Producing sufficient quantities of protein to for a vaccination to produce polyclonal antibodies is a significant burden of this approach.

Active Immunotherapy

Active immunotherapy may avoid the phenomenon of mutational escape seen with passive immune strategies. Such therapy has the potential to generate a broader immune response and thereby recognize the heterogeneous tumor cell population that can arise over time. The difficulty with active immunotherapy lies in convincing the patient's immune system to react against a perceived "self antigen" expressed by the tumor. As with idiotypic protein, many of the antigens expressed by tumors are weak immunogens.

In the instant invention, the unique specificity of the immune system has been adapted to treat B cell malignancies. In the instant invention, the DNA sequence encoding the variable region of the idiotypic immunoglobulins was cloned using primers derived from the 5' end of each unique subfamily of light and heavy immunoglobulin chains together with a constant region primer. Typically, this process uses one of several suitable cloning techniques such as PCR. These constant region primers, in combination with one for the $V_H$ region and one for the $V_L$ region, maybe used to clone the variable regions as a first step in producing a chimeric protein comprising a variable region and a constant region. Alternatively, techniques such as 5' RACE may be used. In the case of one patient described infra, 5' RACE was used to clone the variable regions of the heavy and light immunoglobulin chains in order to produce a chimeric protein. Examples of chimeric proteins include: $V_L/C_\kappa$, $V_L/C_\lambda$, $V_L/IgG_{\gamma1}$, $V_H/IgG_{\gamma1}$, $V_H/C_\kappa$, and $V_H/C_\lambda$. These chimeric proteins are produced in insect cells using a baculovirus vector. The chimeric protein thus comprises a portion of a variable region from an immunoglobulin molecule from a patient and also comprises a portion of a constant region from a source other than the patient. In preferred embodiments, the heavy and light chain constant regions are derived from 9F12 cells. However, other sources for immunoglobulin constant region genes may be used. These chimeric proteins are predicted to be more efficiently produced than using existing systems for producing idiotypic proteins and will be excellent immunogens for use in vaccination protocols.

The present invention fills the great demand for an effective treatment for B cell mediated pathologies and autoimmune diseases. The inventions take advantage of the unique cell surface antigens present on the surface of B cells involved in B cell pathologies, and are prepared in a patient-specific manner. Such vaccines provide exquisite selectivity by being tailored to the markers unique to the pathogenic B cells found in a given patient.

The novel baculovirus/insect cell expression system has proven effective for the efficient production of functional antibodies for immunotherapy from any given patient. This baculovirus expression vector was designed such that only two custom gene-specific primers were needed to amplify any pair of antibody variable regions for easy subcloning and expression as human kappa light chain and $IgG_{\gamma1}$ heavy chain. The incorporation of heterologous secretory signal sequences, which directed the heavy and light chains to the secretary pathway, were incorporated for the expression of large amounts of active immunoglobulin from insect cells. This vector should be useful for the expression of any kappa light chain variable region ($V_L$) in frame with human kappa constant region and secreted via the human placental alkaline phosphatase secretory signal sequence; and any heavy chain variable region ($V_H$) in frame with the human $IgG_{\gamma1}$ constant domain led by the honey bee melittin secretory signal sequence. In other systems, the lambda light chain constant region replaces the kappa constant region. The chimeric protein is then expressed with the $V_L$ region in frame with human lambda constant region and secreted via the human placental alkaline phosphatase secretory signal sequence, along with any heavy chain variable region ($V_H$) in frame with the human $IgG_{\gamma1}$ constant domain led by the honey bee melittin secretory signal sequence. Any monoclonal antibody, mouse or human, either from a monoclonal cell line or identified by phage display cloning, could be easily expressed as whole human $IgG_{\gamma1}/\kappa$ or $IgG_{\gamma1}/\lambda$ in this vector after two simple subcloning steps. Additionally, different immunoglobulin types, including $IgG_{\gamma 2}$, $IgG_{\gamma 3}$, $IgG_{\gamma 4}$, IgA, IgA, $IgA_1$, $IgA_2$, IgM, IgD, IgE heavy chains, or segments thereof, could be used in place of $IgG_{\gamma 1}$. Furthermore, besides those signal sequences described supra, the instant invention may use other secretory signal sequences such as the endogenous secretory sequences associated with the immunoglobulin genes derived from a given patient. Additionally, one of skill in the art would be able to select several different primers that could be used equivalently in this system to produce equivalent results to amplify any pair of antibody variable regions for easy subcloning.

In some instances, utilization of the baculovirus system for the expression of biologically active proteins has been hampered by the inability to efficiently solubilize recombinant proteins without excessive proteolytic degradation. In order to circumvent solubility and proteolysis problems encountered with the expression of recombinant proteins in insect cells, baculovirus transfer vectors were developed for the efficient secretion of biologically active proteins. These vectors that facilitate the secretion of recombinant proteins from host insect cells are constructed by inserting functional secretory leader sequences downstream of the polyhedrin promoter. In-frame insertion of cDNA sequences resulted in the synthesis of proteins containing a heterologous signal sequence which directed the recombinant protein to the secretory pathway. Human and insect leader sequences were both tested to maximize secretion of heterologous proteins from insect cells. The human placental alkaline phosphatase signal sequence (SEQ ID NO:1: MLGPCMLLLLLLLGLR-LQLSLG; DNA sequence is SEQ ID NO:2: ATG GTG GGA CCC TGC ATG CTG CTG CTG CTG CTG CTG CTA GGC CTG AGG CTA CAG CTC TCC CTG GGC) and the honeybee melittin signal sequence (SEQ ID NO:3: MKFLVN-VALVFMVVYISYIYA; DNA sequence is SEQ ID NO:4: ATG AAA TTC TTA GTC AAC GTT GCA CTA GTT TTT ATG GTC GTG TAC ATT TCT TAC ATC TAT GCG) have both proved useful for the secretion of numerous bacterial and human proteins (Mroczkowski et al., *J. Biol. Chem.* 269: 13522-28, 1994 and Tessier et al., *Gene* 98:177-83, 1991).

To tailor the present invention to a particular patient first requires identification and isolation of the genes encoding the unique antigens, and then the means of producing those antigens. This may be accomplished in a number of different ways available to one of skill in the art. For example, a recently developed method that is adapted to the needs of the instant invention uses a novel baculovirus/insect cell expression system and was recently developed for the efficient production of functional antibodies for immunotherapy (see U.S. Provisional Application Ser. No. 60/244,722, entitled "Expression Vectors for Production of Recombinant Immunoglobulin").

Expression of recombinant proteins using the baculovirus system allows the production of large quantities of biologically active proteins without many of the drawbacks associated with proteins made in bacteria, and also avoids the complications of using mammalian cells. For example the immunoglobulin genes from the stable human cell-line 9F12 (ATCC#HB8177), which produces a human IgG1/κ antibody specific for tetanus toxoid, were cloned into a baculovirus dual promoter expression transfer vector. Intact IgG1/κ immunoglobulin was produced in insect cells that behaved similarly to the mammalian antibody in SDS-PAGE analysis and Western blots. The antibody produced by insect cells was glycosylated. The binding affinities of purified Mab9F12 and purified baculovirus expressed antibody were determined to be identical and production levels were determined to be approximately 5-10 μg/ml.

Soluble human immunoglobulin fragments containing specific epitopes of the particular variable regions can be produced in insect host cells via genetic engineering. These soluble recombinant immunoglobulin proteins containing patient-derived particular $V_H$ and/or $V_L$ regions can be used as a therapeutic composition. When administered into the patient, it would specifically induce, in vivo, a cell mediated immune response for altering the B cell mediated pathology.

This technology has also been applied towards the rapid identification and cloning of patient-specific $V_\alpha$ and $V_\beta$ genes expressed by a T cell lymphoma, then expressing these as recombinant $\kappa/V_\alpha$ or $IgG_{\gamma 1}/V_\beta$ molecules in insect cells (see U.S. Provisional Application Ser. No. 60/266,133 entitled "Method and Composition for Altering a T Cell Mediated Pathology"). Molecules produced by this method were formulated and used to induce anti-idiotypic cell-mediated immunity against lymphomas in a patient-specific fashion.

The term "altering" or "alters" refers to the ability of a compound or composition of the invention to modulate a B cell mediated pathology. A compound which alters a B cell pathology may do so by a number of potential mechanisms, including raising antibodies directed at the compound which in turn destroys cells of the B cell pathology, inducing apoptosis in the B cells involved in the pathology, inhibiting further growth and division of cells of the B cell pathology, inducing cell-mediated immunity directed at the cells of the B cell pathology, or otherwise inhibiting the activity of the pathological B cells. The exact mechanism that causes the alteration need not be determined, but only that an alteration in the B cell mediated pathology occurs by some mechanism as a consequence of adding the inventive molecules or compositions.

The term "B cell mediated pathology" or "B cell pathology" refers to those diseases and conditions that arise from inappropriate replication or activity of B cells. In preferred embodiments, the B cell mediated pathology is a B cell lymphoma that results from inappropriate replication of B cells. B cell lymphomas are difficult to treat effectively with the currently available medical methods. Other types of B cell pathologies which involve inappropriate replication of B cells include chronic and acute B cell leukemias, multiple myelomas, and some non-Hodgkin's lymphomas. Other preferred embodiments include a growing number of human diseases that have been classified as autoimmune disease, where the host's own immune system attacks the host's own tissue, such as multiple sclerosis (MS) (Warren and Catz, *Mult. Scler.* 6(5):300-11, 2000), systemic lupus erythematosus (SLE) (Zhang, J. et al., *J. Immunol.* 166(1):6-10, 2001; Odendahl, M. et al., *J. Immunol.* 165(10):5970-79, 2000), anti-Hu associated paraneoplastic neurological syndromes (Rauer, S. and Kaiser, R., *J. Neuroimmunol.* 111(1-2):241-44, 2000); autoimmune hepatitis (AIH) (Ogawa, S. et al., *J. Gastroenterol. Hepatol* (1):69-75, 2000). Other candidate autoimmune diseases for treatment by the present invention include rheumatoid arthritis (RA), myasthenia gravis (MG), autoimmune thyroiditis (Hashimoto's thyroiditis), Graves' disease, inflammatory bowel disease, autoimmune uveoretinitis, polymyositis, scleroderma, and certain types of diabetes. The present treatments for these autoimmune diseases do not cure the disease, but instead only ameliorate the symptoms.

The term "B cell" refers to a cell of the immune system of an organism which is involved in the humoral immunity in normal functioning of a organism (i.e., one that is not experiencing a B cell mediated pathology). B cells are white blood cells that develop from bone marrow and produce antibodies; they are also known as B lymphocytes. In general, B cells are cells involved in antibody production in an organism.

The term "pathology" refers to a state in an organism (e.g., a human) which is recognized as abnormal by members of the medical community. The pathology to be treated in the present invention is characterized by an abnormality in the function of B cells.

The term "patient" refers to an organism in need of treatment for a pathology, or more specifically, a B cell pathology. The term refers to a living subject who has presented at a clinical setting with a particular symptom or symptoms suggesting the need for treatment with a therapeutic agent. The treatment may either be generally accepted in the medical community or it may be experimental. In preferred embodiments, the patient is a mammal, including animals such as dogs, cats, pigs, cows, sheep, goats, horses, rats, and mice. In further preferred embodiments, the patient is a human. A patient's diagnosis can alter during the course of disease progression, either spontaneously or during the course of a therapeutic regimen or treatment.

An "organism" can be a single cell or multi-cellular. The term includes mammals, and, most preferably, humans. Preferred organisms include mice, as the ability to treat or diagnose mice is often predictive of the ability to function in other organisms such as humans. Other preferred organisms include primates, as the ability to treat or diagnose primates is often predictive of the ability to function in other organisms such as humans.

The term "chimeric protein" refers to a protein which comprises a single polypeptide chain comprising segments derived from at least two different proteins. The segments of the chimeric protein must be derived from heterologous proteins, that is, all segments of the chimeric polypeptide do not arise from the same protein. The chimeric proteins of the present invention include proteins containing portions of the $V_H$ or $V_L$ region of an immunoglobulin chain, but do not comprise the entire C region of those chains as found in the B cell clone from which the $V_H$ or $V_L$ regions is derived. Furthermore, the $V_H$ or $V_L$ region may not include the entire variable region, but does include enough to generate an immune response. Chimeric proteins of the present invention may also include proteins in which a segment of the naturally occurring protein has been replaced with an equivalent naturally or non-naturally occurring segment. This includes replacing the $IgG_1$ constant region derived from a patient with the $IgG_1$ constant region from a different source and would also include immunoglobulin constant regions in which a segment of the protein has been replaced with a linker, segment or domain that is partially or entirely manmade. In all cases, however, the gene for the chimeric protein of the instant invention will not be the same as the gene for the immunoglobulins which occur naturally in the patient. The gene for the chimeric protein will be distinguishable from naturally occurring protein for one of the following reasons: (1) it will not be the full length immunoglobulin gene or cDNA from the patient, (2) it will be a different subtype than isolated from the patient, or (3) the nucleic acid sequence encoding the patient's $IgG_1$ constant region will differ from the $IgG_1$ gene used in the expression vector.

The terms "protein," "polypeptide," and "peptide" are used herein interchangeably.

The term "naturally" or "native" refers to a protein as it is isolated from nature. Thus, a naturally occurring protein may refer to a protein as it is found in nature which is encoded by a gene that has not been modified by the use of recombinant techniques. A native protein may refer to a protein as it may be found or synthesized in nature. These terms may also apply to proteins which are produced by biological system such as the bacculovirus virus system of the present invention or by the culture of cells derived from patients. A native protein may alternately refer to an isolated protein which has not been denatured. The term "native" may also refer to the manner in which polypeptide or protein is folded, either alone or in combination with other polypeptides, so that it resembles similar proteins found in nature, or how it is modified after translation ("post-translational modifications") so that it resembles similar proteins found in nature. A naturally-occurring protein may be found only in pathological. B cells from a single patient, nevertheless, this may be considered a naturally-occurring protein.

The term "segment" or "portion" is used to indicate a polypeptide derived from the amino acid sequence of the proteins used for the chimeric proteins having a length less than the full-length polypeptide from which it has been derived. It is understood that such segments may retain one or more characterizing portions of the native polypeptide. Examples of such retained characteristics include: binding with an antibody specific for the native polypeptide, or an epitope thereof.

The terms "$V_H$" and "$V_L$" refer to the variable regions of the polypeptide chains of immunoglobulin molecules, or nucleic acids encoding such polypeptide chains. One skilled in the art realizes the meaning of these terms. The exact sequence of a variable region cannot be predicted and must be determined by isolating the sequence in question. The $V_H$ and $V_L$ regions isolated from particular patients are used in the instant invention. The exact sequence of a kappa (κ) or lambda (λ) light chain is determined by clonal rearrangements of the V regions, J regions and Constant region of the light chain locus. (The kappa and lambda loci are separate and distinct.) The exact sequence of a heavy chain is determined by clonal rearrangements of the V regions, D regions, J regions and Constant region of the heavy chain locus. Additional sequence variation in the variable region arises from imprecision during the recombination process and also is generated by somatic mutations subsequent to the end of the recombination process. The terms "$V_H$" and "$V_L$" also refer to portions or segments of the $V_H$ and $V_L$ regions. A segment of the $V_H$ and $V_L$ region may also include all or substantially all of the V region. The term "substantially all" refers to approximately 90% of the entire variable region, or approximately 80% of the entire variable region. The portion of the $V_H$ and $V_L$ region present must be sufficient to allow the chimeric molecule to operate in the present invention. The terms "$V_H$" and "$V_L$" also refer to functional derivatives of such polypeptide regions as described infra.

The term "immunoglobulin constant region" refers to all or part of that portion of immunoglobulin molecules which are not encoded by the variable regions of immunoglobulins. The term "immunoglobulin constant region" may also refer to the DNA sequence encoding the immunoglobulin constant region. The immunoglobulin constant region includes the segments $C_L$, $C_{H1}$, $C_{H2}$, $C_{H3}$, and the Hinge region. Immunoglobulin types include $IgG_{\gamma 1}$, $IgG_{\gamma 2}$, $IgG_{\gamma 3}$, $IgG_{\gamma 4}$, $IgA_1$, $IgA_2$, IgM, IgD, IgE heavy chains, and κ or λ light chains or segments thereof. Any immunoglobulin constant region segments may be used in the instant invention, provided that the segment allows the immunoglobulin constant region to operate for the purposes of the present invention, for example, or the affinity purification of the chimeric molecule, via binding to Protein G, Protein A, Protein L, or appropriate antibody. Functional derivatives of the immunoglobulin constant region segments, as described infra, may also be used.

The term "immunoglobulin fold" or "immunoglobulin domain" refers to a structural element of the immunoglobulin super family. The immunoglobulin domain is a conserved, repeating structural domain of approximately 110 amino acids each.

Immunoglobulin domains are found in many protein molecules, including antibodies, the T cell antigen receptor, cytokine receptors (e.g., the platelet-derived growth factor receptor with 5 Ig domains), cell adhesion molecules (e.g., ICAM-1/CD54), and many others. Two immunoglobulin domains are found in each TCR; one in the variable region and one in the constant region. Two immunoglobulin domains are found in antibody light chains and four are found in IgG heavy chains. The present invention contemplates the replacement of one or two domains of the constant region with domains from a different molecule, such as an immunoglobulin molecule, to produce a modified (chimeric) constant region which may have different properties such as binding to other molecules.

The terms "$IgG_1$, $IgG_2$, $IgG_3$, $IgG_4$, IgA, $IgA_1$, $IgA_2$, IgM, IgD, IgE" refer to classes and subclasses of human immunoglobulins. The terms may refer to either the DNA sequences or the amino acid sequences of the proteins. The class and subclass of an immunoglobulin molecule is determined by its heavy chain. IgG and IgD are different classes of immunoglobulins; $IgG_1$ and $IgG_2$ are different subclasses of immunoglobulin molecules. The term "IgA" may refer to any subclass of IgA molecules. In preferred embodiments, it refers to an $IgA_1$ molecule. In other preferred embodiments, it refers to an $IgA_2$ molecule. In some embodiments, the immunoglobulin heavy chain used may be a chimeric protein that contains amino acids from a second protein.

The term "$IgG_{\gamma1}$" refers to the heavy chain associated with the $IgG_1$ class of immunoglobulins. $IgG_1$ represents approximately 66% of human IgG immunoglobulins Roitt et al., *Immunology*, Mosby, St. Louis, pg. 4.2, 1993).

The terms "kappa constant region," "lambda constant region," "κ constant region," and "λ constant region" refer to the constant regions of kappa (κ) and lambda (λ) light chains that remain constant during the development of the immune system. The terms may refer to either the DNA sequences or the amino acid sequences of the proteins. In some embodiments, portions of the immunoglobulin light chain may be comprised in a chimeric protein that contains amino acids from one or more other proteins.

The term "administering" relates to a method of contacting a compound with or into cells or tissues of an organism. The B cell mediated pathology can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral delivery, decimal application, injection, and aerosol applications.

The B cell mediated pathology can also be prevented or treated by administering a compound of the invention, or an antibody raised to a compound of the invention, to B cells displaying the characteristics of a pathology. The effect of administering a compound on organism function can then be monitored. The organism is preferably a mouse, rat, rabbit, guinea pig, or goat, more preferably a monkey or ape, and most preferably a human.

The term "composition" refers to a mixture that contains the protein of interest. In preferred embodiments, the composition may contain additional components, such as adjuvants, stabilizers, excipients, and the like.

The term "associated with" in reference to the relation of a variable region to a B cell clone refers to the variable region that is found on the immunoglobulins produced by a particular B cell clone.

The term "B cell clone" refers to the clonal descendants of a single B cell. Clonal descendants of B cells express the same idiotype in the produced antibodies as the parental cell. One skilled in the art realizes that clonal descendants of a B cell may have undergone somatic mutation within the variable region of the immunoglobulin gene but still remain part of the B cell clone.

The term "isolating" refers to removing a naturally occurring nucleic acid sequence from its normal cellular environment. Thus, the sequence may be in a cell-free solution or placed in a different cellular environment. The term does not imply that the sequence is the only nucleotide chain present, but that it is essentially free. (about 90-95% pure at least) of non-nucleotide material naturally associated with it, and thus is distinguished from isolated chromosomes. Also, by the use of the term "isolating" in reference to nucleic acid is meant that the specific DNA or RNA sequence is increased to a significantly higher fraction (2- to 5-fold) of the total DNA or RNA present in the solution of interest than in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased. The term "significant" is used to indicate that the level of increase is useful to the person making such an increase, and generally means an increase relative to other nucleic acids of about at least 2-fold, more preferably at least 5- to 10-fold or even more. The term also does not imply that there is no DNA or RNA from other sources. The DNA from other sources may, for example, comprise DNA from a yeast or bacterial genome, or a cloning vector such as pUC19. This term distinguishes from naturally occurring events, such as viral infection, or tumor-type growths, in which the level of one mRNA may be naturally increased relative to other species of mRNA. That is, the term is meant to cover only those situations in which a person has intervened to elevate the proportion of the desired nucleic acid.

Isolated DNA sequences are relatively more pure than in the natural environment (compared to the natural level this level should be at least 2- to 5-fold greater, e.g., in terms of mg/mL). Individual sequences obtained from PCR may be purified to electrophoretic homogeneity. The DNA molecules obtained from this PCR reaction could be obtained from total DNA or from total RNA. These DNA sequences are not naturally occurring, but rather are preferably obtained via manipulation of a partially purified naturally occurring substance (e.g., messenger RNA (mRNA)). For example, the construction of a cDNA library from mRNA involves the creation of a synthetic substance (cDNA) and pure individual cDNA clones can be isolated from the synthetic library by clonal selection from the cells carrying the cDNA library. The process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

The term "gene encoding" refers to a sequence of nucleic acids which codes for a protein or polypeptide of interest. The nucleic acid sequence may be either a molecule of DNA or RNA. In preferred embodiments, the molecule is a DNA molecule. In other preferred embodiments, the molecule is a RNA molecule. When present as a RNA molecule, it will comprise sequences which direct the ribosomes of the host cell to start translation (e.g., a start codon, ATG) and direct the ribosomes to end translation (e.g., a stop codon). Between the start codon and stop codon is an open reading frame (ORF). One skilled in the art is very familiar with the meaning of these terms.

The term "insect cell lines" refers to cell lines derived from insects and susceptible to infection by the bacculovirus. One skilled in the art is familiar with such cell lines and the techniques needed to utilize them. Representative examples of insect cell lines include *Spodoptera frugiperda* (sf9) and *Trichoplusia ni* (Hi-5) cell lines.

The terms "*Trichoplusia ni* (High-5) cells" and "*Spodoptera frugiperda (sf9)* cells" refers to insect cell lines used in combination with baculovirus expression vectors. One skilled in the art is familiar with these cell lines and how to obtain them.

The term "inserting" refers to a manipulation of a DNA sequence via the use of restriction enzymes and ligases whereby the DNA sequence of interest, usually encoding the gene of interest, can be incorporated into another nucleic acid molecule by digesting both molecules with appropriate restriction enzymes in order to create compatible overlaps and then using a ligase to join the molecules together. One skilled in the art is very familiar with such manipulations and examples may be found in Sambrook et al. (Sambrook, Fritsch, & Maniatis, "Molecular Cloning: A Laboratory Manual", 2nd ed., Cold Spring Harbor Laboratory, 1989), which is hereby incorporated by reference in its entirety including any drawings, figures and tables.

The term "adjuvant" refers to a substance which is provided with the antigen or immunogen of choice, e.g., the protein or polypeptide to which an immune response is desired, to enhance the immune response when one attempts to raise an immune response in an animal against the antigen or immunogen of choice. One skilled in the art is familiar with appropriate adjuvants to select and use. Adjuvants approved for human use include aluminum salts and MF59 (Singh and O'Hagan, *Nature Biotech* 17:1075-81, 1999). Other adjuvants are being developed (Id.) and may be used in conjunction with the present invention.

The term "keyhole-limpet hemocyanin" or "KLH" refers to a protein which is isolated from keyhole limpets which is commonly used as a carrier protein in the immunization process. One skilled in the art is familiar with the meaning of the term keyhole limpet hemocyanin.

The term "cytokine" refers to a family of growth factors, soluble (glyco)proteins, secreted primarily from leukocytes. Cytokines stimulate both the humoral and cellular immune responses, as well as the activation of phagocytic cells. Cytokines are synthesized, stored and transported by various cell types not only inside of the immune system (lymphokines, interleukins, monokines, tumor necrosis factors, interferons) but also by other cells which are associated with the study of hematology (colony-stimulating factors), oncology (transforming growth factors), and cell biology (peptide growth factors, heat shock and other stress proteins).

Cytokines secreted from lymphocytes are termed lymphokines, while those secreted by monocytes or macrophages are referred to as monokines. Many of the lymphokines are also referred to as interleukins (ILs), since they are not only secreted by leukocytes but they are also able to affect the cellular responses of leukocytes. Specifically, interleukins are growth factors targeted to cells of hematopoietic origin.

The term "growth factor" refers to a protein that binds receptors on the surface of a cell and subsequently activates cellular proliferation and/or differentiation. Many growth factors are quite versatile and can act to stimulate cellular division in a wide variety of cell types, while others are specific to a particular cell-type.

The term "chemokine" refers to a group of small proinflammatory cytokines which function as chemoattractants and activators for leukocytes and represent a superfamily of over 30 chemotactic cytokines. They orchestrate the activation and migration of immune system cells from the blood or bone marrow to the site of infection and damaged tissue. Chemokines also play an essential role in the growth and proliferation of primitive stem cells found in bone marrow which in turn develop into mature immune cells. Chemokines are involved in a wide range of acute and inflammatory diseases and exert their action by binding to receptors of the seven-transmembrane-helix class.

Chemokines frequently range from 8 to 11 kDa in molecular weights, are active over a concentration range of 1 to 100 ng/ml, and are produced by a wide variety of cell types. The production of chemokines typically is induced by exogenous irritants and endogenous mediators such as IL-1, TNF-alpha, and PDGF. The chemokines bind to specific cell surface receptors and can be considered second-order cytokines that appear to be less pleiotropic than first-order proinflammatory cytokines because they are not potent inducers of other cytokines and exhibit more specialized functions in inflammation and repair.

The term "granulocyte-macrophage colony-stimulating factor" or "GM-CSF" refers to a small (less than 20 kDa) secreted protein. It binds to specific cell surface receptors and functions as species-specific stimulator of bone marrow cells. It stimulates the growth and differentiation of several hematopoietic cell lineages including dendritic cells, granulocytes, macrophages, eosinophils, and erythrocytes. In particular, this cytokine also plays a role in shaping cellular immunity by augmenting T-cell proliferation (Santoli et al., *J. Immunol.* 141(2):519-26, 1988), increasing expression of adhesion molecules on granulocytes and monocytes (Young et al., *J. Immunol.* 145(2):607-15, 1990; Grabstein et al., *Science* 232 (4749):506-08, 1986), and by augmenting antigen presentation (Morrissey et al., *J. Immunol* 139(4):I.1.13-9, 1986; Heufler et al., *J. Exp. Med.* 167(2):700-05, 1988; Smith et al., *J. Immunol.* 144(5):1777-82, 1990).

The term "monocyte chemotactic protein-3" or "MCP-3" refers a chemokine primarily produced by monocytes. MCP-3 has a wide spectrum of chemotactic activity and attracts monocytes, dendritic cells, lymphocytes, natural killer cells, eosinophils, basophils, and neutrophils. The cDNA was cloned in 1993 by Minty et al., *Eur Cytokine Netw* 4(2):99-110, 1993, and Opdenakker et al., *Biochem Biophys Res Commun.,* 191(2):535-42, 1993. Its properties have been recently reviewed by Proost et al., *J. Leukoc Biol.* 59(1):67-74, 1996.

The term "expression vector" refers to a recombinant DNA construct which is designed to express a selected gene of interest, usually a protein, when properly inserted into the expression vector. One skilled in the art understands the term. Expression vectors commonly include a promotor at the 5' end of the site where the gene of interest is inserted and a terminator region at 3' end of the site. Frequently the gene of interest is inserted into the appropriate site by means of selected restriction enzyme cleavage sites. The term "expression vector" also refers to a DNA construct such as described above into which the gene of interest encoding the product of interest has already been inserted.

The term "baculovirus expression vector" refers to a DNA construct which is designed to express a selected gene when used in the baculovirus system. Any of the potential baculoviruses or expression vectors designed to function in the baculovirus system may be used in the instant invention. In a similar fashion, the term "expression vector" is a genus which encompasses the particular embodiment of baculovirus expression vectors, but "expression vectors" may function in cells and cell lines aside from, or in addition to, insect cell lines.

The term "allow the expression of" refers to placing an expression vector into an environment in which the gene of interest will be expressed. This commonly means inserting the expression vector into an appropriate cell type where the promotor and other regions necessary for gene expression will be recognized by the host cell's components and will cause the expression of the gene of interest. The expression normally consists of two steps: transcription and translation. Expression can also be conducted in vitro using components derived from cells. One skilled in the art is familiar with these techniques, and such techniques are set forth in Sambrook et al. (Sambrook, Fritsch, & Maniatis, "Molecular Cloning: A Laboratory Manual", 2nd ed., Cold Spring Harbor Laboratory, 1989). In, the preferred embodiment, the expressed product is a protein or polypeptide. In other, preferred embodiments, the expressed product is $V_H/IgG_{\gamma1}$, $V_L/C_\kappa$, $V_L/C_\lambda$, or $V_L/IgG_{\gamma1}$.

The term "secretory signal sequence" refers to a peptide sequence. When this sequence is translated in frame as a peptide attached to the amino-terminal end of a polypeptide of choice, the secretory signal sequence will cause the secretion of the polypeptide of choice by interacting with the machinery of the host cell. As part of the secretory process, this secretory signal sequence will be cleaved off, leaving only the polypeptide of interest after it has been exported. In preferred embodiments, the honey bee melittin secretory signal sequence is employed. In other preferred embodiments, the human placental alkaline phosphatase secretory signal sequence is employed. The present invention is not limited by these secretory signal sequences and others well known to those skilled in the art may be substituted in place of, and in addition to, these. The term "secretory signal sequence" also refers to a nucleic acid sequence encoding the secretory peptide.

The term "ELISA" refers to "Enzyme-Linked ImmunoSorbent Assay" in which the presence or concentration of a protein is determined by its binding to the plastic well of an ELISA plate followed by its subsequent detection by antibodies specific for the protein to be quantified or detected.

The term "promoter controls" refers to an arrangement of DNA in an expression vector in which a promoter is placed 5' to a gene of interest and causes the transcription of the DNA sequence into an mRNA molecule. This mRNA molecule is then translated by the host cell's machinery. One skilled in the art is very familiar with the meaning of this term.

The terms "protein A," "protein G," and "protein L" refer to specific bacterial proteins which are capable of specifically binding immunoglobulin molecules without interacting with an antigen binding site. Protein A is a polypeptide isolated from *Staphylococcus aureus* that binds the Fc region of immunoglobulin molecules. Protein G is a bacterial cell wall protein with affinity for immunoglobulin G (IgG), which has been isolated from a human group G streptococcal strain (G148). Protein L is an immunoglobulin light chain-binding protein expressed by some strains of the anaerobic bacterial species *Peptostreptococcus magnus.*

The term "B cell lymphoma" refers to a cancer that arises in cells of the lymphatic system from B cells. B cells are white blood cells that develop from bone marrow and produce antibodies. They are also known as B lymphocytes.

The term "refractory low grade B cell lymphoma" refers to a low grade B cell lymphoma that has not responded to treatment. The term "low grade B cell lymphoma" refers to a lymphoma that tends to grow and spread slowly, including follicular small cleaved cell lymphoma. Also called indolent lymphomas due to their slow growth.

The term "follicular B cell lymphoma" refers to a type of non-Hodgkin's lymphoma. It is an indolent (slow-growing) type of lymphoma.

The term "isolating" as refers to a protein or polypeptide, refers to removing a naturally occurring polypeptide or protein from its normal cellular environment or refers to removing a polypeptide or protein synthesized in an expression system (such as the baculovirus system described herein) from the other components of the expression system. Thus, the polypeptide sequence may be in a cell-free solution or placed in a different cellular environment. The term does not imply that the polypeptide sequence is the only amino acid chain present, but that it is essentially free (about 90-95% pure at least) of non-amino acid-based material naturally associated with it.

By the use of the term "enriched" in reference to a polypeptide is meant that the specific amino acid sequence constitutes a significantly higher fraction (2- to 5-fold) of the total amino acid sequences present in the cells or solution of interest than in normal or diseased cells or in the cells from which, the sequence was taken. This could be caused by a person by preferential reduction in the amount of other amino acid sequences present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acid sequences of about at least 2-fold, more preferably at least 5- to 10-fold or even more. The term also does not imply that there is no amino acid sequence from other sources. The other source of amino acid sequences may, for example, comprise amino acid sequence encoded by a yeast or bacterial genome, or a cloning vector such as pUC19. In preferred embodiments, the amino acid sequence is a chimeric protein as described above. The term is meant to cover only those situations in which man has intervened to increase the proportion of the desired amino acid sequence.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment. Compared to the natural level this level should be at least 2-to 5-fold greater (e.g., in terms of mg/mL). Purification of at least one order of magnitude, preferably two or three orders, and more preferably four or five orders of magnitude is expressly contemplated. The substance is preferably free of contamination at a functionally significant level, for example 90%, 95%, or 99% pure.

The term "operatively linked" refers to an arrangement of DNA in which a controlling region, such as a promoter-or enhancer, is attached to a connected DNA gene of interest so as to bring about its transcription, and hence allowing its translation. The term "operatively linked" may also refer to a DNA sequence encoding a processing signal, such as a secretory signal sequence, connected to a gene encoding a polypeptide to form a single open reading frame. Following transcription and translation, the secretory signal sequence has the potential to bring about the export of the translated polypeptide. One skilled in the art is familiar with-the meaning of this term.

Functional Derivatives of Useful Chimeric Proteins

Also provided herein are functional derivatives of a polypeptide or nucleic acid of the invention. By "functional derivative" is meant a "chemical derivative," "fragment," or "variant," of the polypeptide or nucleic acid of the invention, as these terms are defined below. A functional derivative retains at least a portion of the function of the protein, for example, reactivity with an antibody specific for the protein or binding activity mediated through noncatalytic domains, which permits its utility in accordance with the present invention. It is well known in the art that due to the degeneracy of the genetic code numerous different nucleic acid sequences can code for the same amino acid sequence. Equally, it is also well known in the art that conservative changes in amino acid can be made to arrive at a protein or polypeptide that retains the functionality of the original. In both cases, all permutations are intended to be covered by this disclosure.

Included within the scope of this invention are the functional equivalents of the herein-described isolated nucleic acid molecules. The degeneracy of the genetic code permits substitution of certain codons by other codons that specify the same amino acid and hence would give rise to the same protein. The nucleic acid sequence can vary substantially since, with the exception of methionine and tryptophan, the known amino acids can be coded for by more than one codon. Thus, portions or all of the genes of the invention could be synthesized to give a nucleic acid sequence significantly different from a sequence that is found in nature. The encoded amino acid sequence thereof would, however, be preserved.

A "chemical derivative" of the complex contains additional chemical moieties not normally a part of the protein. Covalent modifications of the protein or peptides are included within the scope of this invention. Such modifications may be introduced into the molecule by reacting targeted amino acid residues of the peptide with an organic derivatizing agent that is capable of reacting with selected side chains or terminal residues, as described below. It may also consist of attaching carbohydrates to the protein in addition to the normal carbohydrates attached by the bacculovirus expression system of the invention.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect or reversing the charge of the lysinyl residues. Other suitable reagents for derivatizing primary amine containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine α-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimide (R'—N—C—N—R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include the in vitro glycosylation of polypeptides or proteins.

Derivatization with bifunctional agents is useful, for example, for cross-linking the component peptides of the protein to each other or to other proteins in a complex to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[p-azidophenyl] dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the α-amino groups of lysine, arginine, and histidine side chains (Creighton, T. E., Proteins: Structure and Molecular Properties, W.H. Freeman & Co., San Francisco, pp. 79-86, 1983), acetylation of the N-terminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein complex and the like. Moieties capable of mediating such effects are disclosed, for example, in Remington's Pharmaceutical Sciences, 18th ed., Mack Publishing Co., Easton, Pa. (1990).

A functional derivative of a protein with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., *DNA* 2:183, 1983) wherein nucleotides in the DNA coding the sequence are modified such that a modified coding sequence is modified, and thereafter expressing this recombinant DNA in a prokaryotic or eukaryotic host cell, using techniques such as those described above. Alternatively, proteins with amino acid deletions, insertions and/or substitutions may be conveniently prepared by direct chemical synthesis, using methods well-known in the art. The functional derivatives of the proteins typically exhibit the same qualitative biological activity as the native proteins.

Uses of the Chimeric Proteins of the Invention

Other aspects of the invention relate to uses for the instant chimeric proteins. Preferred uses include pharmaceutical and veterinary applications, wherein an effective amount of chimeric protein according to the invention (preferably in a composition according hereto) is administered to a patient. In this way, the chimeric protein contacts cells of the patient, which contacting thereafter elicits the desired biological response. Methods for using the instant chimeric proteins include methods of eliciting an immune response in an organism, methods of raising antibodies (B cell immune response) in an organism, methods of inducing a T cell immune response by an organism, and methods for treating B cell pathologies. The invention also includes methods for treatment of subjects in order to increase the immune response capable of altering a B cell pathology by administering a chimeric protein of the invention.

Typically, such methods are accomplished by delivering to the organism an effective amount of a chimeric protein according to the invention. "Effective amount" refers to an amount that results in the desired biological response being elicited. What constitutes such an amount will vary, and depends on a variety of factors, including the particular chimeric protein, the desired biological response to be elicited, the formulation of the chimeric protein, the age, weight, gender, and health of the organism to be treated, the dosage regimen, the condition or disease to be treated or prevented, etc. Organisms to which the instant chimeric proteins and compositions may be administered include mammals, preferably a mammal selected from the group consisting of a bovine, canine, equine, feline, ovine, porcine, and primate animal. Particularly preferred organisms are humans.

The compounds described herein can be administered to a human patient per se, or in pharmaceutical compositions where it is mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., latest edition.

1. Routes of Administration.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. One of skill in the art will understand the various modifications that would be made to adapt the composition to a particular route of administration.

Alternately, one may administer the compound in a local rather than systemic manner, for example, via injection of the compound directly into a solid tumor, often in a depot or sustained release formulation.

2. Composition/Formulation.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Suitable carriers include excipients such as, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for compositions may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

3. Effective Dosage.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al., "The Pharmacological Basis of Therapeutics," Ch. 1 p.1, 1975).

Dosage amount and interval may be adjusted individually to provide plasma levels of the active moiety which are sufficient to maintain the required effect, or minimal effective concentration (MEC). The MEC will vary for each compound. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

4. Packaging.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the polynucleotide for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, treatment of rheumatoid arthritis, treatment of diabetes, and the like.

EXAMPLES

In the following description, reference will be made to various methodologies known to those skilled in the art of immunology, cell biology, and molecular biology. Publications and other materials setting forth such known methodologies to which reference is made are incorporated herein by reference in their entireties as though set forth in full.

1. Tissue Processing for Non-Hodgkin's Lymphoma Idiotype (ID) Identification and Cloning:

Tumor samples from a peripheral lymph node were biopsied as clinically indicated under sterile conditions and used to generate patient idiotype-specific recombinant chimeric immunoglobulin proteins. Remaining lymph node biopsy material was stored in liquid nitrogen in tissue cell bank for future use.

a. Cell Isolation: Single cell suspensions of patient lymph node biopsies were obtained by forcing the biopsied lymphoma tissue through a disposable 0.38 mm steel mesh screen while submerged in sterile PBS. The dispersed cells were washed twice in PBS, then resuspended and counted. A 10% fraction of the cells were processed for total RNA extraction and the remaining cells were archived in liquid nitrogen following resuspension in RPMI 1640 tissue culture media containing 30% (v/v) fetal bovine serum and 10% (v/v) DMSO. All processing of clinical samples was performed in a biological safety cabinet.

b. Total RNA Preparation: Total RNA from homogenized lymph node cells was isolated using RNeasy Kit® (Qiagen) as per manufacturer's instruction. Total RNA was quantitated by spectrophotometry.

c. cDNA Synthesis: Approximately 2.0 µg total RNA was used as template for first strand cDNA synthesis using the SuperScript™ Preamplification System ( GIBCO™-BRL) according to manufacturer's recommendation. Oligo(dT) provided with the kit was used to prime the cDNA.

d. PCR Amplification of Genes Encoding Lymphoma Heavy and Light Chains: Both heavy and light chains from the lymphoma-specific immunoglobulins were identified as follows. Aliquots of the single stranded lymphoma cDNA were combined with a series of $V_H$ and $V_L$ leader sequence-specific oligonucleotide sense primers representing all known $V_H$, $V_\kappa$, and $V_\lambda$ subfamilies as listed in Table 1, paired with IgM, IgG, IgA, or $Ig_\kappa$ and $Ig_\lambda$ constant region specific antisense primers. These samples were then amplified by PCR and analyzed by agarose gel electrophoresis.

Parallel reactions were conducted using cDNA prepared from the patient's peripheral blood lymphocytes. A comparison of PCR products generated by each pair of primers derived from samples containing normal PBL or lymph node biopsy cDNA would lead to the identification of the candidate tumor specific $V_H$ and $V_\kappa$ or $V_\lambda$ subfamily over-represented in the lymphoma, and the isotype of the heavy and light chains. Candidate tumor V region gene products were then excised, and their nucleic acid sequence was determined to assess clonality. For each patient, two independent analyses were performed from starting cellular fractions.

One microliter of the cDNA reaction (representing 5% of the total cDNA reaction volume) was amplified for 35 cycles in 50 µl volume using the HotStarTaq™ Master Mix Kit (Qiagen). Cycling conditions: 95° C. 15 min, 65° C. 4 min, 72° C. 1 min, followed by 94 ° C. 1 min, 61° C. 30 sec, 72° C. 1 min for 34 cycles; and a final extension step at 72° C. for 7 min. A 10 µl aliquot of each reaction is analyzed by electrophoresis on a 1% agarose gel with ethidium bromide.

TABLE 1

Primer Sequences Used for Amplification of Lymphoma Heavy and Light Chains

'(GA)' means either a G or an A,
'(TC)' means either a T or a C.

| PRIMER NAME | PRIMER SEQUENCE (5' 3') |
| --- | --- |
| 491$V_{H1}$L | TCACCATGGACTGGACCTGGAG<br>SEQ ID NO:38 |
| 492$V_{H2}$L.1 | ACCATGGACATACTTTGTTCCACGC<br>SEQ ID NO:39 |
| 493$V_{H2}$L.2 | ACCATGGACACACTTTGCTCCACGC<br>SEQ ID NO:40 |
| 494$V_{H3}$L.1 | ACCATGGAGTTTGGGCTGAGCTG<br>SEQ ID NO:41 |
| 495$V_{H3}$L.2 | ACCATGGAACTGGGGCTCCGCTG<br>SEQ ID NO:42 |
| 496$V_{H4}$L | AAGAACATGAAACACCTGTGGTTCTTC<br>SEQ ID NO:43 |
| 497$V_{H5}$L | ATCATGGGGTCAACCGCCATCCT<br>SEQ ID NO:44 |
| 498$V_{H6}$L | ACAATGTCTGTCTCCTTCCTCATC<br>SEQ ID NO:45 |
| 516$V_{\kappa1}$L | ACATGAGGGTCCCCGCTCAGC<br>SEQ ID NO:46 |
| 517$V_{\kappa2}$L | TCAGCTCCTGGGGCTGCTAATG<br>SEQ ID NO:47 |
| 515$V_{\kappa3}$L | CTTCCTCCTGCTACTCTGGCTC<br>SEQ ID NO:48 |
| 518$V_{\kappa4}$L | GCAGACCCAGGTCTTCATTTCTC<br>SEQ ID NO:49 |
| 519$V_{\kappa5}$L | CCAGGTTCACCTCCTCAGCTTC<br>SEQ ID NO:50 |

TABLE 1-continued

Primer Sequences Used for Amplification of Lymphoma Heavy and Light Chains

'(GA)' means either a G or an A,
'(TC)' means either a T or a C.

| PRIMER NAME | PRIMER SEQUENCE (5' 3') |
|---|---|
| 520 $V_{\kappa 6}L$ | GGTTTCTGCTGCTCTGGGTTCC<br>SEQ ID NO:51 |
| 522 $V_{\lambda 1}L$ | TCACTG(TC)(GA)CAGGGTCCTGGGC<br>SEQ ID NO:52 |
| 523 $V_{\lambda 2}L$ | ACTCAGG(GA)CACAGG(GA)TCCTGG<br>SEQ ID NO:53 |
| 524 $V_{\lambda 3}.1$ | TTGCTTACTGCACAGGATCCGTG<br>SEQ ID NO:54 |
| 525 $V_{\lambda 3}L.2$ | CTTGCTCACTTTACAGGTTCTGTG<br>SEQ ID NO:55 |
| 526 $V_{\lambda 3}L.3$ | CTCACTCTTTGCATAGGTTCTGTG<br>SEQ ID NO:56 |
| 527 $V_{\lambda 3}L.4$ | TCAACCTCTACACAGGCTCTATTG<br>SEQ ID NO:57 |
| 528 $V_{\lambda 3}L.5$ | CTCACTCTCTGCACAG(GT)CTCTG(AT)G<br>SEQ ID NO:58 |
| 529 $V_{\lambda 4}.L1$ | CATTTTCTCCACAGGTCTCTGTGC<br>SEQ ID NO:59 |
| 530 $V_{\lambda 4}L.2$ | CCTCCACTG(GC)ACAGGGTCTCTC<br>SEQ ID NO:60 |
| 531 $V_{\lambda 5}L$ | CTCTCACTGCACAGGTTCCCTC<br>SEQ ID NO:61 |
| 532 $V_{\lambda 6}L$ | CGCTCACTGCACAGGTTCTTGG<br>SEQ ID NO:62 |
| 533 $V_{\lambda 7}L$ | CTTGCTGCCCAGGGTCCAATTC<br>SEQ ID NO:63 |
| 534 $V_{\lambda 8}L$ | TGCTTATGGATCAGGAGTGGATTC<br>SEQ ID NO:64 |
| 535 $V_{\lambda 9}L$ | CAGTCTCCTCACAGGGTCCCTC<br>SEQ ID NO:65 |
| 536 $V_{\lambda 10}L$ | TCACTCACTCTGCAGTGTCAGTG<br>SEQ ID NO:66 |
| IgG Constant-E | CTGAGTTCCACGACACCGTCAC<br>SEQ ID NO:69 |
| IgM Constant-E | GGGAATTCTCACAGGAGACGAGG<br>SEQ ID NO:70 |
| $C_\kappa$-E | TTGGAGGGCGTTATCCACCTTC<br>SEQ ID NO:71 |
| $C_\lambda$-E | GAAGTCACTTATGAGACACACCAG<br>SEQ ID NO:72 |
| IgG Constant-I | GGAAGTAGTCCTTGACCAGGCAG<br>SEQ ID NO:73 |
| IgM Constant-I | GGGAAAAGGGTTGGGCCCGATGCAC<br>SEQ ID NO:74 |
| $C_\kappa$-I | GGGAAAAGGGTTGGGCCCGATGCAC<br>SEQ ID NO:75 |
| $C_\lambda$-I | GGAACAGAGTGACACTGGGTGCAGCCTTGGGCTG<br>SEQ ID NO:76 |
| Cλ Downstream | TGCCGTCGGCAGGAGGTATTTCATTATGACTGTCTCCTTGCTATTATGAACATTCTGTAGGGGCCA<br>SEQ ID NO:77 |
| Cλ - 5' | GTCAGCCCAAGGCTGCACCCAGTGTCACTCTGTTCC<br>SEQ ID NO:78 |
| Cλ - 3' | CGTATCAAGCTTTTACTATGAACATTCTGTAGGGCCAC<br>SEQ ID NO:79 |
| λ-stuff 1 | CCTTTGATAACACCCA<br>SEQ ID NO:80 |
| λ-stuff 1' | GTGTTATCAAAGG<br>SEQ ID NO:81 |
| γ1-stuff 1 | 5'CTAGTTTGATAAGGGCC3'<br>SEQ ID NO:82 |
| γ1-stuff 1' | 5'CTTATCAAA3'<br>SEQ ID NO:83 |
| κ-Stuff 1 | 5'-CCTTTGATAACACCAA3'<br>SEQ ID NO:84 |
| κ-Stuff 1' | 5'- -3'<br>SEQ ID NO:85 | e. Cloning and Sequencing of PCR Products: PCR products from reactions determined to contain the tumor specific variable sequences for heavy and light chains were cloned directly into plasmid pCR2.1®-TOPO® as per manufacturer's recommendations, and introduced into Top10™ competent *E. coli* cells (Invitrogen). Twenty four miniprep DNA plasmids were prepared from carbenicillin resistant bacterial colonies using the QIAprep® Spin Miniprep™ Kit (Qiagen), and quantitated by spectrophotometry. Two hundred ng of each plasmid was sequenced using the Cy5/Cy5.5 Dye Primer Cycle Sequencing Kit™ (Visible Genetics). Following the completion of the sequencing reactions, samples were electrophoresed on the OpenGene™ Automated DNA Sequencing System and the data was processed with GeneObjects™ software package (Visible Genetics). Additional analysis including sequence alignments were performed using the SEQUENCHER™ Version 4.1.2 DNA analysis software (GENE Codes Corp.). A V-region derived sequence could be considered tumor specific if it was present in 75% of the samples, for example, if 18 or greater of the 24 form a consensus group when analyzed using the above software utilizing the default parameters. Two independent biopsy samples would be compared when available.

f. cDNA Synthesis and Generation of 5' RACE Products: Due to the occurrence of mutations in the $V_H$ and $V_L$ sequences, it is not possible at times to identify tumor-specific immunoglobulin rearrangements. As an alternative to the sequence-specific PCR strategy supra, one can employ a 5' RACE PCR strategy to identify tumor specific immunoglobulin (Ig) rearrangements. All steps for first strand cDNA synthesis to the generation of Ig specific PCR products are performed according to manufacturer's directions (5' RACE system for Rapid Amplification of cDNA Ends, version 2.0, GIBCO™ BRL), with slight modification. Approximately 2.5 μg of total RNA is used as template for each first strand cDNA synthesis in the presence of specific antisense primers complimentary to the immunoglobulin heavy and the light chains' constant region utilized by the B cell population of interest (SEQ ID NO:69 for IgG, SEQ ID NO:70 for IgM, SEQ ID NO:71 for $C_\kappa$, and SEQ ID NO:72 for $C_\lambda$). The cDNA reactions are purified over GlassMAX™ spin cartridges, generating a final volume of 50 μl each. A 10 μl aliquot of each purified cDNA is oligo(dC) tailed with terminal deoxynucleotidyl transferase in a 25 μl volume, generating the templates to be used for subsequent PCR reactions. The PCR set up utilizes an upstream primer containing a poly(G) track provided by the manufacturer and an Ig specific antisense primer interior to that used for cDNA first strand synthesis (SEQ ID NO:73 for IgG, SEQ ID NO:74 for IgM, SEQ ID NO:75 for $C_\kappa$, and SEQ ID NO:76 for $C_\lambda$). Five μl of template is amplified in a 50 μl volume as follows: 95° C. for 15 min, 55° C. for 4 min, 72° C. for 1 min, followed by 94° C. for 1 min, 55° C. for 30 sec, 72° C. for 1 min for 34 cycles, and a final extension step at 72° C. for 7 min. The final PCR products are separated by electrophoresis on a 1% agarose gel with ethidium bromide and the band of the appropriate size (~500-600 bp) is isolated and cloned into the pCR2.1-TOPO plasmid as described in 1e, supra.

Figure 2:
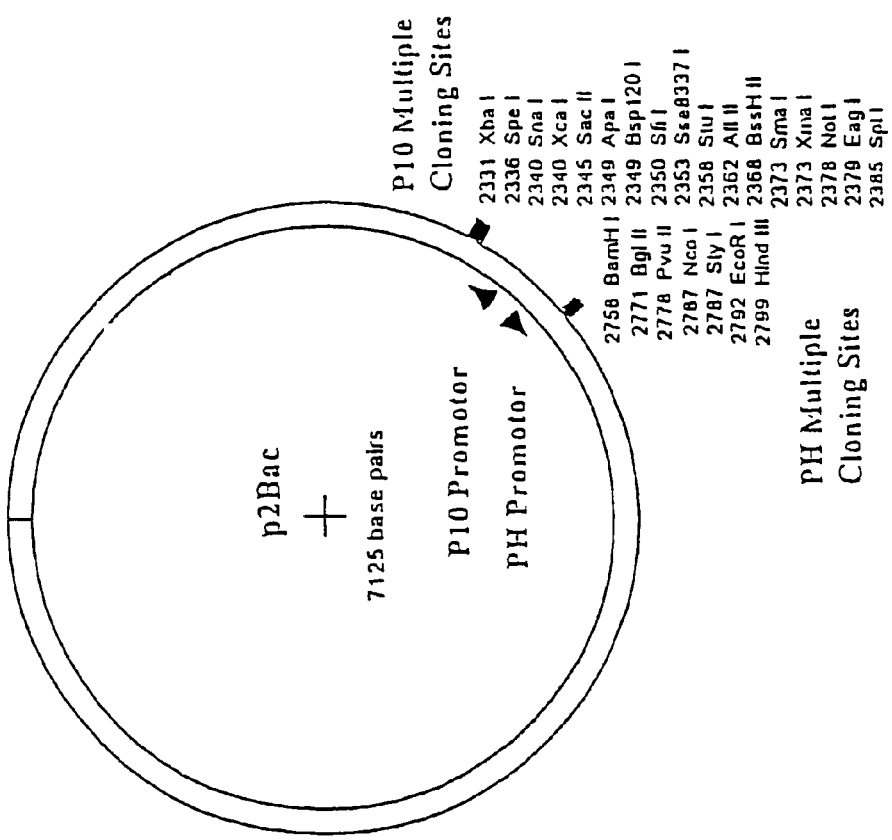
FIG. 2: Plasmid map of a baculovirus expression vector p2Bac with multiple cloning sites.

2. Construction of Baculovirus Expression Vectors pTRABacHuLC$_\kappa$HC$_{\gamma 1}$ and pTRABacHuLC$_\lambda$HC$_{\gamma 1}$ a. Cloning of Secretory Signal Sequences into p2Bac: The base vector for the pTRABacHuLC$_\kappa$HC$_{\gamma 1}$ and pTRABacHuLC$_\kappa$HC$_{\gamma 1}$ constructs was p2Bac (FIG. 2, SEQ ID NO:5, Invitrogen, Carlsbad, Calif.). Two secretory signal sequences were cloned into this base vector, and the first intermediate baculovirus expression vector p2BacM was created. In general, the vector p2Bac was first modified utilizing complimentary oligonucleotides encoding the amino terminal domain of the honey bee melittin secretory signal sequence positioned to be under transcriptional control of the baculoviral AcNPV P10 promoter. For melittin sequence cloning, 2 μg p2Bac was digested with Not I and Spe I for 4 hours at 37° C. The linear vector was purified following electrophoresis through a 1% agarose gel using Qiaex® II resin (Qiagen, Chatsworth, Calif.). The purified DNA was then eluted with 50 μl water and the DNA concentration was determined. One μg each of primers Me1S/N (SEQ ID NO:15) and Me1N/S (SEQ ID NO:16) were mixed in 10 μl digestion buffer M (Roche Molecular Biochemicals, Indianapolis, Ind.), and heated to 70° C. for 5 min, then cooled to room temperature to anneal complimentary primers. Ten percent of the annealed primers was digested in 20 μl reaction with Not I and Spe I for 4 hours at 37° C., and the digested primers were purified following electrophoresis through a 15% polyacrylamide gel with Qiaex® II resin, and the concentration of the DNA for annealed primers was determined. The DNAs of p2Bac vector and annealed melittin fragment were ligated at 1:10 vector to insert ratio. The ligation product was transformed using competent XL1-Blue E. coli (Stratagene, San Diego, Calif.) and plated on a LB-carbenicillin agar plate for overnight growing at 37° C. Miniprep colonies were prepared by standard protocols, and the plasmids were sequenced to check the construction. The resulting vector p2BacM contained the melittin secretory signal sequence.

Figure 5A:
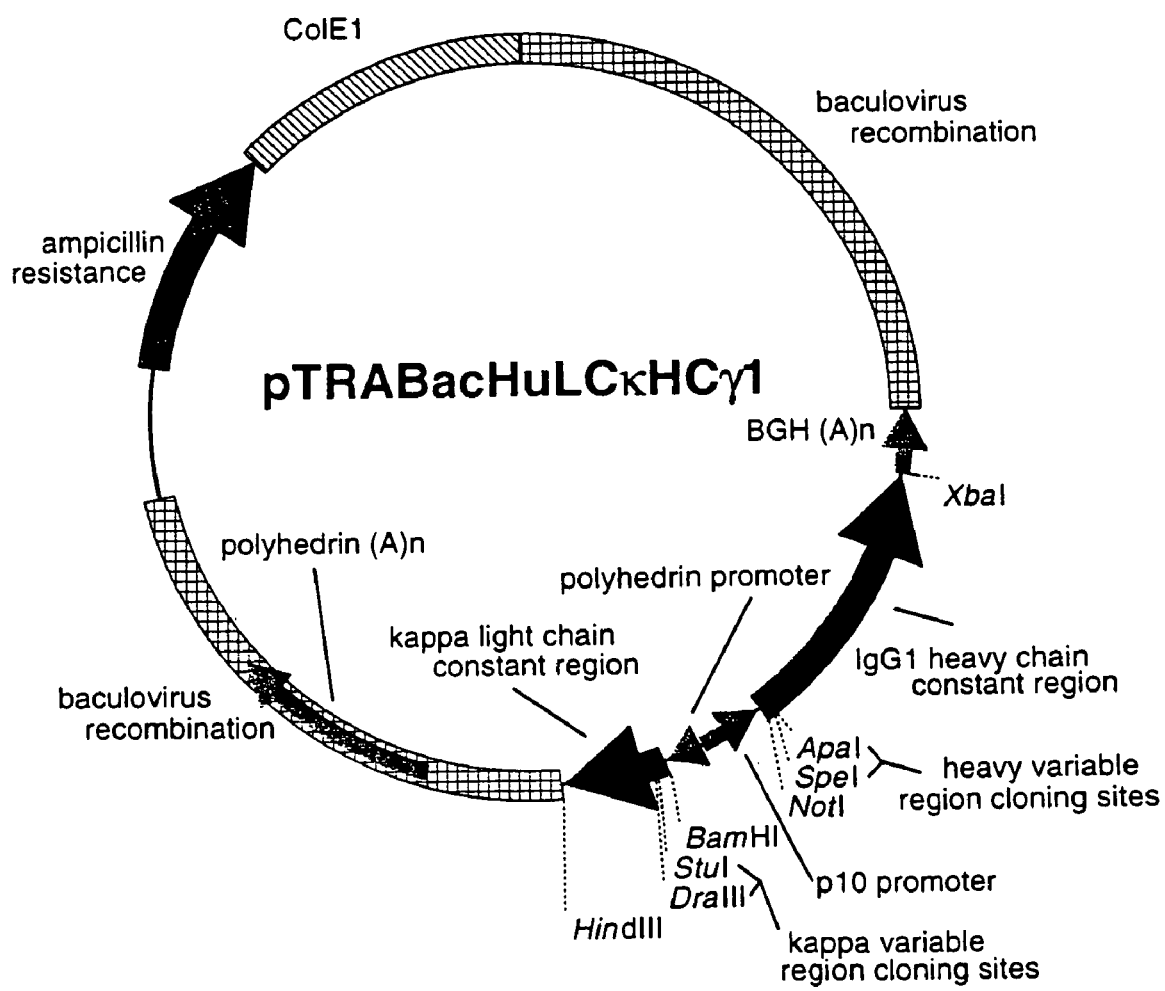
FIG. 5a: Plasmid map of recombinant baculovirus expression vector pTRABacHuLC$_\kappa$HC$_{\gamma1}$ with $IgG_{\gamma1}$ constant regions.

The p2BacM vector was further modified similarly to encode for the amino terminal domain of the human placental alkaline phosphatase secretory signal sequence under transcriptional control of the AcNPV polyhedron promoter, creating a second intermediate baculovirus expression vector p2BacMA. The procedure used to introduce the alkaline phosphatase sequence was generally cloned as follows: 2 μl p2BacM plasmid was digested with Bam HI and Eco RI, the linear vector was gel purified from agarose gel with Qiaex® II resin and eluted in 50 μl water. The DNA concentration of the vector was determined. One μl each of primers APB/E (SEQ ID NO:17) and APE/B (SEQ ID NO:18) were mixed in 10 μl digestion buffer M, and heated to 70° C. for 5 min and then cooled down to room temperature to anneal complimentary primers. Ten percent of the annealed primers was digested in a 20 μl reaction with Bam HI and Eco RI for 4 hours at 37° C. The digested primers were then purified from 15% polyacrylamide gel with Qiaex® II resin. The DNA concentration of the digested primers was also determined. The linear p2BacM vector and alkaline phosphatase fragment were then ligated at 1:10 vector to insert ratio, and the ligation product was transformed using competent XL1-Blue E. coli and plated on a LB-carbenicillin agar plate for overnight growing at 37° C. Miniprep colonies were prepared and the plasmids were sequenced to check the construction. The resulting intermediate vector p2BacMA would contain a secretory signal sequence for a human placental alkaline phosphatase. The p2BacMA plasmid was further transformed into SCS-110 E. coli strain (Stratagene) lacking dcm methylase activity for subsequent cloning of the κ constant region into methyl-sensitive Stu I site.

b. Amplification and Cloning of Constant Regions of IgG$_{\gamma 1}$ and Light Chains: The human kappa (κ) constant and the human IgG$_{\gamma 1}$ constant domains of human monoclonal antibody 9F12 were PCR amplified from RNA extracted from the human cell line 9F12 (ATCC#HB8177). The κ constant region was cloned behind the alkaline phosphatase signal sequence. The IgG$_{\gamma 1}$ constant region was inserted downstream from the melittin secretory signal sequence thus creating the vector (pTRABacHuLC$_\kappa$HC$_{\gamma 1}$, FIG. 5a). A vector containing the human lambda (λ) light chain constant region (pTRABacHuLC$_\lambda$HC$_{\gamma 1}$, FIG. 5b) was produced by replacing the κ light chain constant region with a λ light chain constant region. The light chains were isolated by RT-PCR from a chronic lymphocytic leukemia cellular RNA preparation. The detailed description of the cloning procedures are as follows:

c. Amplification of 9F12 κ and IgG$_{\gamma 1}$ constant region fragments: Total RNA from 9F12 cells (ATCC#HB8177) was extracted using the RNeasy Kit® (Qiagen) as per the manufacturer's instruction. A single stranded cDNA was synthesized using SuperScript™ reverse transcriptase (GIBCO™ BRL, Rockville, Md.) with oligo(dT) primers. One twentieth of the synthesized single strand cDNA was amplified in 100 μl PCR reactions with Expand High Fidelity™ Taq (Roche) using κ and IgG$_{\gamma 1}$ specific oligonucleotides (SEQ ID NO:21 plus SEQ ID NO:22 and SEQ ID NO:19 plus SEQ ID NO:20, respectively). The fragments from amplified 9F12 immunoglobulin were purified from 1.5% SeaKem® agarose with Qiaex® II resin and eluted with 50 μl water. The DNA concentrations for the fragments were determined. The purified 9F12 immunoglobulin fragments were ligated separately into the TA-II (Invitrogen) PCR cloning vector. The ligation products were transformed using competent XLI-Blue E. coli and plated on a LB-carbenicillin agar plate for overnight growing at 37° C. Minprep colonies were prepared and the plasmid DNA was sequenced.

d. Insertion of the 9F12 κ Constant Region into the Expression Vector: For κ constant domain, 5 μg plasmid DNA containing a κ constant region and 2 μg of DNA for the vector p2BacMA purified from SCS110 E. coli were digested with Stu I and Hind III. A 320 bp fragment containing κ constant region and a 7.1 kb fragment containing p2BacMA vector were gel purified with Quiex II and eluted in 50 μl water. The DNA concentrations for both fragments were determined. The purified fragments were then ligated with Rapid Ligation Kit (Roche). The ligation products were transformed using competent XL1-Blue E. coli and plated on a LB-carbenicillin agar plate for overnight growing at 37° C. Miniprep bacterial colonies were prepared and the recombinant DNA was sequenced to verify proper κ constant region insertion. The resulting plasmid vector was pTRABacLC$_κ$.

e. Addition of the IgG$_{γ1}$ Constant Domain to the Vector: The IgG$_{γ1}$ constant domain was added to the vector by first digesting 5 μg of plasmid DNA containing IgG$_{γ1}$ constant region and 2 μg plasmid DNA for the vector pTRABacLC$_κ$ with Spe I and Xba I. A 1 kb fragment of IgG$_{γ1}$ constant region and a 7.4 kb fragment of pTkAacLC$_κ$ vector were gel purified from agarose plugs with Quiex II and eluted in 50 μl water. The DNA concentrations for both fragments were determined. The purified fragments were then ligated with Rapid Ligation Kit (Roche). The ligation products were transformed using competent XL1-Blue E. coli and plated on a LB-carbenicillin agar plate for overnight growing at 37° C. Miniprep colonies were prepared and the ligation and orientation of the IgG$_{γ1}$ insertion were determined by restriction analysis and sequencing of the restriction sites. The resulting recombinant vector was pTRABacHuLC$_κ$HC$_{γ1}$.

This plasmid, pTRABacHuLC$_κ$HC$_{γ1}$, was further refined to add translational stop codons between the melittin secretory sequence, and the C$_{γ1}$ region sequence and the alkaline phosphatase secretory sequence and the C$_κ$ region sequence, respectively. To accomplish these modifications, the pTRABacHuLC$_κ$HC$_{γ1}$ vector was linearized following digestion with Spe I.+Apa I. The linearized vector was then ligated with annealed complimentary primers γ1-stuff 1 (SEQ ID NO:82) and γ1-stuff 1' (SEQ ID NO:83) to introduce the in-frame stop codons. The vector resulting from this modification was subsequently linearized following digestion with Stu I (AGGCCT)+Dra III (CACnnnGTG) and then ligated with annealed complimentary primers κ-stuff 1 (SEQ ID No. 84) and κ-stuff 1' (SEQ ID NO:81) to introduce the in-frame stop codons. The net effect of these modifications are indicated in the sequences shown in FIGS. 6C & 6D, respectively. (The added sequences are highlighted by a double underline and bold.)

f. Addition of the λ Constant Region to the Vectors: Total RNA from purified peripheral blood lymphocytes (PBL) obtained from a chronic lymphocytic leukemia (CLL) patient displaying a λ light chain idiotype was extracted using the RNeasy kit® (Qiagen).

Figure 5B:
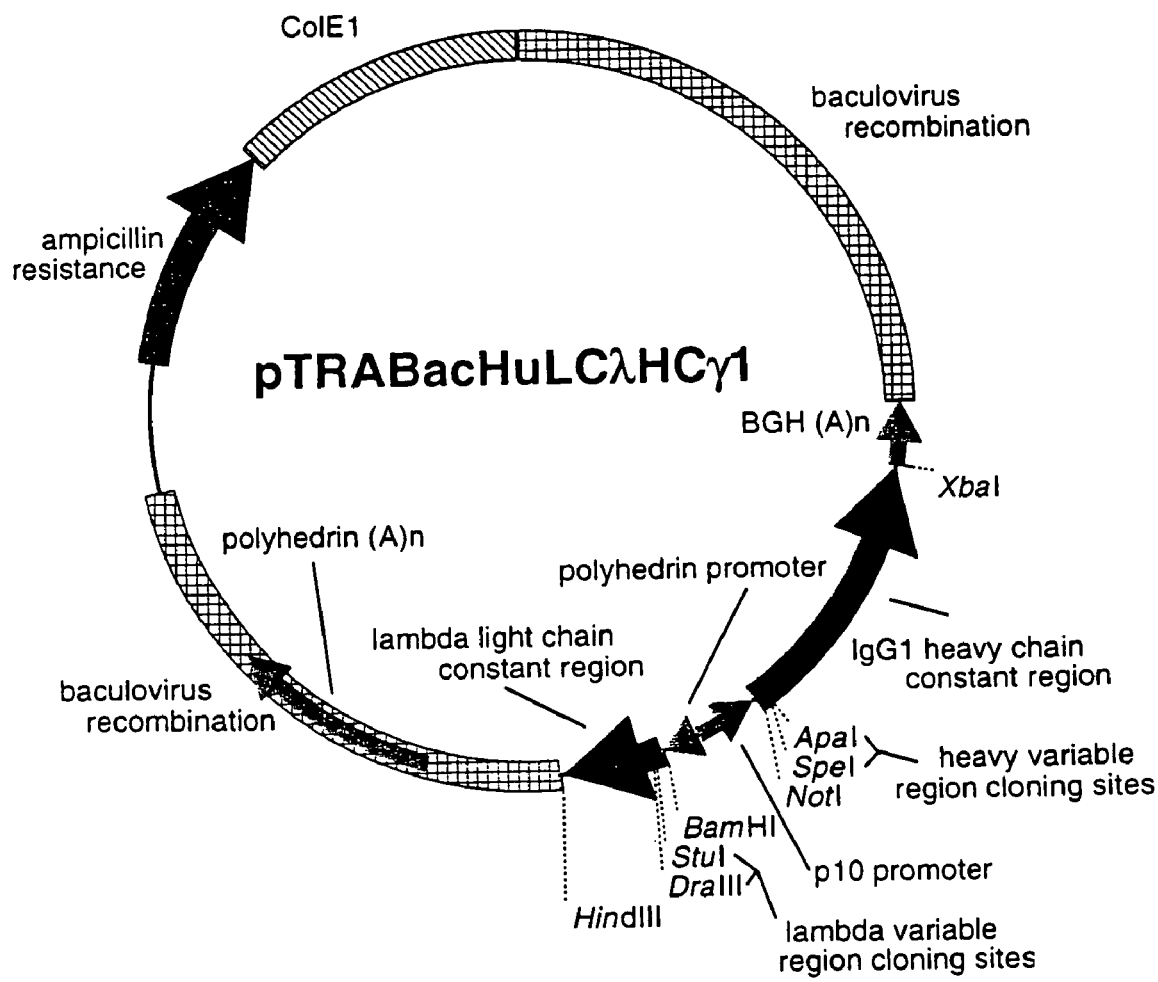
FIG. 5b: Plasmid map of recombinant baculovirus expression vector pTRABacHuLC$_\lambda$HC$_{\gamma1}$ with $IgG_{\gamma1}$ constant regions.

Approximately 2.0 μg total RNA was used as template for first strand cDNA synthesis using the SuperScript™ Preamplification System (Gibco BRL) according to manufacturer's recommendation. Oligo(dT) was used for priming. One twentieth of the synthesized single stranded cDNA was amplified in a PCR reaction using an upstream primer identical to a portion of the Vλ signal sequence (SEQ ID NO:54) and a downstream primer (SEQ ID NO:77) complimentary to the last several codons of the λ constant region as well as a portion of the 3' untranslated region. The PCR products were cloned into the pCRII vector (Invitrogen) and sequenced to confirm identity. A plasmid containing the correct λ constant region sequence was chosen as a template for a second PCR. In this reaction a sense oligonucleotide, Cλ-5' (SEQ ID NO:78), containing an engineered Dra III restriction site, corresponding the sequence in the λ constant region immediately downstream of Jλ and a Hind III containing antisense oligonucleotide primer, Cλ-3' (SEQ ID NO:79) spanning the STOP codon immediately following the λ constant region were utilized. The resulting PCR product was cloned into the pCR2.1-TOPO vector and sequenced. A fragment containing the λ constant region sequence was released upon Hind III restriction from some of the plasmids, depending on orientation of the insert. This restriction fragment was gel isolated and cloned into pTRABacHuLCκHCγ1 (FIG. 5A), following linearization following Hind III digestion, generating an intermediate plasmid containing both the λ and κ constant regions. Restriction of this plasmid with Stu I and Dra III resulted in the removal of the κ sequences. This linearized plasmid was then ligated with annealed complimentary primers λ-stuff 1 (SEQ ID NO:80) and λ-stuff 1' to generate the final version of pTRABacHuLCλHCγ1 (FIG. 5B).

3. Insertion of Genes for Patient-Derived Idiotype V$_H$ ND/or V$_L$ Regions into an Expression Vector Using either pTRABacHuLC$_κ$HC$_{γ1}$ or pTRABacHuLC$_{80}$HC$_{γ1}$, it was possible to insert genes for any V$_L$ region containing the unique cloning sequences Stu I and Dra III between the alkaline phosphatase signal sequence and the κ or λ constant region, and genes for any V$_H$ region containing the unique cloning sequences Spe I and Apa I between the melittin secretory signal sequence and the IgG$_{γ1}$ constant region (See FIG. 5A and 5B). The resulting expression vector could then be utilized for transduction into Spodoptera frugiperda (Sf 9) insect cells to produce recombinant budded baculovirus. The recombinant baculovirus was then serially amplified in Sf 9 cells to produce a high titer recombinant baculovirus stock. This high titer recombinant baculovirus stock was then used to infect Trichoplusia ni High Five™ cells for subsequent chimeric IgG protein production. A list of all oligonucleotide primers used in the construction of pTRABacHuLC$_κ$HC$_{γ1}$ or pTRABacHuLC$_γ$HC$_{γ1}$ can be found in Table 2.

After the tumor derived sequences for V$_H$ and/or V$_L$ regions are isolated as described above, oligonucleotide primers including the terminal 40 nucleotides of the melittin leader peptide (for Ig heavy chain cloning) (SEQ ID NO:8—CAGATCACTA GTTTTTATGG TCGTGTACAT TTCTTACATC TATGCG], the terminal 28 nucleotides of the alkaline phosphatase leader peptide (for Ig light chain cloning) (SEQ ID NO:9—CTGAGTAGGC CTGAGGCTAC AGCTCTCCCT GGGC), and the first 21 to 24 nucleotides of the respective V$_H$ or V$_L$ region proteins are prepared. Reverse oligonucleotide primers from the heavy or light chain constant region are used (IgG: SEQ ID NO:10—GGAAGTAGTC CTTGACCAGG CAG; IgM: SEQ ID NO:11—GGGAAAAGGG TTGGGCCCGA TGCAC; Igκ: SEQ ID NO:12—GATGAAGACA CTTGGTGCAG CCACAG; Igλ: SEQ ID NO:13: GGAACAGAGT GACACTGGGT GCAGCCTTGG GCTG). Recombinant plasmids identified previously as having the clonal V$_H$ or V$_L$ sequences are used as templates for a second round of PCR. Cycling conditions were as described supra.

Plasmid templates were combined with an IgG$_{γ1}$, IgM, Igλ, or Igκ constant region primer complementary to codon encoding amino acids 141-149, 115-123, 108-119, and 109-117 respectively and the appropriate leader/V region fusion primer. For example, for one patient, the primers used were SEQ ID NO:67 for V$_{H3}$ and SEQ ID NO:68 for V$_{κ3}$ (SEQ ID NO:67: CAGATCACTA GTTTTTATGG TCGTGTACAT TTCTTACATC TATGCGGAGA TGAAATTGGT GGAGTCTGGG; SEQ ID NO:68: CTGAGTAGGC CTGAGGCTAC AGCTCTCCCT GGGCGAAGTT GTGT-TGACTC AGTCTCC). Cycling conditions were as described above.

a. Light Chain Variable Region Insertion into Expression Vector: A PCR derived $V_L$ product and 2 µg of the corresponding pTRABacHuLC$_\kappa$HC$_{\gamma 1}$ or pTRABacHuLC$_\lambda$HC$_{\gamma 1}$ cassette vector digested with Stu I and Dra III. The 350 by DNA fragment from the patient derived $V_L$ region and the 8.4 kb fragment for the linear pTRABacHuLC$_\kappa$HC$_{\gamma 1}$ or pTRABacHuLC$_\lambda$HC$_{\gamma 1}$ vector were purified from agarose gel plugs with Qiaex® II resin and eluted in 50 µl water. The DNA concentrations for both fragments were determined and then the fragments ligated using Rapid Ligation kit (Roche). The ligation products were used to transform competent XL1-Blue E. coli which were subsequently plated on a LB-carbenicillin agar plate for overnight growing at 37° C. Miniprep colonies were prepared and the recombinant DNA plasmids were verified by restriction analysis and sequencing. The resulting vector designated pTRABac(NHL-$V_L$)LC$_\kappa$HC$_{\gamma 1}$ or pTRABac(NHL-$V_L$HC$_{\gamma 1}$.

b. Heavy Chain Variable Region Insertion into Expression Vector: A PCR derived $V_H$ product and 2 µg of the pTRABac(NHL-$V_L$)$_{LC\kappa}$HC$_{\gamma 1}$ or pTRABac(NHL-$V_L$LC$_\lambda$HC$_{\gamma 1}$ cassette vector were digested with Spe I and Apa I. The 350 by DNA fragment from the patient derived $V_H$ region and the 8.8 kb fragment for the linear pTRABac(NHL-$V_L$)LC$_\kappa$HC$_{\gamma 1}$ or pTRABac(NHL-$V_L$)LC$_\kappa$HC$_{\gamma 1}$ vector were purified from agarose gel plugs with Qiaex II resin and eluted in 50 µl water. The DNA concentrations for both fragments were determined and then the fragments ligated using Rapid Ligation kit (Roche). The ligation products were used to transform competent XL1-Blue E. coli which were subsequently plated on a LB-carbenicillin agar plate for overnight growing at 37° C. Miniprep colonies were prepared and the recombinant DNA plasmids were verified by restriction analysis and sequencing. The resulting vector is designated pTRABac(NHL-$V_L$)LC$_\kappa$(NHL-$V_H$)HC$_{\gamma 1}$, pTRABac(NHL-$V_L$)LC$_\lambda$(NHL-$V_H$)HC$_{\gamma 1}$ and is assigned a reference number corresponding to a patient, e.g., FV8786-001.

TABLE 2

Primer Sequences Used for Construction of pTRABacHuLC$_\kappa$HC$_{\gamma l}$ and pTRABacHuLC$_\lambda$HC$_{\gamma l}$ Baculovirus Transfer Vectors.

| PRIMER NAME | PRIMER SEQUENCE (5' 3') |
|---|---|
| 1. Melittin N-terminus (MelS/N and MelN/S) | ACTAGTGCAACGTTGACTAAGAATTTCAT GCGGCCGC (SEQ ID NO:15) GCGGCCGCATGAAATTCTTAGTCAACGTT GCACTAGT (SEQ ID NO:16) |
| 2. Human Placental Alkaline Phosphatase N-terminus (APB/E and APE/B) | GCGGATCCATGGTGGGACCCTGCATGCTG CTGCTGCTGCTGCTGCTAGGCCTggaatt CC (SEQ ID NO:17) GGAATTCCAGGCCTAGCAGCAGCAGCAGC AGCAGCATGCAGGGTCCCACCATGGATCC GC (SEQ ID NO:18) |
| 3. IgG$_\gamma$ Heavy Chain Constant: Upstream Downstream | TGTGACTAGTATGTATCGGCCCATCGGTC TTCCCCCT (SEQ ID NO:19) TTTCTAGACTATTATTTACCCGGAGACAG GGAGAG (SEQ ID NO:20) |

TABLE 2-continued

Primer Sequences Used for Construction of pTRABacHuLC$_\kappa$HC$_{\gamma l}$ and pTRABacHuLC$_\lambda$HC$_{\gamma l}$ Baculovirus Transfer Vectors.

| PRIMER NAME | PRIMER SEQUENCE (5' 3') |
|---|---|
| 4. Kappa Light Chain Constant: Upstream | CTAGGCCTATGTATCACCAAGTGTCTTCA TCTTCCCGCCATCT (SEQ ID NO:21) |
| Downstream | CCCAAGCTTCTATTAACACTCTCCCCTGT TTGAAGCT (SEQ ID NO:22) |

4. Transfection of Insect Cell Lines with Variable Region-Containing Expression Vectors and Production of Recombinant Chimeric Proteins:

a. Insect Cell Growth: Two established insect cell lines (Sf9 and High-5) were transfected with modified baculoviral vectors to produce recombinant chimeric $V_H$/immunoglobulin and/or $V_L$/immunoglobulin proteins. All insect cells were grown at 28° C. in ESF-921 Serum Free Insect Media (Expression Systems LLP) containing 50 µg/L gentamycin in disposable sterile vented shaker flasks (Coming), at 140-150 rpm, with no more than 50% liquid volume. Cells were passaged every 2 to 3 days. Frozen cells were thawed (Cryo-preservation media: 10% DMSO, 40% ESF-921 medium, 50% High-5 conditioned media) from a working cell bank for each lot of product or every six weeks to assure a continuous stock of exponentially growing cells that was not retractile to infection by baculovirus.

b. Sf9 Cell Transfection and Recombination Assay: The modified baculovirus expression vectors containing genes for $V_H$ and/or $V_L$ regions and genes encoding immunoglobulin heavy and/or light chain constant regions were co-transfected into Sf9 cells using the BacVector-3000™ transfection kit (Invitrogen). Ten individual plaques are picked from agarose overlays. Virus from isolated plaques are used to infect T-25 flasks seeded with Sf-9 cells at 50% confluency in 5 ml ESF-921 media. Clonal viral isolates amplified in T-25 flasks are tested by PCR, using two primers (SEQ ID NO:36 —TT-TACTGTTT TCGTAACAGT TTTG) and (SEQ ID NO:37—GGTCGTTAAC AATGGGGAAG CTG) to assure clonality of the isolated plaques and that there was no wild type virus contamination. In general, 200 ng recombinant transfer vector plasmid was co-transfected with triple-cut Bac- Vector-3000 as described in the Bac Vector® manual (Novagen) using the Eufectin lipid reagent supplied. This transfection mixture was subjected to serially 5-fold dilutions. One hundred microliter aliquots were plated in 60 mm tissue culture dishes containing 2.5×10$^6$ adherent Sf9 cells. After 1 hour, cells were overlaid with 4 ml of a 1% agarose solution in ESF-921 culture medium. Ten individual clones were picked from the transfected cells grown in agarose overlays after staining for live cells using Neutral Red (Sigma, St. Louis, Mo.) at t=144 hours post transfection. Virus was eluted from plaque plugs overnight in 1 ml ESF-921 media. T-25 flasks were seeded with Sf-9 cells at 50% confluency in 5 ml ESF-921 media, and infected with 0.5 ml of eluted clonal virus. Ninety-six hours post infection, 0.5 ml media was removed from T-25 flasks; the cells were removed by centrifugation and the supernatant was assayed for immunoglobulin activity by dot blotting on nitrocellulose. The absence of wild type virus was also tested by PCR as follows.

Infectious supernatant (10 μl) containing recombinant baculovirus was added to 90 μl of lysis buffer containing 10 mM Tris pH 8.3, 50 mM KCl, 0.1 mg/ml gelatin, 0.45% Nonidet® P-40, and 0.45% Tween-20, containing 6 μg Proteinase-K. The mixture was heated for 1 hour at 60° C. and the Proteinase-K was denatured by incubation at 95° C. for 10 min. Twenty five μl of the heated mixture was removed to a fresh PCR tube after cooling, and another 25 μl of the mixture containing 10 mM Tris pH 8.3, 50 mM KCl, 0.1 mg/ml gelatin, 0.45% NP-40, 0.45% Tween-20, 400 μM each dNTP, 5 mM $MgCl_2$, 50 pM each PCR primer (final), and 2.5 U Taq polymerase (Roche) was added. The viral DNA was amplified for 40 cycles at: 92° C. for 1 min., followed by 58° C. for 1 min. and 72° C. for 1 min. The recombinant baculovirus primers PH forward (SEQ ID NO:36) and PH reverse (SEQ ID NO:37) were used to amplify the polyhedron locus expressing the light chain gene. PCR products were analyzed following electrophoresis through an agarose gel. Recombinant baculovirus would amplify a 1300 by fragment, while wild type baculovirus would produce a ~800 by fragment with these primer sets. Recombinant virus contaminated with wild type virus would amplify both fragment sizes.

c. Preparation of High Titer Viral Stocks in Sf9 Insect Cells: Two ml from a T-25 primary culture was transferred to a T-75 flask containing SUP cells at 50% confluency in 10 ml ESF-921 media, and cells were grown for 120 hours at 28° C. Five ml of secondary T-75 cultures was transferred to a 150 ml shaker flask containing 50 ml of Sf9 cells at $2 \times 10^6$ cells/ml, and cells were grown for 120 hours at 28° C. 25 ml was transferred from the 150 ml shaker flask into 500 ml of Sf-9 cells at $2 \times 10^6$ cells/ml in a one liter shaker flask, and was grown at 28° C. When the cultures reached 20%, viable cells as determined by trypan blue staining (approximately 120 to 144 hours post infection), the viral culture was harvested by centrifugation at 3000×g, distributed into 50 ml sterile tubes, and half of the tubes were stored at 4° C with the rest at −80° C. This harvested 500 ml high titer ($>1 \times 10^8$ pfu/ml) viral stock was then used to infect High-5 insect cells for immunoglobulin production. Viral titers (pfu/ml) were determined using a Baculovirus Rapid Titer Kit (Clontech, Palo Alto, Calif.).

d. Production of Id in High-5 Insect Cells: High-5 insect celis (BTI-TN-5B1-4) secreted higher levels (2-20X) of recombinant immunoglobulin compared to Sf9 cells, and were chosen for chimeric protein production. Early log phase High-5 cells ($1.0$-$2.0 \times 10^6$ cells/ml) were seeded in 1 liter disposable culture flasks with vented closures at $5 \times 10^5$ cells/ml in ESF921 Media (Expression Systems LLP). The flasks were shaken at 140-150 rpm at 28° C., and the volume of media in the flasks was adjusted over time to no greater than 500 ml. When the cell densities reached 1.5-2.5 cell/ml in 500 ml media, the flasks were infected with high titer recombinant baculovirus stock at a multiplicity of infection (MOI) approximating 0.5:1 (pfu:cells). The flasks were then shaken at 140-150 rpm at 28° C.; the culture was harvested 96 hours post-infection.

5. Purification of the Chimeric Protein Comprising a $V_H$-Immunoglobulin and a $V_L$-Immunoglobulin:

Cells and debris were removed by centrifugation for 60 min. at approximately 5,000×g, followed by filtration through a 0.2μ PES sterile filter unit. Chimeric proteins were purified from cleared tissue culture media by affinity chromatography with a Protein-A HiTrap™ cartridge (Amersham Pharmacia, Piscataway, N.J.), followed by ion-exchange chromatography utilizing FPLC technology (Amersham Pharmacia). The purified chimeric proteins were size separated and buffer exchanged into PBS by FPLC chromatography. All reagents used for protein purification were of USP biotechnology grade (GenAr, Mallinckrot Baker, Parris, Ky.) and endotoxin tested by the manufacturer. Sterile USP grade water was used to make all buffers and other solutions. Buffers and other solutions were prepared in a biological safety cabinet, and filter sterilized through 0.2 μm PES filter units.

a. Protein A Sepharose™ Affinity Purification of the Chimeric Proteins: Tissue culture medium was removed from growing culture flasks and spun for 60 min. at 5,000×g to sediment cells and debris. The supernatant was sterilized by filtration using a 0.2 μ PES filter unit. Tris buffer (1M, pH 7.4) was added to the filtered medium containing $V_H$ and/or $V_L$-immunoglobulin chimeric proteins to a final concentration of 20 mM. The buffered tissue culture supernatant was loaded onto a 5 ml HighTrap recombinant Protein A Sepharose™ affinity cartridge at a flow rate of 1 to 5 ml/min with a P1 peristaltic pump (Amersham Pharmacia) collecting the flow-through in a clean flask. The column was washed with 25 ml PBS (pH 7.4) at 5 ml/min. The direction of the flow was reversed and the column was washed with an additional 25 ml PBS. The column was eluted in reverse at 1 ml/min with 0.05 M citric acid (pH 3.5) collecting 1 ml fractions. Other protein columns including but not limited to protein G, protein L, or any proteins that are able to bind to an immunoglobulin binding domain could be used in the same manner.

b. Ion Exchange Chromatography: A 5 ml HiTrap™ SP Sepharose cation exchange cartridge was equilibrated with 50 ml of 25 mM citric acid (pH 3.5) and 20 mM NaCl. The Protein A eluted VH and/or VL-IgG chimeric proteins were loaded directly onto the equilibrated High Trap SP Sepharose column using a peristaltic pump at a flow rate of 1 ml/min. The column was washed with 25 ml 50 mM citric acid (pH 3.5) and 20 mM NaCl (Buffer A) at 2 ml/min. The column was eluted with a linear gradient (0% Buffer B to 100% Buffer B) to collect 1 ml fractions at 1 ml/min. (Buffer B=100 mM Na carbonate (pH 10.0) and 1M NaCl). The ion exchange eluted fractions containing $V_H$ and/or $V_L$-IgG chimeric proteins were analyzed spectrophotometrically by their OD280. The peak fractions were pooled.

c. Size Exclusion Chromatography: The pooled Ig fraction from SP ion-exchange was then loaded onto a HiPrep™ Sephacryl 26/60 S200 Hi Resolution column (Pharmacia) that had been equilibrated in 5 column volumes of PBS (pH7.2) following a pre-wash in 100 ml sterile water. The chimeric Ig proteins were eluted in PBS at a flow rate of 0.5 ml/min and collected in 1 ml fractions. The major Ig peak was apooled a sterile filtered through a 0.2μ filter.

6. Idiotypic Protein and Keyhole Limpet Hemocyanin (KLH) Conjugation.

Once purified, the idiotypic protein was conjugated to GMP grade KLH (VACMUNE®, Biosyn Corporation) via glutaraldehyde crosslinking. At least 5 mg of purified, sterile idiotypic protein as described, supra, was combined with an equal weight of KLH in a sterile 15 ml conical tube and the final volume was adjusted to 9 ml in PBS. One ml of 1% glutaraldehyde (25% Grade 1 aqueous solution, Sigma) was added dropwise to a final concentration of 0.1%. The tube was then slowly rocked for 4 hours at room temperature. The conjugate was dialyzed in sterile DispoDialyzers® (Spectrum Labs) against 2 liters sterile PBS, with three buffer changes over at least 24 hours in a biological safety hood. The final IgG/KLH conjugate in PBS is aseptically removed from the dialysis chambers and transferred into a sterile tube, mixed, then aliquoted in vials. Each vial of final product was labeled with the lot number, patient identifier, vial number and date vialed. Ten percent of the final vialed lot was tested for sterility and a vial was tested for the presence of endotoxin. One vial was retained for archival purposes.

7. Product Tests a. DNA Sequence of Baculovirus Containing Production Lot Supernatant: A 1 ml aliquot of sample of infected insect cell production culture supernatant was harvested and cleared of cellular debris by spinning at 3000 rpm for 5 min in a desktop centrifuge. At least 0.1 ml of this cleared supernatant containing baculovirus particles was combined at a volume ratio of 1 to 9 with lysis buffer (10 mM Tris pH 8.3, 50 mM KCl, 0.1 mg/ml gelatin, 0.45% Nonidet® P-40, and 0.45% Tween-20), subjected to proteolysis with proteinase K (final concentration 60 µg/ml) for 1 h at 60° C., followed by denaturation for 15 min at 95° C. Twenty-five µl of this lysate was then combined with an additional 25 µl of the above lysis buffer containing 400 µM each dNTP, 5 mM MgCl$_2$, 25 pmol forward and reverse oligonucleotide primers (see Table 3; SEQ ID NO:34 and SEQ ID NO:31 for $V_H$ Identification and SEQ ID NO:35 and SEQ ID NO:36 for $V_L$ identification, respectively), and 2.5 U Taq polymerase (Roche). Cycling conditions for the PCR of $V_L$ are: initial denaturation for 2 min at 92° C., followed by 40 cycles of 1 min each at 92° C., 58° C., and 72° C., with a final extension of 7 min at 72° C. For the PCR of $V_H$, cycling conditions are the same except that the annealing temperature is 64° C. PCR products were assessed for expected size and quantity by agarose gel electrophoresis. Subsequently, two or more nested primers were used to directly sequence the PCR products. (See Table 3; SEQ ID NO:30 and SEQ ID NO:34 for $V_H$ identification, SEQ ID NO:28 and SEQ ID NO:35 for $V_\kappa$ identification, and SEQ ID NO:88 and SEQ ID NO:35 for Vλ identification, respectively.) The complete $V_H$ and $V_L$ nucleotide sequences was determined using the OpenGene™ Automated DNA Sequencing System (Visible Genetics) and sequencing analysis software, as described above and compared with the V-gene sequences of the pTRABac(NHL-FV-8786-XXX) vector corresponding to that patient's idiotype.

b. Superose™ 6 Gel Filtration Chromatography: Gel filtration chromatography of the purified Id was performed to assess protein purity. Gel filtration chromatography was performed using a Superose™ 6 HR 10/30 FPLC column (Amersham Pharmacia) with PBS as the liquid phase. Peak integration was performed on the largest 20 peaks by the FPLC software using the following criteria to reject a peak from being included in area evaluation: height less than 0.01 Au; width less than 0.05 ml; area less than 0.01 Au/ml. Fractions of each column run were collected and assayed for human immunoglobulin specific activity by capture ELISA, and compared to the OD$_{280}$ chromatogram.

c. Immunoglobulin Assay; Anti Human IgG ELISA: Microtiter plate wells were coated with 100 µl of a 3 µg/ml dilution of Goat anti-Human IgG heavy chain specific antibody (Roche) in carbonate buffer overnight at 4° C., and washed 2 times with 100 µl TBS (50 mM Tris, 150 mM NaCl, pH 7.5). Wells were blocked with of 200 µl TBSB (TBS+1% BSA) for 1 hour at 22° C.

Each chromatogram fraction corresponding to human peak in TBSB was tested. One hundred µl of diluted sample was added in 2-fold serial dilutions to wells in replicates, and incubated 1 hour at 22° C. The assay was repeated with purified Human IgG1/κ or IgG1/λ standards (Sigma, St. Louis, Mo.). The wells were washed 4 times with 200 µl TBST (TBS+0.1% Tween 20). The detection antibody was diluted (Goat-anti-Human κ or λ-HRP (Fischer, Pittsburgh, Pa.)1:2000 in TBSB, 100 µl was added to wells, and incubated for 1 hour at 22° C. The wells were washed 6 times with 200 µl TBST. One hundred µl of substrate (TMB 1 component, KPL Inc., Gaithersburg, Md.) was added to wells, developed 30 min. and assayed at OD$_{620}$.

d. Idiotypic Protein Release Criteria: (1) The DNA sequence of idiotype-variable genes in baculovirus from production supernatant must be identical to the DNA sequence in the production vector. (2) The idiotypic protein concentration was greater than 0.5 mg/ml based on OD$_{280}$. (3) The major peak area was greater than 90% of area in evaluated peaks on Superose 6 analytical chromatography. (4) The major chromatographic peak corresponds to the human IgGκ (or λ) ELISA activity peak.

The final vaccine product, Id-KLH, was tested for endotoxin levels by a kinetic turbidity microplate assay or a Limulus Amoebocyte Lysate (LAL) assay and had a level below 350 endotoxin units (EU) per ml. Ten percent of the lot was tested for sterility on a 14-day test and tests negative or was discarded.

Table 3 shows a summary of primer sequences used for establishing final product identity.

TABLE 3

Primer Sequences Used for Establishing Final Product Identity

| PRIMER NAME | PRIMER SEQUENCE (5' 3') |
|---|---|
| 1. Human Placental Alkaline Phosphatase Internal | AAATGATAACCATCTCGC (SEQ ID NO:25) |
| 2. Human Placental Alkaline Phosphatase External | TTTACTGTTTTCGTAACAGTTTTG (SEQ ID NO:26) |
| 3. Kappa Light Chain Constant Antisense | TTGGAGGGCGTTATCCACCTTC (SEQ ID NO:27) |
| 4. Kappa Light Chain Constant Downstream Internal | CTGTAAATCAACAACGCACAG (SEQ ID NO:28) |
| 5. Kappa Light Chain Constant Downstream External | CAACAACGCACAGAATCTAG (SEQ ID NO:29) |
| 6. Melittin Internal | GGGACCTTTAATTCAACCCAACAC (SEQ ID NO:30) |
| 7. Melittin External | AAACGCGTTGGAGTCTTGTGTGC (SEQ ID NO:31) |

TABLE 3-continued

Primer Sequences Used for Establishing Final Product Identity

| PRIMER NAME | PRIMER SEQUENCE (5' 3') |
|---|---|
| 8. IgG$_{\gamma l}$ Heavy Chain Constant Downstream Internal | GGAAGTAGTCCTTGACCAGGCAG (SEQ ID NO:32) |
| 9. IgG$_{\gamma l}$ Heavy Chain Constant Downstream Middle | CTGAGTTCCACGACACCGTCAC (SEQ ID NO:33) |
| 10. IgG$_{\gamma l}$ Heavy Chain Constant Downstream External | TAGAGTCCTGAGGACTGTAGGAC (SEQ ID NO:34) |
| 11. Kappa & Lambda Downstream: | 5'-GGTCGTTAACAATGGGGAAGCTG-3' (SEQ ID NO:35) |
| 12. PH forward | 5'-TTTACTGTTTTCGTAACAGTTTTG-3' (SEQ ID NO:36) |
| 13. PH reverse | 5'-GGTCGTTAACAATGGGGAAGCTG-3' (SEQ ID NO:37) |
| 14. Lambda Constant Internal | 5'-GAAGTCACTTATGAGACACACCAG-3' (SEQ ID NO:88) |

8. Use of Chimeric Protein of the Invention for Treatment of Non-Hodgkin's B-Cell Lymphoma:

$V_H$ and $V_L$ regions were obtained from a patient with Non-Hodgkin's B-Cell Lymphoma. Using the 5' RACE method described supra, genes encoding these regions were cloned and inserted into the expression vector and expressed by the methods of the instant invention. Table 5 contains the DNA sequences of the Vh and Vl regions used for the expression vector. The Apa I and Dra III sites used for cloning are indicated by underlining.

TABLE 5

Variable region sequences obtained from a patient.

VH A/07

GACATGTTGTTGGTGGAATCGGGGGGAGGCCTGGTCCAGCCGGGGGAGTC
CCTGAGACTCTCCTGTGTGGCCTCTAGATTCACCTTTAGAACGTTTTGGA
TGACCTGGGTCCGCCAACTTCCAGGGAAGGGGCTGGAGTGGGTGGCCAAT
ATAAATCAAGATGGCAGTCAGACGTATCATGCGGACTCTGTAAAGGGCCG
ATTTACCATCTCCAGAGACAACGGCAGGAACTCCCTATTTTTACAAATGA
CAAGTCTGAGAGTCGCGGACACGGCTATATATTACTGTGCGACTAATGAA
ACGTCCAGTGGCCTGGACTGCTGGGGCCAAGGAACCCTGGTCACTGTCTC
CTCAGCTTCCACCAAGGGCCC
SEQ ID NO:86

VK A/L6

GAAATCGTGTTGACACAGTCTCCAGCCACCCTGTCTTCGTCTCCAGGAGA
CAGAGTCGCCCTCTCCTGCAGGGCCAGTCAGAGTGTAAGAAGTTACTTAA
GTTGGTATCAACAGAAGGCTGGCCAGGCTCCCAGGCTCCTCATCCATAAT
GCATCCAGTAGGGCCACTGGCATCCCGCCCAGATTCAGTGGCAGTGGGTC
TGGGACAGACTTCACTCTCACCATCAGTCGCCTAGAGACTGAAGATGCTG
CAGTTTATTACTGTCAGCAACTTTATTTCTGGCCTCCGATATTATTTTTC
GGCCCTGGGACCAAAGTGAATATCACACGAACTGTGGCTGCACCAAGTG
SEQ ID NO:87

The isolated recombinant chimeric immunoglobulin protein produced for this patient from the genetic information detailed above was conjugated to KLH and administered with GM-CSF five times over a six-month period as described supra. A CT scan was performed on the neck and pelvis areas of the patient prior to administration of the therapy and 9 months later. A comparison of the sum of the diameters of 6 tumor masses revealed a 60% reduction nine months following therapy initiation. (Note that these figures are not adjusted to accommodate the size of the lymph node prior to diagnosis of the disease (See, Cheson et al., *J. Clin. Oncol.*, 17(4):1244, 1999.)

TABLE 6

Reduction in size of lymph nodes following treatment.

| | PRIOR TO TXT. (Product of diameters; cm$^2$) | 9 MONTHS POST TXT. (Product of diameters; cm$^2$) |
|---|---|---|
| LYMPH NODE 1 | 6.16 | 2.8 |
| LYMPH NODE 2 | 5.0 | 1.6 |
| LYMPH NODE 3 | 3.3 | 1.17 |
| LYMPH NODE 4 | 3.78 | 1.44 |
| LYMPH NODE 5 | 1.92 | 1.0 |
| LYMPH NODE 6 | 1.08 | 0.80 |
| SUM OF DIAMETERS | 21.24 | 8.81 |

The invention claimed is:

1. A composition comprising two different proteins produced by a process comprising the steps of: (a) isolating a gene encoding a full length sequence of a human $V_H$ region isolated from a B cell clone of a human patient having a B cell mediated pathology selected from the group consisting of refractory low grade lymphoma and follicular B cell lymphoma; (b) linking said gene encoding said entire $V_H$ region and a gene encoding at least a portion of an immunoglobulin constant region in an expression vector to form a gene encoding the first of said different proteins; (c) isolating a gene encoding a full length sequence of a human $V_L$ region isolated from a B cell clone of said patient having said B cell mediated pathology selected from the group consisting of refractory low grade lymphoma and follicular B cell lymphoma; (d) linking said gene encoding said entire $V_L$ region and a gene encoding at least a portion of an immunoglobulin constant region into said expression vector to form a gene encoding the second of said different proteins; (e) introducing said expression vector into insect cells, wherein said expression vector contains two separate expression cassettes each having a baculovirus promoter and a heterologous secretory signal sequence, wherein (i) said promoters are selected from the group consisting of p10 promoter and polyhedrin promoter, and (ii) said secretory signal sequences are selected from the group consisting of human placental alkaline phosphatase secretory signal sequence, honey bee melittin secretory signal sequence, and the endogenous secretory signal sequence associated with the immunoglobulin genes isolated from said patient; and (f) allowing the expression of said two different proteins having the same $V_H$ and $V_L$ amino acid sequences as said patient; wherein said composition elicits an active immune response.

2. A composition comprising two separate and distinct proteins produced by a process comprising the steps of: (a) isolating a gene encoding a full length sequence of a human $V_H$ region isolated from a B cell clone of a human patient having a B cell mediated pathology selected from the group consisting of refractory low grade lymphoma and follicular B cell lymphoma; (b) linking said gene encoding said entire $V_H$ region and a gene encoding at least a portion of an immunoglobulin constant region in an expression vector to form a gene encoding the first of said separate and distinct proteins; (c) isolating a gene encoding a full length sequence of a human $V_L$ region isolated from a B cell clone of said patient having said B cell mediated pathology selected from the group consisting of refractory low grade lymphoma and follicular B cell lymphoma; (d) linking said gene encoding said entire $V_L$ region and a gene encoding at least a portion of an immunoglobulin constant region into an expression vector to form a gene encoding the second of said separate and distinct proteins; (e) introducing said expression vectors into insect cells, wherein said expression vectors contain two separate expression cassettes each having a baculovirus promoter and a heterologous secretory signal sequence, wherein (i) said promoters are selected from the group consisting of p10 promoter and polyhedrin promoter, and (ii) said secretory signal sequences are selected from the group consisting of human placental alkaline phosphatase secretory signal sequence, honey bee melittin secretory signal sequence, and the endogenous secretory signal sequence associated with the immunoglobulin genes isolated from said patient; and (f) allowing the expression of said two separate and distinct proteins having the amino acid sequences as said patient; wherein said composition elicits an active immune response.

3. The composition of claim 1 or claim 2, wherein said first protein is further conjugated to a carrier protein.

4. The composition of claim 1 or claim 2, wherein said second protein is further conjugated to a carrier protein.

5. The composition of claim 4 wherein said carrier protein is a keyhole-limpet hemocyanin (KLH).

6. The composition of claim 1 or claim 2 wherein said composition is administered to a patient.

7. The composition of claim 1 or claim 2 wherein said composition is administered to said patient together with a cytokine or a chemokine.

8. The composition of claim 7 wherein said composition is administered to said patient together with a cytokine wherein said cytokine is granulocyte-macrophage-colony stimulating factor (GM-CSF).

9. The composition of claim 1 or claim 2 wherein said gene encoding said first of said proteins comprising said entire $V_H$ region and a first immunoglobulin constant region is controlled by a p10 promoter in an expression vector, and said gene encoding said second of said proteins comprising said entire $V_L$ region and a second first immunoglobulin constant region is controlled by a polyhedrin promoter in an expression vector.

10. The composition of claim 2 wherein said gene comprising said entire $V_H$ and $V_L$ region and said gene encoding said immunoglobulin constant region in an expression vector is controlled by either a p10 promoter or a polyhedrin promoter.

11. The composition of claim 1 or claim 2 wherein one of said genes encoding said immunoglobulin constant regions is a gene encoding at least a portion of a human κ or λ constant region.

12. The composition of claim 1 or claim 2 wherein said gene encoding one of said immunoglobulin constant regions is a gene encoding at least a portion of an immunoglobulin constant region selected from the group consisting of a human $IgG_{\gamma 1}$ constant region, a human $IgG_{\gamma 2}$ constant region, a human IgG$_{\gamma3}$ constant region, a human IgG$_{\gamma4}$ constant region, a human IgA$_1$ constant region, a human IgA$_2$ constant region, a human IgM constant region, a human IgD constant region, a human IgE constant region, a human κ, chain constant region, and a human λ chain constant region.

13. The composition of claim 12 wherein one of said genes encoding said immunoglobulin constant regions is a gene encoding at least a portion of a human IgG$_{\gamma1}$ gene.

14. The composition of claim 1 or claim 2 wherein said proteins are isolated using a protein selected from the group consisting of protein A, protein G, protein L, an anti-immunoglobulin antibody, and other proteins being able to bind to an immunoglobulin binding domain.

15. The composition of claim 1 or claim 2 wherein said proteins are analyzed for expression by ELISA.

16. The composition of claim 1 or claim 2 wherein said proteins are used to treat a B cell mediated pathology selected from the group consisting of refractory low grade lymphoma and follicular B cell lymphoma.

17. The composition of claim 1 wherein said expression vector is a baculovirus expression vector.

18. The composition of claim 2 wherein said expression vectors are baculovirus expression vectors.

19. The composition of claim 1 wherein said expression vector is a baculovirus expression vector that comprises a honey bee melittin secretory signal sequence and a human placental alkaline phosphatase secretory signal sequence.

20. The composition of claim 2 wherein one of said expression vectors is a baculovirus expression vector that comprises a honey bee melittin secretory signal sequence and the other of said expression vectors is a baculovirus expression vector that comprises a human placental alkaline phosphatase secretory signal sequence.

21. The composition of claim 1 wherein said expression vector is a baculovirus expression vector that comprises a baculovirus p10 promoter and polyhedrin promoter, wherein said p10 promoter controls a honey bee melittin secretory signal sequence, and wherein said polyhedrin promoter controls a human placental alkaline phosphatase secretory signal sequence.

22. The composition of claim 1 wherein said expression vector is a baculovirus expression vector that comprises a baculovirus p10 promoter and polyhedrin promoter, wherein said p10 promoter controls a honey bee melittin secretory signal sequence, and wherein said polyhedrin promoter controls a secretory signal sequence selected from the group consisting of a human placental alkaline phosphatase secretory signal sequence and a honey bee melittin secretory signal sequence.

23. The composition of claim 1 wherein said proteins are produced in insect cells selected from the group consisting of the *Trichoplusia ni* cell line and the *Spodoptera frugiperda* cell line.

24. A composition produced by expression of a gene encoding a first of two different proteins and by expression of a gene encoding a second of the different proteins from an expression vector in insect cells; wherein said expression vector comprises both: (a) a gene encoding said first of the different proteins wherein said gene encoding said first of said different proteins comprises a gene encoding the full length of a human V$_H$ region from B cells of a human patient having a B cell mediated pathology selected from the group consisting of refractory low grade lymphoma and follicular B cell lymphoma and a gene encoding at least a portion of an immunoglobulin constant region; (b) a gene encoding said second of the different proteins wherein said gene encoding said second of the different proteins comprises a gene encoding the full length of a human V$_L$ region from B cells of a human patient having a B cell mediated pathology selected from the group consisting of refractory low grade lymphoma and follicular B cell lymphoma and a gene encoding at least a portion of an immunoglobulin constant region, wherein said composition comprising the two different proteins having the same V$_H$ and V$_L$ amino acid sequences as said patient elicits an active immune response.

25. A composition produced by expression of a gene encoding a first of two separate and distinct proteins from a first expression vector in insect cells and by expression of a gene encoding a second of the separate and distinct proteins from a second expression vector in insect cells (a) wherein said first expression vector comprises: a gene encoding said first of the separate and distinct proteins wherein said gene encoding said first of the separate and distinct protein comprises a gene encoding the full length of a human V$_H$ region from B cells of a human patient having a B cell mediated pathology selected from the group consisting of refractory low grade lymphoma and follicular B cell lymphoma and a gene encoding at least a portion of an immunoglobulin constant region; (b) wherein said second expression vector comprises: a gene encoding said second of the separate and distinct proteins wherein said gene encoding said second of the separate and distinct proteins comprises a gene encoding the full length of a human V$_L$ region from B cells of a human patient having a B cell mediated pathology selected from the group consisting of refractory low grade lymphoma and follicular B cell lymphoma and a gene encoding at least a portion of an immunoglobulin constant region, wherein said composition comprising the two separate and distinct proteins having the same V$_H$ and V$_L$ amino acid sequences as said patient elicits an active immune response.

26. The composition of claim 24 or claim 25 wherein said expression vectors are baculovirus expression vectors.

27. The composition of claim 24 wherein said expression vector is a baculovirus expression vector that comprises a honey bee melittin secretory signal sequence and a human placental alkaline phosphatase secretory signal sequence.

28. The composition of claim 24 wherein said expression vector is a baculovirus expression vector that comprises a baculovirus p10 promoter and polyhedrin promoter, wherein said p10 promoter controls a honey bee melittin secretory signal sequence, and wherein said polyhedrin promoter controls a human placental alkaline phosphatase secretory signal sequence.

29. The composition of claim 24 wherein said expression vector is a baculovirus expression vector that comprises a baculovirus p10 promoter and polyhedrin promoter, wherein said p10 promoter controls a honey bee melittin secretory signal sequence, and wherein said polyhedrin promoter controls a secretory signal sequence selected from the group consisting of a human placental alkaline phosphatase secretory signal sequence and a honey bee melittin secretory signal sequence.

30. The composition of claim 24 or claim 25, wherein said first of the proteins is conjugated to a carrier protein.

31. The composition of claim 24 or claim 25, wherein said second of the proteins is conjugated to a carrier protein.

32. The composition of claim 31 wherein said proteins are conjugated to a keyhole-limpet hemocyanin (KLH).

33. The composition of claim 24 or claim 25 wherein said composition is administered to said patient.

34. The composition of claim 24 or claim 25 wherein said composition is administered to said patient together with a cytokine or a chemokine.

35. The composition of claim 34 wherein said composition is administered to said patient together with a cytokine wherein said cytokine is granulocyte-macrophage-colony stimulating factor (GM-CSF).

36. The composition of claim 24 or claim 25 wherein said gene encoding said first of the proteins comprising a full length $V_H$ region and a first immunoglobulin constant region is controlled by a p10 promoter, and said gene encoding said second of the proteins comprising a full length $V_L$ region and a second first immunoglobulin constant region is controlled by a polyhedrin promoter.

37. The composition of claim 24 or claim 25 wherein said gene comprising said full length $V_H$ region or full length $V_L$ region and said gene encoding said immunoglobulin constant region is controlled by either a p10 promoter or a polyhedrin promoter.

38. The composition of claim 24 or claim 25 wherein one of said genes encoding at least a portion of said immunoglobulin constant regions is a gene encoding at least a portion of a human κ or λ constant region.

39. The composition of claim 24 or claim 25 wherein said gene encoding at least a portion of said immunoglobulin constant regions is a gene encoding at least a portion of an immunoglobulin constant region selected from the group consisting of a human $IgG_{\gamma 1}$ constant region, a human $IgG_{\gamma 2}$ constant region, a human $IgG_{\gamma 3}$ constant region, a human $IgG_{\gamma 4}$ constant region, a human $IgA_1$ constant region, a human $IgA_2$ constant region, a human IgM constant region, a human IgD constant region, a human IgE constant region, a human k chain constant region, and a human l chain constant region.

40. The composition of claim 39 wherein one of said genes encoding at least a portion of said immunoglobulin constant regions is a gene encoding a human $IgG_{\gamma 1}$.

41. The composition of claim 24 or claim 25 wherein said proteins are produced in insect cells selected from the group consisting of the *Trichoplusia ni* cell line and the *Spodoptera frugiperda* cell line.

42. The composition of claim 24 or claim 25 wherein said proteins are isolated using a protein selected from the group consisting of protein A, protein G, protein L, an anti-immunoglobulin antibody, and other proteins being able to bind to an immunoglobulin binding domain.

43. The composition of claim 24 or claim 25 wherein said proteins are analyzed for expression by ELISA.

44. The composition of claim 24 or claim 25 wherein said composition is used to treat a B cell mediated pathology selected from the group consisting of refractory low grade lymphoma and follicular B cell lymphoma.

* * * * *

SEQUENCE LISTING

<160> NUMBER OF SEQ ID NOS: 93

<210> SEQ ID NO 1
<211> LENGTH: 22
<212> TYPE: PRT
<213> ORGANISM: Homo sapiens

<400> SEQUENCE: 1

Met Leu Gly Pro Cys Met Leu Leu Leu Leu Leu Leu Gly Leu Arg
1               5                   10                  15

Leu Gln Leu Ser Leu Gly
            20

<210> SEQ ID NO 2
<211> LENGTH: 66
<212> TYPE: DNA
<213> ORGANISM: Homo sapiens

<400> SEQUENCE: 2
atggtgggac cctgcatgct gctgctgctg ctgctgctag gcctgaggct acagctctcc    60
ctgggc                                                               66

<210> SEQ ID NO 3
<211> LENGTH: 21
<212> TYPE: PRT
<213> ORGANISM: Apis mellifera

<400> SEQUENCE: 3

Met Lys Phe Leu Val Asn Val Ala Leu Val Phe Met Val Val Tyr Ile
1               5                   10                  15

Ser Tyr Ile Tyr Ala
            20

<210> SEQ ID NO 4
<211> LENGTH: 63
<212> TYPE: DNA
<213> ORGANISM: Apis mellifera

<400> SEQUENCE: 4
atgaaattct tagtcaacgt tgcactagtt tttatggtcg tgtacatttc ttacatctat    60
gcg                                                                  63

<210> SEQ ID NO 5
<211> LENGTH: 7125
<212> TYPE: DNA
<213> ORGANISM: Autographa californica nucleopolyhedrovirus
<220> FEATURE:
<223> OTHER INFORMATION: Expression vector

<400> SEQUENCE: 5
gcagttcgtt gacgccttcc tccgtgtggc cgaacacgtc gagcgggtgg tcgatgacca    60
gcggcgtgcc gcacgcgacg cacaagtatc tgtacaccga atgatcgtcg ggcgaaggca   120
cgtcggcctc caagtggcaa tattggcaaa ttcgaaaata tatacagttg gttgtttgc    180 gcatatctat cgtggcgttg ggcatgtacg tccgaacgtt gatttgcatg caagccgaaa   240
ttaaatcatt gcgattagtg cgattaaaac gttgtacatc ctcgctttta atcatgccgt    300
cgattaaatc gcgcaatcga gtcaagtgat caaagtgtgg aataatgttt ctttgtatt    360 cccgagtcaa gcgcagcgcg tattttaaca aactagccat cttgtaagtt agtttcattt   420
aatgcaactt tatccaataa tatattatgt atcgcacgtc aagaattaac aatgcgcccg    480
ttgtcgcatc tcaacacgac tatgatagag atcaaataaa gcgcgaatta aatagcttgc    540
gacgcaacgt gcacgatctg tgcacgcgtt ccggcacgag ctttgattgt aataagtttt    600
tacgaagcga tgcatgacc cccgtagtga caacgtcac gcccaaaaga actgccgact    660
acaaaattac cgagtatgtc ggtgacgtta aaactattaa gccatccaat cgaccgttag    720

-continued

```
tcgaatcagg accgctggtg cgagaagccg cgaagtatgg cgaatgcatc gtataacgtg      780
tggagtccgc tcattagagc gtcatgttta gacaagaaag ctacatattt aattgatccc      840
gatgatttta ttgataaatt gaccctaact ccatacacgg tattctacaa tggcggggtt      900
ttggtcaaaa tttccggact gcgattgtac atgctgttaa cggctccgcc cactattaat      960
gaaattaaaa attccaattt taaaaaacgc agcaagagaa acatttgtat gaaagaatgc     1020
gtagaaggaa agaaaaatgt cgtcgacatg ctgaacaaca agattaatat gcctccgtgt     1080
ataaaaaaaa tattgaacga tttgaaagaa aacaatgtac cgcgcggcgg tatgtacagg     1140
aagaggttta tactaaactg ttacattgca aacgtggttt cgtgtgccaa gtgtgaaaac     1200
cgatgtttaa tcaaggctct gacgcatttc tacaaccacg actccaagtg tgtgggtgaa     1260
gtcatgcatc ttttaatcaa atcccaagat gtgtataaac caccaaactg ccaaaaaatg     1320
aaaactgtcg acaagctctg tccgtttgct ggcaactgca agggtctcaa tcctatttgt     1380
aattattgaa aataaaaaca attataaatg ctaaatttgt tttttattaa cgatacaaac     1440
caaacgcaac aagaacattt gtagtattat ctataattga aaacgcgtag ttataatcgc     1500
tgaggtaata tttaaaatca ttttcaaatg attcacagtt aatttgcgac aatataattt     1560
tattttcaca taaactagac gccttgtcgt cttcttcttc gtattccttc tcttttttcat    1620 ttttctcctc ataaaaatta acatagttat tatcgtatcc atatatgtat ctatcgtata     1680
gagtaaattt tttgttgtca taaatatata tgtctttttt aatggggtgt atagtaccgc     1740
tgcgcatagt ttttctgtaa tttacaacag tgctattttc tggtagttct tcggagtgtg     1800
ttgctttaat tattaaattt atataatcaa tgaatttggg atcgtcggtt ttgtacaata     1860
tgttgccggc atagtacgca gcttcttcta gttcaattac accattttt agcagcaccg      1920 gattaacata actttccaaa atgttgtacg aaccgttaaa caaaaacagt tcacctccct     1980
tttctatact attgtctgcg agcagttgtt tgttgttaaa ataacagcc attgtaatga      2040 gacgcacaaa ctaatatcac aaactggaaa tgtctatcaa tatatagttg ctgatatctc     2100
cccagcatgc ctgctattgt cttcccaatc ctccccctttg ctgtcctgcc ccaccccacc    2160
ccccagaata gaatgacacc tactcagaca atgcgatgca atttcctcat tttattagga    2220
aaggacagtg ggagtggcac cttccagggt caaggaaggc acgggggagg ggcaaacaac    2280
agatggctgg caactagaag gcacagtcga ggctgatcag cgagctctag tctagactag    2340
tataccgcgg gccctgcagg ccttaaggcg cgcccgggcg ccgcgtacg attgtaaata     2400 aaatgtaatt tacagtatag tattttaatt aatatacaaa tgatttgata ataattctta    2460
tttaactata atatattgtg ttgggttgaa ttaaaggtcc cggcatcctc aaatgcataa    2520
tttcatagtc ccccttgttg taagtgatgc gtatttctga atctttgtaa aatagcacac    2580
aagactccaa cgcgtttggc gttttatttt cttgctcgag gatatcatgg agataattaa    2640
aatgataacc atctcgcaaa taataagta ttttactgtt ttcgtaacag ttttgtaata     2700
aaaaaaccta taaatattcc ggattattca taccgtccca ccatcgggcg tgctagcgga    2760
tccgagctcg agatctgcag ctggtaccat ggaattcgaa gcttgtcgtt ggatggaaag    2820
gaaaagagtt ctacagggaa acttggaccc gcttcatgga agacagcttc cccattgtta    2880
acgaccaaga agtgatggat gttttccttg ttgtcaacat gcgtcccact agacccaacc    2940
gttgttacaa attcctggcc caacacgctc tgcgttgcga cccgactat gtacctcatg     3000 acgtgattag gatcgtcgag ccttcatggg tgggcagcaa caacgagtac cgcatcagcc    3060
tggctaagaa gggcggcggc tgcccaataa tgaaccttca ctctgagtac accaactcgt    3120
```

```
tcgaacagtt catcgatcgt gtcatctggg agaacttcta caagcccatc gtttacatcg    3180
gtaccgactc tgctgaagag gaggaaattc tccttgaagt ttccctggtg ttcaaagtaa    3240
aggagtttgc accagacgca cctctgttca ctggtccggc gtattaaaac acgatacatt    3300
gttattagta catttattaa gcgctagatt ctgtgcgttg ttgatttaca gacaattgtt    3360
gtacgtattt taataattca ttaaatttat aatctttagg gtggtatgtt agagcgaaaa    3420
tcaaatgatt ttcagcgtct ttatatctga atttaaatat taaatcctca atagatttgt    3480
aaaataggtt tcgattagtt tcaaacaagg gttgttttc cgaaccgatg gctggactat    3540
ctaatggatt ttcgctcaac gccacaaaac ttgccaaatc ttgtagcagc aatctagctt    3600
tgtcgatatt cgtttgtgtt ttgttttgta ataaaggttc gacgtcgttc aaaatattat    3660
gcgcttttgt atttctttca tcactgtcgt tagtgtacaa ttgactcgac gtaaacacgt    3720
taaataaagc tagcttggac atatttaaca tcgggcgtgt tagctttatt aggccgatta    3780
tcgtcgtcgt cccaaccctc gtcgttagaa gttgcttccg aagacgattt tgccatagcc    3840
acacgacgcc tattaattgt gtcggctaac acgtccgcga tcaaatttgt agttgagctt    3900
tttggaatta tttctgattg cgggcgtttt tgggcgggtt tcaatctaac tgtgcccgat    3960
tttaattcag acaacacgtt agaaagcgat ggtgcaggcg gtggtaacat ttcagacggc    4020
aaatctacta atggcggcgg tggtggagct gatgataaat ctaccatcgg tggaggcgca    4080
ggcggggctg gcggcggagg cggaggcgga ggtggtggcg gtgatgcaga cggcggttta    4140
ggctcaaatg tctctttagg caacacagtc ggcacctcaa ctattgtact ggtttcgggc    4200 gccgttttg gtttgaccgg tctgagacga gtgcgatttt tttcgtttct aatagcttcc     4260
aacaattgtt gtctgtcgtc taaaggtgca gcggttgag gttccgtcgg cattggtgga     4320
gcgggcggca attcagacat cgatggtggt ggtggtggtg gaggcgctgg aatgttaggc    4380
acgggagaag gtggtggcgg cggtgccgcc ggtataattt gttctggttt agtttgttcg    4440
cgcacgattg tgggcaccgg cgcaggcgcc gctggctgca caacggaagg tcgtctgctt    4500
cgaggcagcg cttggggtgg tggcaattca atattataat tggaatacaa atcgtaaaaa    4560
tctgctataa gcattgtaat ttcgctatcg tttaccgtgc cgatatttaa caaccgctca    4620
atgtaagcaa ttgtattgta aagagattgt ctcaagctcc gcacgccgat aacaagcctt    4680
ttcattttta ctacagcatt gtagtggcga gacacttcgc tgtcgtcgac tcgagttcta    4740
tagtgtcacc taaatcgtat gtgtatgata cataaggtta tgtattaatt gtagccgcgt    4800
tctaacgaca atatgtccat atggtgcact ctcagtacaa tctgctctga tgccgcatag    4860
ttaagccagc cccgacaccc gccaacaccc gctgacgcgc cctgacgggc ttgtctgctc    4920
ccggcatccg cttacagaca agctgtgacc gtctccggga gctgcatgtg tcagaggttt    4980
tcaccgtcat caccgaaacg cgcgagacga aagggcctcg tgatacgcct atttttatag    5040
gttaatgtca tgataataat ggtttcttag acgtcaggtg gcacttttcg gggaaatgtg    5100
cgcggaaccc ctatttgttt attttttctaa atacattcaa atatgtatcc gctcatgaga    5160
caataaccct gataaatgct tcaataatat tgaaaaagga agagtatgag tattcaacat    5220
ttccgtgtcg cccttattcc cttttttgcg gcattttgcc ttcctgtttt tgctcaccca    5280
gaaacgctgg tgaaagtaaa agatgctgaa gatcagttgg gtgcacgagt gggttacatc    5340
gaactggatc tcaacagcgg taagatcctt gagagttttc gccccgaaga acgttttcca    5400
atgatgagca cttttaaagt tctgctatgt ggcgcggtat tatcccgtat tgacgccggg    5460
caagagcaac tcggtcgccg catacactat tctcagaatg acttggttga gtactcacca    5520
```

```
gtcacagaaa agcatcttac ggatggcatg acagtaagag aattatgcag tgctgccata    5580
accatgagtg ataacactgc ggccaactta cttctgacaa cgatcggagg accgaaggag    5640
ctaaccgctt ttttgcacaa catggggggat catgtaactc gccttgatcg ttgggaaccg   5700
gagctgaatg aagccatacc aaacgacgag cgtgacacca cgatgcctgt agcaatggca    5760
acaacgttgc gcaaactatt aactggcgaa ctacttactc tagcttcccg gcaacaatta    5820
atagactgga tggaggcgga taaagttgca ggaccactts tgcgctcggc ccttccggct    5880
ggctggttta ttgctgataa atctggagcc ggtgagcgtg ggtctcgcgg tatcattgca    5940
gcactggggc cagatggtaa gccctcccgt atcgtagtta tctacacgac ggggagtcag    6000
gcaactatgg atgaacgaaa tagacagatc gctgagatag gtgcctcact gattaagcat    6060
tggtaactgt cagaccaagt ttactcatat atactttaga ttgatttaaa acttcatttt    6120
taatttaaaa ggatctaggt gaagatcctt tttgataatc tcatgaccaa aatcccttaa    6180
cgtgagtttt cgttccactg agcgtcagac cccgtagaaa agatcaaagg atcttcttga    6240
gatccttttt ttctgcgcgt aatctgctgc ttgcaaacaa aaaaaccacc gctaccagcg    6300
gtggtttgtt tgccggatca agagctacca actcttttc cgaaggtaac tggcttcagc     6360
agagcgcaga taccaaatac tgtccttcta gtgtagccgt agttaggcca ccacttcaag    6420
aactctgtag caccgcctac atacctcgct ctgctaatcc tgttaccagt ggctgctgcc    6480
agtggcgata agtcgtgtct taccgggttg gactcaagac gatagttacc ggataaggcg    6540
cagcggtcgg gctgaacggg gggttcgtgc acacagccca gcttggagcg aacgacctac    6600
accgaactga gatacctaca gcgtgagcat tgagaaagcg ccacgcttcc cgaagggaga    6660
aaggcggaca ggtatccggt aagcggcagg gtcggaacag gagagcgcac gagggagctt    6720
ccagggggaa acgcctggta tctttatagt cctgtcgggt ttcgccacct ctgacttgag    6780
cgtcgatttt tgtgatgctc gtcagggggg cggagcctat ggaaaaacgc cagcaacgcg    6840
gcctttttac ggttcctggc cttttgctgg ccttttgctc acatgttctt tcctgcgtta    6900
tcccctgatt ctgtggataa ccgtattacc gcctttgagt gagctgatac cgctcgccgc    6960
agccgaacga ccgagcgcag cgagtcagtg agcgaggaag cggaagagcg cccaatacgc    7020
aaaccgcctc tccccgcgcg ttggccgatt cattaatgca ggttaacctg cttatcgaa    7080 attaatacga ctcactatag ggagaccggc agatcgatct gtcga                   7125
```

<210> SEQ ID NO 6
<211> LENGTH: 8420
<212> TYPE: DNA
<213> ORGANISM: Unknown Organism
<220> FEATURE:
<223> OTHER INFORMATION: Description of Unknown Organism: pTRABacHuLCHC1
      DNA sequence

<400> SEQUENCE: 6

```
gcagttcgtt gacgccttcc tccgtgtggc cgaacacgtc gagcgggtgg tcgatgacca     60
gcggcgtgcc gcacgcgacg cacaagtatc tgtacaccga atgatcgtcg ggcgaaggca    120
cgtcggcctc caagtggcaa tattggcaaa ttcgaaaata tatacagttg ggttgtttgc    180
gcatatctat cgtggcgttg ggcatgtacg tccgaacgtt gatttgcatg caagccgaaa    240
ttaaatcatt gcgattagtg cgattaaaac gttgtacatc ctcgctttta atcatgccgt    300
cgattaaatc gcgcaatcga gtcaagtgat caaagtgtgg aataatgttt tctttgtatt    360
cccgagtcaa gcgcagcgcg tattttaaca aactagccat cttgtaagtt agtttcattt    420
aatgcaactt tatccaataa tatattatgt atcgcacgtc aagaattaac aatgcgcccg    480
```

```
ttgtcgcatc tcaacacgac tatgatagag atcaaataaa gcgcgaatta aatagcttgc    540
gacgcaacgt gcacgatctg tgcacgcgtt ccggcacgag ctttgattgt aataagtttt    600
tacgaagcga tgacatgacc cccgtagtga caacgatcac gcccaaaaga actgccgact    660
acaaaattac cgagtatgtc ggtgacgtta aaactattaa gccatccaat cgaccgttag    720
tcgaatcagg accgctggtg cgagaagccg cgaagtatgg cgaatgcatc gtataacgtg    780
tggagtccgc tcattagagc gtcatgttta gacaagaaag ctacatattt aattgatccc    840
gatgatttta ttgataaatt gaccctaact ccatacacgg tattctacaa tggcggggtt    900
ttggtcaaaa tttccggact gcgattgtac atgctgttaa cggctccgcc cactattaat    960
gaaattaaaa attccaattt taaaaaacgc agcaagagaa acatttgtat gaaagaatgc   1020
gtagaaggaa agaaaaatgt cgtcgacatg ctgaacaaca agattaatat gcctccgtgt   1080
ataaaaaaaa tattgaacga tttgaaagaa acaatgtac cgcgcggcgg tatgtacagg    1140
aagaggttta tactaaactg ttacattgca acgtggttt cgtgtgccaa gtgtgaaaac    1200
cgatgtttaa tcaaggctct gacgcatttc tacaaccacg actccaagtg tgtgggtgaa   1260
gtcatgcatc ttttaatcaa atcccaagat gtgtataaac caccaaactg ccaaaaaatg   1320
aaaactgtcg acaagctctg tccgtttgct ggcaactgca agggtctcaa tcctatttgt   1380
aattattgaa tataaaaaca attataaatg ctaaatttgt tttttattaa cgatacaaac   1440
caaacgcaac aagaacattt gtagtattat ctataattga aaacgcgtag ttataatcgc   1500
tgaggtaata tttaaaatca ttttcaaatg attcacagtt aatttgcgac aatataattt   1560 tatttcaca taaactagac gccttgtcgt cttcttcttc gtattccttc tcttttcat     1620 ttttctcctc ataaaaatta acatagttat tatcgtatcc atatatgtat ctatcgtata   1680
gagtaaattt tttgttgtca taaatatata tgtcttttt aatggggtgt atagtaccgc    1740
tgcgcatagt ttttctgtaa tttacaacag tgctattttc tggtagttct tcggagtgtg   1800
ttgctttaat tattaaattt atataatcaa tgaatttggg atcgtcggtt ttgtacaata   1860
tgttgccggc atagtacgca gcttcttcta gttcaattac accatttttt agcagcaccg   1920
gattaacata acttttccaaa atgttgtacg aaccgttaaa caaaaacagt tcacctccct   1980
tttctatact attgtctgcg agcagttgtt tgttgttaaa aataacagcc attgtaatga   2040
gacgcacaaa ctaatatcac aaactggaaa tgtctatcaa tatatagttg ctgatatctc   2100
cccagcatgc ctgctattgt cttcccaatc ctcccccttg ctgtcctgcc ccaccccacc   2160
ccccagaata gaatgacacc tactcagaca atgcgatgca atttcctcat tttattagga   2220
aaggacagtg ggagtggcac cttccagggt caaggaaggc acgggggagg ggcaaacaac   2280
agatggctgg caactagaag gcacagtcga ggctgatcag cgagctctag tctagactat   2340
tatttacccg gagacaggga gaggctcttc tgcgtgtagt ggttgtgcag agcctcatgc   2400
atcacggagc atgagaagac gttccccctgc tgccacctgc tcttgtccac ggtgagcttg   2460
ctgtagagga agaaggagcc gtcggagtcc agcacgggag gcgtggtctt gtagttgttc   2520
tccggctgcc cattgctctc ccactccacg gcgatgtcgc tgggatagaa gcctttgacc   2580
aggcaggtca ggctgacctg gttcttggtc agctcatccc gggatggggg cagggtgtac   2640
acctgtggtt ctcggggctg ccctttggct ttggagatgg ttttctcgat ggggggctggg   2700 agggctttgt tggagacctt gcacttgtac tccttgccat tcagccagtc ctggtgcagg   2760
acggtgagga cgctgaccac acggtacgtg ctgttgtact gctcctcccg cggctttgtc   2820
ttggcattat gcacctccac gccgtccacg taccagttga acttgacctc agggtcttcg   2880
```

```
tggctcacgt ccaccaccac gcatgtgacc tcaggggtcc gggagatcat gagggtgtcc    2940
ttgggttttg gggggaagag gaagactgac ggtcccccca ggagttcagg tgctgggcac    3000
ggtgggcatg tgtgagtttt gtcacaagat ttgggctcaa ctttcttgtc caccttggtg    3060
ttgctgggct tgtgattcac gttgcagatg taggtctggg tgcccaagct gctggagggc    3120
acggtcacca cgctgctgag ggagtagagt cctgaggact gtaggacagc cgggaaggtg    3180
tgcacgccgc tggtcagggc gcctgagttc acgacaccg tcaccggttc ggggaagtag    3240
tccttgacca ggcagcccag ggccgctgtg cccccagagg tgctcttgga ggagggtgcc    3300
aggggggaaga ccgatgggcc cactagtgca acgttgacta agaatttcat gcggccgcgt    3360
acgattgtaa ataaaatgta atttacagta tagtatttta attaatatac aaatgatttg    3420
ataataattc ttatttaact ataatatatt gtgttgggtt gaattaaagg tcccggcatc    3480
ctcaaatgca taatatcata gtccccttg ttgtaagtga tgcgtatttc tgaatctttg    3540
taaaatagca cacaggactc caacgcgttt ggcgttttat tttcttgctc gaggatatca    3600
tggagataat taaaatgata accatctcgc aaataaataa gtattttact gttttcgtaa    3660
cagtttgta ataaaaaaac ctataaatat tccggattat tcataccgtc ccaccatcgg    3720
gcgtgctagc ggatccatgg tgggaccctg catgctgctg ctgctgctgc tgctaggcct    3780
caccaagtgt cttcatcttc ccgccatctg atgagcagtt gaaatctgga actgcctctg    3840
ttgtgtgcct gctgaataac ttctatccca gagaggccaa agtacagtgg aaggtggata    3900
acgccctcca atcgggtaac tcccaggaga gtgtcacaga gcaggacagc aaggacagca    3960
cctacagcct cagcagcacc ctgacgctga gcaaagcaga ctacgagaaa cacaaagtct    4020
acgcctgcga agtcacccat cagggcctga gctcgcccgt cacaaagagc ttcaacaggg    4080
gagagtgtta ataagaagctt gtcgttggat ggaaaggaaa agagttctac agggaaactt    4140
ggacccgctt catggaagac agcttcccca ttgttaacga ccaagaagtg atggatgttt    4200
tccttgttgt caacatgcgt cccactagac ccaaccgttg ttacaaattc ctggcccaac    4260
acgctctgcg ttgcgacccc gactatgtac ctcatgacgt gattaggatc gtcgagcctt    4320
catgggtggg cagcaacaac gagtaccgca tcagcctggc taagaagggc ggcggctgcc    4380
caataatgaa ccttcactct gagtacacca actcgttcga acagttcatc gatcgtgtca    4440
tctgggagaa cttctacaag cccatcgttt acatcggtac cgactctgct gaagaggagg    4500
aaattctcct tgaagtttcc ctggtgttca agtaaaggga gtttgcacca gacgcacctc    4560
tgttcactgg tccggcgtat taaaacacga tacattgtta ttagtacatt tattaagcgc    4620
tagattctgt gcgttgttga tttacagaca attgttgtac gtattttaat aattcattaa    4680
atttataatc tttagggtgg tatgttagag cgaaaatcaa atgattttca gcgtctttat    4740
atctgaattt aaatattaaa tcctcaatag atttgtaaaa taggtttcga ttagtttcaa    4800
acaagggttg ttttttccgaa ccgatggctg gactatctaa tggattttcg ctcaacgcca    4860
caaaacttgc caaatcttgt agcagcaatc tagctttgtc gatattcgtt tgtgttttgt    4920
tttgtaataa aggttcgacg tcgttcaaaa tattatgcgc ttttgtattt ctttcatcac    4980
tgtcgttagt gtacaattga ctcgacgtaa acacgttaaa taaagctagc ttggacatat    5040
ttaacatcgg gcgtgttagc tttattaggc cgattatcgt cgtcgtccca accctcgtcg    5100
ttagaagttg cttccgaaga cgattttgcc atagccacac gacgcctatt aattgtgtcg    5160
gctaacacgc ccgcgatcaa atttgtagtt gagcttttg gaattattc tgattgcggg    5220
cgttttgggg cgggtttcaa tctaactgtg cccgatttta attcagacaa cacgttagaa    5280
```

-continued

```
agcgatggtg caggcggtgg taacatttca gacggcaaat ctactaatgg cggcggtggt    5340
ggagctgatg ataaatctac catcggtgga ggcgcaggcg gggctggcgg cggaggcgga    5400
ggcggaggtg gtggcggtga tgcagacggc ggtttaggct caaatgtctc tttaggcaac    5460
acagtcggca cctcaactat tgtactggtt tcgggcgccg tttttggttt gaccggtctg    5520
agacgagtgc gattttttc gtttctaata gcttccaaca attgttgtct gtcgtctaaa    5580
ggtgcagcgg gttgaggttc cgtcggcatt ggtggagcgg gcggcaattc agacatcgat    5640
ggtggtggtg gtggtggagg cgctggaatg ttaggcacgg gagaaggtgg tggcggcggt    5700
gccgccggta taatttgttc tggtttagtt tgttcgcgca cgattgtggg caccggcgca    5760
ggcgccgctg gctgcacaac ggaaggtcgt ctgcttcgag gcagcgcttg gggtggtggc    5820
aattcaatat tataattgga atacaaatcg taaaaatctg ctataagcat tgtaatttcg    5880
ctatcgttta ccgtgccgat atttaacaac cgctcaatgt aagcaattgt attgtaaaga    5940
gattgtctca agctccgcac gccgataaca agccttttca ttttttactac agcattgtag    6000 tggcgagaca cttcgctgtc gtcgactcga gttctatagt gtcacctaaa tcgtatgtgt    6060
atgatacata aggttatgta ttaattgtag ccgcgttcta acgacaatat gtccatatgg    6120
tgcactctca gtacaatctg ctctgatgcc gcatagttaa gccagccccg cacccgcca    6180 acaccgctg acgcgccctg acgggcttgt ctgctcccgg catccgctta cagacaagct    6240
gtgaccgtct ccgggagctg catgtgtcag aggttttcac cgtcatcacc gaaacgcgcg    6300
agaggaaagg gcctcgtgat acgcctattt ttataggtta atgtcatgat aataatggtt    6360
tcttagacgt caggtggcac ttttcgggga atgtgcgcg gaacccctat ttgtttattt     6420
ttctaaatac attcaaatat gtatccgctc atgagacaat aaccctgata atgcttcaa     6480 taatattgaa aaggaagag tatgagtatt caacatttcc gtgtcgccct tattcccttt     6540
tttgcggcat tttgccttcc tgttttgct cacccagaaa cgctggtgaa agtaaaagat    6600
gctgaagatc agttgggtgc acgagtgggt tacatcgaac tggatctcaa cagcggtaag    6660
atccttgaga gttttcgccc cgaagaacgt tttccaatga tgagcacttt taaagttctg    6720
ctatgtggcg cggtattatc ccgtattgac gccgggcaag agcaactcgg tcgccgcata    6780
cactattctc agaatgactt ggttgagtac tcaccagtca cagaaaagca tcttacggat    6840
ggcatgacag taagagaatt atgcagtgct gccataacca tgagtgataa cactgcggcc    6900
aacttacttc tgacaacgat cggaggaccg aaggagctaa ccgcttttt gcacaacatg    6960 ggggatcatg taactcgcct tgatcgttgg gaaccggagc tgaatgaagc cataccaaac    7020
gacgagcgtg acaccacgat gcctgtagca atggcaacaa cgttgcgcaa actattaact    7080
ggcgaactac ttactctagc ttcccggcaa caattaatag actggatgga gcggataaa     7140 gttgcaggac cacttctgcg ctcggccctt ccggctggct ggtttattgc tgataaatct    7200
ggagccggtg agcgtgggtc tcgcggtatc attgcagcac tggggccaga tggtaagccc    7260
tcccgtatcg tagttatcta cacgacgggg agtcaggcaa ctatggatga acgaaataga    7320
cagatcgctg agataggtgc ctcactgatt aagcattggt aactgtcaga ccaagtttac    7380
tcatatatac tttagatgat ttaaaacttc attttaatt taaaggatc taggtgaaga    7440 tccttttga taatctcatg accaaaatcc cttaacgtga gttttcgttc cactgagcgt    7500
cagaccccgt agaaaagatc aaaggatctt cttgagatcc tttttttctg cgcgtaatct    7560
gctgcttgca aacaaaaaa ccaccgctac cagcggtggt ttgtttgccg gatcaagagc    7620
taccaactct ttttccgaag gtaactggct tcagcagagc gcagatacca aatactgtcc    7680
```

-continued

```
ttctagtgta gccgtagtta ggccaccact tcaagaactc tgtagcaccg cctacatacc    7740
tcgctctgct aatcctgtta ccagtggctg ctgccagtgg cgataagtcg tgtcttaccg    7800
ggttggactc aagacgatag ttaccggata aggcgcagcg gtcgggctga acggggggtt    7860
cgtgcacaca gcccagcttg gagcgaacga cctacaccga actgagatac ctacagcgtg    7920
agcattgaga aagcgccacg cttcccgaag ggagaaaggc ggacaggtat ccggtaagcg    7980
gcagggtcgg aacaggagag cgcacgaggg agcttccagg gggaaacgcc tggtatcttt    8040
atagtcctgt cgggtttcgc cacctctgac ttgagcgtcg atttttgtga tgctcgtcag    8100
gggggcggag cctatggaaa aacgccagca acgcggcctt tttacggttc ctggccttttt   8160
gctggccttt tgctcacatg ttctttcctg cgttatcccc tgattctgtg gataaccgta    8220
ttaccgcctt tgagtgagct gataccgctc gccgcagccg aacgaccgag cgcagcgagt    8280
cagtgagcga ggaagcggaa gagcgcccaa tacgcaaacc gcctctcccc gcgcgttggc    8340
cgattcatta atgcaggtta acctggctta tcgaaattaa tacgactcac tatagggaga    8400
ccggcagatc gatctgtcga                                                8420
```

<210> SEQ ID NO 7
<211> LENGTH: 8415
<212> TYPE: DNA
<213> ORGANISM: Unknown Organism
<220> FEATURE:
<223> OTHER INFORMATION: Description of Unknown Organism: pTRABacHuLCHC1
      DNA sequence

<400> SEQUENCE: 7

```
gcagttcgtt gacgccttcc tccgtgtggc cgaacacgtc gagcgggtgg tcgatgacca      60
gcggcgtgcc gcacgcgacg cacaagtatc tgtacaccga atgatcgtcg ggcgaaggca    120
cgtcggcctc caagtggcaa tattggcaaa ttcgaaaata tatacagttg ggttgtttgc    180
gcatatctat cgtggcgttg ggcatgtacg tccgaacgtt gatttgcatg caagccgaaa    240
ttaaatcatt gcgattagtg cgattaaaac gttgtacatc ctcgctttta atcatgccgt    300
cgattaaatc gcgcaatcga gtcaagtgat caaagtgtgg aataatgttt tctttgtatt    360
cccgagtcaa gcgcagcgcg tattttaaca aactagccat cttgtaagtt agtttcatttt  420
aatgcaactt tatccaataa tatattatgt atcgcacgtc aagaattaac aatgcgcccg    480
ttgtcgcatc tcaacacgac tatgatagag atcaaataaa gcgcgaatta aatagcttgc    540
gacgcaacgt gcacgatctg tgcacgcgtt ccggcacgag ctttgattgt aataagtttt    600
tacgaagcga tgacatgacc cccgtagtga caacgatcac gcccaaaaga actgccgact    660
acaaaattac cgagtatgtc ggtgacgtta aaactattaa gccatccaat cgaccgttag    720
tcgaatcagg accgctggtg cgagaagccg cgaagtatgg cgaatgcatc gtataacgtg    780
tggagtccgc tcattagagc gtcatgttta gacaagaaag ctacatattt aattgatccc    840
gatgatttta ttgataaatt gaccctaact ccatacacgg tattctacaa tggcggggtt    900
ttggtcaaaa tttccggact gcgattgtac atgctgttaa cggctccgcc cactattaat    960
gaaattaaaa attccaattt taaaaaacgc agcaagagaa acatttgtat gaaagaatgc   1020
gtagaaggaa agaaaaatgt cgtcgacatg ctgaacaaca agattaatat gcctccgtgt   1080
ataaaaaaaa tattgaacga tttgaaagaa acaatgtac gcgcggcgg tatgtacagg    1140
aagaggttta tactaaactg ttacattgca aacgtggttt cgtgtgccaa gtgtgaaaac   1200
cgatgtttaa tcaaggctct gacgcatttc tacaaccacg actccaagtg tgtgggtgaa   1260
gtcatgcatc ttttaatcaa atcccaagat gtgtataaac caccaaactg ccaaaaaatg   1320
```

-continued

```
aaaactgtcg acaagctctg tccgtttgct ggcaactgca agggtctcaa tcctatttgt    1380
aattattgaa aataaaaca attataaatg ctaaatttgt tttttattaa cgatacaaac    1440
caaacgcaac aagaacattt gtagtattat ctataattga aaacgcgtag ttataatcgc    1500
tgaggtaata tttaaaatca ttttcaaatg attcacagtt aatttgcgac aatataattt    1560
tattttcaca taaactagac gccttgtcgt cttcttcttc gtattccttc tcttttcat     1620
ttttctcctc ataaaaatta acatagttat tatcgtatcc atatatgtat ctatcgtata    1680
gagtaaattt tttgttgtca taaatatata tgtctttttt aatggggtgt atagtaccgc    1740
tgcgcatagt ttttctgtaa tttacaacag tgctattttc tggtagttct tcggagtgtg    1800
ttgctttaat tattaaattt atataatcaa tgaatttggg atcgtcggtt ttgtacaata    1860
tgttgccggc atagtacgca gcttcttcta gttcaattac accatttttt agcagcaccg    1920
gattaacata actttccaaa atgttgtacg aaccgttaaa caaaaacagt tcacctccct    1980
tttctatact attgtctgcg agcagttgtt tgttgttaaa ataacagcc attgtaatga     2040
gacgcacaaa ctaatatcac aaactggaaa tgtctatcaa tatatagttg ctgatatctc    2100
cccagcatgc ctgctattgt cttcccaatc ctccccttg ctgtcctgcc caccccacc      2160
ccccagaata gaatgacacc tactcagaca atgcgatgca atttcctcat tttattagga    2220
aaggacagtg ggagtggcac cttccagggt caaggaaggc acgggggagg ggcaaacaac    2280
agatggctgg caactagaag gcacagtcga ggctgatcag cgagctctag tctagactat    2340
tatttacccg gagacaggga gaggctcttc tgcgtgtagt ggttgtgcag agcctcatgc    2400
atcacggagc atgagaagac gttcccctgc tgccacctgc tcttgtccac ggtgagcttg    2460
ctgtagagga agaaggagcc gtcggagtcc agcacgggag gcgtggtctt gtagttgttc    2520
tccggctgcc cattgctctc ccactccacg gcgatgtcgc tgggatagaa gcctttgacc    2580
aggcaggtca ggctgacctg gttcttggtc agctcatccc gggatggggg cagggtgtac    2640
acctgtggtt ctcggggctg cccttttggct ttggagatgg ttttctcgat gggggctggg    2700
agggctttgt tggagacctt gcacttgtac tccttgccat tcagccagtc ctggtgcagg    2760
acggtgagga cgctgaccac acggtacgtg ctgttgtact gctcctcccg cggctttgtc    2820
ttggcattat gcacctccac gccgtccacg taccagttga acttgacctc agggtcttcg    2880
tggctcacgt ccaccaccac gcatgtgacc tcaggggtcc gggagatcat gagggtgtcc    2940
ttgggttttg gggggaagag gaagactgac ggtcccccca ggagttcagg tgctgggcac    3000
ggtgggcatg tgtgagtttt gtcacaagat ttgggctcaa cttcttgtc caccttggtg      3060
ttgctgggct tgtgattcac gttgcagatg taggtctggg tgcccaagct gctggagggc    3120
acggtcacca cgctgctgag ggagtagagt cctgaggact gtaggacagc cgggaaggtg    3180
tgcacgccgc tggtcagggc gcctgagttc cacgacaccg tcaccggttc ggggaagtag    3240
tccttgacca ggcagcccag ggccgctgtg cccccagagg tgctcttgga ggagggtgcc    3300
aggggggaaga ccgatgggcc cactagtgca acgttgacta agaatttcat gcggccgcgt    3360
acgattgtaa ataaaatgta atttacagta tagtatttta attaatatac aaatgatttg    3420
ataataattc ttatttaact ataatatatt gtgttgggtt gaattaaagg tcccggcatc    3480
ctcaaatgca taatatcata gtccccttg ttgtaagtga tgcgtatttc tgaatctttg     3540
taaaatagca cacaggactc caacgcgttt ggcgttttat tttcttgctc gaggatatca    3600
tggagataat taaatgata accatctcgc aaataaataa gtattttact gttttcgtaa    3660
cagttttgta ataaaaaaac ctataaatat tccggattat tcataccgtc ccaccatcgg    3720
```

```
gcgtgctagc ggatccatgg tgggaccctg catgctgctg ctgctgctgc tgctaggcct    3780
cacccagtgt cactctgttc ccgccctcct ctgaggagct tcaagccaac aaggccacac    3840
tggtgtgtct cataagtgac ttctacccgg gagccgtgac agtggcctgg aaggcagata    3900
gcagccccgt caaggcggga gtggagacca ccacaccctc caaacaaagc aacaacaagt    3960
acgcggccag cagctacctg agcctgacgc ctgagcagtg gaagtcccac aaaagctaca    4020
gctgccaggt cacgcatgaa gggagcaccg tggagaagac agtggcccct acagaatgtt    4080
catagtaaaa gcttgtcgtt ggatggaaag gaaaagagtt ctacagggaa acttggaccc    4140
gcttcatgga agacagcttc cccattgtta acgaccaaga agtgatggat gttttccttg    4200
ttgtcaacat gcgtcccact agacccaacc gttgttacaa attcctggcc aacacgctc    4260 tgcgttgcga ccccgactat gtacctcatg acgtgattag gatcgtcgag ccttcatggg    4320
tgggcagcaa caacgagtac cgcatcagcc tggctaagaa gggcggcggc tgcccaataa    4380
tgaaccttca ctctgagtac accaactcgt tcgaacagtt catcgatcgt gtcatctggg    4440
agaacttcta caagcccatc gtttacatcg gtaccgactc tgctgaagag gaggaaattc    4500
tccttgaagt ttccctggtg ttcaaagtaa aggagtttgc accagacgca cctctgttca    4560
ctggtccggc gtattaaaac acgatacatt gttattagta catttattaa gcgctagatt    4620
ctgtgcgttg ttgatttaca gacaattgtt gtacgtattt taataattca ttaaatttat    4680
aatctttagg gtggtatgtt agagcgaaaa tcaaatgatt ttcagcgtct ttatatctga    4740
atttaaatat taaatcctca atagatttgt aaaataggtt tcgattagtt tcaaacaagg    4800 gttgttttc cgaaccgatg gctggactat ctaatggatt ttcgctcaac gccacaaaac    4860
ttgccaaatc ttgtagcagc aatctagctt tgtcgatatt cgtttgtgtt ttgttttgta    4920
ataaaggttc gacgtcgttc aaaatattat gcgcttttgt atttctttca tcactgtcgt    4980
tagtgtacaa ttgactcgac gtaaacacgt taaataaagc tagcttggac atatttaaca    5040
tcgggcgtgt tagctttatt aggccgatta tcgtcgtcgt cccaaccctc gtcgttagaa    5100
gttgcttccg aagacgattt tgccatagcc acacgacgcc tattaattgt gtcggctaac    5160
acgtccgcga tcaaatttgt agttgagctt tttggaatta tttctgattg cgggcgtttt    5220
tgggcgggtt tcaatctaac tgtgcccgat tttaattcag acaacacgtt agaaagcgat    5280
ggtgcaggcg gtggtaacat ttcagacggc aaatctacta atggcggcgg tggtggagct    5340
gatgataaat ctaccatcgg tggaggcgca ggcggggctg gcggcggagg cggaggcgga    5400
ggtggtggcg gtgatgcaga cggcggttta ggctcaaatg tctctttagg caacacagtc    5460
ggcacctcaa ctattgtact ggtttcgggc gccgttttg gtttgaccgg tctgagacga    5520
gtgcgatttt tttcgtttct aatagcttcc aacaattgtt gtctgtcgtc taaaggtgca    5580
gcgggttgag gttccgtcgg cattggtgga gcggcggca attcagacat cgatggtggt    5640
ggtggtggtg gaggcgctgg aatgttaggc acgggagaag gtggtggcgg cggtgccgcc    5700 ggtataatt gttctggttt agtttgttcg cgcacgattg tgggcaccgg cgcaggcgcc    5760
gctggctgca aacggaagg tcgtctgctt cgaggcagcg cttggggtgg tggcaattca    5820
atattataat tggaatacaa atcgtaaaaa tctgctataa gcattgtaat ttcgctatcg    5880
tttaccgtgc cgatatttaa caaccgctca atgtaagcaa ttgtattgta aagagattgt    5940
ctcaagctcc gcacgccgat aacaagcctt tcatttttta ctacagcatt gtagtggcga    6000
gacacttcgc tgtcgtcgac tcgagttcta tagtgtcacc taaatcgtat gtgtatgata    6060
cataaggtta tgtattaatt gtagccgcgt tctaacgaca atatgtccat atggtgcact    6120
```

```
ctcagtacaa tctgctctga tgccgcatag ttaagccagc cccgacaccc gccaacaccc    6180
gctgacgcgc cctgacgggc ttgtctgctc ccggcatccg cttacagaca agctgtgacc    6240
gtctccggga gctgcatgtg tcagaggttt tcaccgtcat caccgaaacg cgcgagagga    6300
aagggcctcg tgatacgcct attttatag gttaatgtca tgataataat ggtttcttag    6360
acgtcaggtg cacttttcg gggaaatgtg cgcggaaccc ctatttgttt attttctaa    6420
atacattcaa atatgtatcc gctcatgaga caataaccct gataaatgct tcaataatat    6480
tgaaaagga agagtatgag tattcaacat ttccgtgtcg cccttattcc cttttttgcg    6540
gcatttgcc ttcctgtttt tgctcaccca gaaacgctgg tgaaagtaaa agatgctgaa    6600
gatcagttgg gtgcacgagt gggttacatc gaactggatc tcaacagcgg taagatcctt    6660
gagagttttc gccccgaaga acgttttcca atgatgagca cttttaaagt tctgctatgt    6720
ggcgcggtat tatcccgtat tgacgccggg caagagcaac tcggtcgccg catacactat    6780
tctcagaatg acttggttga gtactcacca gtcacagaaa agcatcttac ggatggcatg    6840
acagtaagag aattatgcag tgctgccata accatgagtg ataacactgc ggccaactta    6900
cttctgacaa cgatcggagg accgaaggag ctaaccgctt ttttgcacaa catgggggat    6960
catgtaactc gccttgatcg ttgggaaccg gagctgaatg aagccatacc aaacgacgag    7020
cgtgacacca cgatgcctgt agcaatggca acaacgttgc gcaaactatt aactggcgaa    7080
ctacttactc tagcttcccg gcaacaatta atagactgga tggaggcgga taaagttgca    7140
ggaccacttc tgcgctcggc ccttccggct ggctggttta ttgctgataa atctggagcc    7200
ggtgagcgtg ggtctcgcgg tatcattgca gcactggggc cagatggtaa gccctcccgt    7260
atcgtagtta tctacacgac ggggagtcag gcaactatgg atgaacgaaa tagacagatc    7320
gctgagatag gtgcctcact gattaagcat tggtaactgt cagaccaagt ttactcatat    7380
atactttaga ttgatttaaa acttcatttt taatttaaaa ggatctaggt gaagatcctt    7440
tttgataatc tcatgaccaa aatcccttaa cgtgagtttt cgttccactg agcgtcagac    7500
cccgtagaaa agatcaaagg atcttcttga gatcctttt ttctgcgcgt aatctgctgc    7560
ttgcaaacaa aaaaaccacc gctaccagcg gtggtttgtt gccggatca agagctacca    7620
actctttttc cgaaggtaac tggcttcagc agagcgcaga taccaaatac tgtccttcta    7680
gtgtagccgt agttaggcca ccacttcaag aactctgtag caccgcctac atacctcgct    7740
ctgctaatcc tgttaccagt ggctgctgcc agtggcgata gtcgtgtct taccgggttg    7800
gactcaagac gatagttacc ggataaggcg cagcggtcgg gctgaacggg gggttcgtgc    7860
acacagccca gcttggagcg aacgacctac accgaactga gatacctaca gcgtgagcat    7920
tgagaaagcg ccacgcttcc cgaagggaga aaggcggaca ggtatccggt aagcggcagg    7980
gtcggaacag gagagcgcac gagggagctt ccagggggaa acgcctggta tctttatagt    8040
cctgtcgggt ttcgccacct ctgacttgag cgtcgatttt tgtgatgctc gtcagggggg    8100
cggagcctat ggaaaaacgc cagcaacgcg gcctttttac ggttcctggc cttttgctgg    8160
ccttttgctc acatgttctt tcctgcgtta tcccctgatt ctgtggataa ccgtattacc    8220
gcctttgagt gagctgatac cgctcgccgc agccgaacga ccgagcgcag cgagtcagtg    8280
agcgaggaag cggaagagcg cccaatacgc aaaccgcctc tccccgcgcg ttggccgatt    8340
cattaatgca ggttaacctg gcttatcgaa attaatacga ctcactatag ggagaccggc    8400
agatcgatct gtcga                                                    8415
```

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 8
cagatcacta gttttatgg tcgtgtacat ttcttacatc tatgcg                46

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 9
ctgagtaggc ctgaggctac agctctccct gggc                            34

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 10
ggaagtagtc cttgaccagg cag                                        23

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 11
gggaaaaggg ttgggcccga tgcac                                      25

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 12
gatgaagaca cttggtgcag ccacag                                     26

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 13
ggaacagagt gacactgggt gcagccttgg gctg                            34

<210> SEQ ID NO 14
<211> LENGTH:
<212> TYPE:
<213> ORGANISM:

```
<400> SEQUENCE: 14

000

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 15
actagtgcaa cgttgactaa gaatttcatg cggccgc                                37

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 16
gcggccgcat gaaattctta gtcaacgttg cactagt                                37

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: Primer

<400> SEQUENCE: 17
gcggatccat ggtgggaccc tgcatgctgc tgctgctgct gctgctaggc ctggaattcc       60

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Primer

<400> SEQUENCE: 18
ggaattccag gcctagcagc agcagcagca gcagcatgca gggtcccacc atggatccgc       60

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 19
tgtgactagt atgtatcggc ccatcggtct tcccct                                 37

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 20
tttctagact attatttacc cggagacagg gagag                                  35
```

```
<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 21
ctaggcctat gtatcaccaa gtgtcttcat cttcccgcca tct                43

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 22
cccaagcttc tattaacact ctcccctgtt gaagct                        36

<210> SEQ ID NO 23
<211> LENGTH:
<212> TYPE:
<213> ORGANISM:

<400> SEQUENCE: 23

000

<210> SEQ ID NO 24
<211> LENGTH:
<212> TYPE:
<213> ORGANISM:

<400> SEQUENCE: 24

000

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 25
aaatgataac catctcgc                                            18

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 26
tttactgttt tcgtaacagt tttg                                     24

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 27
ttggagggcg ttatccacct tc                                       22
```

```
<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 28
ctgtaaatca acaacgcaca g                                           21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 29
caacaacgca cagaatctag                                             20

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 30 gggacccttta attcaaccca acac                                       24

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 31
aaacgcgttg gagtcttgtg tgc                                         23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 32
ggaagtagtc cttgaccagg cag                                         23

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 33
ctgagttcca cgacaccgtc ac                                          22

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 34
tagagtcctg aggactgtag gac                                         23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 35
ggtcgttaac aatggggaag ctg                                         23

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 36
tttactgttt tcgtaacagt tttg                                        24

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 37
ggtcgttaac aatggggaag ctg                                         23

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 38
tcaccatgga ctggacctgg ag                                          22

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 39
accatggaca tactttgttc cacgc                                       25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 40
accatggaca cactttgctc cacgc                                       25
```

```
<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 41
accatggagt ttgggctgag ctg                                            23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 42
accatggaac tggggctccg ctg                                            23

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 43
aagaacatga aacacctgtg gttcttc                                        27

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 44
atcatggggt caaccgccat cct                                            23

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 45
acaatgtctg tctccttcct catc                                           24

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 46
acatgagggt ccccgctcag c                                              21

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Primer
```

```
<400> SEQUENCE: 47
tcagctcctg gggctgctaa tg                                            22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 48
cttcctcctg ctactctggc tc                                            22

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 49
gcagacccag gtcttcattt ctc                                           23

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 50
ccaggttcac ctcctcagct tc                                            22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 51
ggtttctgct gctctgggtt cc                                            22

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 52
tcactgyrca gggtcctggg c                                             21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 53
actcaggrca caggrtcctg g                                             21
```

```
<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 54
ttgcttactg cacaggatcc gtg                                             23

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 55
cttgctcact ttacaggttc tgtg                                            24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 56
ctcactcttt gcataggttc tgtg                                            24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 57
tcaacctcta cacaggctct attg                                            24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 58
ctcactctct gcacagkctc tgwg                                            24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 59
cattttctcc acaggtctct gtgc                                            24

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Primer
```

-continued

<400> SEQUENCE: 60
cctccactgs acagggtctc tc					22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 61
ctctcactgc acaggttccc tc					22

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 62
cgctcactgc acaggttctt gg					22

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 63
cttgctgccc agggtccaat tc					22

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 64
tgcttatgga tcaggagtgg attc					24

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 65
cagtctcctc acagggtccc tc					22

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 66
tcactcactc tgcagtgtca gtg					23

-continued

<210> SEQ ID NO 67
<211> LENGTH: 70
<212> TYPE: DNA
<213> ORGANISM: Artificial Sequence
<220> FEATURE:
<223> OTHER INFORMATION: Description of Artificial Sequence: Primer

<400> SEQUENCE: 67
cagatcacta gttttatgg tcgtgtacat ttcttacatc tatgcggaga tgaaattggt    60
ggagtctggg                                                          70

<210> SEQ ID NO 68
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 68
ctgagtaggc ctgaggctac agctctccct gggcgaagtt gtgttgactc agtctcc     57

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 69
ctgagttcca cgacaccgtc ac                                            22

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 70
gggaattctc acaggagacg agg                                           23

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 71
ttggagggcg ttatccacct tc                                            22

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 72
gaagtcactt atgagacaca ccag                                          24

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Primer -continued

<400> SEQUENCE: 73
ggaagtagtc cttgaccagg cag                                        23

<210> SEQ ID NO 74
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 74
gggaaaaggg ttgggcccga tgcac                                      25

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 75
gggaaaaggg ttgggcccga tgcac                                      25

<210> SEQ ID NO 76
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 76
ggaacagagt gacactgggt gcagccttgg gctg                            34

<210> SEQ ID NO 77
<211> LENGTH: 66
<212> TYPE: DNA
<213> ORGANISM: Artificial Sequence
<220> FEATURE:
<223> OTHER INFORMATION: Description of Artificial Sequence: Primer

<400> SEQUENCE: 77
tgccgtcggc aggaggtatt tcattatgac tgtctccttg ctattatgaa cattctgtag  60
gggcca                                                            66

<210> SEQ ID NO 78
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 78
gtcagcccaa ggctgcaccc agtgtcactc tgttcc                          36

<210> SEQ ID NO 79
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 79
cgtatcaagc ttttactatg aacattctgt aggggccac                       39

```
<210> SEQ ID NO 80
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 80
cctttgataa cacccca                                              16

<210> SEQ ID NO 81
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 81
gtgttatcaa agg                                                  13

<210> SEQ ID NO 82
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 82
ctagtttgat aagggcc                                              17

<210> SEQ ID NO 83
<211> LENGTH: 9
<212> TYPE: DNA
<213> ORGANISM: Artificial Sequence
<220> FEATURE:
<223> OTHER INFORMATION: Description of Artificial Sequence: Primer

<400> SEQUENCE: 83 cttatcaaa                                                        9

<210> SEQ ID NO 84
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 84
cctttgataa caccaa                                               16

<210> SEQ ID NO 85
<211> LENGTH:
<212> TYPE:
<213> ORGANISM:

<400> SEQUENCE: 85

000

<210> SEQ ID NO 86
<211> LENGTH: 371
<212> TYPE: DNA
<213> ORGANISM: Homo sapiens

<400> SEQUENCE: 86
gacatgttgt tggtggaatc gggggggaggc ctggtccagc cgggggagtc cctgagactc    60
tcctgtgtgg cctctagatt caccttagaa cgttttgga tgacctgggt ccgccaactt    120
```

```
ccagggaagg ggctggagtg ggtggccaat ataaatcaag atggcagtca gacgtatcat      180
gcggactctg taaagggccg atttaccatc tccagagaca acggcaggaa ctccctattt      240
ttacaaatga caagtctgag agtcgcggac acggctatat attactgtgc gactaatgaa      300
acgtccagtg gcctggactg ctggggccaa ggaaccctgg tcactgtctc ctcagcttcc      360
accaagggcc c                                                          371

<210> SEQ ID NO 87
<211> LENGTH: 349
<212> TYPE: DNA
<213> ORGANISM: Homo sapiens

<400> SEQUENCE: 87
gaaatcgtgt tgacacagtc tccagccacc ctgtcttcgt ctccaggaga cagagtcgcc       60
ctctcctgca gggccagtca gagtgtaaga agttacttaa gttggtatca acagaaggct      120
ggccaggctc ccaggctcct catccataat gcatccagta gggccactgg catcccgccc      180
agattcagtg gcagtgggtc tgggacagac ttcactctca ccatcagtcg cctagagact      240
gaagatgctg cagtttatta ctgtcagcaa ctttatttct ggcctccgat attatttttc      300
ggccctggga ccaaagtgaa tatcacacga actgtggctg caccaagtg                 349

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 88
gaagtcactt atgagacaca ccag                                             24

<210> SEQ ID NO 89
<211> LENGTH: 9182
<212> TYPE: DNA
<213> ORGANISM: Artificial Sequence
<220> FEATURE:
<223> OTHER INFORMATION: Description of Artificial Sequence: Plasmid
      pTRABac/9F12 DNA sequence

<400> SEQUENCE: 89
gcagttcgtt gacgccttcc tccgtgtggc cgaacacgtc gagcgggtgg tcgatgacca       60
gcggcgtgcc gcacgcgacg cacaagtatc tgtacaccga atgatcgtcg ggcgaaggca      120
cgtcggcctc caagtggcaa tattggcaaa ttcgaaaata tatacagttg ggttgtttgc      180
gcatatctat cgtggcgttg ggcatgtacg tccgaacgtt gatttgcatg caagccgaaa      240
ttaaatcatt gcgattagtg cgattaaaac gttgtacatc ctcgcttta atcatgccgt       300 cgattaaatc gcgcaatcga gtcaagtgat caaagtgtgg aataatgttt tctttgtatt      360
cccgagtcaa gcgcagcgcg tattttaaca aactagccat cttgtaagtt agtttcattt      420
aatgcaactt tatccaataa tatattatgt atcgcacgtc aagaattaac aatgcgcccg      480
ttgtcgcatc tcaacacgac tatgatagag atcaaataaa gcgcgaatta atagcttgc      540 gacgcaacgt gcacgatctg tgcacgcgtt ccggcacgag ctttgattgt aataagtttt      600
tacgaagcga tgacatgacc cccgtagtga caacgatcac gcccaaaaga actgccgact      660
acaaaattac cgagtatgtc ggtgacgtta aaactattaa gccatccaat cgaccgttag      720
tcgaatcagg accgctggtg cgagaagccg cgaagtatgg cgaatgcatc gtataacgtg      780
tggagtccgc tcattagagc gtcatgttta gacaagaaag ctacatattt aattgatccc      840
```

```
gatgatttta ttgataaatt gaccctaact ccatacacgg tattctacaa tggcggggtt      900
ttggtcaaaa tttccggact gcgattgtac atgctgttaa cggctccgcc cactattaat      960
gaaattaaaa attccaattt taaaaaacgc agcaagagaa acatttgtat gaaagaatgc     1020
gtagaaggaa agaaaaatgt cgtcgacatg ctgaacaaca agattaatat gcctccgtgt     1080
ataaaaaaaa tattgaacga tttgaaagaa acaatgtac cgcgcggcgg tatgtacagg      1140
aagaggttta tactaaactg ttacattgca aacgtggttt cgtgtgccaa gtgtgaaaac     1200
cgatgtttaa tcaaggctct gacgcatttc tacaaccacg actccaagtg tgtgggtgaa     1260
gtcatgcatc ttttaatcaa atcccaagat gtgtataaac caccaaactg ccaaaaaatg     1320
aaaactgtcg acaagctctg tccgtttgct ggcaactgca agggtctcaa tcctatttgt     1380
aattattgaa taataaaaca attataaatg ctaaatttgt tttttattaa cgatacaaac     1440
caaacgcaac aagaacattt gtagtattat ctataattga aaacgcgtag ttataatcgc     1500
tgaggtaata tttaaaatca ttttcaaatg attcacagtt aatttgcgac aatataattt     1560
tattttcaca taaactagac gccttgtcgt cttcttcttc gtattccttc tcttttttcat    1620 ttttctcctc ataaaaatta acatagttat tatcgtatcc atatatgtat ctatcgtata     1680
gagtaaattt tttgttgtca taaatatata tgtctttttt aatggggtgt atagtaccgc     1740
tgcgcatagt ttttctgtaa tttacaacag tgctattttc tggtagttct tcggagtgtg     1800
ttgctttaat tattaaattt atataatcaa tgaatttggg atcgtcggtt ttgtacaata     1860
tgttgccggc atagtacgca gcttcttcta gttcaattac accatttttt agcagcaccg     1920
gattaacata actttccaaa atgttgtacg aaccgttaaa caaaaacagt tcacctccct     1980
tttctatact attgtctgcg agcagttgtt tgttgttaaa ataacagcc attgtaatga     2040 gacgcacaaa ctaatatcac aaactggaaa tgtctatcaa tatatagttg ctgatatctc     2100
cccagcatgc ctgctattgt cttcccaatc ctccccttg ctgtcctgcc ccaccccacc      2160
ccccagaata gaatgacacc tactcagaca atgcgatgca atttcctcat tttattagga     2220
aaggacagtg ggagtggcac cttccagggt caaggaaggc acgggggagg ggcaaacaac     2280
agatggctgg caactagaag gcacagtcga ggctgatcag cgagctctag tctagactat     2340
tatttacccg gagacaggga gaggctcttc tgcgtgtagt ggttgtgcag agcctcatgc     2400
atcacggagc atgagaagac gttccctgc tgccacctgc tcttgtccac ggtgagcttg      2460
ctgtagagga agaaggagcc gtcggagtcc agcacgggag gcgtggtctt gtagttgttc     2520
tccggctgcc cattgctctc ccactccacg gcgatgtcgc tgggatagaa gcctttgacc     2580
aggcaggtca ggctgacctg gttcttggtc agctcatccc gggatggggg cagggtgtac     2640
acctgtggtt ctcgggctg cccttttggct ttggagatgg ttttctcgat gggggctggg      2700
agggctttgt tggagacctt gcacttgtac tccttgccat tcagccagtc ctggtgcagg     2760
acggtgagga cgctgaccac acggtacgtg ctgttgtact gctcctcccg cggctttgtc     2820
ttggcattat gcacctccac gccgtccacg taccagttga acttgacctc agggtcttcg     2880
tggctcacgt ccaccaccac gcatgtgacc tcaggggtcc gggagatcat gagggtgtcc     2940
ttgggttttg gggggaagag gaagactgac ggtccccca ggagttcagg tgccggtggg      3000
catgtgtgag ttttgtcaca agatttgggc tcaactttct tgtccacctt ggtgttgctg     3060
ggcttgtgat tcacgttgca gatgtaggtc tgggtgccca agctgctgga gggcacggtc     3120
accacgctgc tgagggagta gagtcctgag gactgtagga cagccgggaa ggtgtgcacg     3180
ccgctggtca gggcgcctga gttccacgac accgtcaccg gttcggggaa gtagtccttg     3240
```

```
accaggcagc ccagggccgc tgtgccccca gaggtgctct tggaggaggg tgccagggggg    3300
aagaccgatg ggcccttggt ggaggctgag gagacggtga ccagggttcc ctggcccag      3360
gagtcaaagt agtagtgggc cagccactgt tttcccgctt tcgcacagta ataaacggcc     3420
gtgtcctcgg ctctcaggct gttcaagtgc agatatagcg tgttcatgga attgtctctg    3480
gagatggtca atcggcccgt cacggagtct gcataatatg tggtagttcc tctagcacta    3540
atagccgcga cccactccag ccccatccct ggagcctggc ggacccagct catggcatag    3600
ctgctaaagc tgaatccaga ggctgcacag gagagtctca cggacccccc aggctgtacc    3660
aagcctcccc cagactgcac cagctgcacc tcgtccgcat agatgtaaga aatgtacacg    3720
accataaaaa ctagtgcaac gttgactaag aatttcatgc ggccgcgtac gattgtaaat    3780
aaaatgtaat ttacagtata gtattttaat taatatacaa atgatttgat aataattctt    3840
atttaactat aatatattgt gttgggttga attaaaggtc ccggcatcct caaatgcata    3900
atatcatagt ccccccttgtt gtaagtgatg cgtatttctg aatctttgta aaatagcaca    3960
caggactcca acgcgtttgg cgttttattt tcttgctcga ggatatcatg gagataatta    4020
aaatgataac catctcgcaa ataaataagt atttttactgt tttcgtaaca gttttgtaat    4080
aaaaaaacct ataaatattc cggattattc ataccgtccc accatcgggc gtgctagcgg    4140
atccatggtg ggaccctgca tgctgctgct gctgctgctg ctaggcctga ggctacagct    4200
ctccctgggc atcgacatcc agatgaccca gtctccatcc tccctgtctg catctgtagg    4260
agacagagtc atcatcactt gccgggcaag tcagagtatt agcacctatt taaattggta    4320
tcagcagaaa ccagggaaag cccctaaact cctgatctat tatgcaacca atttgcaaag    4380
tggggtccca tcaaggttca gtggcagtgg atctgggaca gatttcactc tcaccatcag    4440
cagtctgcaa cctgaagatt ttgcgactta ttattgtcaa cagagttcca acaccgtcac    4500
tttcggccct gggaccaaag tggatatgaa gactgtggct gcaccaagtg tcttcatctt    4560
cccgccatct gatgagcagt tgaaatctgg aactgcctct gttgtgtgcc tgctgaataa    4620
cttctatccc agagaggcca agtacagtgg aaggtggat aacgccctcc aatcgggtaa    4680
ctcccaggag agtgtcacag agcaggacag caaggacagc acctcagcc tcagcagcac     4740
cctgacgctg agcaaagcag actacgagaa acacaaagtc tacgcctgcg aagtcaccca    4800
tcagggcctg agctcgcccg tcacaaagag cttcaacagg ggagagtgtt aatagaagct    4860
tgtcgttgga tggaaaggaa aagagttcta cagggaaact tggacccgct tcatggaaga    4920
cagcttcccc attgttaacg accaagaagt gatggatgtt ttccttgttg tcaacatgcg    4980
tcccactaga cccaaccgtt gttacaaatt cctggcccaa cacgctctgc gttgcgaccc    5040
cgactatgta cctcatgacg tgattaggat cgtcgagcc tcatgggtgg gcagcaacaa     5100
cgagtaccgc atcagcctgg ctaagaaggg cggcggctgc ccaataatga accttcactc    5160
tgagtacacc aactcgttcg aacagttcat cgatcgtgtc atctgggaga acttctacaa    5220
gcccatcgtt tacatcggta ccgactctgc tgaagaggag gaaattctcc ttgaagtttc    5280
cctggtgttc aaagtaaagg agtttgcacc agacgcacct ctgttcactg gtccggcgta    5340
ttaaaacacg atacattgtt attagtacat ttattaagcg ctagattctg tgcgttgttg    5400
atttacagac aattgttgta cgtatttta aattcatta aatttataat ctttagggtg     5460
gtatgttaga gcgaaaatca aatgatttc agcgtcttta tatctgaatt taaatattaa    5520
atcctcaata gatttgtaaa ataggtttcg attagtttca aacaagggtt gttttccga     5580
accgatggct ggactatcta atggatttc gctcaacgcc acaaaacttg ccaaatcttg    5640
```

```
tagcagcaat ctagctttgt cgatattcgt ttgtgttttg ttttgtaata aaggttcgac    5700
gtcgttcaaa atattatgcg cttttgtatt tctttcatca ctgtcgttag tgtacaattg    5760
actcgacgta aacacgttaa ataaagctag cttggacata tttaacatcg ggcgtgttag    5820
ctttattagg ccgattatcg tcgtcgtccc aaccctcgtc gttagaagtt gcttccgaag    5880
acgattttgc catagccaca cgacgcctat taattgtgtc ggctaacacg tccgcgatca    5940
aatttgtagt tgagcttttt ggaattattt ctgattgcgg gcgttttttgg gcgggtttca    6000 atctaactgt gcccgatttt aattcagaca acacgttaga aagcgatggt gcaggcggtg    6060
gtaacatttc agacggcaaa tctactaatg gcggcggtgg tggagctgat gataaatcta    6120
ccatcggtgg aggcgcaggc ggggctggcg gcggaggcgg aggcggaggt ggtggcggtg    6180
atgcagacgg cggtttaggc tcaaatgtct ctttaggcaa cacagtcggc acctcaacta    6240
ttgtactggt ttcgggcgcc gttttttggtt tgaccggtct gagacgagtg cgatttttttt    6300 cgtttctaat agcttccaac aattgttgtc tgtcgtctaa aggtgcagcg ggttgaggtt    6360
ccgtcggcat tggtggagcg ggcggcaatt cagacatcga tggtggtggt ggtggtggag    6420
gcgctggaat gttaggcacg ggagaaggtg gtggcggcgg tgccgccggt ataatttgtt    6480
ctggtttagt ttgttcgcgc acgattgtgg gcaccggcgc aggcgccgct ggctgcacaa    6540
cggaaggtcg tctgcttcga ggcagcgctt ggggtggtgg caattcaata ttataattgg    6600
aatacaaatc gtaaaaatct gctataagca ttgtaatttc gctatcgttt accgtgccga    6660
tatttaacaa ccgctcaatg taagcaattg tattgtaaag agattgtctc aagctccgca    6720
cgccgataac aagccttttc attttttacta cagcattgta gtggcgagac acttcgctgt    6780
cgtcgactcg agttctatag tgtcacctaa atcgtatgtg tatgatacat aaggttatgt    6840
attaattgta gccgcgttct aacgacaata tgtccatatg gtgcactctc agtacaatct    6900
gctctgatgc cgcatagtta agccagcccc gacacccgcc aacacccgct gacgcgccct    6960
gacgggcttg tctgctcccg gcatccgctt acagacaagc tgtgaccgtc tccgggagct    7020
gcatgtgtca gaggttttca ccgtcatcac cgaaacgcgc gagaggaaag ggcctcgtga    7080
tacgcctatt tttataggtt aatgtcatga taataatggt tcttagacg tcaggtggca    7140 cttttcgggg aaatgtgcgc ggaacccta tttgtttatt tttctaaata cattcaaata    7200
tgtatccgct catgagacaa taaccctgat aaatgcttca ataatattga aaaggaaga    7260 gtatgagtat tcaacatttc cgtgtcgccc ttattccctt ttttgcggca ttttgccttc    7320
ctgtttttgc tcacccagaa acgctggtga agtaaaaga tgctgaagat cagttgggtg    7380
cacgagtggg ttacatcgaa ctggatctca acagcggtaa gatccttgag agttttcgcc    7440
ccgaagaacg ttttccaatg atgagcactt ttaaagttct gctatgtggc gcggtattat    7500
cccgtattga cgccgggcaa gagcaactcg gtcgccgcat acactattct cagaatgact    7560
tggttgagta ctcaccagtc acagaaaagc atcttacgga tggcatgaca gtaagagaat    7620
tatgcagtgc tgccataacc atgagtgata acactgcggc caacttactt ctgacaacga    7680
tcggaggacc gaaggagcta accgcttttt tgcacaacat gggggatcat gtaactcgcc    7740
ttgatcgttg ggaaccggag ctgaatgaag ccataccaaa cgacgagcgt gacaccacga    7800
tgcctgtagc aatggcaaca acgttgcgca aactattaac tggcgaacta cttactctag    7860
cttcccggca acaattaata gactggatgg aggcggataa agttgcagga ccacttctgc    7920
gctcggccct tccggctggc tggttttattg ctgataaatc tggagccggt gagcgtgggt    7980
ctcgcggtat cattgcagca ctggggccag atggtaagcc ctcccgtatc gtagttatct    8040
```

```
acacgacggg gagtcaggca actatggatg aacgaaatag acagatcgct gagataggtg      8100
cctcactgat taagcattgg taactgtcag accaagttta ctcatatata ctttagattg      8160
atttaaaact tcattttttaa tttaaaagga tctaggtgaa gatcctttt gataatctca       8220
tgaccaaaat cccttaacgt gagttttcgt tccactgagc gtcagacccc gtagaaaaga      8280
tcaaaggatc ttcttgagat cctttttttc tgcgcgtaat ctgctgcttg caaacaaaaa      8340
aaccaccgct accagcggtg gtttgtttgc cggatcaaga gctaccaact cttttccga       8400
aggtaactgg cttcagcaga gcgcagatac caaatactgt ccttctagtg tagccgtagt      8460
taggccacca cttcaagaac tctgtagcac cgcctacata cctcgctctg ctaatcctgt      8520
taccagtggc tgctgccagt ggcgataagt cgtgtcttac cgggttggac tcaagacgat      8580
agttaccgga taaggcgcag cggtcgggct gaacggggggg ttcgtgcaca cagcccagct     8640
tggagcgaac gacctacacc gaactgagat acctacagcg tgagcattga gaaagcgcca      8700
cgcttcccga aggagaaag gcggacaggt atccggtaag cggcagggtc ggaacaggag       8760
agcgcacgag ggagcttcca gggggaaacg cctggtatct ttatagtcct gtcgggtttc      8820
gccacctctg acttgagcgt cgatttttgt gatgctcgtc aggggggcgg agcctatgga      8880
aaaacgccag caacgcggcc tttttacggt tcctggcctt ttgctggcct tttgctcaca      8940
tgttctttcc tgcgttatcc cctgattctg tggataaccg tattaccgcc tttgagtgag      9000
ctgataccgc tcgccgcagc cgaacgaccg agcgcagcga gtcagtgagc gaggaagcgg      9060
aagagcgccc aatacgcaaa ccgcctctcc ccgcgcgttg gccgattcat taatgcaggt      9120
taacctggct tatcgaaatt aatacgactc actatagggga gaccggcaga tcgatctgtc     9180
ga                                                                     9182

<210> SEQ ID NO 90
<211> LENGTH: 8435
<212> TYPE: DNA
<213> ORGANISM: Unknown Organism
<220> FEATURE:
<223> OTHER INFORMATION: Description of Unknown Organism: pTRABacHuLCHC1
      DNA sequence

<400> SEQUENCE: 90
gcagttcgtt gacgccttcc tccgtgtggc cgaacacgtc gagcgggtgg tcgatgacca        60
gcggcgtgcc gcacgcgacg cacaagtatc tgtacaccga atgatcgtcg ggcgaaggca       120
cgtcggcctc caagtggcaa tattggcaaa ttcgaaaata tatacagttg ggttgtttgc       180
gcatatctat cgtggcgttg ggcatgtacg tccgaacgtt gatttgcatg caagccgaaa       240
ttaaatcatt gcgattagtg cgattaaaac gttgtacatc ctcgctttta atcatgccgt       300
cgattaaatc gcgcaatcga gtcaagtgat caaagtgtgg aataatgttt tctttgtatt       360
cccgagtcaa gcgcagcgcg tattttaaca aactagccat cttgtaagtt agtttcattt       420
aatgcaactt tatccaataa tatattatgt atcgcacgtc aagaattaac aatgcgcccg       480
ttgtcgcatc tcaacacgac tatgatagag atcaaataaa gcgcgaatta atagcttgc        540
gacgcaacgt gcacgatctg tgcacgcgtt ccggcacgag ctttgattgt aataagtttt      600
tacgaagcga tgcatgacc cccgtagtga caacgatcac gcccaaaaga actgccgact       660
acaaaattac cgagtatgtc ggtgacgtta aaactattaa gccatccaat cgaccgttag      720
tcgaatcagg accgctggtg cgagaagccg cgaagtatgg cgaatgcatc gtataacgtg      780
tggagtccgc tcattagagc gtcatgttta gacaagaaag ctacatattt aattgatccc      840
gatgatttta ttgataaatt gaccctaact ccatacacgg tattctacaa tggcgggggtt    900
```

```
ttggtcaaaa tttccggact gcgattgtac atgctgttaa cggctccgcc cactattaat      960
gaaattaaaa attccaattt taaaaaacgc agcaagagaa acatttgtat gaaagaatgc     1020
gtagaaggaa agaaaaatgt cgtcgacatg ctgaacaaca agattaatat gcctccgtgt     1080
ataaaaaaaa tattgaacga tttgaaagaa aacaatgtac cgcgcggcgg tatgtacagg     1140
aagaggttta tactaaactg ttacattgca aacgtggttt cgtgtgccaa gtgtgaaaac     1200
cgatgtttaa tcaaggctct gacgcatttc tacaaccacg actccaagtg tgtgggtgaa     1260
gtcatgcatc ttttaatcaa atcccaagat gtgtataaac caccaaactg ccaaaaaatg     1320
aaaactgtcg acaagctctg tccgtttgct ggcaactgca agggtctcaa tcctatttgt     1380
aattattgaa taataaaaca attataaatg ctaaatttgt tttttattaa cgatacaaac     1440
caaacgcaac aagaacattt gtagtattat ctataattga aaacgcgtag ttataatcgc     1500
tgaggtaata tttaaaatca ttttcaaatg attcacagtt aatttgcgac aatataattt     1560
tattttcaca taaactagac gccttgtcgt cttcttcttc gtattccttc tcttttcat     1620 ttttctcctc ataaaaatta acatagttat tatcgtatcc atatatgtat ctatcgtata     1680
gagtaaattt tttgttgtca taaatatata tgtctttttt aatggggtgt atagtaccgc     1740
tgcgcatagt ttttctgtaa tttacaacag tgctattttc tggtagttct tcggagtgtg     1800
ttgctttaat tattaaattt atataatcaa tgaatttggg atcgtcggtt ttgtacaata     1860
tgttgccggc atagtacgca gcttcttcta gttcaattac accattttt agcagcaccg     1920 gattaacata actttccaaa atgttgtacg aaccgttaaa caaaaacagt tcacctccct     1980
tttctatact attgtctgcg agcagttgtt tgttgttaaa aataacagcc attgtaatga     2040
gacgcacaaa ctaatatcac aaactggaaa tgtctatcaa tatatagttg ctgatatctc     2100
cccagcatgc ctgctattgt cttcccaatc ctcccccttg ctgtcctgcc ccaccccacc     2160
ccccagaata gaatgacacc tactcagaca atgcgatgca atttcctcat tttattagga     2220
aaggacagtg ggagtggcac cttccagggt caaggaaggc acggggagg ggcaaacaac     2280 agatggctgg caactagaag gcacagtcga ggctgatcag cgagctctag tctagactat     2340
tatttacccg gagacaggga gaggctcttc tgcgtgtagt ggttgtgcag agcctcatgc     2400
atcacggagc atgagaagac gttccctgc tgccacctgc tcttgtccac ggtgagcttg     2460
ctgtagagga agaaggagcc gtcggagtcc agcacgggag gcgtggtctt gtagttgttc     2520
tccggctgcc cattgctctc ccactccacg gcgatgtcgc tgggatagaa gcctttgacc     2580
aggcaggtca ggctgacctg gttcttggtc agctcatccc gggatggggg cagggtgtac     2640
acctgtggtt ctcggggctg ccctttggct ttggagatgg ttttctcgat gggggctggg     2700
agggctttgt tggagacctt gcacttgtac tccttgccat tcagccagtc ctggtgcagg     2760
acggtgagga cgctgaccac acggtacgtg ctgttgtact gctcctcccg cggctttgtc     2820
ttggcattat gcacctccac gccgtccacg taccagttga acttgacctc agggtcttcg     2880
tggctcacgt ccaccaccac gcatgtgacc tcagggtcc gggagatcat gagggtgtcc     2940
ttgggttttg gggggaagag gaagactgac ggtcccccca ggagttcagg tgctgggcac     3000
ggtgggcatg tgtgagtttt gtcacaagat ttgggctcaa cttcttgtc caccttggtg     3060 ttgctgggct tgtgattcac gttgcagatg taggtctggg tgcccaagct gctggagggc     3120
acggtcacca cgctgctgag ggagtagagt cctgaggact gtaggacagc cggaaggtg     3180 tgcacgccgc tggtcagggc gcctgagttc cacgacaccg tcaccggttc ggggaagtag     3240
tccttgacca ggcagcccag ggccgctgtg cccccagagg tgctcttgga ggagggtgcc     3300
```

```
aggggaaga ccgatgggcc cttatcaaac tagtgcaacg ttgactaaga atttcatgcg    3360
gccgcgtacg attgtaaata aaatgtaatt tacagtatag tattttaatt aatatacaaa    3420
tgatttgata ataattctta tttaactata atatattgtg ttgggttgaa ttaaaggtcc    3480
cggcatcctc aaatgcataa tatcatagtc cccttgttg taagtgatgc gtatttctga    3540
atctttgtaa aatagcacac aggactccaa cgcgtttggc gttttatttt cttgctcgag    3600
gatatcatgg agataattaa aatgataacc atctcgcaaa taaataagta ttttactgtt    3660
ttcgtaacag ttttgtaata aaaaaaccta taaatattcc ggattattca taccgtccca    3720
ccatcgggcg tgctagcgga tccatggtgg gaccctgcat gctgctgctg ctgctgctgc    3780
taggccttg ataacaccaa gtgtcttcat cttcccgcca tctgatgagc agttgaaatc    3840
tggaactgcc tctgttgtgt gcctgctgaa taacttctat cccagagagg ccaaagtaca    3900
gtggaaggtg gataacgccc tccaatcggg taactcccag gagagtgtca cagagcagga    3960
cagcaaggac agcacctaca gcctcagcag caccctgacg ctgagcaaag cagactacga    4020
gaaacacaaa gtctacgcct gcgaagtcac ccatcagggc ctgagctcgc ccgtcacaaa    4080
gagcttcaac aggggagagt gttaatagaa gcttgtcgtt ggatggaaag gaaaagagtt    4140
ctacagggaa acttggaccc gcttcatgga agacagcttc cccattgtta acgaccaaga    4200
agtgatggat gttttccttg ttgtcaacat gcgtcccact agaccccaacc gttgttacaa    4260
attcctggcc caacacgctc tgcgttgcga ccccgactat gtacctcatg acgtgattag    4320
gatcgtcgag ccttcatggg tgggcagcaa caacgagtac cgcatcagcc tggctaagaa    4380
gggcggcggc tgcccaataa tgaaccttca ctctgagtac accaactcgt tcgaacagtt    4440
catcgatcgt gtcatctggg agaacttcta caagcccatc gtttacatcg gtaccgactc    4500
tgctgaagag gaggaaattc tccttgaagt ttccctggtg ttcaaagtaa aggagtttgc    4560
accagacgca cctctgttca ctggtccggc gtattaaaac acgatacatt gttattagta    4620
catttattaa gcgctagatt ctgtgcgttg ttgatttaca gacaattgtt gtacgtattt    4680
taataattca tttaaatttat aatctttagg gtggtatgtt agagcgaaaa tcaaatgatt    4740
ttcagcgtct ttatatctga atttaaatat taaatcctca atagatttgt aaaataggtt    4800
tcgattagtt tcaaacaagg gttgttttc cgaaccgatg gctggactat ctaatggatt    4860
ttcgctcaac gccacaaaac ttgccaaatc ttgtagcagc aatctagctt tgtcgatatt    4920
cgtttgtgtt ttgttttgta ataaaggttc gacgtcgttc aaaatattat gcgcttttgt    4980
atttctttca tcactgtcgt tagtgtacaa ttgactcgac gtaaacacgt taaataaagc    5040
tagcttggac atatttaaca tcgggcgtgt tagctttatt aggccgatta tcgtcgtcgt    5100
cccaaccctc gtcgttagaa gttgcttccg aagacgattt tgccatagcc acacgacgcc    5160
tattaattgt gtcggctaac acgtccgcga tcaaatttgt agttgagctt tttggaatta    5220
tttctgattg cgggcgtttt tgggcgggtt tcaatctaac tgtgcccgat tttaattcag    5280
acaacacgtt agaaagcgat ggtgcaggcg gtggtaacat ttcagacggc aaatctacta    5340
atggcggcgg tggtggagct gatgataaat ctaccatcgg tggaggcgca ggcggggctg    5400
gcggcggagg cggaggcgga ggtggtggcg gtgatgcaga cggcggttta ggctcaaatg    5460
tctctttagg caacacagtc ggcacctcaa ctattgtact ggtttcgggc gccgtttttg    5520
gtttgaccgg tctgagacga gtgcgatttt tttcgtttct aatagcttcc aacaattgtt    5580
gtctgtcgtc taaggtgca gcgggttgag gttccgtcgg cattggtgga gcgggcggca    5640
attcagacat cgatggtggt ggtggtggtg gaggcgctgg aatgttaggc acgggagaag    5700
```

```
gtggtggcgg cggtgccgcc ggtataattt gttctggttt agtttgttcg cgcacgattg   5760
tgggcaccgg cgcaggcgcc gctggctgca caacggaagg tcgtctgctt cgaggcagcg   5820
cttggggtgg tggcaattca atattataat tggaatacaa atcgtaaaaa tctgctataa   5880
gcattgtaat ttcgctatcg tttaccgtgc cgatatttaa caaccgctca atgtaagcaa   5940
ttgtattgta aagagattgt ctcaagctcc gcacgccgat aacaagcctt tcatttttta   6000
ctacagcatt gtagtggcga gacacttcgc tgtcgtcgac tcgagttcta tagtgtcacc   6060
taaatcgtat gtgtatgata cataaggtta tgtattaatt gtagccgcgt tctaacgaca   6120
atatgtccat atggtgcact ctcagtacaa tctgctctga tgccgcatag ttaagccagc   6180
cccgacaccc gccaacaccc gctgacgcgc cctgacgggc ttgtctgctc ccggcatccg   6240
cttacagaca agctgtgacc gtctccggga gctgcatgtg tcagaggttt tcaccgtcat   6300
caccgaaacg cgcgagagga aagggcctcg tgatacgcct atttttatag gttaatgtca   6360
tgataataat ggtttcttag acgtcaggtg gcacttttcg gggaaatgtg cgcggaaccc   6420
ctatttgttt attttctaa atacattcaa atatgtatcc gctcatgaga caataaccct    6480
gataaatgct tcaataatat tgaaaaagga agagtatgag tattcaacat ttccgtgtcg   6540
cccttattcc cttttttgcg gcattttgcc ttcctgtttt tgctcaccca gaaacgctgg   6600
tgaaagtaaa agatgctgaa gatcagttgg gtgcacgagt gggttacatc gaactggatc   6660
tcaacagcgg taagatcctt gagagttttc gccccgaaga acgttttcca atgatgagca   6720
cttttaaagt tctgctatgt ggcgcggtat tatcccgtat tgacgccggg caagagcaac   6780
tcggtcgccg catacactat tctcagaatg acttggttga gtactcacca gtcacagaaa   6840
agcatcttac ggatggcatg acagtaagag aattatgcag tgctgccata accatgagtg   6900
ataacactgc ggccaactta cttctgacaa cgatcggagg accgaaggag ctaaccgctt   6960
ttttgcacaa catgggggat catgtaactc gccttgatcg ttgggaaccg gagctgaatg   7020
aagccatacc aaacgacgag cgtgacacca cgatgcctgt agcaatggca acaacgttgc   7080
gcaaactatt aactggcgaa ctacttactc tagcttcccg gcaacaatta atagactgga   7140
tggaggcgga taaagttgca ggaccacttc tgcgctcggc ccttccggct ggctggttta   7200
ttgctgataa atctggagcc ggtgagcgtg ggtctcgcgg tatcattgca gcactggggc   7260
cagatggtaa gccctcccgt atcgtagtta tctacacgac ggggagtcag gcaactatgg   7320
atgaacgaaa tagacagatc gctgagatag gtgcctcact gattaagcat tggtaactgt   7380
cagaccaagt ttactcatat atactttaga ttgatttaaa acttcatttt taatttaaaa   7440
ggatctaggt gaagatcctt tttgataatc tcatgaccaa aatcccttaa cgtgagtttt   7500
cgttccactg agcgtcagac cccgtagaaa agatcaaagg atcttcttga gatcctttt    7560 ttctgcgcgt aatctgctgc ttgcaaacaa aaaaaccacc gctaccagcg gtggtttgtt   7620
tgccggatca agagctacca actctttttc cgaaggtaac tggcttcagc agagcgcaga   7680
taccaaatac tgtccttcta gtgtagccgt agttaggcca ccacttcaag aactctgtag   7740
caccgcctac atacctcgct ctgctaatcc tgttaccagt ggctgctgcc agtggcgata   7800
agtcgtgtct taccgggttg gactcaagac gatagttacc ggataaggcg cagcggtcgg   7860
gctgaacggg gggttcgtgc acacagccca gcttggagcg aacgacctac accgaactga   7920
gatacctaca gcgtgagcat tgagaaagcg ccacgcttcc cgaagggaga aaggcggaca   7980
ggtatccggt aagcggcagg gtcggaacag gagagcgcac gagggagctt ccaggggga   8040 acgcctggta tctttatagt cctgtcgggt ttcgccacct ctgacttgag cgtcgatttt   8100
```

-continued

| | |
|---|---|
| tgtgatgctc gtcaggggg cggagcctat ggaaaaacgc cagcaacgcg gccttttac | 8160 |
| ggttcctggc cttttgctgg ccttttgctc acatgttctt tcctgcgtta tcccctgatt | 8220 |
| ctgtggataa ccgtattacc gcctttgagt gagctgatac cgctcgccgc agccgaacga | 8280 |
| ccgagcgcag cgagtcagtg agcgaggaag cggaagagcg cccaatacgc aaaccgcctc | 8340 |
| tccccgcgcg ttggccgatt cattaatgca ggttaacctg gcttatcgaa attaatacga | 8400 |
| ctcactatag ggagaccggc agatcgatct gtcga | 8435 |

<210> SEQ ID NO 91
<211> LENGTH: 8429
<212> TYPE: DNA
<213> ORGANISM: Unknown Organism
<220> FEATURE:
<223> OTHER INFORMATION: Description of Unknown Organism: pTRABacHuLCHC1
   DNA sequence

<400> SEQUENCE: 91

| | |
|---|---|
| gcagttcgtt gacgccttcc tccgtgtggc cgaacacgtc gagcgggtgg tcgatgacca | 60 |
| gcggcgtgcc gcacgcgacg cacaagtatc tgtacaccga atgatcgtcg ggcgaaggca | 120 |
| cgtcggcctc caagtggcaa tattggcaaa ttcgaaaata tatacagttg ggttgtttgc | 180 |
| gcatatctat cgtggcgttg ggcatgtacg tccgaacgtt gatttgcatg caagccgaaa | 240 |
| ttaaatcatt gcgattagtg cgattaaaac gttgtacatc ctcgctttta atcatgccgt | 300 |
| cgattaaatc gcgcaatcga gtcaagtgat caaagtgtgg aataatgttt tctttgtatt | 360 |
| cccgagtcaa gcgcagcgcg tattttaaca aactagccat cttgtaagtt agtttcatt | 420 |
| aatgcaactt tatccaataa tatattatgt atcgcacgtc aagaattaac aatgcgcccg | 480 |
| ttgtcgcatc tcaacacgac tatgatagag atcaaataaa gcgcgaatta atagcttgc | 540 |
| gacgcaacgt gcacgatctg tgcacgcgtt ccggcacgag ctttgattgt aataagtttt | 600 |
| tacgaagcga tgacatgacc cccgtagtga aacgatcac gcccaaaaga actgccgact | 660 |
| acaaaattac cgagtatgtc ggtgacgtta aaactattaa gccatccaat cgaccgttag | 720 |
| tcgaatcagg accgctggtg cgagaagccg cgaagtatgg cgaatgcatc gtataacgtg | 780 |
| tggagtccgc tcattagagc gtcatgtta gacaagaaag ctacatattt aattgatccc | 840 |
| gatgatttta ttgataaatt gaccctaact ccatacacgg tattctacaa tggcggggtt | 900 |
| ttggtcaaaa tttccggact gcgattgtac atgctgttaa cggctccgcc cactattaat | 960 |
| gaaattaaaa attccaattt taaaaacgc agcaagagaa acatttgtat gaaagaatgc | 1020 |
| gtagaaggaa agaaaaatgt cgtcgacatg ctgaacaaca agattaatat gcctccgtgt | 1080 |
| ataaaaaaaa tattgaacga tttgaaagaa aacaatgtac cgcgcggcgg tatgtacagg | 1140 |
| aagaggttta tactaaactg ttacattgca aacgtggttt cgtgtgccaa gtgtgaaaac | 1200 |
| cgatgtttaa tcaaggctct gacgcatttc tacaaccacg actccaagtg tgtgggtgaa | 1260 |
| gtcatgcatc ttttaatcaa atcccaagat gtgtataaac caccaaactg ccaaaaatg | 1320 |
| aaaactgtcg acaagctctg tccgtttgct ggcaactgca agggtctcaa tcctatttgt | 1380 |
| aattattgaa taataaaaca attataaatg ctaaatttgt tttttattaa cgatacaaac | 1440 |
| caaacgcaac aagaacattt gtagtattat ctataattga aaacgcgtag ttataatcgc | 1500 |
| tgaggtaata tttaaaatca ttttcaaatg attcacagtt aatttgcgac aatataattt | 1560 |
| tattttcaca taaactagac gccttgtcgt cttcttcttc gtattccttc tctttttcat | 1620 |
| ttttctcctc ataaaaatta acatagttat tatcgtatcc atatatgtat ctatcgtata | 1680 |
| gagtaaattt tttgttgtca taaatatata tgtctttttt aatggggtgt atagtaccgc | 1740 |

-continued

```
tgcgcatagt ttttctgtaa tttacaacag tgctattttc tggtagttct tcggagtgtg    1800
ttgctttaat tattaaattt atataatcaa tgaatttggg atcgtcggtt ttgtacaata    1860
tgttgccggc atagtacgca gcttcttcta gttcaattac accatttttt agcagcaccg    1920
gattaacata actttccaaa atgttgtacg aaccgttaaa caaaaacagt tcacctccct    1980
tttctatact attgtctgcg agcagttgtt tgttgttaaa aataacagcc attgtaatga    2040
gacgcacaaa ctaatatcac aaactggaaa tgtctatcaa tatatagttg ctgatatctc    2100
cccagcatgc ctgctattgt cttcccaatc ctcccccttg ctgtcctgcc ccaccccacc    2160
ccccagaata gaatgacacc tactcagaca atgcgatgca atttcctcat tttattagga    2220
aaggacagtg ggagtggcac cttccagggt caaggaaggc acggggagg ggcaaacaac    2280 agatggctgg caactagaag gcacagtcga ggctgatcag cgagctctag tctagactat    2340
tatttacccg gagacaggga gaggctcttc tgcgtgtagt ggttgtgcag agcctcatgc    2400
atcacggagc atgagaagac gttcccctgc tgccacctgc tcttgtccac ggtgagcttg    2460
ctgtagagga agaaggagcc gtcggagtcc agcacgggag gcgtggtctt gtagttgttc    2520
tccggctgcc cattgctctc ccactccacg gcgatgtcgc tgggatagaa gcctttgacc    2580
aggcaggtca ggctgacctg gttcttggtc agctcatccc gggatggggg cagggtgtac    2640
acctgtggtt ctcggggctg ccctttggct ttggagatgg ttttctcgat ggggctggg    2700 agggctttgt tggagacctt gcacttgtac tccttgccat tcagccagtc ctggtgcagg    2760
acggtgagga cgctgaccac acggtacgtg ctgttgtact gctcctcccg cggctttgtc    2820
ttggcattat gcacctccac gccgtccacg taccagttga acttgacctc agggtcttcg    2880
tggctcacgt ccaccaccac gcatgtgacc tcagggtcc gggagatcat gagggtgtcc    2940
ttgggttttg gggggaagag gaagactgac ggtcccccca ggagttcagg tgctgggcac    3000
ggtgggcatg tgtgagtttt gtcacaagat ttgggctcaa ctttcttgtc caccttggtg    3060
ttgctgggct tgtgattcac gttgcagatg taggtctggg tgcccaagct gctggagggc    3120
acggtcacca cgctgctgag ggagtagagt cctgaggact gtaggacagc cgggaaggtg    3180
tgcacgccgc tggtcagggc gcctgagttc acgacaccg tcaccggttc ggggaagtag    3240
tccttgacca ggcagcccag ggccgctgtg ccccagagg tgctcttgga ggagggtgcc    3300
agggggaaga ccgatgggcc cttatcaaac tagtgcaacg ttgactaaga atttcatgcg    3360
gccgcgtacg attgtaaata aaatgtaatt tacagtatag tattttaatt aatatacaaa    3420
tgatttgata ataattctta tttaactata atatattgtg ttgggttgaa ttaaaggtcc    3480
cggcatcctc aaatgcataa tatcatagtc ccccttgttg taagtgatgc gtatttctga    3540
atctttgtaa aatagcacac aggactccaa cgcgtttggc gttttatttt cttgctcgag    3600
gatatcatgg agataattaa aatgataacc atctcgcaaa taaataagta ttttactgtt    3660
ttcgtaacag ttttgtaata aaaaaaccta taaatattcc ggattattca taccgtccca    3720
ccatcgggcg tgctagcgga tccatggtgg accctgcat gctgctgctg ctgctgctgc    3780
taggcctttg ataacacccca gtgtcactct gttcccgccc tcctctgagg agcttcaagc    3840
caacaaggcc acactggtgt gtctcataag tgacttctac ccgggagccg tgacagtggc    3900
ctggaaggca gatagcagcc ccgtcaaggc gggagtggag accaccacac cctccaaaca    3960
aagcaacaac aagtacgcgg ccagcagcta cctgagcctg acgcctgagc agtggaagtc    4020
ccacaaaagc tacagctgcc aggtcacgca tgaagggagc accgtggaga agacagtggc    4080
ccctacagaa tgttcatagt aaaagcttgt cgttggatgg aaaggaaaag agttctacag    4140
```

```
ggaaacttgg acccgcttca tggaagacag cttccccatt gttaacgacc aagaagtgat    4200
ggatgttttc cttgttgtca acatgcgtcc cactagaccc aaccgttgtt acaaattcct    4260
ggcccaacac gctctgcgtt gcgaccccga ctatgtacct catgacgtga ttaggatcgt    4320
cgagccttca tgggtgggca gcaacaacga gtaccgcatc agcctggcta agaagggcgg    4380
cggctgccca ataatgaacc ttcactctga gtacaccaac tcgttcgaac agttcatcga    4440
tcgtgtcatc tgggagaact tctacaagcc catcgtttac atcggtaccg actctgctga    4500
agaggaggaa attctccttg aagtttccct ggtgttcaaa gtaaaggagt ttgcaccaga    4560
cgcacctctg ttcactggtc cggcgtatta aaacacgata cattgttatt agtacattta    4620
ttaagcgcta gattctgtgc gttgttgatt tacagacaat tgttgtacgt atttttaataa   4680 ttcattaaat ttataatctt tagggtggta tgttagagcg aaaatcaaat gattttcagc    4740
gtctttatat ctgaatttaa atattaaatc ctcaatagat ttgtaaaata ggtttcgatt    4800
agtttcaaac aagggttgtt tttccgaacc gatggctgga ctatctaatg gattttcgct    4860
caacgccaca aaacttgcca aatcttgtag cagcaatcta gctttgtcga tattcgtttg    4920
tgttttgttt tgtaataaag gttcgacgtc gttcaaaata ttatgcgctt ttgtatttct    4980
ttcatcactg tcgttagtgt acaattgact cgacgtaaac acgttaaata aagctagctt    5040
ggacatattt aacatcgggc gtgttagctt tattaggccg attatcgtcg tcgtcccaac    5100
cctcgtcgtt agaagttgct tccgaagacg attttgccat agccacacga cgcctattaa    5160
ttgtgtcggc taacacgtcc gcgatcaaat ttgtagttga gcttttttgga attatttctg   5220 attgcgggcg ttttttgggcg ggtttcaatc taactgtgcc cgattttaat tcagacaaca   5280
cgttagaaag cgatggtgca ggcggtggta acatttcaga cggcaaatct actaatggcg    5340
gcggtggtgg agctgatgat aaatctacca tcggtggagg cgcaggcggg gctggcggcg    5400
gaggcggagg cggaggtggt ggcggtgatg cagacggcgg tttaggctca aatgtctctt    5460
taggcaacac agtcggcacc tcaactattg tactggtttc gggcgccgtt tttggtttga    5520
ccggtctgag acgagtgcga ttttttttcgt ttctaatagc ttccaacaat tgttgtctgt   5580
cgtctaaagg tgcagcgggt tgaggttccg tcggcattgg tggagcgggc ggcaattcag    5640
acatcgatgg tggtggtggt ggtggaggcg ctggaatgtt aggcacggga gaaggtggtg    5700
gcggcggtgc cgccggtata atttgttctg gtttagtttg ttcgcgcacg attgtgggca    5760
ccggcgcagg cgccgctggc tgcacaacgg aaggtcgtct gcttcgaggc agcgcttggg    5820
gtggtggcaa ttcaatatta taattggaat acaaatcgta aaaatctgct ataagcattg    5880
taatttcgct atcgtttacc gtgccgatat ttaacaaccg ctcaatgtaa gcaattgtat    5940
tgtaaagaga ttgtctcaag ctccgcacgc cgataacaag ccttttcatt tttactacag    6000
cattgtagtg gcgagacact tcgctgtcgt cgactcgagt tctatagtgt cacctaaatc    6060
gtatgtgtat gatacataag gttatgtatt aattgtagcc gcgttctaac gacaatatgt    6120
ccatatggtg cactctcagt acaatctgct ctgatgccgc atagttaagc cagccccgac    6180
acccgccaac acccgctgac gcgccctgac gggcttgtct gctcccggca tccgcttaca    6240
gacaagctgt gaccgtctcc gggagctgca tgtgtcagag gttttcaccg tcatcaccga    6300
aacgcgcgag aggaaagggc ctcgtgatac gcctattttt ataggttaat gtcatgataa    6360
taatggtttc ttagacgtca ggtggcactt ttcggggaaa tgtgcgcgga acccctattt    6420
gtttattttt ctaaatacat tcaaatatgt atccgctcat gagacaataa ccctgataaa    6480
```

```
tgcttcaata atattgaaaa aggaagagta tgagtattca acatttccgt gtcgcccttα    6540
ttccctttt  tgcggcattt tgccttcctg tttttgctca cccagaaacg ctggtgaaag    6600
taaaagatgc tgaagatcag ttgggtgcac gagtgggtta catcgaactg atctcaaca    6660
gcggtaagat ccttgagagt tttcgccccg aagaacgttt tccaatgatg agcactttta    6720
aagttctgct atgtggcgcg gtattatccc gtattgacgc cgggcaagag caactcggtc    6780
gccgcataca ctattctcag aatgacttgg ttgagtactc accagtcaca gaaaagcatc    6840
ttacggatgg catgacagta agagaattat gcagtgctgc cataaccatg agtgataaca    6900
ctgcggccaa cttacttctg acaacgatcg gaggaccgaa ggagctaacc gcttttttgc    6960
acaacatggg ggatcatgta actcgccttg atcgttggga accggagctg aatgaagcca    7020
taccaaacga cgagcgtgac accacgatgc ctgtagcaat ggcaacaacg ttgcgcaaac    7080
tattaactgg cgaactactt actctagctt cccggcaaca attaatagac tggatggagg    7140
cggataaagt tgcaggacca cttctgcgct cggcccttcc ggctggctgg tttattgctg    7200
ataaatctgg agccggtgag cgtgggtctc gcggtatcat tgcagcactg gggccagatg    7260
gtaagccctc ccgtatcgta gttatctaca cgacggggag tcaggcaact atggatgaac    7320
gaaatagaca gatcgctgag ataggtgcct cactgattaa gcattggtaa ctgtcagacc    7380
aagtttactc atatatactt tagattgatt taaaacttca ttttttaattt aaaaggatct    7440
aggtgaagat cctttttgat aatctcatga ccaaaatccc ttaacgtgag ttttcgttcc    7500
actgagcgtc agaccccgta gaaaagatca aaggatcttc ttgagatcct ttttttctgc    7560
gcgtaatctg ctgcttgcaa acaaaaaaac caccgctacc agcggtggtt tgtttgccgg    7620
atcaagagct accaactctt tttccgaagg taactggctt cagcagagcg cagataccaa    7680
atactgtcct tctagtgtag ccgtagttag gccaccactt caagaactct gtagcaccgc    7740
ctacatacct cgctctgcta atcctgttac cagtggctgc tgccagtggc gataagtcgt    7800
gtcttaccgg gttggactca agacgatagt taccggataa ggcgcagcgg tcgggctgaa    7860
cggggggttc gtgcacacag cccagcttgg agcgaacgac ctacaccgaa ctgagatacc    7920
tacagcgtga gcattgagaa agcgccacgc ttcccgaagg gagaaaggcg gacaggtatc    7980
cggtaagcgg cagggtcgga acaggagagc gcacgaggga gcttccaggg ggaaacgcct    8040
ggtatcttta tagtcctgtc gggtttcgcc acctctgact tgagcgtcga ttttgtgat    8100
gctcgtcagg gggcggagc  ctatggaaaa acgccagcaa cgcggccttt ttacggttcc    8160
tggccttttg ctggcctttt gctcacatgt tctttcctgc gttatcccct gattctgtgg    8220
ataaccgtat taccgccttt gagtgagctg ataccgctcg ccgcagccga acgaccgagc    8280
gcagcgagtc agtgagcgag gaagcggaag agcgcccaat acgcaaaccg cctctccccg    8340
cgcgttggcc gattcattaa tgcaggttaa cctggcttat cgaaattaat acgactcact    8400
atagggagac cggcagatcg atctgtcga                                      8429
```

<210> SEQ ID NO 92
<211> LENGTH: 120
<212> TYPE: DNA
<213> ORGANISM: Autographa californica nucleopolyhedrovirus

<400> SEQUENCE: 92

```
cttttctata ctattgtctg cgagcagttg tttgttgtta aaaataacag ccattgtaat    60
gagacgcaca aactaatatc acaaactgga aatgtctatc aatatatagt tgctgatatc    120
```

```
<210> SEQ ID NO 93
<211> LENGTH: 230
<212> TYPE: DNA
<213> ORGANISM: Autographa californica nucleopolyhedrovirus

<400> SEQUENCE: 93
tcgagcaaga aaataaaacg ccaaacgcgt tggagtcttg tgtgctattt tacaaagatt       60
cagaaatacg catcacttac aacaaggggg actatgaaat tatgcatttg aggatgccgg     120
gacctttaat tcaacccaac acaatatatt atagttaaat aagaattatt atcaaatcat     180
ttgtatatta attaaaatac tatactgtaa attacatttt atttacaatc                 230
```